United States Patent
Bourke, Jr. et al.

(10) Patent No.: US 10,080,275 B2
(45) Date of Patent: *Sep. 18, 2018

(54) UP AND DOWN CONVERSION SYSTEMS FOR PRODUCTION OF EMITTED LIGHT FROM VARIOUS ENERGY SOURCES INCLUDING RADIO FREQUENCY, MICROWAVE ENERGY AND MAGNETIC INDUCTION SOURCES FOR UPCONVERSION

(71) Applicants: IMMUNOLIGHT, LLC, Detroit, MI (US); DUKE UNIVERSITY, Durham, NC (US)

(72) Inventors: Frederic A. Bourke, Jr., Greenwich, CT (US); Zakaryae Fathi, Raleigh, NC (US); Ian Nicholas Stanton, Durham, NC (US); Michael J. Therien, Durham, NC (US); Paul Rath Stauffer, Durham, NC (US); Paolo Maccarini, Durham, NC (US); Katherine Sarah Hansen, Cary, NC (US); Diane Renee Fels, Morrisville, NC (US); Cory Robert Wyatt, Durham, NC (US)

(73) Assignees: IMMUNOLIGHT, LLC, Detroit, MI (US); DUKE UNIVERSITY, Durham, NC (US)

( * ) Notice: Subject to any disclaimer, the term of this patent is extended or adjusted under 35 U.S.C. 154(b) by 397 days.

This patent is subject to a terminal disclaimer.

(21) Appl. No.: 14/688,687

(22) Filed: Apr. 16, 2015

(65) Prior Publication Data
US 2015/0283392 A1 Oct. 8, 2015

Related U.S. Application Data

(62) Division of application No. 12/943,787, filed on Nov. 10, 2010, now Pat. No. 9,232,618.
(Continued)

(51) Int. Cl.
*H05B 41/28* (2006.01)
*A61L 2/10* (2006.01)
(Continued)

(52) U.S. Cl.
CPC ............ *H05B 41/2806* (2013.01); *A61L 2/10* (2013.01); *A61N 1/40* (2013.01); *A61N 1/44* (2013.01);
(Continued)

(58) Field of Classification Search
CPC ... H01J 9/00; H01J 61/00; A61N 5/00; G01N 33/00; G01N 2033/0003; G01N 33/53;
(Continued)

(56) References Cited

U.S. PATENT DOCUMENTS

| 4,608,222 A | 8/1986 | Brueckner |
| 5,118,422 A | 6/1992 | Cooper et al. |

(Continued)

FOREIGN PATENT DOCUMENTS

| CA | 2 352 266 A1 | 6/2000 |
| CN | 1328474 A | 12/2001 |

(Continued)

OTHER PUBLICATIONS

Combined Office Action and Search Report dated Nov. 27, 2015 in Chinese Patent Application No. 201080061112.8 (submitting English translation only).
(Continued)

*Primary Examiner* — David Porta
*Assistant Examiner* — Djura Malevic
(74) *Attorney, Agent, or Firm* — Oblon, McClelland, Maier & Neustadt, L.L.P.

(57) ABSTRACT

Methods and systems for producing a change in a medium. A first method and system (1) place in a vicinity of the medium at least one upconverter including a gas for plasma
(Continued)

ignition, with the upconverter being configured, upon exposure to initiation energy, to generate light for emission into the medium, and (2) apply the initiation energy from an energy source including the first wavelength $\lambda_1$ to the medium, wherein the emitted light directly or indirectly produces the change in the medium. A second method and system (1) place in a vicinity of the medium an agent receptive to microwave radiation or radiofrequency radiation, and (2) apply as an initiation energy the microwave radiation or radiofrequency radiation by which the agent directly or indirectly generates emitted light in the infrared, visible, or ultraviolet range to produce at least one of physical and biological changes in the medium.

26 Claims, 67 Drawing Sheets

Related U.S. Application Data

(60) Provisional application No. 61/259,940, filed on Nov. 10, 2009.

(51) Int. Cl.
   A61N 1/40    (2006.01)
   A61N 1/44    (2006.01)
   C02F 1/32    (2006.01)
   H01J 65/04   (2006.01)
   A61N 2/00    (2006.01)
   A61N 5/10    (2006.01)

(52) U.S. Cl.
   CPC .............. C02F 1/32 (2013.01); H01J 65/042 (2013.01); A61N 2/00 (2013.01); A61N 5/10 (2013.01); Y02B 20/22 (2013.01); Y02W 10/37 (2015.05)

(58) Field of Classification Search
   CPC ........... G01N 33/551; G01N 33/54346; G01N 33/553; G02B 26/00
   See application file for complete search history.

(56) References Cited

U.S. PATENT DOCUMENTS

| | | | |
|---|---|---|---|
| 5,759,767 A | 6/1998 | Lakowicz et al. | |
| 5,773,609 A | 6/1998 | Robinson et al. | |
| 5,917,605 A | 6/1999 | Colvin, Jr. | |
| 6,344,272 B1 | 2/2002 | Oldenburg et al. | |
| 6,530,944 B2 | 3/2003 | West et al. | |
| 6,699,724 B1 | 3/2004 | West et al. | |
| 6,924,921 B2 | 8/2005 | Lewis et al. | |
| 7,112,306 B2 * | 9/2006 | Obee ......................... A61L 9/20 422/121 |
| 7,294,656 B2 | 11/2007 | Bach et al. | |
| 7,297,374 B1 | 11/2007 | Arney et al. | |
| 7,500,953 B2 | 3/2009 | Oraevsky et al. | |
| 7,604,523 B1 | 10/2009 | Wedding et al. | |
| 7,767,260 B2 | 8/2010 | Peng et al. | |
| 8,138,673 B1 * | 3/2012 | Wedding ................. H01J 11/18 313/567 |
| 8,236,239 B2 | 8/2012 | Bernstein | |
| 8,376,013 B2 | 2/2013 | Bourke et al. | |
| 8,389,958 B2 | 3/2013 | Vo-Dinh et al. | |
| 8,471,217 B2 | 6/2013 | Himmelhaus | |
| 8,502,972 B2 | 8/2013 | Himmelhaus et al. | |
| 8,565,860 B2 | 10/2013 | Kimchy et al. | |
| 2002/0045675 A1 | 4/2002 | Halas et al. | |
| 2002/0103517 A1 | 8/2002 | West et al. | |
| 2002/0119485 A1 | 8/2002 | Morgan | |
| 2002/0127224 A1 | 9/2002 | Chen | |
| 2002/0140381 A1 | 10/2002 | Golkowski et al. | |
| 2003/0034486 A1 | 2/2003 | Korgel | |
| 2003/0066998 A1 | 4/2003 | Lee | |
| 2003/0151376 A9 | 8/2003 | Cao | |
| 2003/0174384 A1 | 9/2003 | Halas et al. | |
| 2003/0206833 A1 | 11/2003 | Obee et al. | |
| 2003/0209836 A1 | 11/2003 | Sherwood | |
| 2003/0219785 A1 | 11/2003 | Hallahan et al. | |
| 2004/0014060 A1 | 1/2004 | Hoheisel et al. | |
| 2004/0036130 A1 | 2/2004 | Lee et al. | |
| 2004/0067431 A1 | 4/2004 | Arney et al. | |
| 2004/0196538 A1 | 10/2004 | Burgener et al. | |
| 2004/0198857 A1 | 10/2004 | Dejneka et al. | |
| 2004/0253138 A1 | 12/2004 | Malak | |
| 2005/0020869 A1 | 1/2005 | Hainfeld et al. | |
| 2005/0129947 A1 | 6/2005 | Peng et al. | |
| 2005/0175540 A1 | 8/2005 | Oraevsky et al. | |
| 2005/0186565 A1 | 8/2005 | Malak | |
| 2005/0253308 A1 | 11/2005 | Sherwood | |
| 2005/0258419 A1 | 11/2005 | Sankaran et al. | |
| 2006/0011862 A1 | 1/2006 | Bernstein | |
| 2006/0119853 A1 | 6/2006 | Baumberg et al. | |
| 2007/0018140 A1 | 1/2007 | Lee et al. | |
| 2007/0059705 A1 | 3/2007 | Lu et al. | |
| 2007/0063154 A1 | 3/2007 | Chen et al. | |
| 2007/0178133 A1 | 8/2007 | Rolland | |
| 2007/0217996 A1 | 9/2007 | Levy et al. | |
| 2007/0218049 A1 | 9/2007 | Chen et al. | |
| 2008/0004364 A1 | 1/2008 | Huo et al. | |
| 2008/0107823 A1 | 5/2008 | Morii et al. | |
| 2008/0115817 A1 | 5/2008 | Defries | |
| 2008/0154431 A1 | 6/2008 | Defries et al. | |
| 2008/0236652 A1 | 10/2008 | Defries et al. | |
| 2008/0248001 A1 | 10/2008 | Bourke | |
| 2008/0271778 A1 | 11/2008 | Defries et al. | |
| 2009/0066948 A1 | 3/2009 | Karpowicz et al. | |
| 2009/0191128 A1 | 7/2009 | Ronda et al. | |
| 2009/0253227 A1 | 10/2009 | Defries et al. | |
| 2009/0263485 A1 * | 10/2009 | Li ........................ G01N 33/587 424/489 |
| 2009/0302235 A1 | 12/2009 | Himmelhaus | |
| 2009/0317295 A1 | 12/2009 | Yonesu et al. | |
| 2010/0135856 A1 | 6/2010 | Pyo et al. | |
| 2010/0203454 A1 | 8/2010 | Brongersma et al. | |
| 2010/0224821 A1 | 9/2010 | Mandelbaum et al. | |
| 2010/0277718 A1 | 11/2010 | Zhang et al. | |
| 2010/0307553 A1 | 12/2010 | Defries et al. | |
| 2011/0213192 A1 | 9/2011 | Levy et al. | |
| 2011/0253909 A1 | 10/2011 | Himmelhaus et al. | |
| 2012/0326089 A1 | 12/2012 | Anderson et al. | |
| 2013/0105709 A1 | 5/2013 | Himmelhaus | |
| 2013/0257270 A1 | 10/2013 | Rojeski | |

FOREIGN PATENT DOCUMENTS

| | | |
|---|---|---|
| CN | 1649632 A | 8/2005 |
| EP | 2130553 A1 | 12/2009 |
| WO | WO 2006/103287 A2 | 10/2006 |
| WO | WO 2008/118234 A2 | 10/2008 |
| WO | WO 2008/124681 A2 | 10/2008 |
| WO | WO 2008118234 A2 | 10/2008 |

OTHER PUBLICATIONS

Tai-zhong Zhang, et al., "Inorganic Photoluminescence Material and Application", Chemical Industry Press, Mar. 31, 2005, 301 Pages.

Chinese Office Action dated Apr. 18, 2016 in Patent Application No. 201080061112.8 (with English Translation).

Combined Taiwanese Office Action and Search Report dated Apr. 12, 2016 in Patent Application No. 099138775 (with English translation of categories of cited documents and English translation of Search Report).

Office Action dated Mar. 10, 2015 in corresponding Taiwan Patent Application No. 099108027 (with English translation).

Office Action dated Jan. 20, 2017 in European Patent Application No. 10830631.7.

(56) References Cited

OTHER PUBLICATIONS

Formality Examination Report dated May 29, 2013 in Saudi Arabian Patent Application No. 113 34 0925 (with partial English language translation).
Office Action dated Nov. 7, 2013 in Saudi Arabian Patent Application No. 82091207.
Office Action dated Jul. 9, 2014 in Pakistan Patent Application No. 209/2010 (submitting English language translation only).
Office Action and Search Report dated Sep. 4, 2014 in Taiwan Patent Application No. 099108027 (with English translation).
International Search Report and Written Opinion of the International Searching Authority dated Mar. 28, 2011, in Patent Application No. PCT/US2010/056178.
T.V. Teperik, et al., "Strong terahertz absorption bands in a scaled plasmonic crystal", Applied Physics Letters, vol. 90, 251910, Jun. 19, 2007, pp. 90-92.
Serena Eley, et al., "A Study of Optical Properties of Zblan Microspheres Produced in Microgravity", NASA Reduced Gravity Student Flight Opportunites Program 2002, Competition, 2002, pp. 1-18.
Partial Supplementary European Search Report dated Sep. 22, 2016 in Patent Application No. 10830631.7.
Office Action dated Jan. 29, 2018 in European Patent Application No. 10830631.7, 5 pages.

\* cited by examiner

- Metastable equilibrium site
- Mono-valent ionic species (Na, K, Li)

Type A          Type X

Figure 54-3A
Figure 54-3B
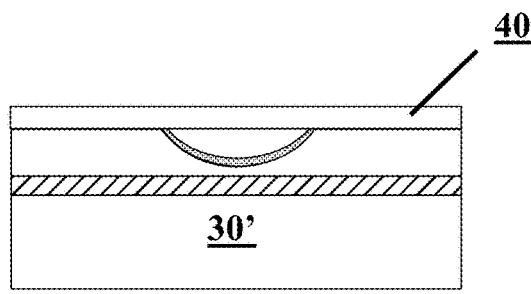
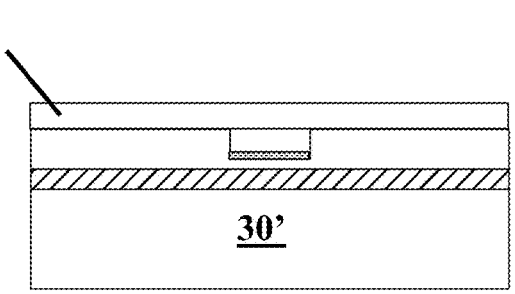
Figure 54-4A
Figure 54-4B
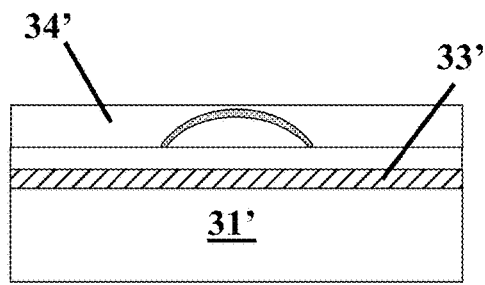
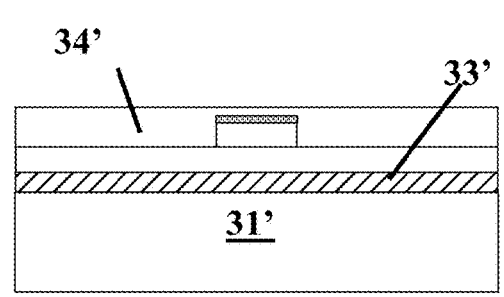

Figure 54-5A
Figure 54-5B
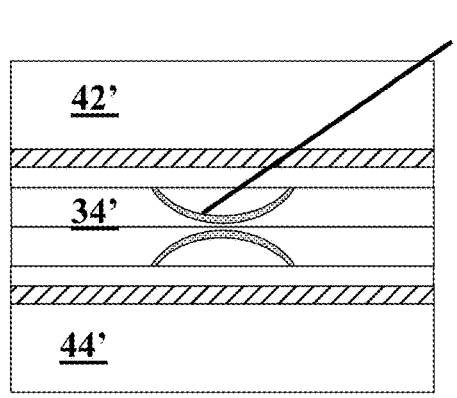
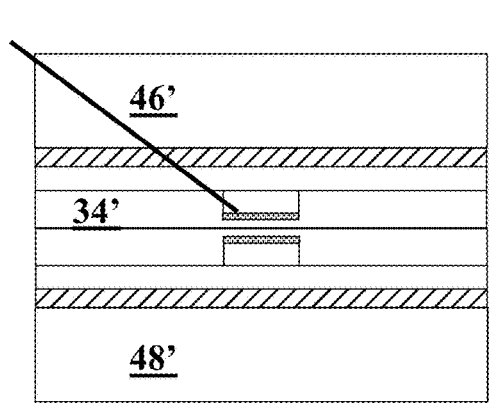
Figure 54-6A
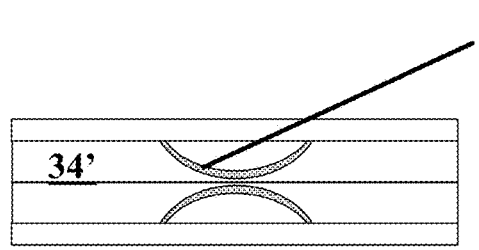
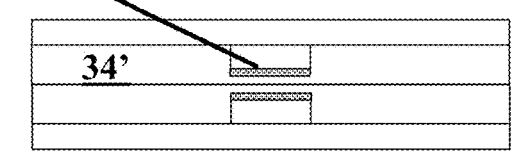
Figure 54-6B
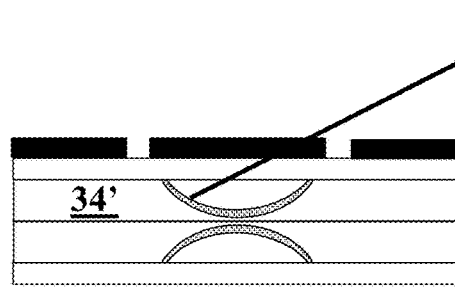
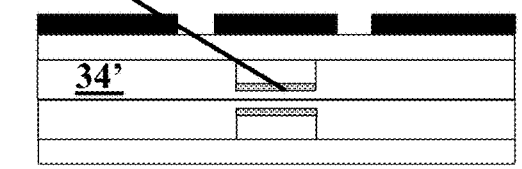

500

Electric Field or Magentic Field Probe

UP AND DOWN CONVERSION SYSTEMS FOR PRODUCTION OF EMITTED LIGHT FROM VARIOUS ENERGY SOURCES INCLUDING RADIO FREQUENCY, MICROWAVE ENERGY AND MAGNETIC INDUCTION SOURCES FOR UPCONVERSION

CROSS REFERENCE TO RELATED APPLICATIONS

This application is a continuation of U.S. Ser. No. 12/943,787 filed Nov. 10, 2010 and is related to Provisional Application Ser. No. 60/954,263, filed Aug. 6, 2007, and 61/030,437, filed Feb. 21, 2008, and U.S. application Ser. No. 12/059,484, filed Mar. 31, 2008, the entire contents of which are hereby incorporated herein by reference. This application is also related to U.S. application Ser. No. 11/935,655, filed Nov. 6, 2007; and Provisional Application Ser. No. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, the entire contents of which are hereby incorporated by reference. This application is related to U.S. provisional patent application 61/161,328, filed Mar. 18, 2009, the entire content of which is hereby incorporated by reference. This application is related to U.S. provisional patent application Ser. No. 12/417,779, filed Apr. 3, 2009, the entire content of which is hereby incorporated by reference. This application is related to PCT application PCT/US2009/050514, filed Jul. 14, 2009, the entire content of which is hereby incorporated by reference. This application is related to U.S. patent application Ser. No. 12/725,108, filed Mar. 16, 2010, the entire content of which is hereby incorporated by reference.

This application is related to and claims priority under 35 U.S.C. 119 to U.S. provisional patent application 61/259,940, filed Nov. 10, 2009, the entire content of which is hereby incorporated by reference.

BACKGROUND OF THE INVENTION

Field of Invention

The invention relates to methods and systems for producing light from lower energy activation sources. The invention also relates to systems and methods for broad band up conversion from the microwave and RF regime to electromagnetic radiation of higher photonic energy in the UV, VIS, and IR regime.

Discussion of the Background

Presently, light (i.e., electromagnetic radiation from the radio frequency through the visible to the X-ray wavelength range) is used in a number of industrial, communication, electronic, and pharmaceutical processes. Light in the infra-red and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules). Both processes play a role in the glowing filament of incandescent lamps, whereas the latter process (electrons within atoms) occurs in fluorescent lamps.

The duality nature of light (or more generally electromagnetic radiation) is such that light is both a wave (characterized by a wavelength and amplitude) and a discrete parcel of energy or photon (characterized by its frequency times the Planck constant (denoted $\hbar$). The higher the frequency the higher the quantized energy carried by the radiation. All energy above the visible is considered in many circumstances to be ionizing radiation as its photons carry sufficient energy to ionize matter.

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ (1 $m/m^2$) in a certain direction per steradian (unit of solid angle) and the irradiance (illuminance) of a surface in $W/m^2$ (1 $m/m^2$ or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infra-red radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many if not all of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Up conversion and down conversion of electromagnetic radiations are very relevant to various industrials fields. Photo-activated chemical reactions find broad use in the industry from catalyzing reactions to Bio-modulation of therapeutic agents. However, UV radiation suffers from a lack of depth of penetration in matter especially biological media, polymers and most solids). For this reason, UV based photo-initiation is limited by direct line of site which prevents volumetric applications.

UV has been limited to reactions taking place on the outer surfaces of materials may they be solids or liquids; organic or inorganic; biological organs, living tissues and composites thereof, structural composites, materials residing inside chemical tanks/reactors for food processing or hydrocarbon chains fractionation (to name a few examples).

Recently, there has been interest in the development of microcavity plasma devices which have been shown to have robust lighting capabilities. These devices are unitarily connected devices driven by a common electrode shared between the microcavities patterned on a common substrate. Lamps have been made from arrays of microcavity plasma devices including dielectric barrier structures in each of the microcavities. The microcavities have used diamond-shaped cross sections and anodized aluminum for the dielectric barriers. The microcavity plasma devices require no ballast. In addition, the microcavity plasma devices have operated at pressures up to one atmosphere and beyond, thereby minimizing or eliminating the pressure differential across the lamp packaging.

Yet, the fact that these devices are unitarily connected devices driven by a common electrode shared between the microcavities patterned on a common substrate restrict utilization of the microcavity devices to discrete device applications such as lamps and recently have been used in transistor structures.

SUMMARY OF THE INVENTION

In one embodiment, there is provided a method for producing a change in a medium. The method (1) places in a vicinity of the medium at least one upconverter including a gas for plasma ignition. The upconverter is configured, upon exposure to initiation energy, to generate light for emission into the medium. The method (2) applies the initiation energy from an energy source including the first wavelength $\lambda_1$ to the medium, wherein the emitted light directly or indirectly produces the change in the medium.

In one embodiment of the invention, there is provided a method for curing of a radiation-curable medium. The method applies initiation energy throughout a composition comprising 1) an uncured radiation-curable medium and 2) at least one upconverter including a gas for ignition and configured, upon exposure to the initiation energy, to generate light for emission into the medium. The light is of a wavelength to cure the uncured medium by polymerization of polymers in the medium. The method cures the radiation-curable medium by activating a photoinitiator in the radiation-curable medium.

In one embodiment of the invention, there is provided a method for producing a change in a medium. The method (1) places in a vicinity of the medium an agent receptive to microwave radiation or radiofrequency radiation, and (2) applies as an initiation energy the microwave radiation or radiofrequency radiation by which the agent directly or indirectly generates emitted light in the infrared, visible, or ultraviolet range to produce at least one of physical and biological changes in the medium.

In one embodiment of the invention, there is provided a system for generating light. The system included a low frequency energy source which radiates a first wavelength $\lambda_1$ of radiation and a receptor having a microscopic dimension and which receives the first wavelength $\lambda_1$ of radiation and generates a second wavelength $\lambda_2$ of the emitted light in the infrared visible or the ultraviolet wavelength range.

In one embodiment of the invention, there is provided a microwave or rf receptor. The receptor includes a freestanding ionizable-gas containment filled with an ionizable gas which upon receipt of first wavelength $\lambda_1$ of microwave or rf energy emits light in the visible or ultraviolet wavelength range.

In one embodiment of the invention, there is provided a microwave or rf receptor. The receptor includes a partitioned structure including at least two reaction components and includes a partition separating the at least two reaction components, whereby mixing of the two reaction components upon microwave or rf radiation at first wavelength $\lambda_1$ produces at least one of a chemiluminescent or bioluminescent reaction for emission of the second wavelength $\lambda_2$.

In one embodiment of the invention, there is provided a method for producing light within the body of a subject. The method places inside the body a gas containment sealed with an ionizable gas, irradiates the body with microwave or rf energy, and ignites a plasma in the gas of the gas containment to thereby produce light within the body of the subject.

In one embodiment of the invention, there is provided a system for treating or diagnosing a human or animal subject. The system includes a gas containment sealed with an ionizable gas. The gas containment is configured to be disposed inside the human or animal subject. The system includes a source of microwave or rf energy configured to broadcast the microwave or rf energy into the human or animal subject. The source of microwave or rf energy at least partially having the capability to generate a plasma in the gas of the gas containment to thereby produce light within the body of the human or animal subject.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIGS. 54-1A to 54-1l are a group of schematics depicting various process for depositing a magnetic membrane structure or coating according to one embodiment of the invention;

DETAILED DESCRIPTION OF THE INVENTION

Figure 1A:
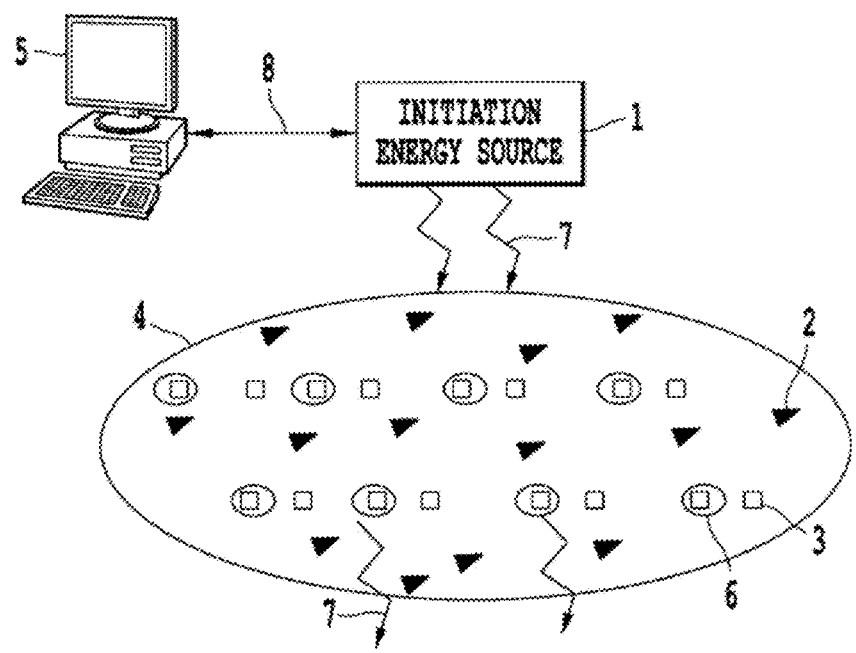
FIG. 1A is a schematic depicting a system according to another embodiment of the invention in which the initiation energy source is directed to a medium having energy modulation agents disbursed within the medium.

The invention is directed to methods and systems for producing electromagnetic radiation having desirable frequency windows (at least one frequency within a desirable frequency range) from other electromagnetic radiation having lower or higher frequency ranges using up converting transitional media or down converting transitional media as the case may apply. In various embodiments of the invention, the produced electromagnetic radiation is then be used to activate an agent in a vicinity of the medium where the up converting transitional media or the down converting transitional media are disposed. In various embodiments, the applied energy is considered to be up converted, as the photon energy carried by radiation 1 has an energy level equal to $hv_1$ (the product of Planck constant and frequency 1) is converted to a higher energy $hv_2$, where $hv_1$ is less than $hv_2$. In various embodiments, the applied energy is considered to be down converted, as energy at $hv_1$, is converted to a lower energy $hv_2$, where $hv_1$ is greater than $hv_2$.

In various embodiments of the invention, there are provided systems and methods for broad band up conversion from the microwave and RF regime to electromagnetic radiation of higher photonic energy in the UV, VIS, and IR regime. The invention can encompasses a variety of applications where the up and down conversions are conducted inside biological media, inside human and animal bodies, and in chemical reactors to name but a few.

The present inventors have realized in particular that such upconversion processing can be used in various materials, chemical, medical, pharmaceutical, or industrial processing. The ultraviolet, visible, and/or near infrared light can then be used to drive photoactivatable reactions in the host medium.

Reference will now be made in detail to a number of embodiments of the invention, examples of which are illustrated in the accompanying drawings, in which like reference characters refer to corresponding elements.

As shown in FIG. 1A, an exemplary system according to one embodiment of the invention may have an initiation energy source 1 directed at medium 4. Activatable agents 2 and energy modulation agents 3 are dispersed throughout the medium 4. The initiation energy source 1 may additionally be connected via a network 8 to a computer system 5 capable of directing the delivery of the initiation energy. In various embodiments, the energy modulation agents 3 are up converters or down converters such as for example fluorescent particles and other luminescent agents discussed below. In various embodiments, the energy modulation agents 3 are a gas containing up converter structures where energy from microwave radiation or radiofrequency radiation directly or indirectly generates emitted light in the infrared, visible, or ultraviolet range to produce physical and/or biological changes in the medium. As used herein, the term "change in the medium" includes but is not limited to the inducement of a photoactivated reaction such as for example drug activation, cell or bacteria or virus or yeast kill, radical generation, sterilization, polymerization, hardening, curing, localized heating from the emitted light, etc. One example of a biological change thus includes the thermal activation or the photo-activation of a therapeutic agent that in turn triggers a response in the cell viability in the medium.

In various embodiments, the energy modulation agents 3 are encapsulated energy modulation agents 6, depicted in FIG. 9A as silica encased energy modulation agents. As shown in FIG. 1A, initiation energy 7 (e.g. in the form of radiation from the initiation energy source 1) permeates throughout the medium 4. In some cases, the initiation energy 7 from the initiation energy source 1 may only permeate partially through the medium. The initiation energy 7 can be completely or partially consumed in the conversion process. Both the initiation and induced radiation (or emission) can represent energy coupled to the medium during the irradiation process.

As discussed below in more detail, the initiation energy source 1 can be an external energy source or an energy source located at least partially in the medium 4. As discussed below in more detail, activatable agents 2 and/or the energy modulation agents 3 can have plasmonics agents which enhance either the applied energy or the energy emitted from the energy modulation agents 3 so as to directly or indirectly produce a change in the medium.

In various embodiments, the initiation energy source 1 may be a linear accelerator equipped with image guided computer-control capability to deliver a precisely calibrated beam of radiation to a pre-selected coordinate. In these embodiments, down conversion can be used to generate internal light inside the medium. In these embodiments, x-rays or high energy particles from these or other sources can be used to directly or indirectly trigger ionization in a gas containing up converter structure of the invention. One example of such linear accelerators is the SmartBeam™ IMRT (intensity modulated radiation therapy) system from Varian medical systems (Varian Medical Systems, Inc., Palo Alto, Calif.). In other embodiments, the initiation energy source 1 may be commercially available components of X-ray machines or non-medical X-ray machines. X-ray machines that produce from 10 to 150 keV X-rays are readily available in the marketplace. For instance, the General Electric Definium series or the Siemens MULTIX series are but two examples of typical X-ray machines designed for the medical industry, while the Eagle Pack series from Smith Detection is an example of a non-medical X-ray machine. As such, the invention is capable of performing its desired function when used in conjunction with commercial X-ray equipment.

In other embodiments, the initiation energy source 1 can be a radio frequency or microwave source or infrared source emitting electromagnetic waves at a frequency which permeates at least a part of the medium and which triggers or produces or enhances secondary radiant energy emission within the medium by interaction with the energy modulation elements 6 therein, for example the gas containing up converter structures of the invention. In other embodiments, the initiation energy source 1 can be an ultraviolet, visible, near infrared (NIR) or infrared (IR) emitter emitting at a frequency which permeates at least a part of the medium 4 and which triggers or produces secondary radiant energy emission within medium 4 by interaction with the energy modulation elements 6 therein.

Figure 1B:
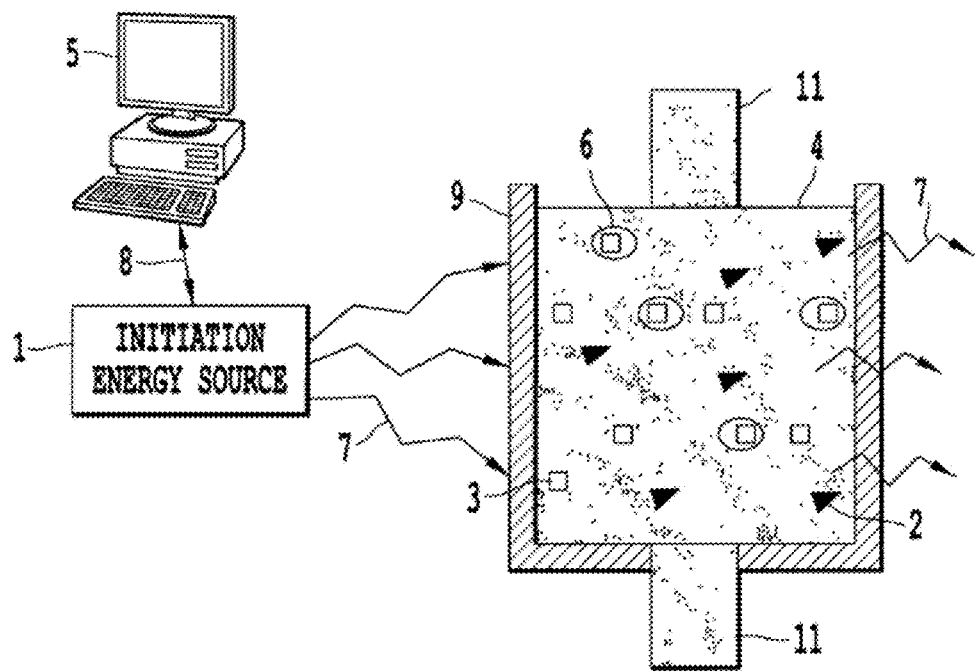
FIG. 1B is a schematic depicting a system according to another embodiment of the invention in which the initiation energy source is directed to a container enclosing a medium having energy modulation agents disbursed within the medium.

FIG. 1B is a schematic depicting another system according to another embodiment of the invention in which the initiation energy source 1 of FIG. 1A is directed to energy modulation elements 6 placed in the vicinity of a fluid medium 4 (e.g., a liquid or other fluid-like medium) and held inside a container 9. As shown in FIG. 1B, the modulation elements 6 by their positioning in the medium have the medium surrounding the modulation elements 6. The modulation elements 6 are inside the medium and therefore intimately in a vicinity of the medium to be activated thereabout each modulation element 6.

Figure 1C:
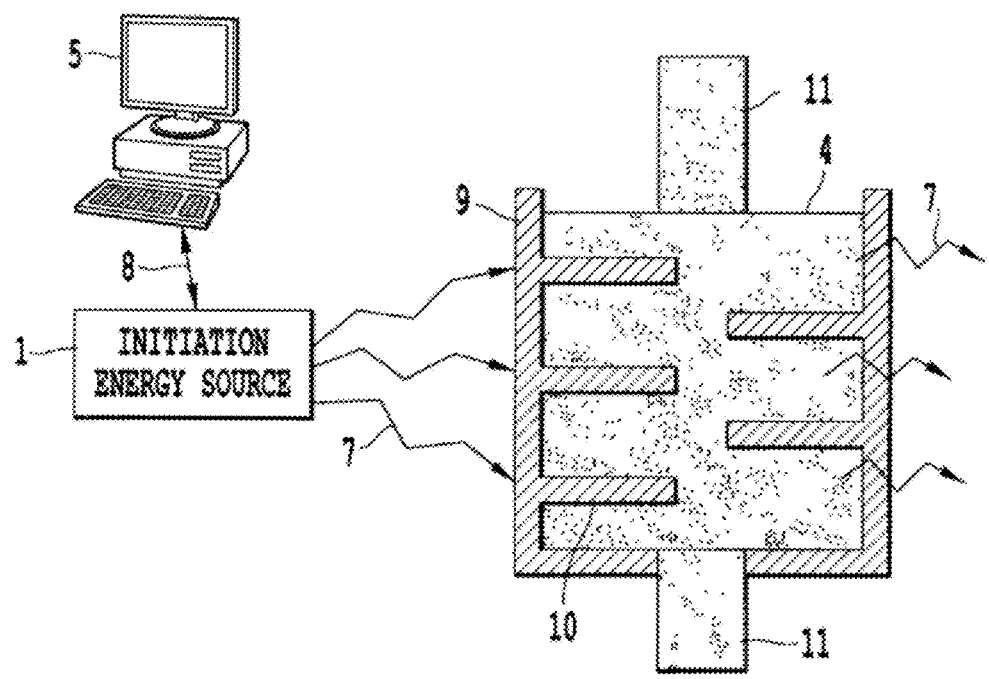
FIG. 1C is a schematic depicting a system according to another embodiment of the invention in which the initiation energy source is directed to a container enclosing a medium having energy modulation agents segregated within the medium.

The container 9 is made of a material that is "transparent" to the initiation energy 7. For example, plastic, quartz, glass, or aluminum containers would be sufficiently transparent to X-rays, while plastic or quartz or glass containers would be transparent to microwave or radio frequency radiation. The energy modulation elements 6 (e.g., the gas containing up converter structures) can be dispersed uniformly throughout the medium or may be segregated in distinct parts of the medium or further separated physically from the medium by encapsulation structures 10, as described below. As shown in FIG. 1C, the encapsulation structures 10 are separated from the medium, and yet are in a vicinity of the medium to be activated. A supply 11 provides the medium 4 to the container 9.

Accordingly, as used herein, "in a vicinity of" refers to the upconverters of the invention, such as for example the modulation elements 6 or the encapsulation structures 10 (e.g., the gas containing up converter structures) being disposed completely inside a medium, partly inside or partly outside a medium, adjacent a medium, or completely outside a medium where light from the upconverters irradiates a part or the whole of the medium.

Alternatively, as shown in FIG. 1C, energy modulation agents such as the gas containing up converter structures of the invention and/or other luminescent materials could be present in the medium in encapsulated structures 10. In one embodiment, the encapsulated structures 10 are aligned with an orientation in line with the external initiation energy source 1. In this configuration, each of the encapsulated structures 10 has itself a "line-of-sight" to the external initiation energy source 1 shown in FIG. 9C without being occluded by other of the encapsulated structures 10. In other embodiments, the encapsulated structures 10 are not so aligned in that direction, but could be aligned perpendicular to the direction shown in FIG. 9C, or could be randomly placed. Indeed, supply of fluid medium 4 could itself be used to agitate the encapsulated structures 10 and mix the fluid medium 4 inside container 9.

Figure 1D:
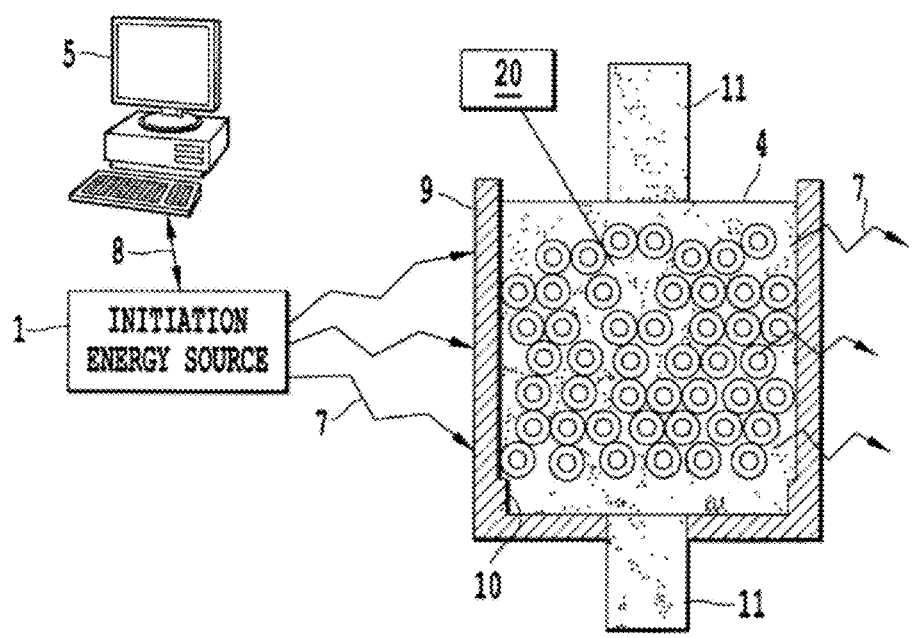
FIG. 1D is a schematic depicting a system according to another embodiment of the invention in which the initiation energy source is directed to a container enclosing a medium having energy modulation agents segregated within the medium in a fluidized bed configuration.

FIG. 1D is a schematic depicting a system according to another embodiment of the invention in which the initiation energy source is directed a container enclosing a medium having energy modulation agents segregated within the medium in a fluidized bed 20 configurations. The fluidized bed 20 includes the encapsulated structures 10 in a configuration where a fluid to be treated is passed between the encapsulated structures 10. The encapsulated structures 10 can include both energy modulation agents such as the gas containing up converter structures of the invention and/or other luminescent materials and/or plasmonics agents as described herein.

In the either configuration of FIGS. 1C and 1D, the medium to be treated in one embodiment would flow by the encapsulated structures 10, or flow along with encapsulated structures 6, and the separation distance between the encapsulated structures 6, 10 would be set a distance smaller than the UV penetration depth in the medium. Thus, as shown in FIGS. 1C and 1D, the medium being treated need not be stationary in order for the encapsulated structures 6, 10 to be in a vicinity of the medium to be treated. In other embodiments, the medium to be treated could be stationary.

In further embodiments of the invention, robotic manipulation devices may also be included in the systems of FIGS. 1A, 1B, 1C, and 1D for the purpose of delivering and dispersing the energy modulation elements 6 in medium 4 or for the purpose of removing old product and introducing new product for treatment into the system.

A suitable initiation source (such as one of microwave sources or radio frequency sources for up conversion) can be used to stimulate light emission in the encapsulated structures 10. In one embodiment of the invention described here, the concentration of light emitters in the medium or the spacing between the encapsulated structures 10 is set such that light emitters are separated from each other in the medium by less than a UV depth of penetration into the medium. Higher concentrations are certainly usable and will generate higher UV fluxes should the energy source have enough intensity to "light" all the luminescent particles.

For a relatively unclouded aqueous medium, UV-B irradiance decreases to 1% after penetration into the water samples between 0.2 m and 1 m, whereas UV-A penetrates on the order of several meters. For such mediums, the concentration of light emitter is more determined by the time needed for the intended UV flux to produce deactivation or activation of an agent in the medium, rather than having to be set based on a concentration of light emitter where the medium itself does not occlude the UV stimulated emission from penetrating throughout the medium. The placement of the light emitter in the vicinity of the medium is not restricted by the optical density of the medium.

Accordingly, the upconverter structures of the invention (as discussed above) can be provided on the interior of sealed quartz or glass tubes or can be provided coated on the surface of spheres or tubes, and further encapsulated with a silicate or another passivation layer. In one embodiment, the gas containing up converter structures of the invention are complexed with the X-ray down converting particles or other energy modulation agents permitting for example X-ray irradiation to also assist in this process.

Broad Band Up Conversion (BUC)

The following embodiments pertain to broad band up conversion (BUC) which converts a low frequency electromagnetic wave (in the microwave or RF regime) to a higher frequency electromagnetic wave (in the IR, VIS, or UV regime) using nano-scale material gas-containing composites.

Upconverting composite (UCC) structures of this embodiment of the invention include gas and gas mixtures contained in capsules of containers having at least one of their dimensions in the following ranges (e.g., 10 cm or 10 mm, 10 microns, 100 nm to 10 nm) that are hollow or porous. In the case of a nano-porous media, the gas is contained inside a nano-particle which, in one embodiment, has nano-pores. The morphology of such particles can be spherical (or substantially spherical). Other non-spherical morphologies may also be used. The mechanism in this embodiment of the invention for up conversion occurs by creating plasmas through the ionization of suitable gas or gas mixtures within the UCC structures.

In other embodiments, the upconverting composite structures of the invention can be millimeter(s) to micron(s) in size.

Plasma is often referred to as the 4th state of matter and naturally occurs when gases are exposed to high intensity electric fields of sufficient magnitude to overcome the work function or the ionization-potential of gases. Plasma is therefore the mixture of a very large number of neutral gas atoms (or molecules) and individual charged, energetic, meta-stable, and unstable species with complex interactions occurring between them. Plasma is in general difficult to create and sustain atmospheric pressures (with one exception being an electrical arc discharge). Stringent pressure and energy transfer conditions typically need to be satisfied before plasma ignition and sustainment can be achieved. In conventional practice, plasma sources have been widely designed for various purposes from lighting applications to chemical vapor deposition.

In general, when a gas in a container, typically at low pressures, is subjected to enough energy to ionize the gas molecules (or atoms) such that a significant number of the gas molecules (or atoms) loose one of more of their valence shell electrons, a plasma can be generated and maintained. Of relevance is the fact that a plasma load (the ionized gas) requires a power transfer to maintain the ionized gas, as wall collisions and recombination of electrons and ions in the gas phase cause a loss of ions from the plasma. In the industry, RF inductive coils operating at 13.56 MHz and microwave energy in the 2.45 GHz range have been used to couple power into a plasma and maintain ionization.

From a practical stand point, a plasma can be treated as a conductor because of its large population of energetically charged particles (both the negative charges (i.e.; electrons) and the positive charges (i.e.; ions)) with the plasma conductivity being defined by the charge density and the electron mobility. An ionized gas includes on average an equal number of positive and negative charges. For most plasmas, the extent of ionization is small, typically only 1 charge particle per 700 to 10,000 neutral atoms or molecules.

The negative charge carriers are mostly electrons. Energy transfer (loss) from electrons is inefficient. Thus, electrons attain high energy (e.g., 2-50 eV). This permits high-temperature type of reactions (which make free radicals) in a low temperature neutral gas to occur. The electron energy is channeled into inelastic electron-neutral collisions which supply new charge species to the plasma and which generate light emission.

In one embodiment of the invention, a plasma in one of the UCC structure becomes the light source to trigger the activation of agents in the medium surrounding the UCC structures.

In one embodiment of the invention, in the presence of a static magnetic field, a charged particle resonates around magnetic lines of force at a particular frequency, known as its rotation of cyclotron frequency. The cyclotron frequency at which an electron enters the ECR is given as:

$$\omega ce = q*B/m$$

While in the static magnetic field, if the particle is subjected to a time varying electric field with a frequency equal to the cyclotron frequency of the particle, and if the electric field is perpendicular to the magnetic field (or at least has a component that is perpendicular to the electric field), then the charge will absorb the energy of the electric field quite effectively. This occurrence is widely referred to as ECR.

It is known that the gyrating electrons assume a helical path about the magnetic field lines. For a microwave frequency of 2.45 GHz, the required B field strength for ECR is 875 Gauss (assuming and provided the electric field is perpendicular to the magnetic field). Electrons that enter the precession are referred to as "hot-electrons," and their kinetic energy is transferred to the valence electrons of the discharge gas. This energy transfer can be done after single or multiple collisions). The plasma formed can be sustainable or unsustainable. A discharge can be sustained when the loss mechanism (diffusion and recombination) are balanced by ionization in a steady state. An ECR plasma is usually conducted at low pressures in the mTorr region. Power absorption takes place even if the excitations of the electric field are outside of the ECR frequency. This is known as joule or collision or Ohmic heating and can take place at high pressure (e.g., 100 mTorr or higher).

Inductively coupled plasmas which operate in the RF regime are typically operated at 13.56 MHz or 27 MHz. The frequencies are not restricted by any fundamental law of nature, but rather set to a frequency band clear of other radio communications. Microwave-generated plasmas can be operated over a broad range from above 300 MHz all the way to 100 GHz, although the spectrum accessed is only this frequencies supplied from commercially available sources.

In one embodiment of the invention, the gases in the UCC structures have a low work function (or ionization potential). In its simplest definition, ionization is the ability of a photon to detach at least one electron from an atom or molecule. Furthermore, the ionization of a substance depends on the energy of individual photons, and not on their number.

UV radiation has very low penetration depth and resonates with the electrons involved in covalent bonding between adjacent atoms. X-ray radiation is deeply penetrating and resonates with tightly bound electrons (the inner core electrons) and induces transitions between allowable electronic energy states. X-rays and gamma rays (due to the higher characteristic photon energy) can excite electrons and can ionize almost any molecule or atom. Far ultraviolet light can ionize many atoms and molecules (a well known mechanism and well studied detrimental effect on living cells).

Across the electromagnetic spectrum, the spectral ranges and energy states depend on the frequency and the matter exposed to the radiation. Near UV, visible light, IR, microwaves and radio waves are in general considered non-ionizing radiation. In other words, ionization (especially in solids) is not generally produced by radiation with wavelengths longer than 200 nm.

In general, low frequency radiation in the RF and microwave regime couples energy through free rotation of molecules or the dipolar polarization of parts of molecules (side groups). IR couples with the vibration of molecules, the optical through UV couples to the outer electronic states of atoms and molecules. Soft X-ray and X-rays couple with core electronic states of atoms and gamma rays couples with nuclear states. Upon light generation from a source, the emitted spectrum of the radiant energy can be broad, or it can have well defined lines at certain wavelengths (depending of the mechanism responsible for the radiation processes).

In one embodiment of the invention, gases of a particular polarity (molecular charge asymmetry) are chosen as the coupling media to implement the upconverting process. Gases benefit from a high degree of rotational freedom as compared to other molecules (whose mobility is hindered through their bondage to a network). Furthermore, gases typically have a low ionization potential, as compared to crystalline solids. In this embodiment, the chemical composition of the UCC structures is selected not only to contain gas and gas mixtures but also to permit microwave coupling and UV or VIS transmission (for secondary light emission), and/or to be compatible with metallization processes, and/or to be amenable to surface treatments which may functionalize the surface for solvation, conjugation and other effects.

It is well established that the ratio of Na to Al in silicates determines the short range order/structure of these materials, and hence the silicate cages left within them. Other material chemistries (not containing sodium) are also suitable in different embodiments of the invention to contain desirable gas and gas mixtures. In some embodiments, the UCC structures include ionization-assisting materials attached to increase microwave coupling efficiency and therefore facilitate the ionization process of the gas mixtures associated with the UCC. Ionization-assisting materials can possess high electron mobility and density; these materials include carbon-nano-tubes (CNTs) and graphene amongst others. These attached or associated materials would serve as electron pumps (as it is well established that microwave couples to CNTs and graphene through electrical conductivity).

Microwaves are electromagnetic waves whose frequencies range from 300 MHz (Megahertz) to 300 GHz (Gigahertz). Their corresponding wavelengths range from one meter to sub-millimeters. The lower end of the microwave region borders radio frequencies, while the upper end is adjacent to infrared frequencies. Microwaves are widely used in modern society.

Microwave radiation obeys the laws of electromagnetism according to the well known Maxwell's equations (which are the four basic laws of electromagnetism). When a material is exposed to microwave energy, the following set of equations can be used to characterize the electromagnetic properties:

Conductive materials (Ohm's law): $J=\sigma E$ (where $\sigma$ is the conductivity of the material).

Dielectric materials: $D=\varepsilon E$ where $\varepsilon$ is the permittivity of the material which can also be written: $\varepsilon=\varepsilon_0 k'$ where $\varepsilon_0$ is the permittivity of empty space and $k'$ is the dielectric constant of the material.

Magnetic materials: $B=\mu H$ where $\mu$ is the permeability of the material which can also be written as $\mu=\mu_0 \mu_r$ where $\mu_0$ is the permeability of empty space and $\mu_r$ is the relative permeability of the material, where D is the flux of the electric induction,
B is the magnetic flux density,
H is the magnetic field vector, and
J is the conduction current density.

In one upconversion embodiment, plasmas in the UCC structures are created through the ionization of suitable gas or gas mixtures within the UCC. In one embodiment of the invention, the attachment of a CNT material and graphene can facilitate the plasma ignition and plasma sustainment while the UCC is exposed to microwave and/or radio frequency RF radiation. This process can be facilitated further by the presence of a magnetic field applied with a proper orientation. The application of MW and RF can be from a wide range of sources including magnetrons, Klystrons, Gyrtrons, Traveling Wave Tubes and Solid Sate Amplifiers and possible a helix sustaining a strong alternating field such as those in inductive coupling.

The optimal microwave frequency will be application dependent. The plasma generation process triggered by microwave ionization of gases occurs, in one embodiment, under the presence of a magnetic field having a proper orientation vis-à-vis the RF/MW field (i.e., orthogonal disposition). Once the gas in the UCC structure is ionized, electrons in the plasma can be made to enter a precession movement. The magnetic field strength required to force precession of electrons is much less than that required for the precession of ions (due primarily to the difference in mass between electron and ions). The magnetic field strength can be therefore selected to resonate with electrons while bypassing ions.

The added elastic collisions (due to induced precession movements) reduce the MW energy required for generating and maintaining the plasma. Higher MW frequencies typically results in higher disassociation rates and lower electronic temperatures compared to lower RF/MW frequencies. Conversely, the higher the frequency of the incident microwave energy the less the penetration depth is. In one embodiment, as discussed in more detail later, MRI equipment can be used in conjunction with microwave equipment for triggering plasma intensification, therefore taking advantage of the well established equipment base in the field of MRI.

The chemical properties of the UCC structures can be imparted through surface modifications, which can be tailored for specific applications. For example, the UCC surface can be coated with thin metallic coatings and can be functionalized for attaching molecular structures that, in one embodiment, can undergo chemical changes after UV irradiation from the UCC structures. Various divers applications for the resultant upconverted light were discussed above and other applications are discussed hereafter.

A metalized and/or functionalized UCC structure is referred to herein as a UCC-MF. A UCC-MF outputting in the UV is abbreviated herein as UCC-MF-UV. Molecular structures attached to the UCC-MF surfaces can be a tag used for subsequent chemical tracing purposes, a catalyst for initiating other chemical reactions, a therapeutic agent for subsequent bio-modulation.

In one application pertaining to in-vivo photo-initiated modulation of a therapeutic agent, the upconverting composite would be mm, micron and nano meters. For reaching the nucleus the composite is made very small (nanometer scale) and can deeply penetrate inside biological tissue of animals or humans. More specifically, in this embodiment, the UCC structure would be designed to diffuse and penetrate a cell or even to penetrate the nucleus of a cell of a specific organ or "the target site."

In one application pertaining to in-vivo photo-initiated modulation of a therapeutic agent, the upconverting composite would be larger and placed nearby or proximate the specific organ or "the target site."

In one embodiment of the invention, when the UCC (perhaps with an attached therapeutic agent) is at a target site, a deeply penetrating MW radiation along with an applied magnetic field are used to ignite the gas mixture of the UCC. The gas mixture subsequently generates UV light necessary to modulate the therapeutic agent(s). One specific example would be for activation of psoralen.

Nano-UCC(s) have the potential to optimize psoralen excitation in vivo. The emission band tuning can be achieved through the UCC synthesis (gas mixtures and gas containment material selection) which would permit sensitization of the broad family of psoralen derivatives that can be fabricated.

Other application areas could use gasses of different emission characteristics. These applications could include: the sterilization of surrounding media, the photoactivation of resins in curing and bonding applications, as well as to other application areas discussed above or below or known to be photoactivatable. In those applications, the known emission characteristics of plasma gases are used to select which gases to contain in the UCC structures.

The paper "Emission Characteristics of a Glow Discharge in a Mixture of Heavy Inert Gases with Iodine Vapor," by A. K. Shuaibov and I. A. Grabovaya. Uzhgorod National University, Uzhgorod, 88000 Ukraine, Optics and Spectroscopy, Vol. 98, No. 4, 2005, pp. 510-513. Translated from Optika i Spektroskopiya, Vol. 98, No. 4, 2005, pp. 558-561, the entire contents of which are incorporated herein by reference, describes the emission characteristics of a low-pressure UV excimer-halogen lamp pumped by a longitudinal DC glow discharge. In that paper, the discharge was initiated in mixtures of heavy inert gases with iodine vapor at a total pressure of 100-2000 Pa and with a power deposited into the plasma of 10-100 W. Current-voltage characteristics of the glow discharge and emission spectra of the plasma in the region of 190-360 nm were reported. The radiation intensity at the resonance line of the iodine atom (206.2 nm) and the intensity at the peaks of the XeI(B-X) (253 nm) and I2(B-X) (342 nm) emission bands were analyzed as functions of the pressure and partial composition of the mixtures of Ar, Kr, and Xe with iodine vapor, as well as the electric power of the glow discharge.

In one embodiment of the invention, mixtures such as these can be used in the UCC structures of the invention which, upon plasma generation, would emit similar emission lines. The light emission spectrum of the plasma can be controlled by adapting the gas composition.

The paper "Plasma technology: a solution for UV curing on 3-dimensional substrates," by Tunja Jung, Peter Simmendinger, Katia Studer, Wolfgang Tobisch, presented at: Radtech e|5: UV & EB Technology Conference 2006. (RadTech International, NA, Apr. 23-26, 2006, Lakeside Center at McCormick Place Chicago, Ill.), the entire contents of which are incorporated herein by reference, describes that, by adapting process parameters such as the type of the gas, it is possible to emit UV light between 200 and 380 nm. This paper described the use of these radiations to induce photoinitiated polymerization. Arc-lamps were used for the UV-curing applications, with emissions not significantly different from the emissions of the plasma process described above. In this paper, during the plasma process, the light was emitted throughout the chamber. In other words, UV-plasma curing required placing the coated substrate in the light source. As previously mentioned, in one embodiment of the invention, the light emission spectrum of the plasma can be controlled by adapting the gas composition.

Figure 2:
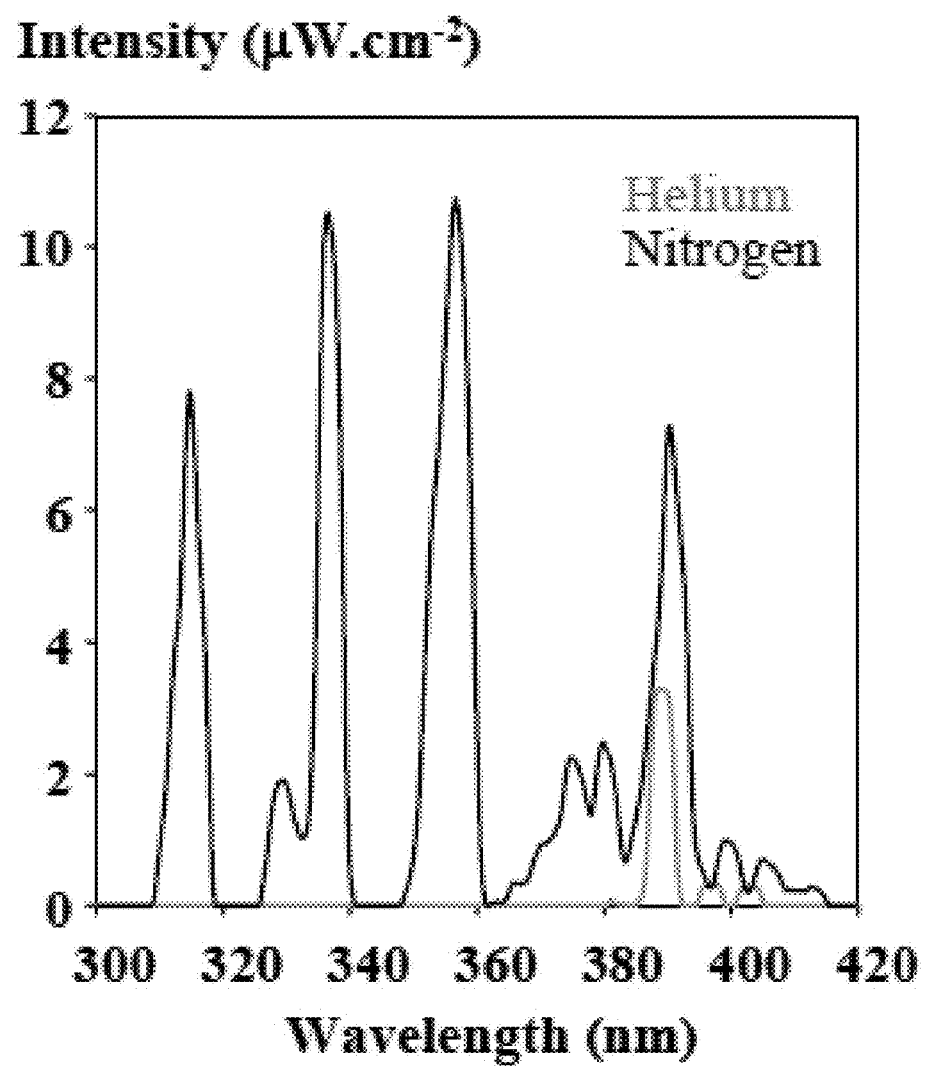
FIG. 2 shows that the UV emission induced by a nitrogen and a helium plasma are different.

FIG. 2 (reproduced from that paper) shows that the UV emission induced by a nitrogen and a helium plasma are different. Depending on the spectral photosensitivity of the UV-curable formulation, it is therefore necessary to check whether the UV emission of the plasma overlaps the absorption of the photoinitiator in the coating system. The emission properties of plasmas can be customized by modifying the gas contents and pressure and thus can be adapted to specific technical application requirements. The systems shown in FIGS. 32 and 33 (discussed below) can be used to engineer the desired emission from the UCC structures before introduction of the UCC structures into the target medium or site.

Figure 3:
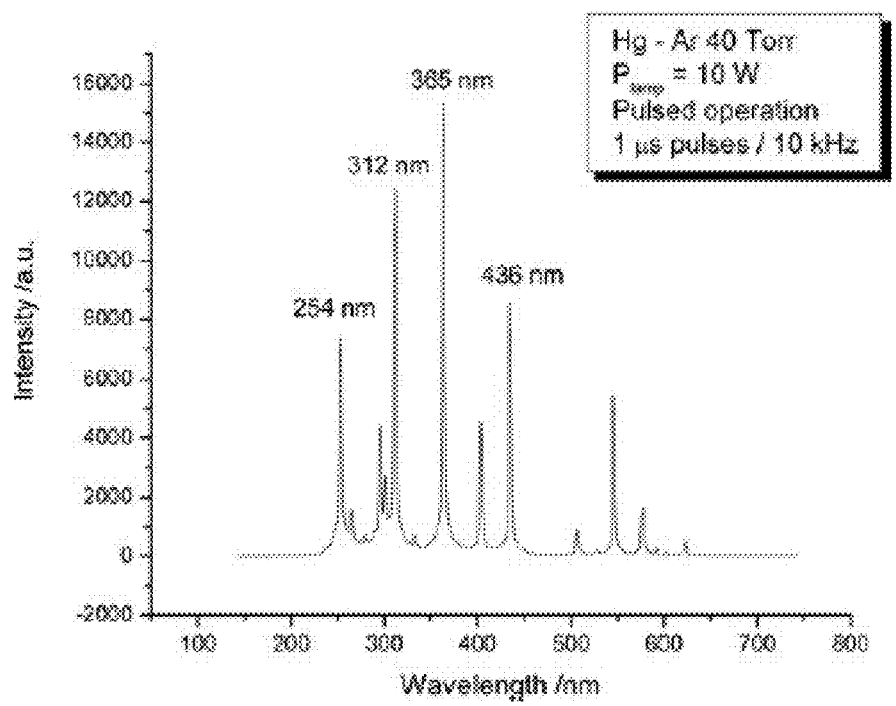
FIG. 3 show that the UV and VIS emissions from the low-pressure mercury-argon discharge.

In another study published in the INSTITUTE OF PHYSICS PUBLISHING JOURNAL OF PHYSICS D: APPLIED PHYSICS. J. Phys. D: Appl. Phys. 37 (2004) 1630-1638 PII: S0022-3727(04)74779-8. entitled: "Relative enhancement of near-UV emission from a pulsed low-pressure mercury discharge lamp, using a rare gas mixture," by S Kitsinelis, R Devonshire, M Jinno, K H Loo, D A Stone and R C Tozer, the entire contents of which are incorporated herein by reference. In this paper, the physical reasons for the enhancement of near-UV and visible emissions from a low-pressure mercury-argon discharge under pulse drive conditions are explained. FIG. 3 (reproduced from that paper) shows the UV and VIS emissions from the low-pressure mercury-argon discharge. A small admixture of Krypton as the buffer gas leads to maximizing radiative emissions. The conditions of operation that maximize the enhancement of near-UV and visible radiation, including the effect of the buffer gas, are described. This paper describes that, for a pulsed discharge, electron-ion recombination followed by cascade radiative transitions is the process responsible for most of the 365 nm emission and that argon with a small admixture of krypton (as the buffer gas composition) leads to maximum radiative emission. The gases can be tuned though mixtures of proper ratios to emit at any frequency within UVA.

In one embodiment of the invention, mixtures such as these are used in the UCC structures of the invention which upon plasma generation inside emit similar emission lines.

Figure 4:
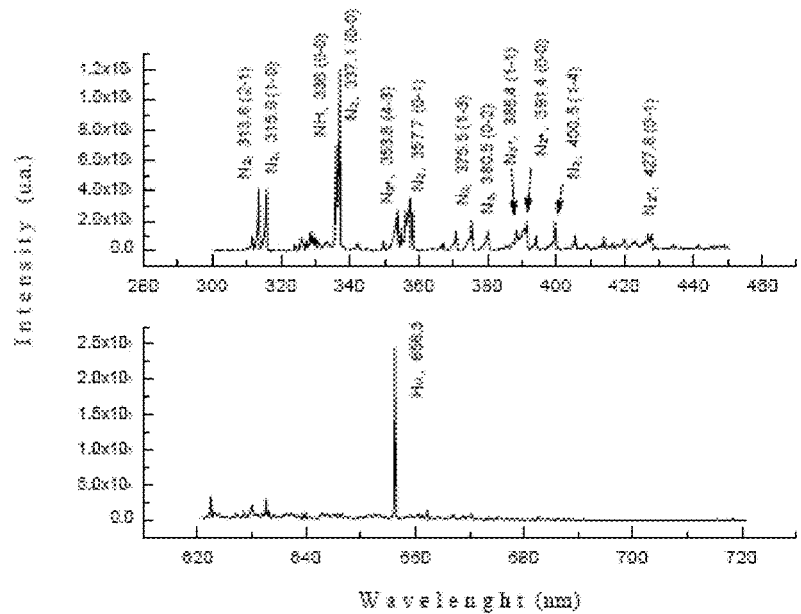
FIG. 4 shows emission lines from a nitrogen/hydrogen plasma covering the UVA target range.

Ammonia and argon gasses are also of special interest. Ammonia has been used to create MASERs due to its response to microwave energy. It absorbs microwave energy, and in various embodiments significant rotational energy can be pumped into ammonia molecules. Most gasses including argon can be ionized using microwave radiation and using a Tesla coil or a combination thereof. These two gases can be used as a base from which other gases can be added to produce specific UV or VIS or IR spectral emissions of interest. FIG. 4 shows emission lines from a nitrogen/hydrogen plasma which would be expected to have similar emission lines.

In one embodiment of the invention, upconverting of low frequency radiation (microwave or RF) into high frequencies uses non-solid emission media (i.e. the gases in the UCC structures). The advantages of using microwave reside in two main factors: a) the depth of penetration of low frequency radiation far exceeds the penetration depth of IR and UV and b) the low frequency regime is inherently non-ionizing (low energy photons) and does not trigger adverse immune responses like in the case of high intensity high dosage x-rays or gamma rays.

Examples of Broad Band UCC Structures of the Invention:

In one embodiment of the invention, a hollow gas-filled container (of a range on the order of millimeters to microns to sub-microns in a principle diameter) is designed to be deployed within an object or dispersed in a medium. In one example, the object can be a target organ or tissue in a patient near a sight where for example a photosensitive chemotherapeutic agent (e.g., psoralen) has been localized. In one example, the medium can be a UV-activated resin or epoxy for joining two objects together, such as two semiconductor substrates or two semiconductor die or two circuit board elements or a combination of these being joined. In one example, the object being treated can be a crack in a structural member such as a bridge structure or a highway member in which the crack has been pre-filled with the UV-activated resin or epoxy This UCC "capsule" structure once in the target or medium is exposed to a combination of microwave energy and/or high magnetic field in order to produce light (for example UV, VIS, or IR light or a combination thereof) from the plasma gas in the gas-filled container to activate an agent in the medium such as for example a chemotherapeutic agent or a photoactivatable resin. In some applications, the generated light is used to sterilize or pasteurize the target medium, separate from or including using the generated light to activate a chemotherapeutic agent or a photoactivatable resin.

In one embodiment of the invention, an applied magnetic field can range in strength from 0.01 Tesla to 11 Tesla. In other embodiments, no magnetic fields are applied. In other embodiments, higher magnetic field strengths can be utilized. In one embodiment of the invention, the magnetic field can be substantially uniform and/or can be oriented along the axis of current-carrying coils producing the magnetic field. Such an axis oriented along the axis of current-carrying coils will be referred to herein as a main magnetic axis. Such coils can be made of superconductors, which in various embodiments can be cryogenically cooled.

In one embodiment of the invention, the RF and/or microwave energy can vary from 13 kHz to 300 GHz with incident powers varying from about 1 W to 10 kW. These RF and microwave sources can operate in a continuous mode or a pulsed mode with high peak powers and/or low duty cycles. Various RF and microwave devices, capable of either pulsed or CW operation, are well known in the art, and devices generating this types of pulsed or CW RF and/or microwave radiation are suitable for the invention.

In one embodiment of the invention, the volume of the UCC capsule structure can range broadly from the cubic nanometer scale to the cubic centimeter scale. In the lower size scale, the volume of the gas container can range between 30,000 $nm^3$ and 250,000 $nm^3$ with wall thicknesses in the range of 10 to 100 Å. The UCC capsule structure can be made even larger in volume, with larger wall thicknesses, for the same purpose described above; i.e., for the purpose of containing a gas to be exposed to microwave and/or magnetic fields. In one embodiment of the invention, some of the walls of the UCC capsule structure can be made thicker than others. In one embodiment of the invention, one wall is deliberately made very thin (as will be discussed in more detail below).

In one embodiment of the invention, the shape of the gas container in the UCC capsule structure can also vary, without diminishing its functionality; in many cases a sphere, cylinder, or ellipsoid is more suited for microwave coupling and/or plasma generation. In one embodiment of the invention, the shape of the walls can also enhance the structural integrity of the container; e.g., spheres and ellipsoids tend to be structurally superior to prismatic shapes, ceteris paribus.

The gas containers described here, in one embodiment of the invention, are designed to be exposed to the combination of a strong magnetic field along with pulses of electromagnetic fields.

Figure 49A:
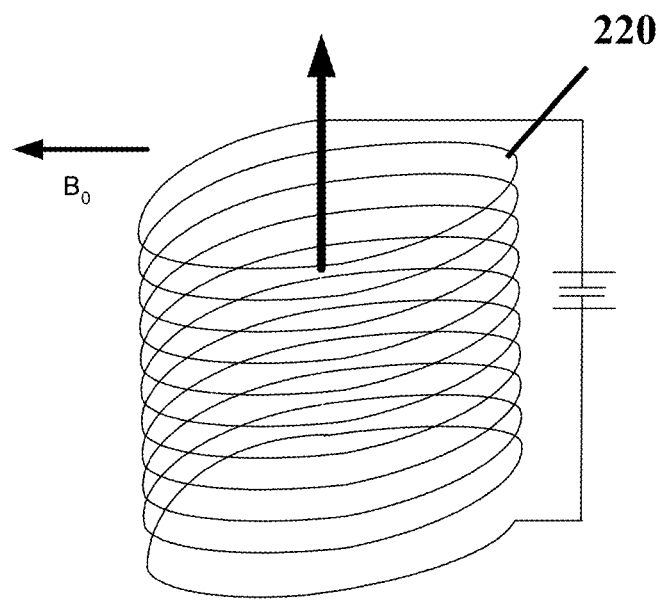
FIG. 49A is a schematic of a multi-turn solenoidal coil showing the projection of the magnetic field along the longitudinal axis.
Figure 49B:
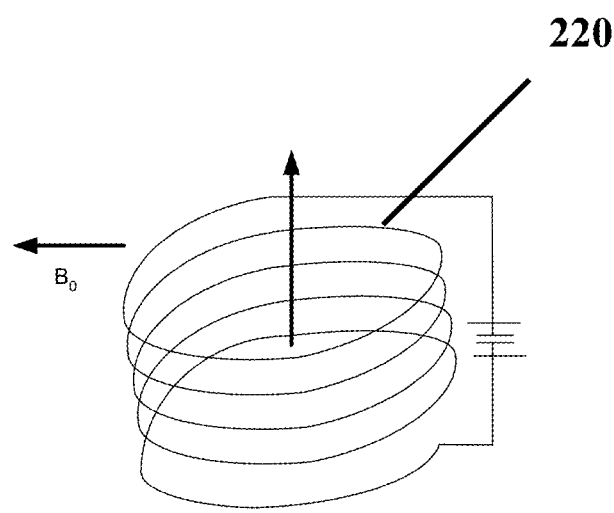
FIG. 49B is a schematic of another multi-turn solenoidal coil showing the projection of the magnetic field along the longitudinal axis.
Figure 50:
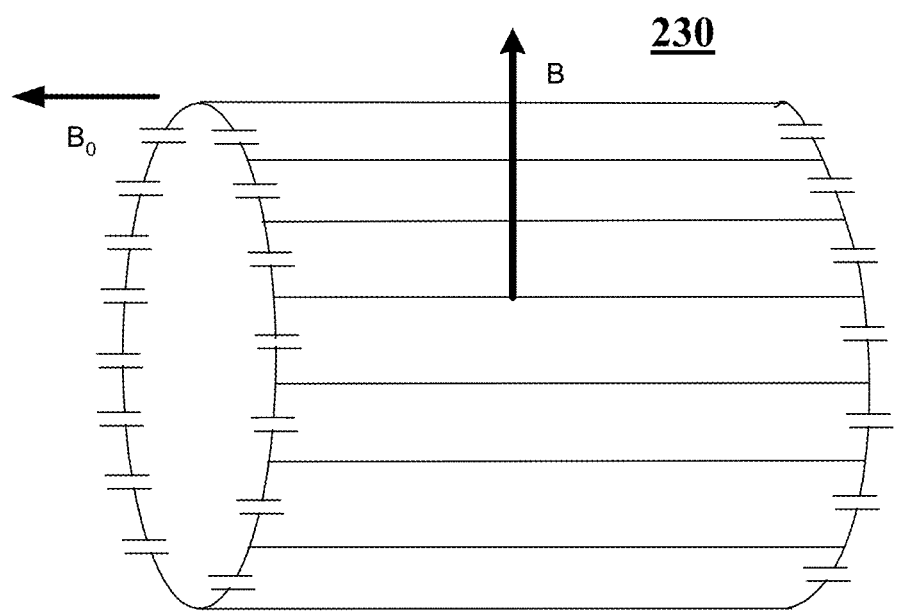
FIG. 50 is a schematic of bird cage coil showing the projection of the magnetic field in a radial direction.

In one embodiment of the invention, the magnetic gradients referred to above are produced using coils located in different positions along the axis of the strong magnetic field and the axis of these coils are oriented perpendicular to the axis of the strong and uniform magnetic field. The pulsed and short lived magnetic field gradients are therefore designed to be able to orient and reorient magnetic dipoles 90 and 180E from the central axis. FIGS. 49 and 50 (below) provide more details of various magnetic field applicators.

In the absence of a material, the magnetic flux is expressed as B=$\mu_0$ H, where H is called the magnetic field strength and $\mu_0$ is a constant called the permeability of free space. Inserting a specimen into the coil carrying a current (and hence having an axial magnetic field flux B) does influence the magnetic field. Generally, the orbital and spin magnetic moments within atoms respond to an applied magnetic field. The flux lines are perturbed by the presence of the specimen. The resultant equation becomes expressed as $$B=\mu_0(H+M),$$

where magnetization M is defined as the magnetic moment per unit volume. For a given material of volume V, the magnetization is therefore the ratio of the magnetic moment divided by the volume:

$$M=\mu_m/V$$

Magnetic materials tend to concentrate flux lines. Examples magnetic materials include materials containing high concentrations of magnetic atoms such as iron, cobalt and nickel. On the other hand, diamagnetic materials tend to repel flux lines weakly. Examples of diamagnetic materials include water, protein, fat and other genetic materials. Magnetic susceptibility $\chi$ is expressed the ratio of:

$$\chi=M/H$$

The permittivity of diamagnetic materials is below 1. The permittivity for Paramagnetic materials is above. The permittivity for ferromagnetic, ferromagnetic and anti-ferromagnetic materials is between 100 to 1,000,000.

As for paramagnetic gases, applying a magnetic field would tend to orient the dipole moments. In other words, the gas attains a magnetization. With higher temperatures, however, the thermal energy k*T may exceed the torque alignment applied by the magnetic flux onto the gas dipoles.

In one embodiment of the invention, the energy recipe defined (i.e., the combination of RF and/or microwave energy along with in some cases a magnetic field) for irradiation of the UCC structures includes parameters such as for example the magnitude and direction of the strong magnetic field, the frequency, power, the electric field strength, the magnetic field strength, a direction of the RF/microwave coils that produce the gradients, and continuous vs. pulsed operation (with defined peak powers and duty cycles). In one embodiment of the invention, these energy recipe parameters are computer controlled, as shown in FIG. 51 (below).

Different energy recipes will likely be required for different UCC structures or for different gas containers in the UCC structures or the UCC capsule structures. (Unless specifically set forth differently a UCC structure will refer to any of the UCC capsule structures or the other gas containment structures discussed herein.) In one embodiment of the invention, the energy recipe is designed to trigger ionization of gases in the UCC structures. Once ionized, the gases enter a plasma phase of matter. In one embodiment of the invention, the plasma ignition need not be sustained for a long period of time. If the chemo-therapeutic agent and the UCC are properly oriented and good energy transfer with minimized scattering; then, Plasma maintenance for even a microsecond can generate substantial amounts of UV, VIS, or NIR light. If on the other hand UV light is not properly directed then more UV light is required to trigger the chemo-therapeutic agent.

In one embodiment of the invention, the UCC structures (filled with preselected gasses or gas combinations) can emit in the UVA range upon plasma ignition. One especially suitable emission for chemotherapeutic treatment is emission at about 360 nm+/−50 nm. Accordingly, the gases and gas mixtures are selected to work in conjunction with the gas container and the available energy recipes to produce the desired light emission and the various examples here are provide solely for illustrative purposes.

In one embodiment of the invention, the walls of the UCC structures are UV transmissive so that the UV emissions from the interior gas (or gasses) pass from the inside of the gas container to the outside of the gas container with minimal losses due to absorption, scattering or other mechanisms. The size of the wall (and its absorption characteristics) will be a design consideration for the UCC structures. In one embodiment of the invention, the walls of the UCC structures are transmissive to X-rays or high energy electron beams which can be used to trigger plasma ignitions in the UCC structures of the invention. X-ray and RF can be applied at the same time. X-ray radiation can be applied to the UCC. The UC's inner walls can have a thin coating of a material able to interact with X-ray photon to generate secondary electrons.

In one embodiment of the invention, the gas container material is be able to: withstand the electron temperatures during plasma ignition, withstand the pressure build up resulting from the temperature rise, permit both the magnetic field and the RF and microwave energy to interact with gases while bypassing the walls of the container and/or transfer a substantial part of the generated UV radiation to the outside of the gas container. Any desirable frequency with the UVA can be triggered using the appropriate set of gases.

In one embodiment of the invention, gases such as Ne, Xe, He, Hg, $H_2$, $N_2$, Ar, Kr (or combinations thereof) can be used. For example, gas mixtures Ne+He, Ne+He+5% Xe, Ne+5-10% Xe can be used as well other combinations and other mixture ratios. The percent Xe addition listed above is by atomic percent. Hg+Ar emit at the 360 nm; Ne+1% Ar also emits at 365 nm. A small admixture of Krypton as the buffer gas can lead to radiative emission enhancements. Furthermore; other gas combinations can be used, including iodine vapor with various impurities.

The properties of a plasma can be customized by modifying process parameters (magnetic field strength, microwave power and frequency) or impurities of the reactive gases leading to plasma formation.

The range of pressure in the gas container can be between 0.01 and 100 Torr. Other ranges considered more practical include a pressure between 0.5 and 5 Torr. Though other pressures are suitable, the structural integrity of the gas containers may be best suited for this range of 0.5 and 5 Torr based on theoretical calculations. The size and shape of the container will partially determine the pressure range selected. Furthermore, the mean free path of the electrons decreases with increasing pressures and vice-versa. Hence, at low pressures, sustaining plasma may be frustrated by electron diffusion and loss the interior wall surfaces of the gas containers.

Alignment through a magnetic field (especially with 0.1 Tesla and above magnetic field strength) along with the ionization of the microwave field, in one embodiment of the invention, provides one control mechanism for energy conversion that is not typically available in the absence of the magnetic field. Upon the RF/MW frequencies being tuned and applied orthogonal to an applied magnetic field, the electrons in the plasmas in the UCC structures can enter an electron cyclotron resonance or can gain kinetic energy without entering ECR. In either case the plasma disassociation rate is enhanced in the presence of a B field regardless of its orientation. This is because various electrons travel on random trajectories once they are generated; so that, certain electrons will find themselves in favorable trajectories to a gain and increase in their kinetic energy. Under certain conditions of orthogonal B and E fields, the electrons can be confined to a circular trajectory leading to their magnetically induced confinement.

The magnetic field forces the precession of the liberated electrons which in turn collide with the various gases and impart further energy, permitting ionization and plasma maintenance. The presence of the magnetic field permits a lower overall externally imposed electromagnetic energy to have to be used. The lowering of the total energy required to obtain UV output is very beneficial in view of the fact that the gas container may be disposed inside an animal or human tissue (in vivo or in vitro).

In one embodiment of the invention, the UCC structure can be functionalized and attached to a drug delivery vehicle and sent throughout the body to target tumor site. The UCC structure can play the role of a UV light source to trigger desirable reactions through photo-initiation. Photo-initiation is a known mechanism used in various medicinal, pharmaceutical and chemical reactions. In one embodiment of the invention, the photo initiation can be performed at 360 nm (+/−50 nm) to trigger for example psoralen (and psoralen derivatives with bio-therapeutic functionality) inside a diseased cell or nucleus. The benefits of psoralen are known, but few techniques have been able to activate psoralen inside a UV skin depth of a biological sample.

The energy required to trigger psoralen is in the range of about 2 photons at 360 nm (+/−50 nm). In the 360 nm range, the following calculation illustrates one example of a suitable gas container gaseous mixture:

| Chemical Species & Gas Mixtures | Electronic Emission λ = nm | Energy per photon (J) E = (h * C)/(λ) | E (ev) | Energy per mole (J/mol) # particles per mol = 6.02E+23 | Energy (kcal/mole) 1k cal = 4.18 kJ |
|---|---|---|---|---|---|
| $H_2 + N_2$ (Plasma) | 360 | 5.51799E−19 | 3.44E+00 | 3.32E+05 | 1.39E+03 |

Assuming a van der walls radius to 3 Angstroms (0.3 nm)

| Effective Atomic Radius nm | Capsule volume nm$^3$ | Number of particles inside Volume | ionized to neutral atoms 1:700 | hV for 360 nm energy (J) | hV for 360 nm energy eV |
|---|---|---|---|---|---|
| 0.3 | 49,244 | 164,148 | 23.450 | 5.51799E−19 | 3.44E+00 |

| Energy Output of the capsule, eV | Charging time in one second | Number of excitations per sec | Output efficiency (UV transmission) | Capsule Output eV |
|---|---|---|---|---|
| 8.08E+01 | 1.00E+04 | 8.08E+05 | 0.75 | 6.06E+06 |

If one assumes that the ionized to neutral atom ratio is close to 1:10,000 then the energy output of the capsule is calculated to be 4.24 H $10^5$ eV.

In one embodiment of the invention, to improve the efficiency of the coupling energy and to minimize scattering a protrusion can be designed onto the gas container to facilitate the attachment of the drug and to collimate and maximize the UV delivery with minimal scattering In one embodiment of the invention, the gas container can be coated with a metal coating such as a Au or Ag coating through vapor deposition or through wet chemistry. The metal coating permits plasmonic effects which enhance the light output of the capsule (and possibly alter its output frequency).

In one embodiment of the invention, the interior wall of the gas container can be treated with plasma or wet chemistry to facilitate the ionization of the gases, prior to filling and sealing the gas containers. Gas mixtures can be chosen to have an affinity for one another to lower the work function and facilitate plasma ignition.

For various embodiments of the invention, the container can be under negative pressure below atmospheric pressure and down to the mTorr pressure range. A hollow nano-meter size container can be filled with gases which emit in the UV The gas container can be fused silica structure, a micro-balloon or a porous ceramic The container can be UV transmissive. Quartz is reported to be around 75% transmission in the UVA range, and represents one material suitable for the invention.

Various methods can be used to produce gas containers in various sizes ranging from the centimeter range to the nanometer range. In one embodiment of the invention, nano-meter size containers can be made through the various techniques described below. For the purposes of terminology in describing such a method, a starting wafer is defined as the wafer upon which the various patterning, etching, metal vapor deposition, bonding, gas filling, sealing, surface modification and all other processing steps intended for building the UCC structures of the invention.

Construction of the UCC Structures of the Invention

One way to build the UCC structures would be to form the container volume through suitable etching recipes, and then seal the starting wafer using another wafer to cap the volume formed therein. In this example, the gas container may have rounded parts (due to etching), and a substantially planar wafer can be used as a sealant wafer.

More complex methods can be used to build these and other gas containers. Such steps can include: forming suitable groves and patterns on two different starting silicate wafers and then aligning and mating these wafers with the appropriate "hollowed out" features to form the gas container. The sealing can be done by heat or can be done using chemistries that allow silicates to bond at or near room temperature.

One important part of the fabrication of the of the gas containers is the use of a structural wafer under the starting wafer. This structural wafer acts as a fixture and holds the starting wafer using a release layer. Either wet etching or dry etching can be used to form desirable concave features in the starting wafers. Wet etching can use for example chemicals such as hydrofluoric acid, nitric acid, acetic acid. Typically, the isotropic etching pattern resulting from wet etching is a disadvantage in semiconductors; however, the undercutting that takes place under the resist (i.e., the etching downward and sideways) is actually advantageous in this case since the undercutting permits rounded edges to be formed. Also, since wet etching is isotropic, it can be used to form patterns that are disposed in the plane of the starting wafer. In one embodiment of the invention, this procedure can produce a glass container with rounded internal walls.

Figure 5:
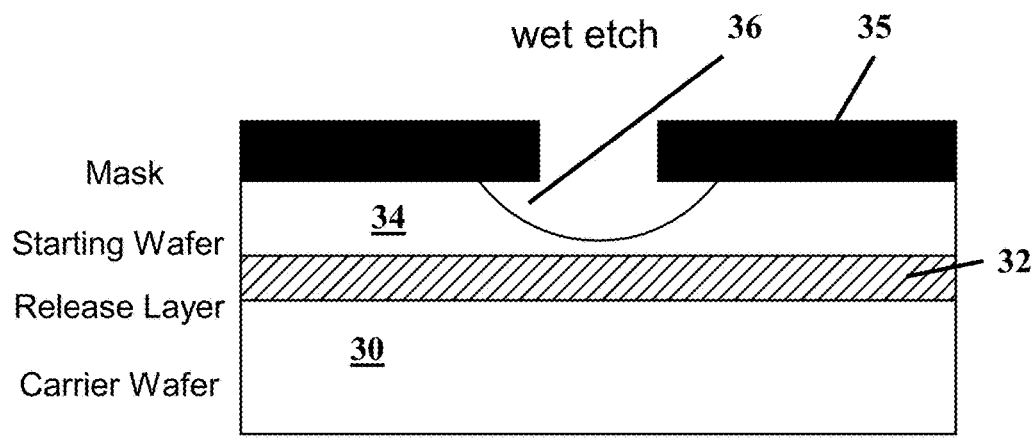
FIG. 5 is a schematic of a wet etch pattern illustrating the undercutting that takes place under the resist (the etching is downward and sideways)

FIG. 5 is a schematic of a wet etch pattern illustrating the undercutting that takes place under the resist to form the depicted concave structures. This figure shows a carrier wafer 30 having a release layer 32 and starting wafer 34 disposed thereon. A mask 35 is deposited and thereafter has an opening defined thereon to expose the starting wafer 32. A wet etch is used to generate the undercut portions 36.

Figure 6A:
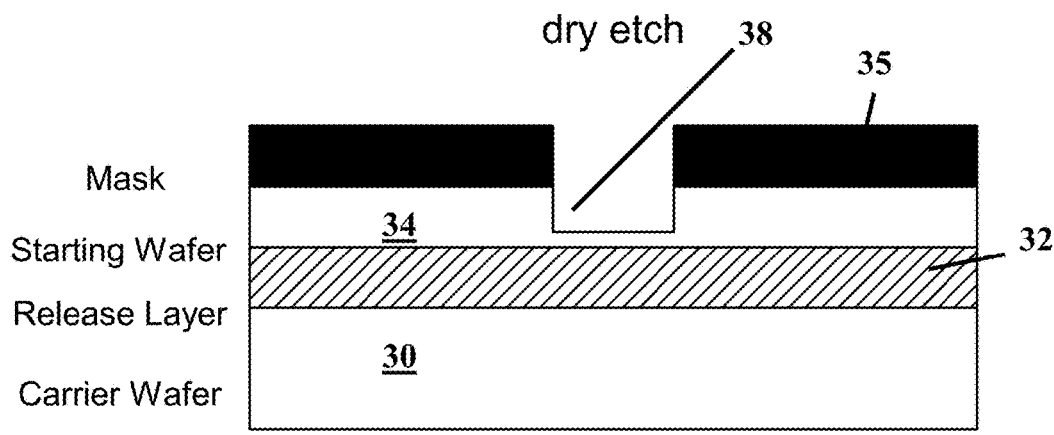
FIG. 6A is a schematic of a dry etch pattern (resulting in well defined trenches)

Plasma etching is anisotropic and leads to a trench definition having more rectangular edges than typically possible with wet etching. The use of RF generated plasmas coupled to RF power supplies is a known, effective, and efficient method suitable for the invention. Gaseous etchants such as fluorine and chlorine based gases can be used. Other etching gasses include: $BCl_3$, $Cl_2$, $CF_4$, $CHClF_2$, $CHF_3$, $CH_2F_2$, $CH_3F$, $C_2F_6$, $C_3F_8$, $C_4F_8$, HBr, HCl, HF, $NF_3$, $SiF_3$, $SiF_4$, $SF_6$ or combinations thereof. Additives such as argon, oxygen, hydrogen, and nitrogen (which are typically included between 1 and 10 ppm levels) can be added to the etching gas. The etching rate can be controlled using temperature and energy. The rates of etching can be between 10 and 350 Angstroms per min. FIG. 6A is a schematic of a dry etch pattern (resulting in well defined trenches). This figure shows a carrier wafer 30 having a release layer 32 and starting wafer 34 disposed thereon. A mask 34 is deposited and thereafter has an opening defined thereon to expose the starting wafer 32. A dry etch is used to generate the trench-like portions 38. This method using plasma etching to form the concave structures would be used when square sided walls are not considered an impediment for the UCC container.

Figure 6B:
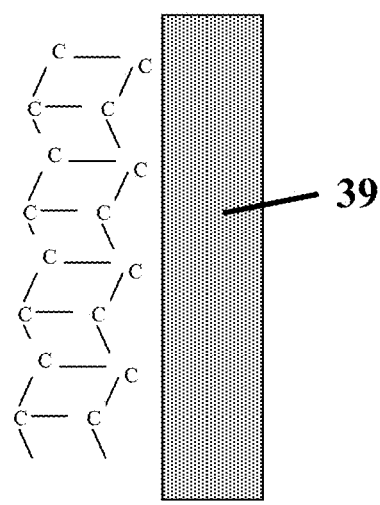
FIG. 6B is a schematic depicting carbon-carbon bonds forming a saturated surface on a wall 39 of one of the UCC structures.
Figure 7:
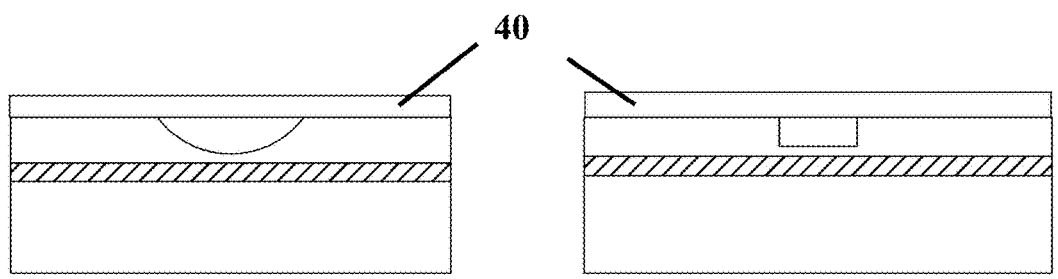
FIG. 7 is a schematic showing how after removal of the patterning resist, the starting wafer can be capped with a flat quartz wafer (for example) to form gas containers.

Hydrogen additives increase selectivity toward etching $SiO_2$. Some of hydrogen additives can influence the surface chemistry of the quartz wall left behind (called the side wall passivation or side wall protection). This side wall blocking passivation forms when (for example) the carbon atoms contained within the reactive etchant species mentioned above enter into chemical bonding with each others and form carbon-carbon bonds resulting in a saturated surface. FIG. 6B shows a schematic depicting carbon-carbon bonds forming a saturated surface on a wall 39 of one of the UCC structures. The carbon atoms from the side wall protection layer on the side wall of the trenches may enter into the plasma mix (when the glass containers are infused with the desirable gases and sealed) and possibly shift our UV emission output. On the other hand, in another embodiment of the invention, an oxide rich surface can be retained through an oxygen plasma burn to remove the carbons prior to sealing the containers. The strong electronegative potential of oxygen may lower the ionization potential of the gases subsequently stored in the quartz container. Since dry etching is anisotropic, it can be used to form patterns that are disposed across the surface of the starting wafer in any pattern defined by the mask on the starting wafer. This can lead to a glass container with rounded internal sidewalls. Regardless, the container can then be sealed from the top (as shown in FIG. 7) with a plate 40 to form a small scale cap (after the proper gases have been infused inside the nanometer containers).

The wall chemistry left behind after etching of the walls of the gas containers may play an important role in the functionality of the gas containers. The walls can have a surface energy that favors the ionization of the gases contained within the containers. In other cases, the surface energy will be unfavorable to plasma ignition. The ionized gases inside the glass containers would be repulsed, attracted by the electrostatic forces residing on the surfaces of the walls. These may be important consideration in view of the small physical dimensions contemplated in the invention.

In the case of dry etch chemistry, the sidewall protection film described above (which varies in thickness between 10-30 Å) is left behind from many etchant chemistries that are used. Accordingly, dry etching can be considered as a plasma treatment that can produce an interior surface of the gas container that can range from an oxidized surface on one end of the spectrum to a polymerized surface at the other end of the spectrum. As a plasma treatment, this treatment can occur as an additional step after wet chemistry is used to form the concave structures. By ranking order, the chemistries that can be used and lead from oxidizing to polymerizing include $NF_3$, $CF_4$, $CF_3Cl$, $CF_3Br$, $C_2F_6$, $CHF_3$, $C_3F_8$, $C_4F_{10}$ and $C_2F_4$. On one side of the spectrum, the addition of an oxidant is desirable (such as $O_2$). On the other side of the spectrum in order to consume the oxidants, $H_2$ can be used and is desirable in some cases.

Further surface modification of the walls of the gas containers can be performed for other purposes that would be beneficial, such as for example plasma formation, luminosity and mechanical integrity.

Figure 8A:
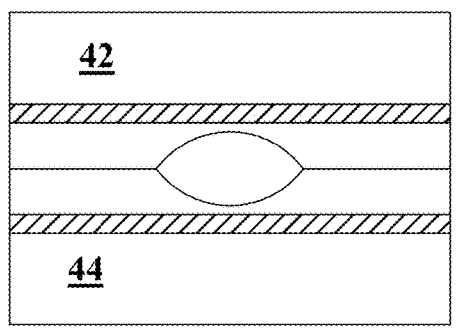
FIG. 8A is a schematic showing how after removal of resist, two mirror imaged wafers (using a wet etch) are mated to form the gas containers.
Figure 8B:
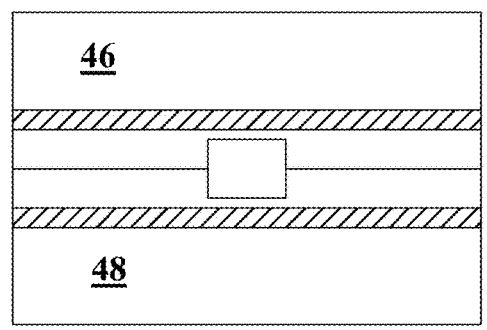
FIG. 8B is a schematic showing how after removal of resist, two mirror imaged wafers (using a dry etch) are mated to form the gas containers.

FIG. 7 is a schematic showing how after removal of the patterning resist, the starting wafer can be capped with the plate 40 (e.g., a flat quartz wafer) to form gas containers. Both wet and dry etching can be used. FIG. 8A is a schematic showing another embodiment of the invention and depicting how after removal of resist, two mirror imaged wafers 42, 44 (using a wet etch) are mated to form the gas containers. This method is more complex but desirable. A more rounded container can be obtained prior to removing the release layer. FIG. 8B is a schematic showing how after removal of resist, two mirror imaged wafers 46, 48 (using a dry etch) are mated to form the gas containers.

Figure 9:
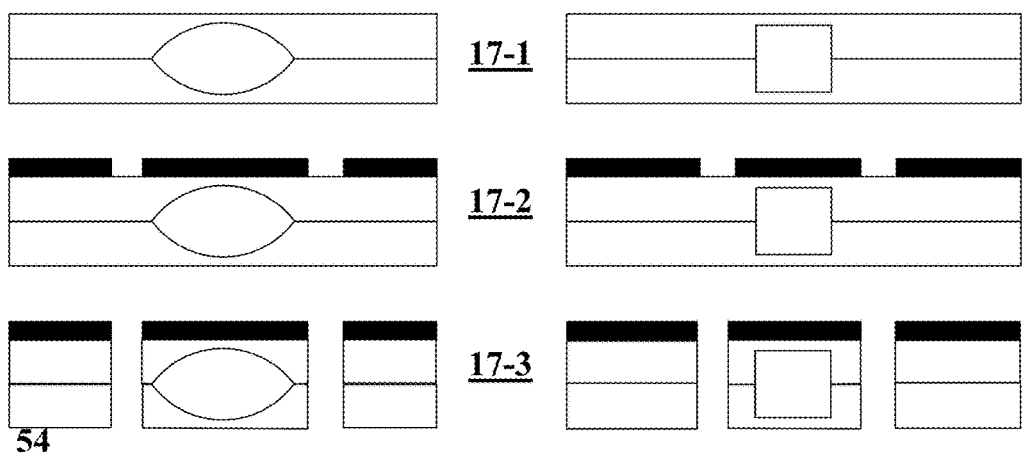
FIG. 9 is a process schematic showing the release layer being removed, followed by patterning.
Figure 10:
FIG. 10 is a process schematic showing two versions of the gas containers of the invention made using the large scale repeatable and reproducible processes.

FIG. 9 is a process schematic showing the release layer 32 having been removed, followed by (or proceeding) patterning at step 17-1, the masking and patterning at step 17-2, and the etching at step 17-3 to release and separate the UCC structures from each other. In this embodiment, a dry etch is used to obtain the gas containers. FIG. 10 is a process schematic showing two gas containers 50, 52 of the invention made using the large scale repeatable and reproducible processes discussed above.

Figure 11:
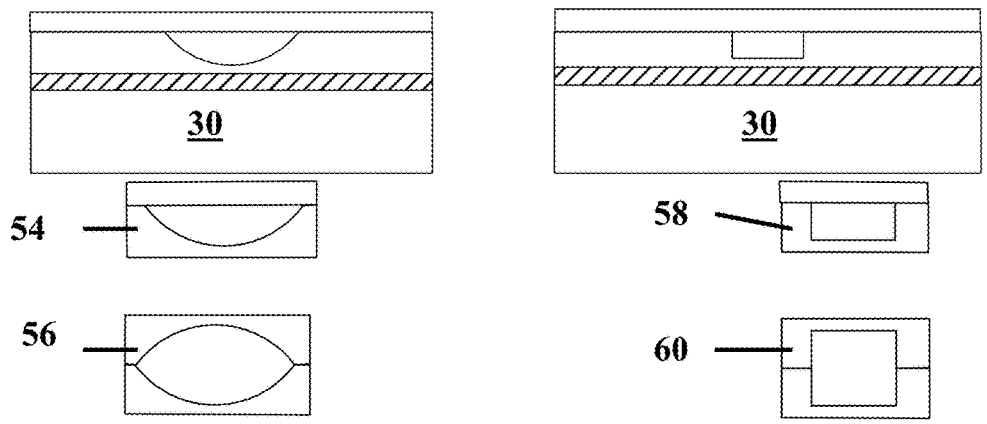
FIG. 11 is a schematic showing different shapes of the gas containers depending on how the starting wafer is capped and how the trenches are formed.

FIG. 11 is a schematic showing different shaped gas containers depending on how the starting wafer is capped and how the trenches are formed. FIG. 11 shows a half-spherical containment 54, a spherical containment 56, a capped rectilinear containment 58, and mated rectilinear containment 60.

Figure 12:
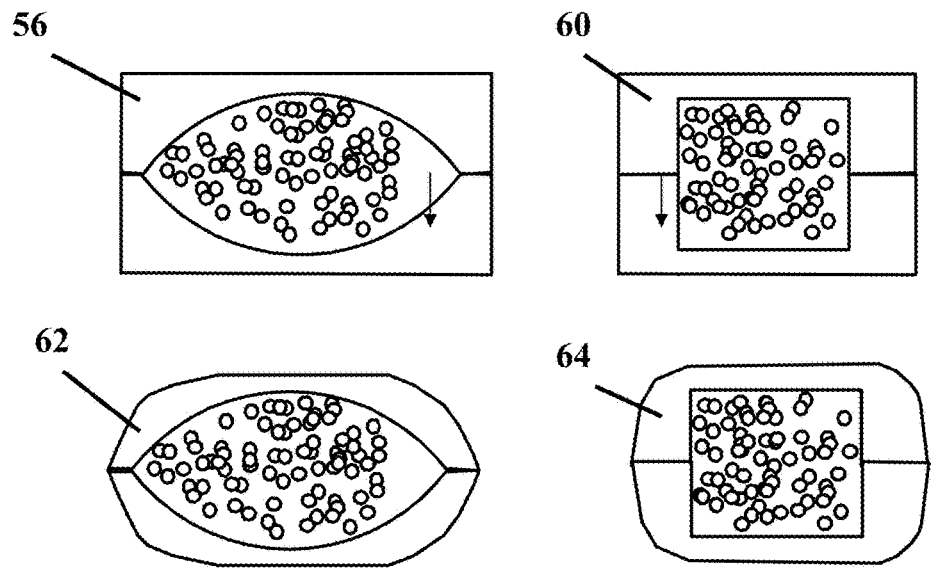
FIG. 12 is a process schematic showing the filling of the gas containers with the appropriate gases prior to sealing.

FIG. 12 is a process schematic showing the filling of the gas containers 56, 60 with the appropriate gases prior to sealing. The gas containers can be treated using HF to etch the edges. Gases such as Ne, Xe, He, Hg, $H_2$, $N_2$, Ar, Kr can be used as the fill gases. Also gas mixtures Ne+He, Ne+He+ 5% Xe, Ne+5-10% Xe can be used. The percent Xe addition is by atomic percent. Hg+Ar emit at the 360 nm; Ne+1% Ar also emits at 365 nm. Furthermore, other gas combinations can be used, including iodine vapor with various impurities. After the gas fill, the gas containers can be treated to an HF bath solution to treat their edges to produce the UCC structures 62, 64.

Figure 13:
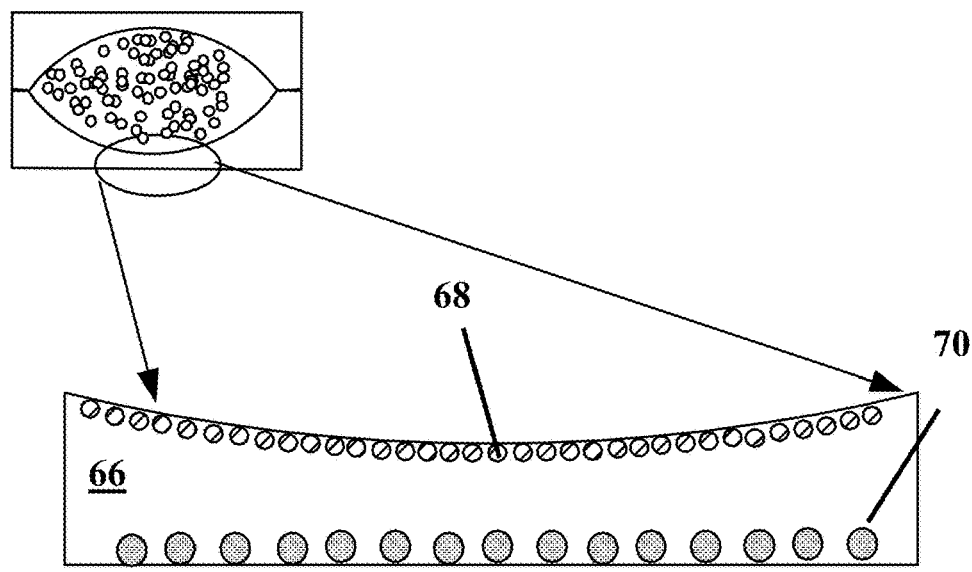
FIG. 13 is a schematic showing the internal wall of the glass containers being surface modified using Li and/or Na.

FIG. 13 is a schematic showing the wall 66 of glass containment 50 being surface modified on the interior using Li and/or Na interior surface moieties 68. In one embodiment of the invention, the internal wall of the gas containers can be surface modified by diffusing lithium and sodium into the silicate container. Both sodium and lithium are relatively small ions. This treatment is best performed when the two halves of the gas containers are still open. The diffusion of lithium and sodium to the internal walls can increase the positive charges of the internal walls which would repulse a portion of the population of positively charged ions produced during the plasma ignition. Furthermore, if lithium and or sodium are leached out of the glass wall and into the plasma, these ions can release significant light and hence trigger more energy generation. Ion beam processes can be used to supply the lithium and sodium ions onto the interior walls of the gas containers of the invention. In these cases, an anneal stage is added to ensure proper diffusion of the Li and Na ions. Sodium would lower the ionization potential of gases and gas mixtures.

In one embodiment of the invention; the outer walls of the glass container can be strengthened using external additives 70 such as potassium. In one embodiment of the invention; potassium can be used to create compressive stresses that increase the structural integrity of the wall 66. The potassium surface modification of the outside walls is expected to done after the containers have been sealed and released. The outside wall of the glass container of the invention can be strengthened using potassium diffusion. This technique can increase the strength of the gas container of the invention. The strength of the gas containers can be thus engineered. In turn, the strengthening of the glass containers increases its structural integrity and permits the use of the gas filled containers at different pressures.

Once the two halves of the gas containers are mated and the gas containers are sealed, a series of patterning and etching can be done to release the gas containers, through deep and fast dry etching. Once the containers are singulated from the starting wafer, their surfaces can be etched (by time and temp in an HF bath) to reduce the wall thickness and round the edges. When the gas containers are subjected to an HF treatment, the chemical strengthening using potassium diffusion is done subsequently to the etching of their outer surfaces.

Figure 14:
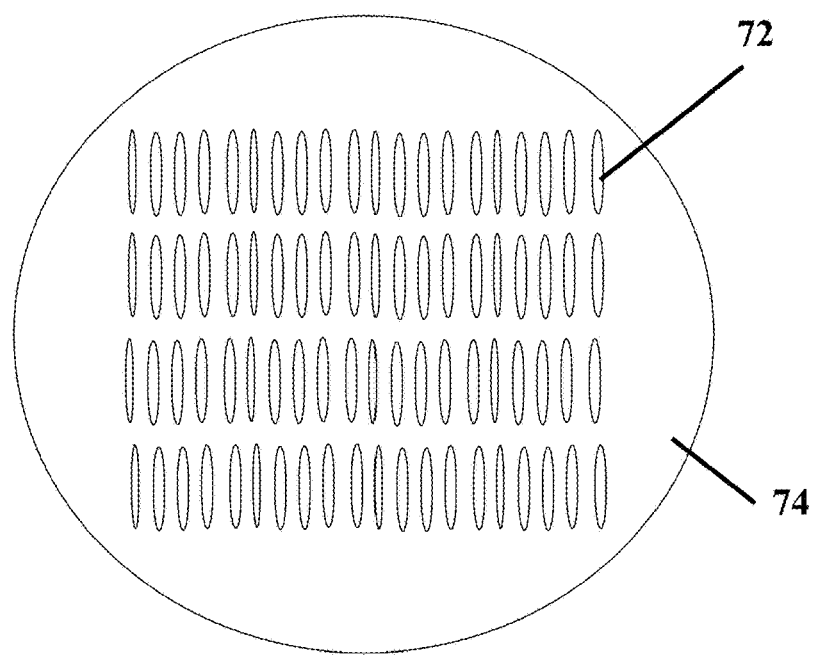
FIG. 14 is a schematic showing the production of the gas containers carried our using standard semiconductor processes where over 100,000 up gas container converters can be made per 150 mm wafer.

Regardless, FIG. 14 is a schematic showing the production of a plurality of gas containers 72 carried our using standard semiconductor processes where over 100,000 gas container converters can be made per 150 mm wafer 74.

In one embodiment of the invention, a metal coating such as Au or Ag for plasmonic activity can be applied at the wafer level using metal vapor deposition or can be applied through wet chemistry (after the gas containers have been singulated). Prior to metal coating, a choice is typically made as whether or not to undergo the chemical strengthening step using potassium diffusion.

In one embodiment of the invention, various means can be used to create nano-porosity on the interior or exterior surface of the gas containers of the invention.

Further surface modification where by the gas containers (with or without down converters contained within) can have a dielectric layer and a metallic shell and possibly an additional protective layer. The wet chemistry processes described before are applicable to the gas containers. This final protective layer can be made of bio-compatible chemistries that facilitate drug delivery within biological living bodies.

Figure 53:
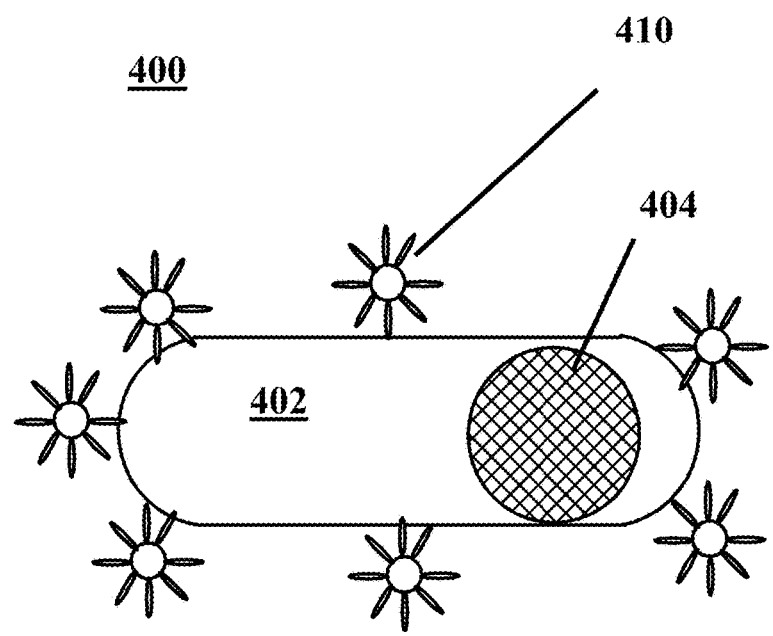
FIG. 53 is a schematic of a UCC structure including a capsule-type region for holding an upconverting gas and a down converting media where an activatable agent is attached thereto.

In another embodiment of the invention, the gas containers are coated with a material having magnetic properties or to have an ultra-nano-particle having magnetic properties (that fits within the gas container similar to the illustration provided in FIG. 53.)

As noted earlier, a combination of microwave and strong magnetic fields can be used to ignite plasma and generate UV light. A well known source of magnetic field with all the desirable magnetic gradient and controls is available in MRI machines with superconducting magnets enabling up to 11 Tesla. In one embodiment of the invention, an applicator of RF and or microwave energy is provided having a proper applicator design, antenna, high frequency coil, and a mirror for quasi-optic. The microwave and RF applicators that can be used in this invention include but are not limited to waveguide applicators, direct microwave irradiation using antennas, stray field applicators, capacitive parallel plates, coaxial lines, quasi-optical microwave devices, coils and solenoids and other RF and Microwave devices that can be derivatives of the fundamental microwave and RF designs. Discussed below are schematic illustrations of various microwave and RF hardware.

In one embodiment of the invention, the coils used for applying the magnetic gradient and all other modifications to the MRI machine are removable, so that after the light therapy permitted in one application of the invention, the MRI machine can be returned to normal functional state. It is possible to use microwave designs that place the generators and power supplies outside the MRI machines to avoid any undesirable effects caused through coupling of the magnetic field of the MRI with the components and subsystems of the microwave system. The microwave energy is then transmitted via an appropriate waveguide from the generator to the patient table.

In one embodiment of the invention, the waveguide passes through the walls of the MRI main tunnel in which case special MRI equipment designs have be made to optimize the microwave energy delivery. This is especially the case if microwaves using quasi-optical technologies (where a microwave beam is launched using a waveguide and reflected and focused through a mirror to target a tumor area in the patient. The microwave applicators have to be made from non magnetic materials to avoid coupling to the magnetic field of the MRI. Aluminum and copper waveguides and electrodes are therefore preferred In one embodiment of the invention, an X-ray machine having a source, a programmable controller and radiation containment is used in conjunction with the MRI machine. Once the magnetic tracers (embedded in the silicate containers encapsulating gases as well as a down converting media) confirm that the therapeutic agents have been delivered to target, the patient is subjected to an appropriate X-ray recipe consisting of energy dose and pulse width.

Yet another embodiment of the invention is to combine suitable microwave applicators and X-ray hardware with MRI machines. Furthermore, high power LASER sources in the IR regime can be used in MRI machines.

The various radiation energy sources can be used in combination or solo as the treatment may necessitate.
Examples of Gas Containers Having Carbon Nanotubes:

In one embodiment of the invention, the gas containers include carbon nano-tubes (CNTs) inside the UCC structures. In one embodiment of the invention, a single-wall nano tube (SWNT) or a double-wall carbon nano-tube (DWNT) is attached to the internal or external wall of the gas container (preferably to the inside wall and preferably protruding inside the volume of the gas container). The CNT structure facilitates plasma ignition inside the gas containers.

The electronic properties of SWNTs are sensitive to the adsorption of certain gases. The charge transfer and gas-induced charge fluctuation are expected to significantly change the transport properties of the SWNT in the presence of an electric field. Furthermore, various gas molecules adsorbed to SWNT can be either charge donors or acceptors to the nano-tubes. Of special interest is the fact that $NH_3$, $N_2$, $H_2$, $CH_4$ fall in the charge donor category, and thus can be used as gasses inside the gas containers of the invention. $O_2$ for instance (which is not necessarily used in this example) would act as a charge acceptors and would make the nano-tubes p-type conductors.

In effect, the CNT not only can concentrate the electric field inside the gas container but also can lower the ionization potential of gaseous species. The CNTs can be attached to the gas containers using a series of steps all of which are well established and practiced in the semiconductor industry.

Figure 15:
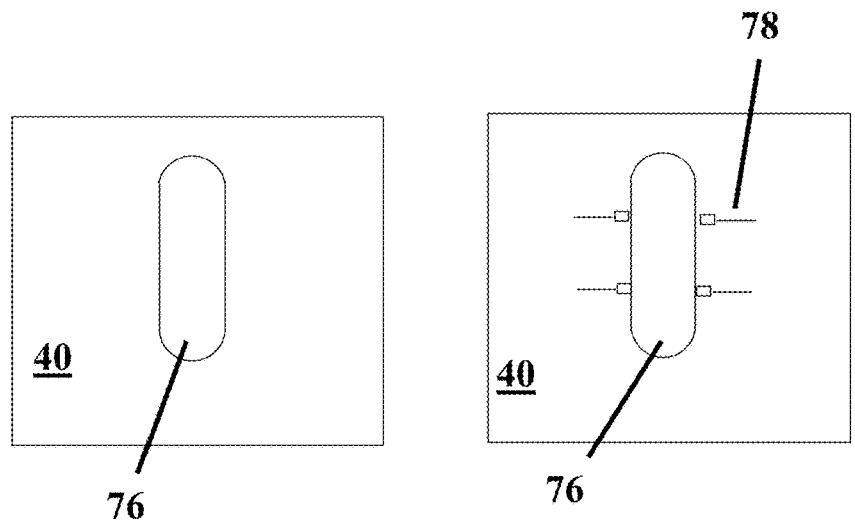
FIG. 15 is a schematic showing metal traces deposited through patterning and sputtering to position electrical pads that would be negatively biased for the subsequent placement of carbon-nano-tubes (CNTs) through fluidic self assembly.

First, the desirable position of the CNT is defined, followed by patterning, masking and metallization. FIG. 15 is a schematic showing metal traces 76 deposited through patterning and sputtering to position electrical pads that would be negatively biased for subsequent placement of Carbon-Nano-Tubes 78 (through Fluidic Self Assembly). The metal traces 76 would be formed for example of the underside of plate 40, such that when plate 40 is sealed to form the containments, the Carbon-Nano-Tubes 78 will be in place. The metallization can be done using various techniques including, evaporation, metal organic chemical vapor deposition, and sputtering. One suitable method would be sputtering. The sputtering process is widely used in semiconductors and can be applied in this example to deposit metal traces of desirable geometry along the surface of the starting wafer and/or in the concave cavities formed in the starting wafer surface.

Sputtering is based on simple principles. A vacuum chamber is filled with argon gas. Plasma is struck and the argon ions are accelerated with a biasing voltage into the target material (Al or another metal of choice such as Au). Metal atoms are knocked off the target and land on the wafers. Parameters such as pressure, bias voltage, generator and sputtering target can change the rate of deposition.

Au traces can be deposited from a Au coated sputtering target through a patterned mask onto the surface of the starting wafer and/or in the concave cavities formed in the starting wafer surface. Al traces can be deposited from an Al coated sputtering target. Cu traces can be deposited from a Cu coated sputtering target. At least two metal traces (one on each side of the gas container) can branch out from the concave quartz starting wafer structure.

Figure 16:
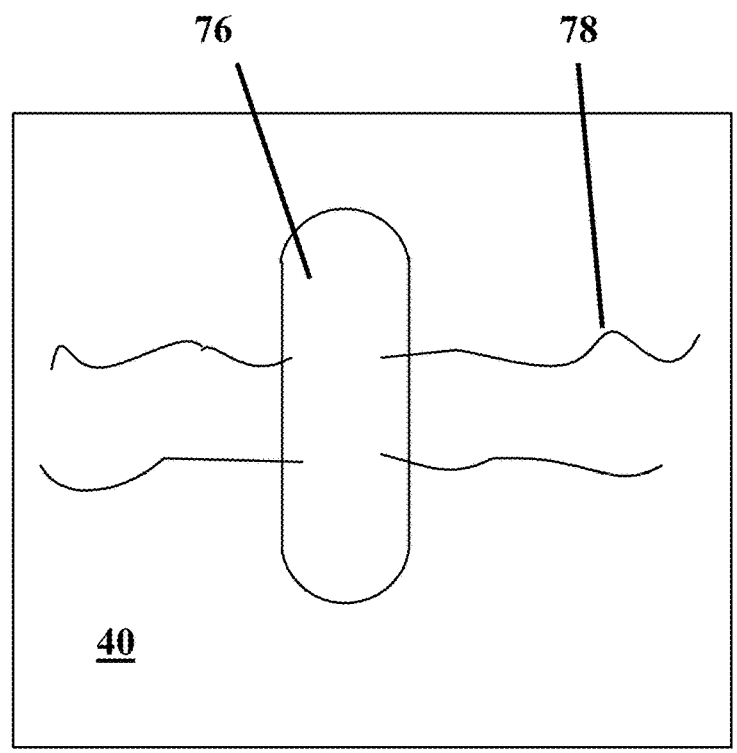
FIG. 16 is a schematic showing CNTs attached using a metallization process (e.g., sputtering)

A quartz wafer plate 40 having the metal traces 76 is introduced in a non polar liquid bath and a negative bias is applied to the traces 76 (through a pre-deposited common trace with an electrical pad on the perimeter of the wafer for applying the bias). The SWCNTs 78 are released in the non polar solution through a process similar to fluidic self assembly, known in the art. After settling and assuming the desirable positions, the quartz wafer is elevated slowly to above the surface of the non polar liquid (used for dipping). The wafer is then subjected to a conformal coating to keep all the CNTs 78 in place. For example, another sputtering step is applied and the CNT are now fixed in the designated groves. The mask would then be removed. Indeed, FIG. 16 is a schematic showing CNTs 78 attached using a metallization process (e.g., sputtering). This method can yield a repeatable and reproducible assembly from the nano to the micron scale. Upon removing the photo-resist, the carbon nano tubes are held on place by virtue of the metal coatings. Besides CNTs, aluminum or copper filings or nanorods or nanoparticles can be added into the UCC structures.

With the CNTs in place, the gas containers are ready for gas filling and subsequently sealing. Upon the quartz surface of the quartz starting wafer, a conformal coating of a silane adhesion promoter is dispensed. The silane adhesion promoter is designed for silica to open the Si—O—Si molecular bridge network on at least a near surface of the quartz wafers.

The sealing is performed by bringing the top wafer in close proximity to and aligned with the bottom wafer hosting the CNT 78 (in this case only the bottom wafer has CNT). The wafers are then sealed by having a fixture that holds the wafers in close proximity under pressure for example of 17 KN. This bonding can be done at or near room temperature.

The bonded wafers are then ready for another series of patterning and masking steps to singulate and release the various gas containers through deep and fast dry etching. Once the containers are singulated their surfaces can be etched (by time and temp in an HF bath) to reduce the wall thickness and round the edges (as described above). This fabrication process of forming the gas containers and releasing the gas containers using standard lithographic patterning and other recognized semiconductor metal deposition and etching processes can occur with or without CNT inclusion.

Figure 17:
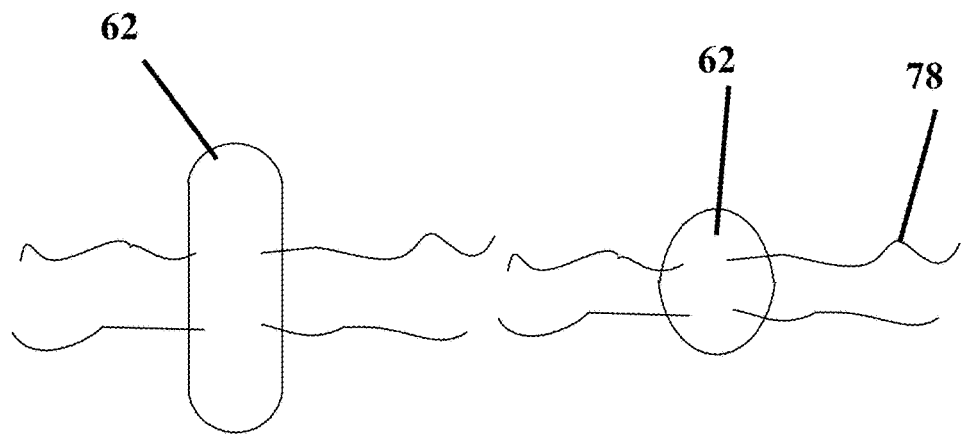
FIG. 17 is a schematic showing that the shape of the up converters can be controlled and showing that spherical or elongated shapes can be manufactured in a reproducible manner.
Figure 18:
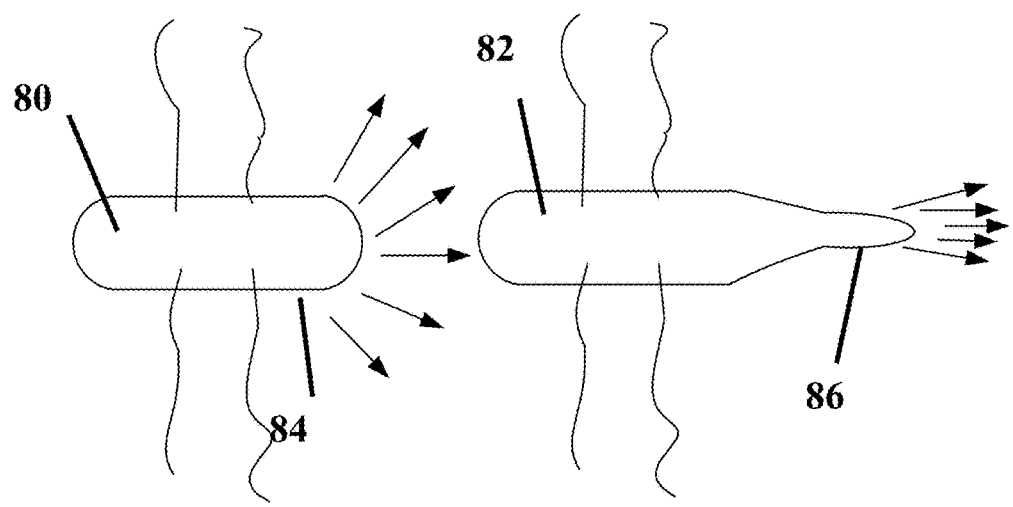
FIG. 18 is a schematic showing that the shape of the up converters can be further engineered for maximizing UV output and collimation to be directed to an agent in the medium of the upconverting container.

FIG. 17 is a schematic showing that the shape of the UCC structures 62 can be controlled and showing that spherical or elongated shapes can be manufactured in a reproducible manner. FIG. 18 is a schematic showing that the shape of the UCC structures 62 can be further engineered for maximizing UV output, and collimation to be directed to an agent in the medium of the up converting container can be realized. The UCC structures 80 and 82 have respective longitudinal ends 84 and 86, where light from the ionized gas in the UCC structure will be directed or concentrated. In other words, minimizing scattering and orienting the solid angle output can be performed through controlling the shape of the walls of the UCC structures.

Once the UCC structures are characterized in term of UV output; and, the sights of maximum UV output (or UV ports) have been identified, the UCC structures can be further functionalized by adding biding agents to the UV ports (on the outer walls of the UCC). These binding agents are used to fixate a chemical moiety such a psoralen in the proper conformation to the sight of maximum UV output in order to achieve photo-initiation of the chemo-therapeutic agent at the right site and with the least number of UV photons. Furthermore, additional exposure of the psoralen to UV radiation is designed to break the binder so that the psoralen is released (detached) from the UCC structure.

Examples of Double Metallic Coated Structures:

Sub-wavelength particles with metallic coatings exhibit very useful properties due to the local field enhancements created through optical excitations by the collective oscillation of the electrons, which are localized along the interface. A plasmonic phenomenon results in the concentration of electromagnetic fields at the interface of the metal and the fluorescent crystalline material. This results in enhanced fluorescence and results in a frequency shift. The intensification and the frequency shift depend on the dielectric, the fluorescence material, the size of the metalized particles, and the thickness of the coating among other parameters. The enhanced fluorescence that takes place is predominantly occurring at the outer surfaces of the crystals.

Dual shell metallic coated fluorescent materials have gained interest recently in view of the potential of added intensification, and in view of other potentially useful inductive coupling between concentric metal shells.

Figure 19:
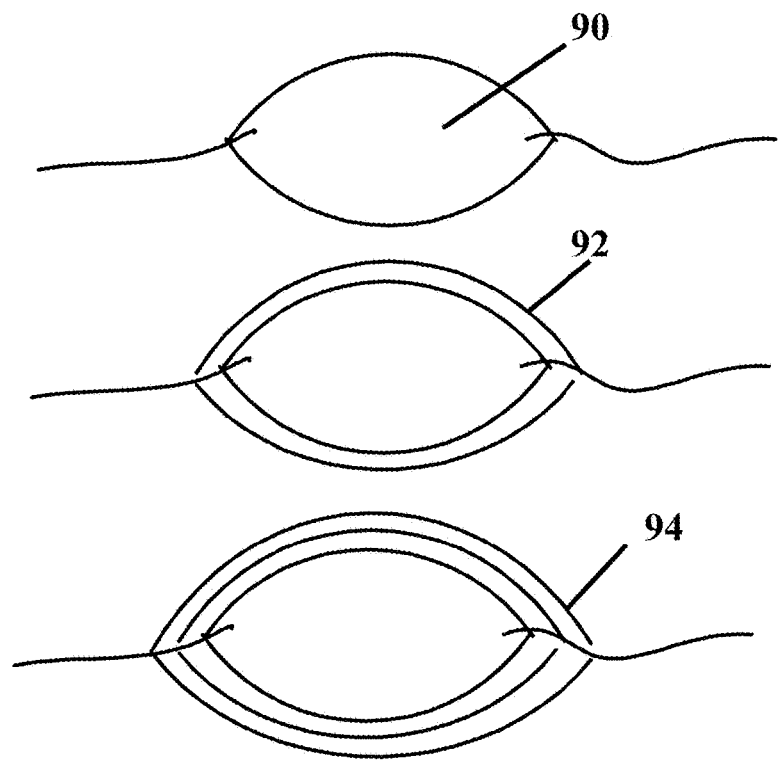
FIG. 19 is a schematic showing a novel method for producing single and double metallic shell coatings not using wet chemistries.

In one embodiment of the invention, there is provided a method by which a dual shell coating can be prepared. FIG. 19 is a schematic showing a novel method for producing single and double shell coatings. A plasmonic coating 92 can be applied to a UCC structure 90 with or without CNT. A second coating 94 can further be applied to UCC structure 90 with or without CNT. Though the method is exemplified specifically for the gas container of the invention, the method is applicable to other metalized solid crystalline particles with plasmonic properties.

Similar to as before, a patterned wafer with electrical pads formed therein is connected to a common ground plane using conventional vias. So that only the electrical pads are electrically conductive, the areas between the electrical pads are insulated using an organic or inorganic material (such as $SiO_2$ or polymers). The patterned wafer is placed inside a liquid bath using a non polar liquid. The electrical pads are connected to a negative bias creating a potential around the area of the electrical pad.

The metalized glass containers (as described above but now free standing) can be introduced into a solution of supersaturated solution for the purpose of partial hydrolysis of organo-metallic compounds. The hydrolysis of TEOS and TMOS are well known and are used for the purpose of illustrating a simple method of creating a dual shell with highly efficient semiconductor tools.

Starting with a metal alkoxides $Si(OR)_4$ where R is an alcohol radical, one can promote the hydrolysis and condensation. The hydrolysis can be promoted by either an acid or base conditions. Acid catalyzed gels are preferred in this case since these gels create chain like behavior in their viscosity.

At one stage in the polymerization process, the gas containers with acidic functionalized attached can be passed on top of the non-polar liquid bath, with the wafer in a reversed biased condition. The glass containers would be electrostatically drawn to the electrical pads for the wafer.

The wafer can be then elevated above the top surface and partially dried. The wafer will then be taken to a CVD for depositing $SiO_2$ using standard silicate deposition processes. The top part of the gas containers can be fully coated and the lateral sides can be partially coated.

The glass containers would therefore be coated partially (and not fully since the glass containers lay on top of the electrodes). A second wafer with an adhesive but compliant release layer would be brought into proximity and aligned with the wafer containing the gas containers. The second wafer is then introduced to the CVD tool for depositing $SiO_2$ to coat the top parts of the gas container and partially coat the lateral side of the glass container. CVD tools have the capability of wafer tilting to optimize the coating uniformity.

The $SiO_2$ deposition recipe is designed to permit the formation of a relatively uniform $SiO_2$ coating since the top and bottom part get fully coated (once) and the lateral parts get coated partially each time, but go through the process twice.

The last step is metallization (as was described before); the sputtering process can be used effectively while the gas containers are held at the wafer level.

Figure 20:
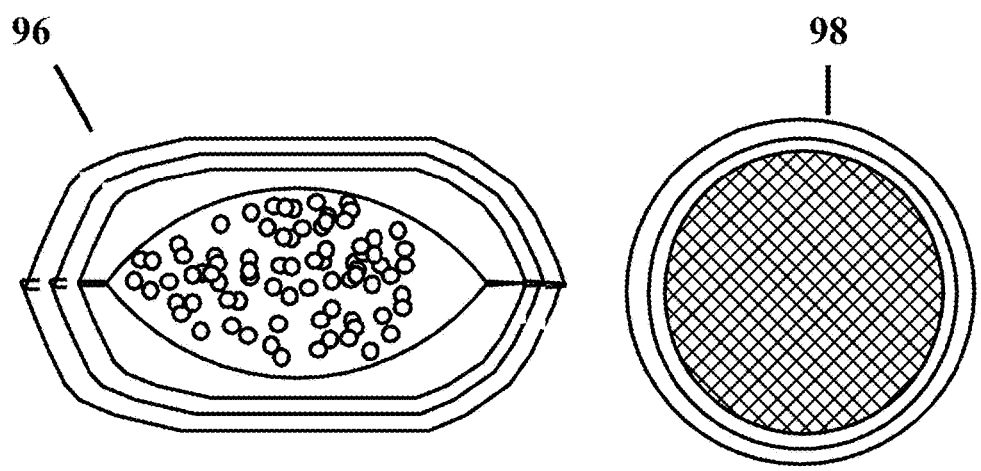
FIG. 20 is a schematic of a double metallic shell that is applicable to the gas containers of the invention as well as solid state crystalline solids used for down or upconverters.

A dual shell metallization can therefore be synthesized using existing semiconductor processes and can be arguably more repeatable and reproducible. FIG. 20 is a schematic showing how this novel method produces dual shell metallization on upconverter gas containers 96 or on solid state crystalline doped up converters 98, as described in more detail below.

Figure 21:
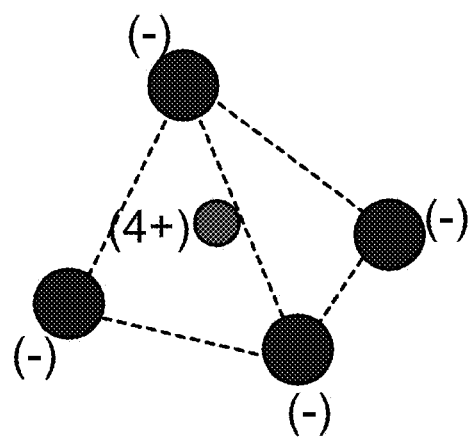
FIG. 21 is a schematic of a silicon tetrahedral building block of all silicates [$Si^{4+}$(red) and $O^{2-}$(blue)]
Figure 22:
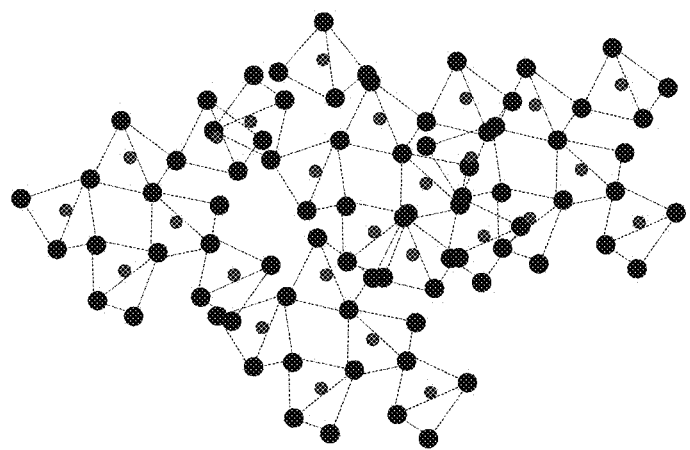
FIG. 22 is a schematic representation of amorphous $SiO_2$.
Figure 23:
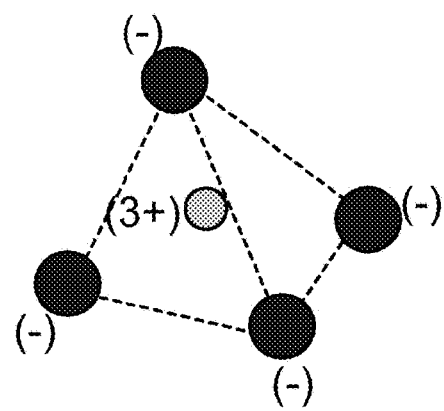
FIG. 23 is schematic representation of amorphous silicate where aluminum (Al) is substituted for some Si to produce a charge deficiency.
Figure 24:
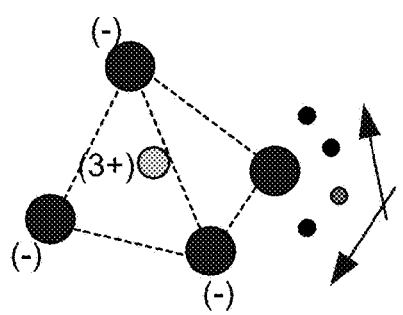
FIG. 24 is schematic representation of the metastable equilibrium of various alkali and alkaline earth metals around non-bridging oxygen.

Alternative Gas Containment Structures:

Silicates: FIG. 21 is a schematic of the fundamental silicon tetrahedral building block of all silicates [$Si^{4+}$(red) and $O^{2-}$(blue)]. FIG. 22 is a schematic representation of amorphous $SiO_2$ network. FIG. 23 is schematic representation of amorphous silicate where aluminum (Al) is substituted for some Si to produce a charge deficiency. The tetrahedral configuration formed is no longer electrically neutral, and some of the bridging oxygen sites become non-bridging oxygen sites. The concentration of non bridging oxygen increases in direct proportionality the $Al^{3+}$ concentration. FIG. 24 is schematic representation of this substituted amorphous silicate structure further modified with ionic species. All these structures are suitable as UCC structures of the invention.

In some glasses, to maintain charge neutrality (and avoid attracting various airborne polar molecules and gases) alkali and alkaline earth metals (sodium, potassium, and calcium) are added to the silicate structure. These ionic species break the silicate network and get trapped in meta-stable equilibriums around non-bridging oxygen sites. These alkali ions become active in the microwave field (and can jump over longer distances due to the wider and more spaced available meta-stable equilibrium sites).

Figure 25:
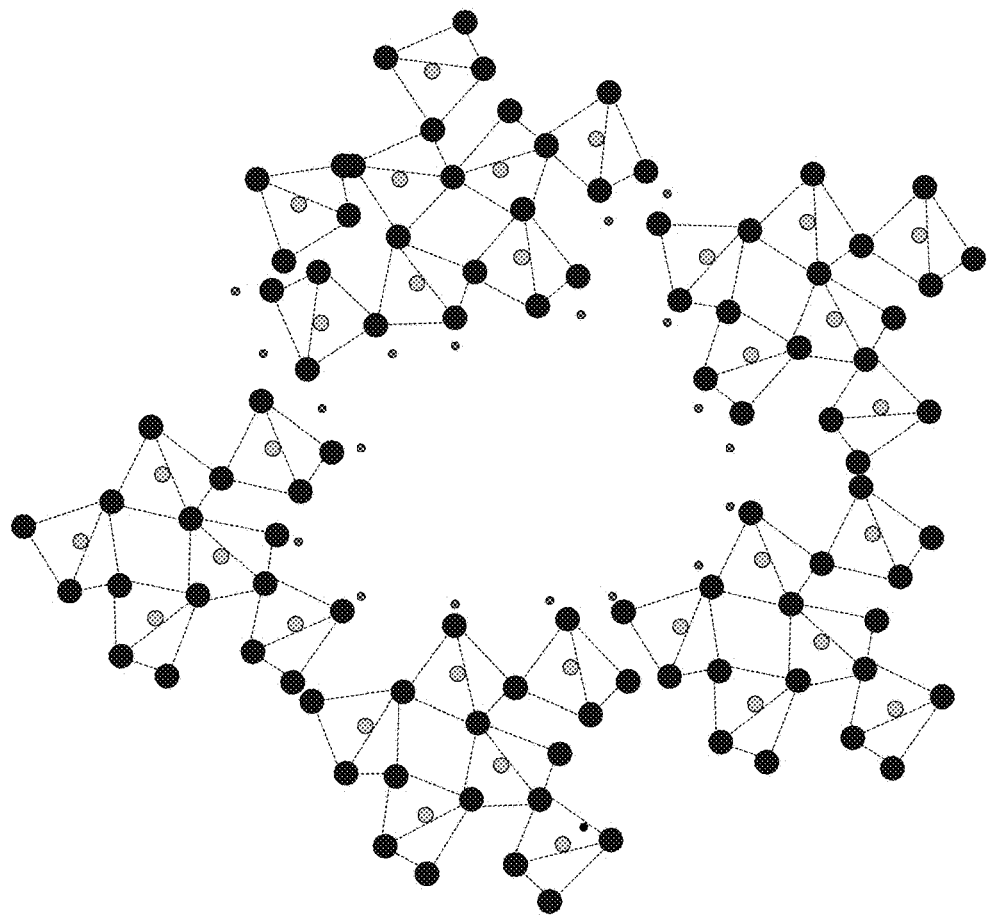
FIG. 25 is schematic representation of showing the complexities of a caged substituted silicate structure.
Figure 26:
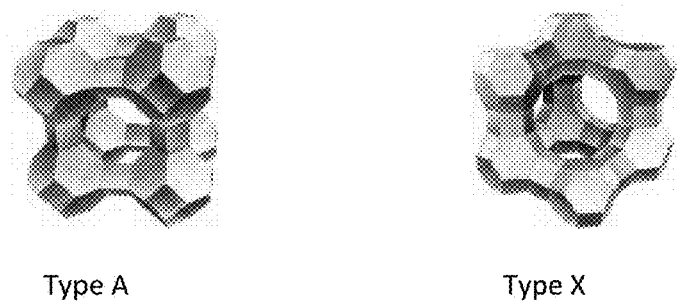
FIG. 26 is schematic representation of zeolites composed of alumino-silcate structures.

FIG. 25 is schematic representation showing the complexities of a caged substituted silicate structure. At the proper ratio of sodium to aluminum, large silicates cages are formed. At a molar ratio (Na/Al=1) the sodium alumino silicate glasses exhibit significant microwave absorption and diffusion. FIG. 24 is schematic representation of zeolites composed of alumino-silcate structures. The crystallographic structure of two zeolites formed by varying tetrahedras of ($AlO_4$) and ($SiO_4$) is shown. All these structures are suitable as UCC structures of the invention.

Unlike the previous example, charge neutrality is deliberately prevented and Zeolite exhibit useful properties as getter materials. Zeolites are widely used as adsorbents. The tetrahedras result in unique structures of special interest in the invention. Molecular sieves are manufactured by crystallization from aluminum hydroxide, sodium hydroxide and water-glass. In one embodiment, water glass can be used as a sealant for the porous particles.

Under a crystallization process, the required sodium alumino-silicate structure is formed. The formed zeolite crystals can be ion exchanged to further adjust the pore size. Molecules larger than the pore opening of the molecular sieve can not be adsorbed, smaller molecules can. Molecular polarity can be used to control/assist absorption. Gases with one degree of polarity may diffuse faster (e.g., ammonia is very suitable for the diffusion process and microwave coupling).

It is possible to prepare phosphorous modified Zeolites/ molecular sieves through an exchange process wherein a partially hydrogen, ammonium exchanged sodium zeolite sieve is combined with $H_3PO_4$ and subsequently treated at elevated temperature and steam to react the proper site leading to the obtainment of a zeolite with $P_2O_5$ in 2% to 5% by weight. The technology is described in U.S. Pat. No. 5,378,670 which referenced in its entirety in the invention. Various other catalysts that contain phosphorous or phosphorous compounds can be used to derive phosphorous zeolites molecular sieves. These catalysts are described in various patents including U.S. Pat. Nos. 4,498,975; 4,504,382; 4,839,319; 4,970,185; and 5,110,776. All these patents are hereby referenced in their entirety.

Figure 27:
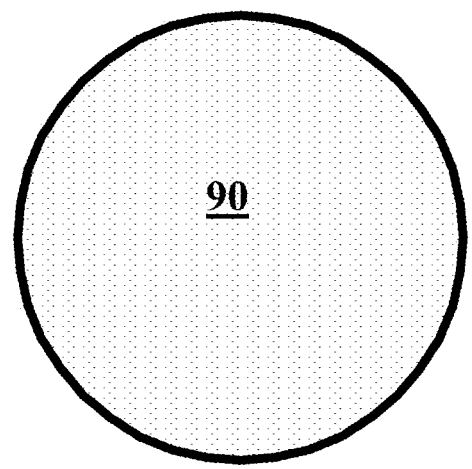
FIG. 27 is schematic representation of an Alkali-Alumino-Silicate nano-particle containing nano-pores (or silicate cages)
Figure 28:
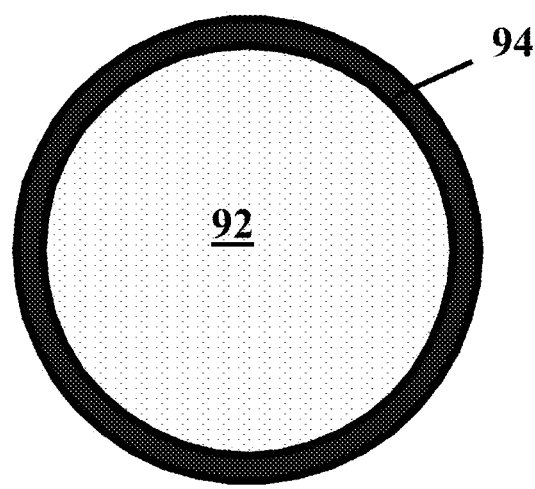
FIG. 28 is schematic representation of an alumino silicate nano-particle coated with nano-diamond film or diamond like carbon or highly conductive graphene material.
Figure 29:
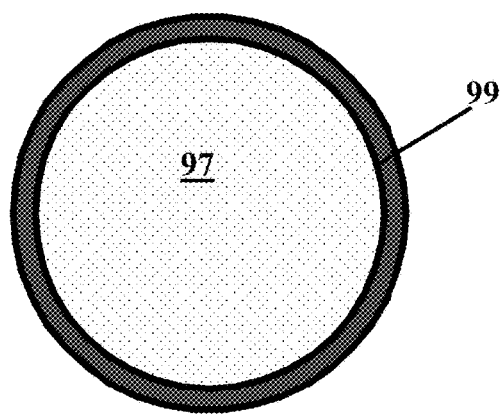
FIG. 29 is schematic representation of a nano-particle coated with an organic film (for possible bioluminescence.

FIG. 27 is schematic representation of an alkali-aluminosilicate nano-particle 90 in one embodiment of the invention containing therein nano-pores (or silicate cages). These particles can be synthesized in various ways, and some structures are commercially available under different brand names. FIG. 28 is schematic representation of an alumino silicate nano-particle 92 in one embodiment of the invention having a coating 94, such as for example coated with nano-diamond film or diamond like carbon or highly conductive graphene material. FIG. 29 is schematic representation of a nano-particle 97 in one embodiment of the invention coated with an organic film 99 (for possible bioluminescence). All these structures are suitable as UCC structures of the invention.

Figure 30:
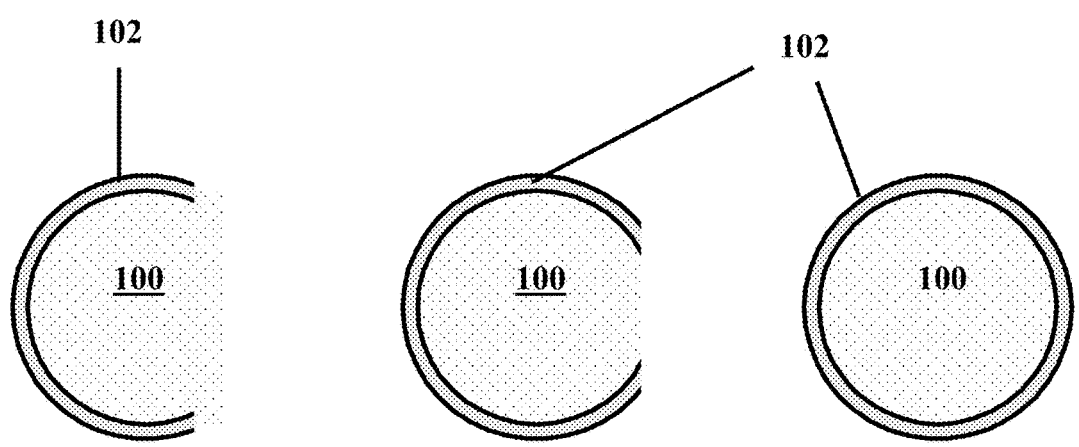
FIG. 30 is schematic representation of a partially coated to fully coated Sodium-Alumino-Silicate particles the coating illustrated with Au for plasmonics generation.
Figure 31:
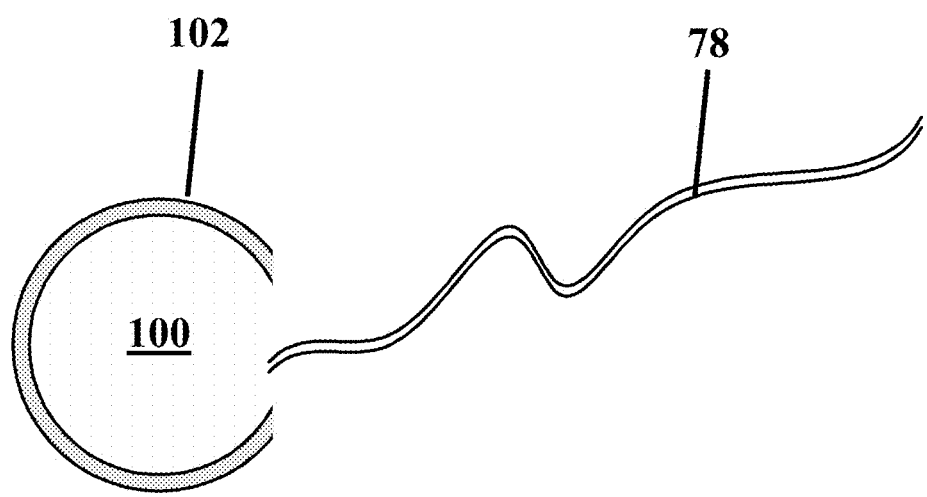
FIG. 31 is schematic representation of a carbon-Nano-Tube (CNT)

FIG. 30 is schematic representation of a partially coated to fully coated sodium-alumino-silicate particles 100 in one embodiment of the invention, the coating 102 is by way of illustration a metal coating (e.g., Au or Ag) for plasmonics generation. FIG. 30 shows the coating 102 as a completely or partially encasing coating. FIG. 31 is schematic representation of a carbon-nano-tube (CNT) 78 in one embodiment of the invention, which can be attached to a porous or hollow nano-particle 100 containing therein appropriate gas or gas mixtures. All these structures are suitable as UCC structures of the invention.

A single or double wall CNTs can be used in any of the noted embodiments. As discussed earlier in the context of gas contained UCC structures, CNTs are very receptive to microwave energy and can act as an electronic pump to stimulate the generation of plasma As noted above, ammonia and argon are of special interest. Ammonia has been used to create MASERs due to its response to microwave energy. It absorbs microwave energy, and in various embodiments significant rotational energy can be pumped into ammonia molecules. Argon can be ionized using microwave radiation and a Tesla coil or a combination thereof. These two gases can be used as a base from which other gases can be added to produce specific UV or VIS or IR spectral emissions of interest. Commercially available silicate porous structures can be filled with the appropriate gases using a series of cycles of heat treatment under vacuum followed by back purge at elevated temperatures (this will assist the diffusion process). As discussed in relation to FIGS. 2-4, a variety of gases can be used. The plasma generation can be carried out using microwave energy of various frequencies and magnetic field strengths.

Figure 32:
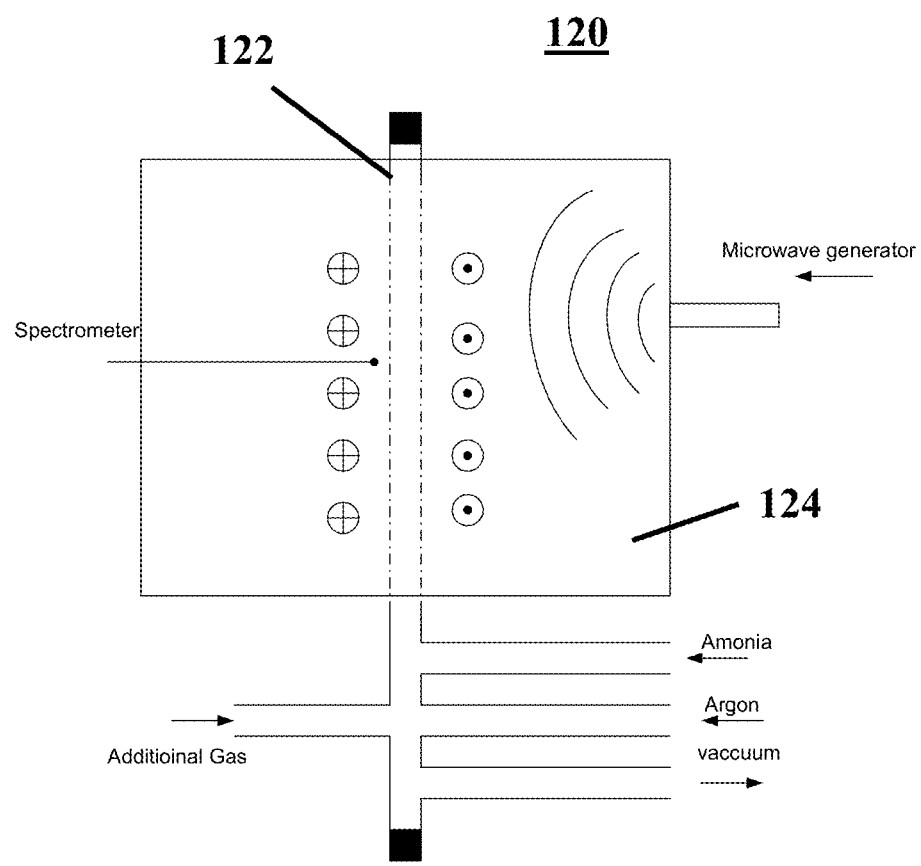
FIG. 32 is schematic representation of a microwave construction with an electromagnet for testing gas emissions.
Figure 33:
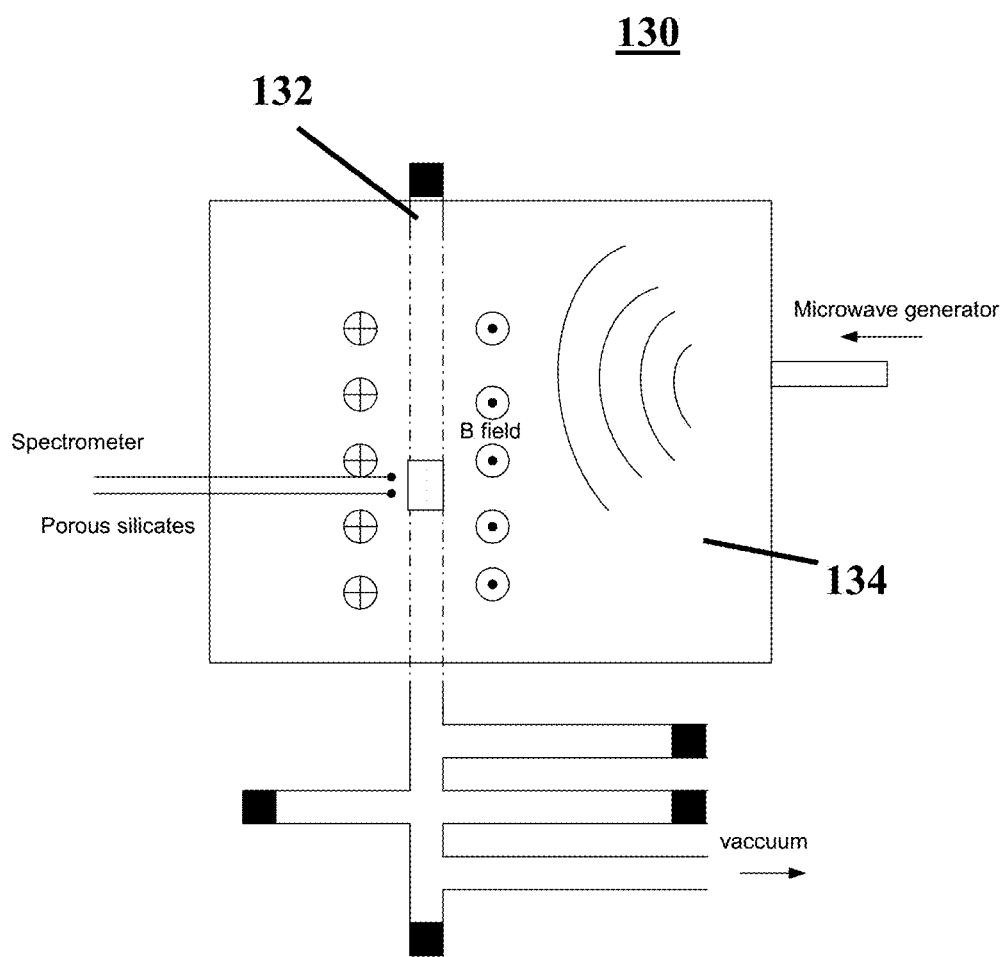
FIG. 33 is schematic representation of a microwave construction for testing nano-particles for emissions after they have been filled with gas and sealed (no external gases)

The gases for diffusion are selected to have appropriate emission characteristics for activation or treatment of agents in the medium about the UCC structures. FIG. 32 is schematic representation of a microwave system 120 for producing pure-gas emissions from various UCC structures of the invention. FIG. 32 shows a sealed tube 122 of reduced pressure extending through a microwave applicator 124. Different test gases can be introduced and optical emission data from plasmas of those gases measured by the spectrometer. Once a particular gas having an appropriate emission wavelength is identified, the UCC structures can be filled with the candidate gas. FIG. 33 is schematic representation of a microwave system 130 for comparison of different nano-particles for emissions (no external gases). Here, the gas-filled UCC structures are held by rod 132 in the microwave applicator 134. Optical emission data from plasmas in the gas-filled UCC structures are measured by the spectrometer. This microwave system 134 permits one to readily compare emission spectra to that intended for a particular application. Furthermore, the microwave system of FIG. 33 represents schematically a system for applying microwave energy (and optionally a magnetic field) to the UCC structures disposed in a medium placed inside the microwave system of FIG. 33.

Various silicate structures can be utilized for the UCC structures of the invention.

Silica Gel: Silica gel including randomly linked spherical polymerized silicate particles are utilized in various embodiments of the invention. The properties of silica gels result from the size and state of aggregation of the primary particles and their surface chemistry. Gels with nearly 100% $SiO_2$ purity with tailor-made pore systems and surface properties are used to "trap" the microwave-excitable gas inside.

For preparation, sulfuric acid and sodium silicate are mixed under controlled conditions to build the primary particles of the desired size, which polymerize and form the raw gel from which all types of silica gels are made. By controlling the washing, ageing, and drying conditions, the physical parameters such as porosity (pore size and distribution) and surface area can be adjusted to produce a range of different silica gel types. Silica gels are available in a wide range of particle sizes, each type having a well-defined particle size distribution.

Various chemical and thermal treatments can be used to improve the characteristics of silica gels as filter materials by controlling their internal surface areas and surface chmistries. These silica gels can be engineers to control their pore size and distribution as well as their internal surface chmistries. The following patent application US 2005/0205102 A1 is referenced in its entirety. The use of special catalysts and hydrothermal treatments is well documented in the literature for example, Czarney et al, Przem. Chem. 46 (4), 203-207 (1967) provide a study on pore structures following the various hydro-treatments and catalysts.

Silica gel compositions containing alkali metals and alkali metal alloys are described in patent application US 2009/

0041614 A1. The use of Sodium (Na), Potassium (K), Rubidium (Rb) and Cesium (Cs). Sodium and Potassium (and their compounds) are preferred and are of special interest in the invention. Of particular interest is the reported reducing capability of the surface chemistry and how it reacts with Si—O—H groups to release hydrogen.

Precipitated Silicates: Precipitated silica include a three-dimensional network of coagulated primary silica particles. The latter grow to sizes higher than 4-5 nm before they coagulate. Precipitated silicates are synthesized by acidifying sodium silicate. Sulfuric acid is used as the acid source. A stirring vessel containing water is used, and the precipitation is carried out under alkaline conditions. The choice of agitation, duration of precipitation, the addition rate of reactants, their temperature and concentration, and pH can vary the properties of the silica. U.S. Pat. Nos. 4,422,880, 4,132,806, 4,015,996, and 4,122,161 are referenced in their entirety.

Precipitated silicas distinguish from silica gels on the basis of pore structure. Precipitates typically have a broad meso/macroporous pore structure reflected in the pore size distribution, whereas gels generally have a more narrow microporous or mesoporous structure.

These precipitated silicates once filed with a working gas are suitable as UCC structures of the invention.

Commercial products: VYCOR® glass code 7930 is an open-cell, porous glass which exhibits suitable absorbing properties for the invention. Due to its porosity, this material has an internal surface area of approximately 250 square meters per gram. This porous glass is widely used in transistors, microminiature relays and other small devices. It has practical application in any sealed device that requires freedom from foreign contaminants. The open-cell network allows permeability on a selective basis—the species must be smaller than the microscopic pores to pass through the porous glass. The homogeneous pore diameters can be controlled to average between 40 and 200 Angstroms. These commercial glasses once filed with a working gas are suitable as UCC structures of the invention.

Figure 34:
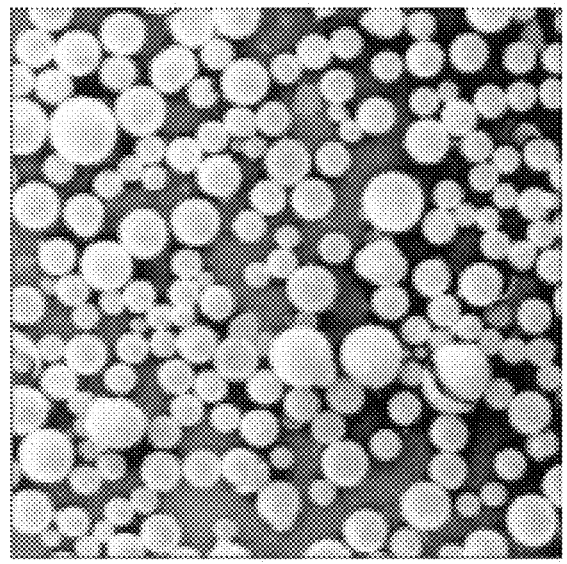
FIG. 34 is a micrograph of iron oxide nanoparticles.

Hollow Spheres (Cenospheres): Cenospheres are hollow spheres comprised largely of silica and alumina and filled with air and/or gases. Cenospheres are a naturally occurring by-product of the burning process at coal-fired power plants, and they have most of the same properties as manufactured hollow-sphered products. The departure from all other chemistries presented before is that cenospheres have Iron Oxide as part of their chemistry (Silica (55%-65%), Alumina (25%-35%), Iron Oxide (1%-5%), Titania (0.5%-1.5%)). Size of theses hollow spheres are very large compared to what may be needed in the biomedical application but spheres in the range of 10-350 microns may find use in other applications not limited to extremely small sizes. FIG. 34 is micrograph of Iron Oxide nanoparticles. The following patent documents pertaining to cenospheres are incorporated herein in their entirety by reference: U.S. Pat. Appl. Publ. No. 20080190327 and U.S. Pat. No. 6,506,819.

These cenospheres once filed with a working gas can be suitable as UCC structures of the invention through a gas diffusion process at elevated temperatures.

Figure 35:
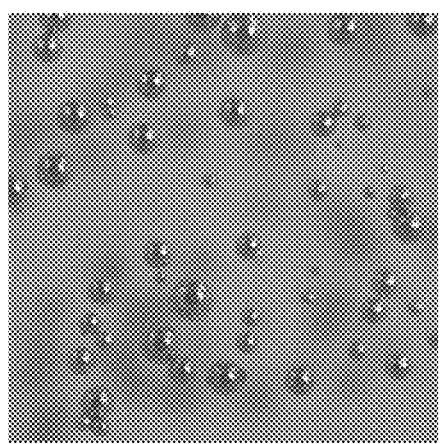
FIG. 35 is micrograph of conducto spheres.
Figure 35:
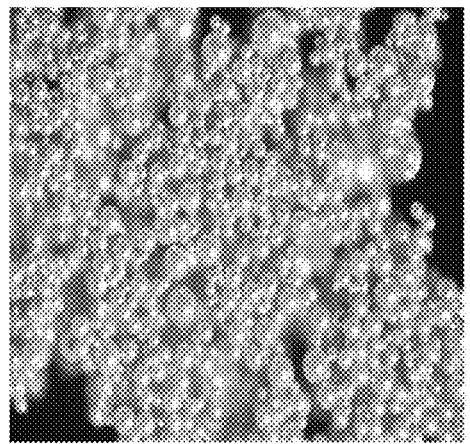

Conductospheres: Conductospheres are hollow glass microspheres coated with silver. These materials are typically incorporated into paints, adhesives and composites to provide these materials with electrical conductivity and to shield against electromagnetic interference (EMI) and radio frequency interference (RFI). Conductospheres are expected to be microwave receptors in aggregate forms. FIG. 35 is micrograph of Conducto spheres.

Conducto spheres exist in various products. Product B-55 Microsphere Material Base is an aluminosilicate in the range of 56 microns in median particle diameter and average Silver Thickness of 75 nm. Product M-18 Microsphere Material Base is a hollow glass in the range of 19 microns in median particle diameter and average Silver Thickness of 60 nm.

These conductospheres once filed with a working gas can be suitable as UCC structures of the invention through a gas diffusion process at elevated temperatures.

Alternative Hollow Spheres: Hollow $Ni_3Si_2O_5(OH)_4$ nanospheres can be synthesized via a facile deposition process at room temperature. The demonstrated diameters of the products is currently in the range of 300-320 nm, and the average wall thickness is about 10 nm.

These hollow spheres once filed with a working gas can be suitable as UCC structures of the invention.

Receptor Structures:

In one embodiment of the invention, there is provided a system for generating light. The system includes a low frequency energy source which radiates a first wavelength $\lambda_1$ of radiation and includes a receptor having outside dimensions of millimeters or below and which receives the first wavelength $\lambda_1$ of radiation and generates a second wavelength $\lambda_2$ of the emitted light in the infrared visible or the ultraviolet wavelength range. The receptor in various embodiments can have an outside dimension less than 1 cm, less than 1 mm, or less than 1 micron.

The receptor in one embodiment can have microscopic dimensions. As used in this context, microscopic refers to a dimensional scale on the order of 900 microns or less, including nanometer size structures ranging in size from a few nm to 1000 nm. In one embodiment, the receptor has microscopic dimensions are less than 400 nm so as to not represent significant scattering centers for visible light. In one embodiment, the receptor has microscopic dimensions are less than 50 nm so as to diffuse through porous and semi permeable medium such as in living cells or biological matter.

The receptor can include an ionizable-gas containment including an ionizable gas. The receptor in one embodiment can be a free-standing microwave or rf receptor, not attached to the circuitry delivering the microwave or rf power to ionize the gas contained in the receptor. The free-standing microwave or rf receptor of this invention is configured to be disposable in a medium nominally transparent to microwave or rf radiation and nominally opaque to UV or visible light. Accordingly, the walls of the free-standing microwave or rf receptor of this invention are nominally transparent to both microwave or rf radiation and transparent to UV or visible light.

The free-standing microwave or rf receptors of the invention thus differ from plasma shells previously developed. For example, U.S. Pat. Appl. Publ. No. 2007/0132387 (the entire contents of which are incorporated herein by reference) describes plasma shells encased between circuitry elements whose DC voltages produce plasmas inside the shells. For example, U.S. Pat. No. 7,604,523 (the entire contents of which are incorporated herein by reference) describe a number of techniques in the art and improvements thereon for forming plasma shells including the choice of ionizable gas and the incorporation of secondary electron emitters. The techniques in U.S. Pat. No. 7,604,523 produce plasma shells with average diameters of about 1 mil to 20 mils (where one mil equals 0.001 inch) or about 25 microns to 500 microns where 25.4 microns (micrometers) equals 1 mil or 0.001 inch. Plasma-shells can be manufactured up to 80 mils or about 2000 microns in diameter or greater. The thickness of the wall of each hollow plasma-shell in U.S. Pat. No. 7,604,523 is sufficient to retain the gas inside, but thin enough to allow passage of photons emitted by the gas discharge.

Accordingly, the techniques described in U.S. Pat. Appl. Publ. No. 2007/0132387 and U.S. Pat. No. 7,604,523 for the formation of plasma shells including the surface treatments, the gas selection, and the incorporation of secondary electron emitters materials are suitable for the formation of the free-standing microwave or rf receptors of this invention, where the techniques applied there are selected to provide walls for the free-standing microwave or rf receptors of this invention is nominally transparent to both microwave or rf radiation and transparent to UV or visible light.

The receptor can include a free space region within the containment which upon ionization of the gas emits at least the second wavelength $\lambda_2$. The ionizable-gas containment can have an outside dimension less than 1 cm, less than 1 mm, or less than 1 micron, less 100 nm, less than 50 nm, or less than 20 nm. The ionizable-gas containment can be a silicate glass containing network formers (Aluminum, Lead, Phosphate) and modifiers (Sodium, Lithium, Calcium).

The ionizable-gas containment can be a porous structure permeable to microwave or rf radiation. The porous structure can be at least one of a silicate glass, an alkali glass, a sodium glass, and a phosphate glass. The porous structure can be an ion-exchanged glass structure. The porous structure can have an outside water glass to seal an ionizable gas inside.

The ionizable-gas containment can be at least one of a silica gel, a precipitate silicate, a cenosphere, a conductosphere, or a hollow sphere. The ionizable-gas containment can be filed completely or partially with at least one of hydrogen, argon, nitrogen, xenon, ammonia, iodine vapor; mercury vapor; an organic gas, and hydrogen-nitrogen mixtures, and mixtures thereof. In one embodiment, other low ionization materials such as sodium and barium strontium oxide can be included inside the ionizable-gas containment. The ionizable-gas containment can include a microwave or rf coupler to promote electron emission into the free space region. The microwave or rf coupler can be at least one of a carbon structure, a carbon nanotube, a single wall carbon nanotube, a double wall carbon nanotube, grapheme, and metal materials or nanomaterials made of aluminum or copper.

The receptor can include a partitioned structure including at least two reaction components and a partition separating the at least two reaction components whereby mixing of the two reaction components upon microwave radiation at first wavelength $\lambda_1$ produces at least one of a chemiluminescent or bioluminescent reaction for emission of the second wavelength $\lambda_2$. The reaction components can include bioluminescent or chemiluminescent reagents.

The partition cam be a microwave-activatable material which, upon activation, opens the partition to mix the at least two reaction components. The partition can be at least one of a microwave susceptible material which heats upon microwave exposure, or a rf susceptible material which heats upon rf exposure, or a magnetic susceptible material which is inductively moved upon exposure to a magnetic inductive field. The partition can be material having a melting point material less than 30° C. The partitioned structure can be a biodissovable material. The partition can be a material having a melting point greater than 30° C.

The receptor can be a structure including a shell and at least one interior void. This structure can be for example a cenosphere and a conductosphere. The interior void can be filled with at least one argon, neon, xenon, helium, ammonia, or an organic molecule.

The system for generating light includes a microwave or rf applicator which directs radiation of the first wavelength $\lambda_1$ into an object including the microwave receptor. The microwave or rf applicator can be one of a waveguide applicator, a microwave or rf antenna, or a microwave beam source. The microwave beam source can be a focused beam source concentration radiation of the first wavelength $\lambda_1$ into a region of the object where the microwave receptors reside. The first wavelength $\lambda_1$ radiation can be in a range of 1 KHz to 100 GHz.

The receptor can be configured to emit for the second wavelength $\lambda_2$ radiation in a range from NIR to UV. The receptor can be configured to emit for the second wavelength $\lambda_2$ radiation which activates psoralen. The receptor can be configured to emit for the second wavelength $\lambda_2$ radiation which photoactivates a resin material. The receptor can be configured to emit for the second wavelength $\lambda_2$ radiation which is capable of sterilizing a medium in vicinity of the microwave receptor. The receptor can be configured to emit for the second wavelength $\lambda_2$ radiation which photoactivates a photo-activatable adhesive connecting members together such as for example at least one of a semiconductor device, a printed circuit board, or a semiconductor wafer. The receptor can be configured to emit for the second wavelength $\lambda_2$ radiation which photoactivates photograftable materials. The receptors can be a plurality of receptors forming a fluidized bed for treating a fluid about the receptors.

Viewed from a different perspective, the receptors can be considered structures for disposition in an homogeneous or inhomogeneous medium, or nearby an homogeneous or inhomogeneous medium, whose reception of electromagnetic field energy results in the production of emitted light. The receptors described above make use of materials and/or combination of materials to assist in energy conversion inside a medium such as for example a living body from one window of wavelengths and/or electrical fields of amplitudes and/or or currents flux densities to another window of wavelengths.

In one embodiment, the flux density (electrical or magnetic or both) propagated in for example a polarizable biological media (e.g., an elemental volume inside the human body) induce in the materials and/or combination of materials of the receptors a conversion of the incident energy into emitted energy which radiates from the receptors. This conversion may be more appropriately characterized in terms of the reactions of the materials and/or combination of materials of the receptors with induced currents around the receptors especially at low RF frequencies of 100 MHz and below. In this low frequency regime, ionic currents can take place, and these ionic current could in turn trigger biomodulated responses.

Viewed from another perspective, the receptors can be considered structures for disposition in an homogeneous or inhomogeneous medium whose reception of electromagnetic field energy results in a receptor response. The receptor response can be as noted above the initiation of a plasma contained in the receptor, the initiation of a bioluminescent or chemiluminescent reaction, the melting or dissolving of a member of the receptor, etc. The receptor response can be the triggering of a microelectronic device included in the receptor. In which case, emitted light may or may not be output from the receptor.

Microwave or RF Applicator Configurations:

For the purposes of illustration and to simplify discussion of the basic concepts, incident wave propagation is considered along a z-axis of a Cartesian coordinate reference system in the following description. One consequence of Maxwell's equations is the self-propagation properties of electromagnetic waves. A time-varying magnetic field produces a time-varying electric field, which in turn creates a time-varying magnetic field. In a Cartesian reference system (x,y,z), with the assumption that propagation is along the z axis, both E and H are sinusoidally propagating along the z axis at the phase velocity of the wave.

The media to be treated in the invention can include various regions across which the incident microwave energy is going through to reach the desired target site (tumor site for example). The incident wave goes through various absorption and reflections at each interface and various microwave delivery methods are envisaged.

Figure 36:
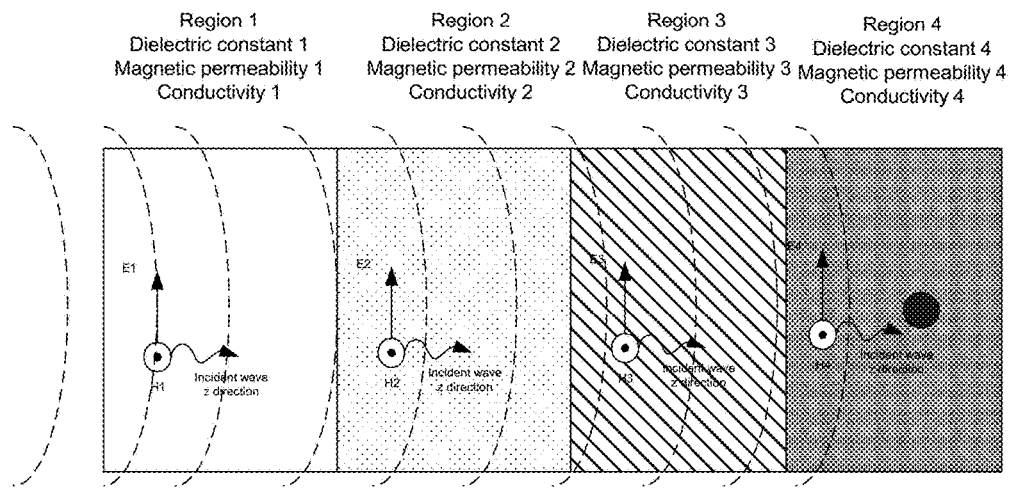
FIG. 36 is schematic of direct irradiation in a biological media.

FIG. 36 is schematic of direct irradiation in a biological media. As shown in FIG. 36, the incident microwave will in all likelihood travel through different biological media (i.e., regions 1, 2, and 3) such as blood vessels and bone before arriving at the target medium (i.e., region 4). This method can be used for example to deliver microwave energy to a tumor site but may not necessarily be appropriate for the deliver of microwave energy to other target regions. In this direct irradiation method of the invention, a microwave antenna can direct the microwave energy, and a high intensity microwave power can be used to power the UCCs inside the tumor site at region 4.

Figure 37:
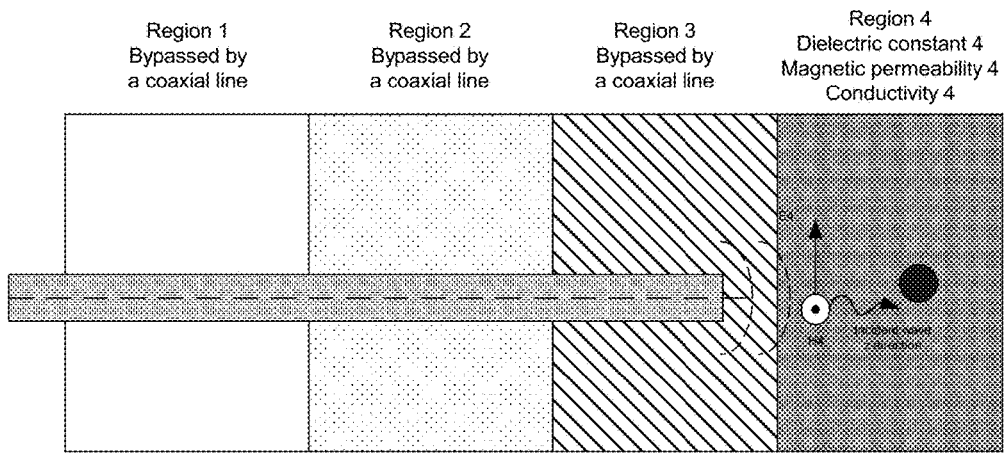
FIG. 37 is schematic of coaxial irradiation in a biological media.

FIG. 37 is schematic of coaxial irradiation in a biological media. This embodiment of the invention may result in tissue damage due to coax insertion to proximity of the tumor site. However, this embodiment avoids unnecessarily exposing regions 1, 2, and 3 to microwave irradiation when delivering microwave energy to region 4.

Figure 38:
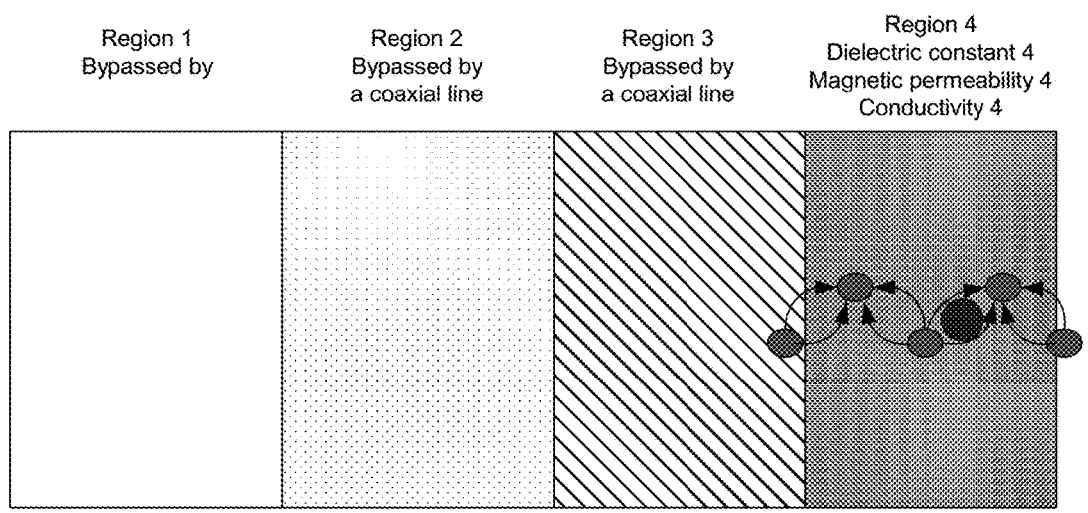
FIG. 38 is schematic of the effects of RF stray fields in a biological media.

FIG. 38 is schematic of the effects of RF stray fields in a biological media which results in tissue damage due to stray field probes insertion. The stray field applicators can be powered with solid state amplifiers and can be operated at low frequencies compared to microwave applicators (from 1 MHz to 400 MHz)

U.S. Pat. No. 5,187,409 (describing the HE 11 quasi-optic) is incorporated herein by reference in its entirety. The HE 11 is a quasi optical mode of propagation for microwave energy with special orientation of the electric and field and magnetic field in the plane of the target. The divergent output of a waveguide is focused through a parabolic mirror to a minimal beam waist size close to one wavelength, which at 28 GHz is close to 10 mm. A highly concentrated beam can be obtained from a 28 GHz Gyrotron output. The peak power of this source is 40 W per $mm^2$ and has been shown to ionize air. Such powers would be detrimental to biological tissue, but could be acceptable for the irradiation of other media such as for example the above-noted resin curing applications. Of course, lower powers could be used for irradiating biological tissue.

In one embodiment of the invention, the microwave energy can propagate as if it were a focused light wave. Thus, biological tissue in regions 1, 2, and 3 receive a lower level of microwave radiation exposure than what would have occurred with the configuration depicted in FIG. 36 to obtain the same intensity of microwave energy in region 4. Other quasioptical modes outputs are possible including TE02 and TE01; however, these modes do not have the same energy distribution and can not as easily be focused using a mirror. The following patents are incorporated herein in their entirety by reference: U.S. Pat. Nos. 3,010,088 and 3,188,588 which provide descriptions of these modes.

Gas Reaction Upconverter Structures

Figure 39:
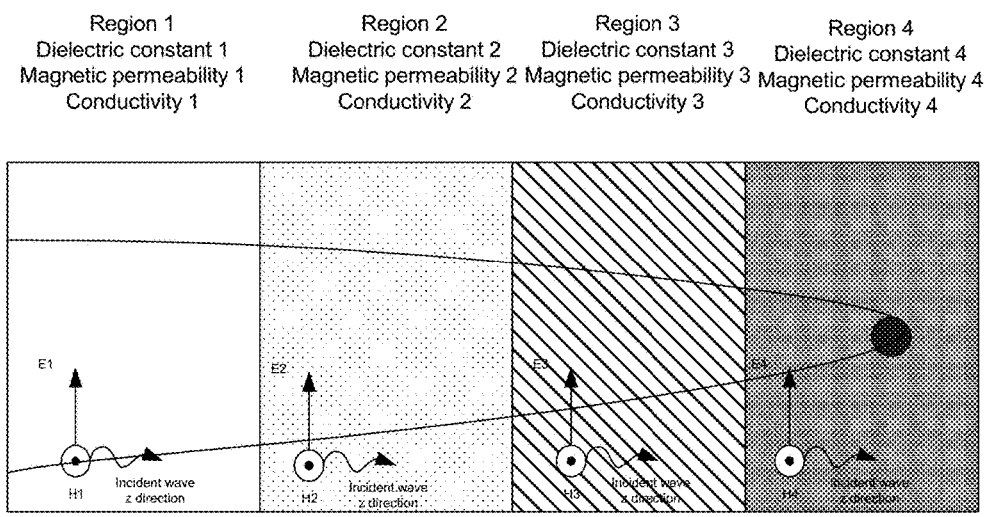
FIG. 39 is schematic of the effects of RF stray fields in a biological media.
Figure 40:
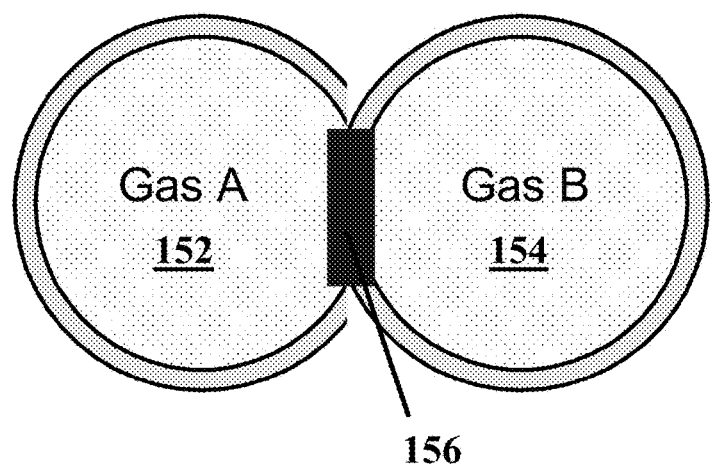
FIG. 40 is schematic overview of other Broad Band Frequency Up-Conversion Methods and Materials through Gas Reaction which shows two nano-particles necked together through an interface material to form a multichamber gas reactor.

The upconverter structures in the embodiments below do not rely on plasma formation to generate light emission. Rather, in these embodiments, an applied source of microwave, RF, magnetic induction, or ultrasound energy reacts with the UCC structures to indirectly promote chemiluminescent or bioluminescent reactions. FIG. 39 is schematic overview of other Broad Band Frequency Up-Conversion Methods and Materials through Gas Reactions, dielectric lensing, multilayered composites and organic Bioluminescence. FIG. 40 depicts a UCC structure 150 having two compartment 152 and 154 separated by an interface material 156. Each UCC structure compartment in one embodiment of the invention contains a reactive component. Once the interface material 156 is compromised, the two components undergo in one embodiment of the invention an exothermic reaction and emit light during the reaction time to for example bio-modulate a therapeutic agent but not long enough to over heat the surrounding tissue. Molecules excited via oxidation chain reactions in the presence of catalysts can also be used. In other applications, the emitted light from the UCC structure 150 activates photo-activatable agents about the medium of the UCC structures. The interface material 156 can be a water glass ($2Na_2O.SiO_2$) which can provide a build-in time delay prior to dissolution.

Figure 41:
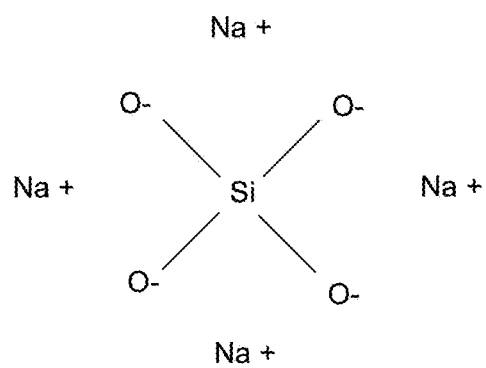
FIG. 41 is a schematic depicting a general water glass composition.

An example of a water glass composition can be as follows: $Na_2O$ (17 to 18%), $SiO_2$ (36 to 38%) and Iron Dioxide (0.05%). FIG. 41 is a schematic depicting a general water glass composition.

The interface material 156 in one embodiment of the invention can be a magnetic material such that magnetic induction ruptures the interface material. Such magnetic sheets or film compositions could be made of Fe—Si—Al flakes on a polymeric membrane with low melting points and engineered to have excellent permeability and magnetic absorption.

However, other magnetic film materials can be used such as $BaFe_{10.5}Mn_{1.5}O_{19}$ thin films. These films can be deposited by Alternating Target Laser Ablation Deposition (AT-LAD) of $BaFe_2O_4$, $Fe_2O_3$, $MnFe_2O_4$ Targets. The technique is well documented in IEEE transactions on Magnetics, Vol 44, No 11, November 2008 p-2966-2969 authored by Anton L. Geiler et al, the entire contents of which are incorporated herein by reference. The following patent is incorporated herein in its entirety by reference: U.S. Pat. No. 5,483,037.

Figure 42:
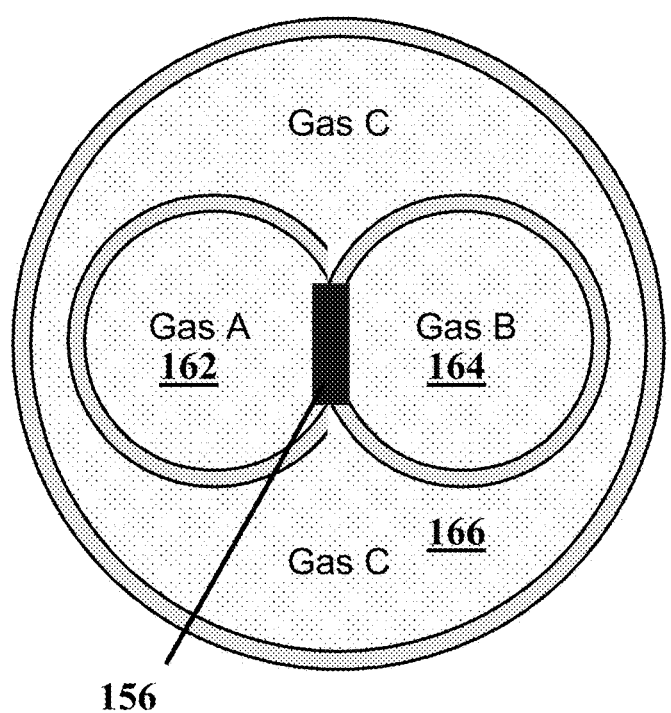
FIG. 42 is schematic of another nano-particle structure (a tri-chamber gas reactor)
Figure 43:
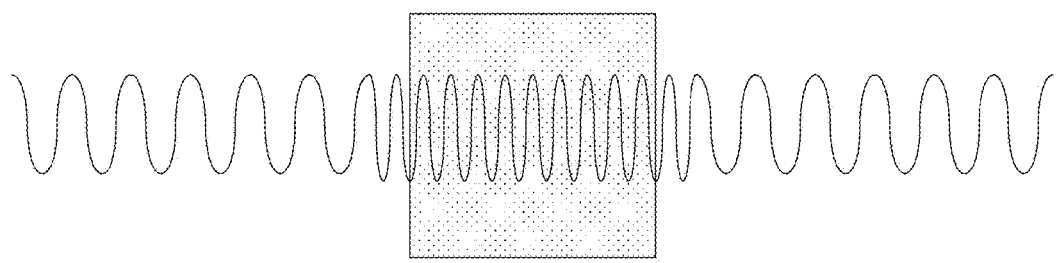
FIG. 43 is schematic of a light wave propagation in different media.
Figure 44:
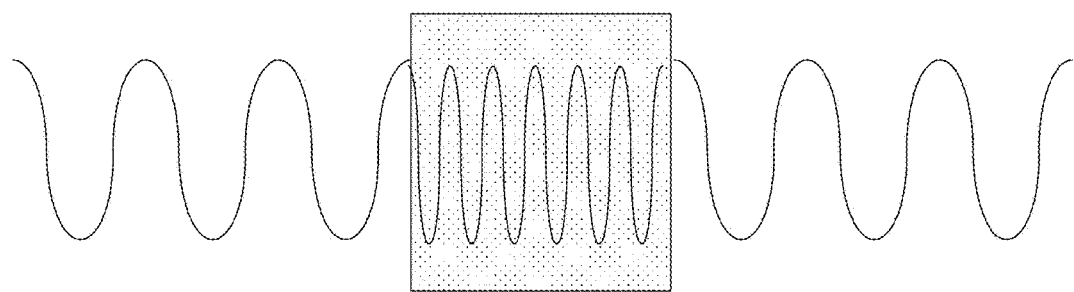
FIG. 44 is schematic of a Φ-wave propagation in different media.
Figure 45:
FIG. 45 is schematic of a multi-layer dielectric lens.
Figure 46:
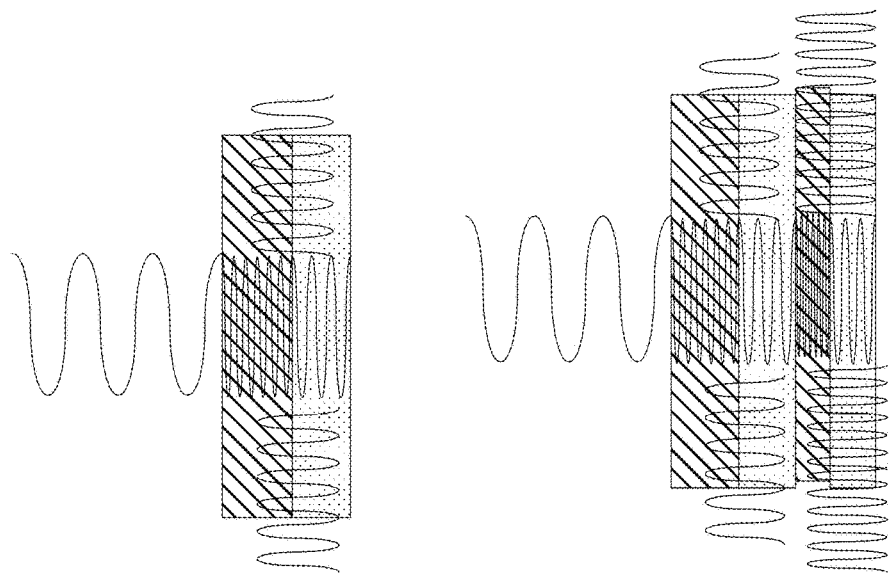
FIG. 46 is schematic of a Φ-wave propagating through a multi-layer dielectric lens.
Figure 47:
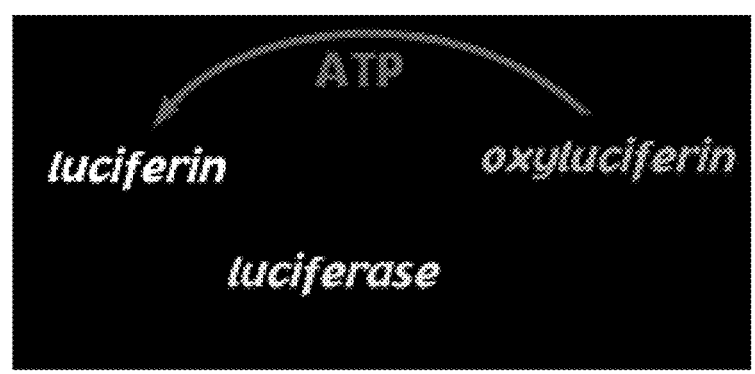
FIG. 47 is schematic of luciferin and luciferase.
Figure 48:
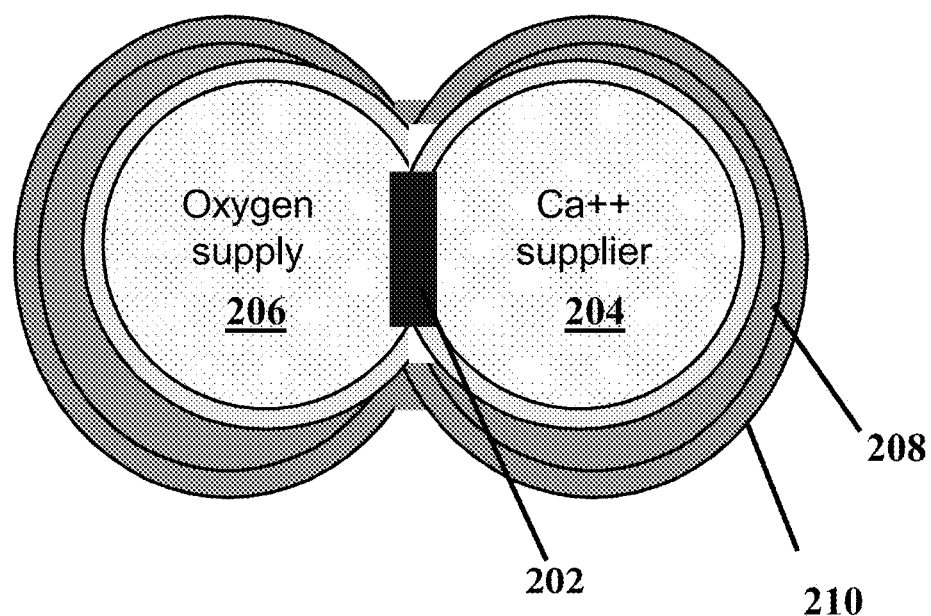
FIG. 48 is schematic of an encapsulated structure of the invention for bioluminescence.

In a similar fashion, a triple component capsule structure could be made for more reactive gas reactions (or chain reactions). FIG. 42 is schematic of another UCC structure 160 of the invention having multiple compartments 162, 164, 166.

The UCC structures shown in FIGS. 41 and 42 could be made with the lithographic patterning and processes described above. For the sake of illustration, the structures shown in FIGS. 41 and 42 could be viewed as a top-view of patterned concavities in starting wafer 34, where the wet or dry chemistries described above (along with proper masking) is used to form these structures. Deposition and patterning can be used to deposit the interface material between the separate cavities.

For example, an interface material made of a polymer loaded with graphite powder would be particularly susceptible to absorbing microwave or RF energy and heat. For example, an interface material made of a polymer loaded with magnetic powder would be particularly susceptible to being ruptured upon exposure to an induction field. For example, an interface material made of a polymer of different viscoelastic properties than the silica wall would be particularly susceptible to being ruptured upon exposure to ultrasounds.

The cavities can be selectively masked and filled with their respective reactive components.

Dielectric Lensing: A visible light propagating at the speed of light slows down when it enter a glass. The speed of light inside glasses is reduced yet there no energy transfer. This is because in glasses the wavelength of a propagating wave is smaller than in free space. The index of refraction is the ratio of the speed of light in free space to inside the glass (n>1). In the visible, the index of refraction of metals nears infinity. FIG. 43 is schematic of light wave propagation in different media.

In the visible, one considers the index of refraction. There is equivalency between the index of refraction (in the visible) and the dielectric constant (in the microwave regime). An electromagnetic wave propagating in free space has a characteristic wavelength $\lambda_0$. When this wavelength enters a dielectric material with high permittivity and low loss, the amplitude of the wave is maintained, but the wavelength is reduced $\lambda_d$. In other words, there is little if any energy-transfer, but the wave shrinks between free space and the dielectric ($\lambda_d<\lambda_0$).

FIG. 44 is schematic of Φ-wave propagation in different media. In the microwave regime, one considers the dielectric constant. Metallic films of sufficiently small thickness do not reflect microwaves but rather absorb or transmit the energy. Similarly to light, metals have an infinitely high dielectric constant, and therefore the wavelength of an incident microwave frequency shrinks a great amount prior to being reflected, absorbed or transmitted. However, when a metallic film (of a prescribed thickness) is coated on top of an appropriate dielectric (of a suitable dielectric constant and low loss factor) a plasmonic effect can take place.

When a quartz sphere is metallically coated, the plasmonic effect (discussed above) results in a shorter wavelength out put from a sphere. When the metal is coated on top of the same dielectric but in a planar configuration, then the same phenomenon occurs and planar plasmons are generated.

The thickness of the metal and the dielectric material influence the output wavelength. For these reasons, engineered layered structures of thin metals on top of quartz or intrinsic silicon can create significant dielectric lensing and shrink the incident wave significantly. However, the passage across layers is accompanied by some energy loss.

Dielectric lensing can create focusing and help stimulate up conversion by directing the microwave energy to a selected region of the target object. Though the frequency increases, the amplitude decreases, and if one can afford some energy loss during this conversion, then an upconversion method utilizing dielectric lensing to deliver the microwave energy in a focused region is suitable for various embodiments of the invention.

FIG. 45 is schematic of a multi-layer dielectric lens. FIG. 46 is schematic of a Φ-wave propagating through a multi-layer dielectric lens. This schematic representation shows that the incident wave is reduced in wavelength for every paired metallic and dielectric layer (but scattered in multiple waves). Thus, a dielectric lensing structure in one embodiment of the invention can be constructed as a multilayered structure utilizing processes similar to that in semiconductor photolithography and development, CVD, ALD and metallization, described above. The dielectric lensing can be used to focus RF and MW energy and shorten the incident wavelengths which would help the coupling efficiency to certain organs in the body.

Organic Molecules for Bioluminescence: In bioluminescence or chemiluminescence, the energy for driving the emitted luminescent light is supplied by a chemical reaction rather than from a source of light. The basic reaction follows the sequence illustrated below with reference to FIGS. 47-48. FIG. 47 is schematic of luciferin and luciferase:

The luciferase catalyzes the oxidation of luciferin;

Resulting in light and an inactive "oxyluciferin";

To produce more luciferin, energy must be provided to the system, here shown as "ATP."

Sometimes, the luciferin and luciferase (as well as a co-factor such as oxygen) are bound together in a single unit called a "photoprotein." This molecule can be triggered to produce light when calcium is added to it. FIG. 48 is a schematic of an encapsulated structure 200 of the invention for bioluminescence. As before, an interface material 202 separates compartments 204 and 206. Bioluminescent coatings 208, 210 can be applied to the encapsulated structure 200. The coatings can obtain oxygen and calcium from nano-particles. In these cases calcium rich glass composition or glass composition with surface treatment to add calcium would be desirable. Techniques for stimulating or entering the triggering process by microwave "activation" as above can be used.

Microwave Generation and Applicators for Delivery of Microwave Radiation and/or Magnetic Flux to Target Media In general, microwave appliances have three major components: a microwave generator, a waveguide and an applicator. Microwaves can be generated by several methods. Microwave signal transmission can be performed using transmission lines or waveguides. There are many types of microwave applicators, each usually designed for a specific use.

Reliable microwave sources (generators) are available nowadays including magnetrons, klystrons, Gyrotrons, traveling wave tubes (TWT), backward wave oscillators (BWO), Cross-Field Amplifiers (CFA), Solid State High Power Amplifiers and masers.

Magnetrons are widely used due to their proliferation as domestic appliance. Magnetrons: The magnetron is a diode in which the magnetic field is perpendicular to the electric field existing between the cathode and anode. The magnetic field is created by either permanent magnets or by electromagnets. The electrons are emitted from the heated cathode and travel toward the anode at a velocity proportional to the existing difference in potential. The anode is generally at ground potential while the cathode is at a high negative potential.

Due to the applied magnetic field, the electrons do not travel in straight paths. The charged species traveling at a given velocity through the lines of a magnetic field are subjected to a right angle force called Lorentz's force. The intensity of this force is directly proportional to the velocity of the charged species and the intensity of the existing magnetic field. Its direction is perpendicular to the plane formed by the magnetic and the electric fields causing displacement of the charged species. If the magnetic field applied in the magnetron is intense enough (the cut-off value of the magnetic field) the electrons completely miss the anode and no current circulates in the magnetron.

If the magnetic field strength is adjusted to the cut-off value, and the electrons fail to reach the anode, the magnetron can produce oscillations by virtue of the currents induced electrostatically by the moving electrons. The frequency of the oscillations is related to the time it takes the electrons to complete their travel from the cathode toward the plate and back again. The electrons rotating at a constant velocity give up energy in the microwave frequency and radio frequency range. The microwave energy is coupled by means of a probe from one of the resonant cavities into an output coupling antenna where it is launched into a waveguide.

There are two types of magnetrons; conventional and coaxial. In turn, the conventional magnetrons can be subdivided into three types (cyclotron-frequency, negative resistance and multi-cavity) based on how energy is transferred to the RF field.

For the cyclotron-frequency magnetron, the diode includes a cathode cylinder inside an anode cylinder. It is positioned between the poles of a magnet such that the magnetic lines are perpendicular to the electric field established between the anode and the cathode. The cyclotron-frequency magnetron operates by virtue of resonance between the period of RF oscillation and the rotational motion of the electron.

The negative-resistance magnetron is also referred to as the split-anode magnetron, because the anode is split in half. The split plane is parallel to the axis of the anode. This type of magnetron operates on the principle of the static negative resistance characteristic between the anode sections. It is capable of great output and operates at high frequencies The multi-cavity magnetron consists of a cylindrical anode structure containing a number of equally spaced cavity resonators. An electron traveling between the cathode and the anode of such a tube is subjected to accelerating and decelerating forces resulting in a spiral motion around the anode, with the electron influenced by all the cavities. This magnetron's function depends on the mean velocity of the electron being synchronized with the velocity of the traveling-wave component of the RF interaction field between the cathode and anode. The multi-cavity magnetron is the microwave tube most commonly used in the microwave ovens and microwave processing systems.

The coaxial magnetron is actually an extension of the conventional magnetron structure (cathode surrounded by an anode) with the addition of a third element, a coaxial cavity that surrounds the anode forming the inner walls. The coaxial magnetron has improved performance over conventional magnetrons. The advantages include: operating mode control, lower fields, decreased arcing, very high quality factor, Q, and ease of tuning. The disadvantages of this tube are its size and weight.

Klystrons: A klystron is a tube based on the velocity modulation of an electron beam. Klystrons can generate, receive, and amplify radio and/or microwave signals. The two basic types of klystrons are the multi-cavity and reflex.

The klystron, in the microwave range, performs the same functions that ordinary vacuum tubes do at the RF range. It takes advantage of the transit time of the electrons. Electrons are emitted by the cathode and are drawn toward a plate by virtue of a difference in potential. The electrons are focused by either magnetic or electrostatic means. A series of resonant cavities are aligned next to each other and are bonded by grids and separated from each others by drift tubes. The electrons are drawn to the first resonant cavity in which an RF or MW signal is injected. The electrons couple to the signal and are accelerated in a one half-cycle and are retarded in the other, thus speed modulation is achieved. Bunches of accelerated and decelerated electrons are formed in the first drift tube. The second resonant cavity becomes the host of an RF or MW signal and an electric field is established in the entrance of the second draft tube, which results in a second modulation of the beam. The RF or MW energy is extracted at the last cavity.

Traveling wave tubes (TWTs): A traveling wave tube performs the same functions as its predecessors, however, it has an extremely wide bandwidth. This broadband amplifier is capable of sweeping a range of frequencies of up to an octave in bandwidth. A bandwidth of one octave is one in which the upper frequency is twice the lower frequency.

The TWT includes for its major parts: the electron gun assembly, the RF interaction circuit, the focusing magnets, and the collector. When the cathode is heated it emits a continuous stream of electrons which are drawn to the anode, and focused into a narrow beam by a magnetic field.

At the same time, the electrons are fed into a tightly wound helix. An RF signal is injected inside the system. The speed with which the RF energy progresses along the length of the tube is determined primarily by the pitch of the helix. The velocity of the RF energy is made synchronous with the velocity of the electrons, resulting in an interaction between the electron beam and the RF signal. Some of the electrons are accelerated under the influence of the alternating electric field, others are slowed. As these velocity-modulated electrons progress through the helix they form bunches, resulting in the amplification of the RF (MW) signal. Some materials processing systems that use high power traveling wave tubes (up to 2.25 KW) are now widely available. Of all microwave tubes, only the traveling wave tube (TWT) offers a broad bandwidth operation.

Backward wave oscillators and cross field amplifiers: The last two ways of generating MW energy are by backward wave oscillators (BWO) and cross field amplifiers (CFA). The BWO is used as a local oscillator for the internal mixing circuitry of spectrum analyzers. The BWO are being replaced in many applications by solid state sources. The CFAs are small, light, and operate at low voltage. The CFA is capable of generating high peak powers.

MASER (Microwave Amplification by Stimulated Emission of Radiation): When MASERs were invented (1950s), they offered a completely new and revolutionary method for producing microwaves. The principle of operation of the MASER is based on the use of stimulated emission of electromagnetic radiation in a medium of molecules or atoms with more particles in the upper (excited) state than in the lower state (that is, with an inverted population).

When the particles of the system interact with radiation of frequency equal to the difference between their ground and excited energy state, the particles are forced to the upper state due to radiation (energy) absorption. When the particles already in the upper state interact with the radiation, they fall to the lower energy state by emitting radiation of the same frequency as the incident radiation (stimulated emission).

However, in the case of an inverted population, a net excess of emitted radiation takes place over the absorbed radiation, and an amplification process occurs. The radiation emitted in this manner is monochromatic (because of the well defined particles transitions) and coherent (because it is forced by the driving field). The effective coupling between the particles and the radiation is achieved by the use of a suitable resonant microwave cavity.

Molecular roto-vibrational states (such as those of excited ammonia gas molecules) or paramagnetic levels in solid materials (such as the Zeeman levels of paramagnetic ions) provide the means by which population inversion is achieved for MASER applications. The frequency of the MASER is therefore dependent on the nature of the molecule (the number of excited energy levels and the distance between them).

Gyrotrons & Solid State Amplifiers: Gyrotrons & Solid State Amplifiers are also well known microwave sources that can be used in the invention.

Waveguides: A transmission line can be defined as a device that transfers energy from one point to another with a minimum loss. In essence, all transmission lines are waveguides since they are designed to guide the energy wave along a certain direction.

The open two-wire line, the coaxial line, the rectangular waveguide and the circular waveguide are all used in industry to satisfy specific needs. The two-wire transmission line consists of two parallel conductors insulated from each other. An open two wire line has three types of losses: a) radiation losses, b) dielectric losses and c) copper losses.

At low frequencies, and over short transmission distances, the open two wire line finds a world wide application, namely the television (TV) twin-lead used to connect an antenna to a TV receiver. The coaxial line is composed of two concentric conductors separated by an insulating material.

Coaxial lines are either rigid or flexible. The dielectric in the rigid coaxial line is usually air. The dielectric in flexible coaxial lines is usually polyethylene. The coaxial lines allow low-loss transmission. There are small dielectric losses in the low frequency coaxial lines, but there are significant dielectric and copper losses as frequency increases. But, the coaxial lines offer a compact form factor and can be used for insertion into biological organs.

Waveguides are shielded, capable of low-loss microwave transmission and offer several advantages over the two wire lines or the coaxial lines. A waveguide requires no center conductor and its dielectric is usually air. Waveguides are hollow metallic tubes and are available in different geometric configurations. Waveguide configuration include rectangular, circular and elliptical.

Electromagnetic energy does not move straight down the rectangular waveguide as an electromagnetic wave; instead, the electromagnetic energy progresses down the guide by a series of reflections off the internal surface of the narrow dimension.

There are two basic modes of transmission inside rectangular waveguides: 1) the transverse electric (TE) mode and 2) the transverse magnetic (TM) mode. The TE mode of propagation corresponds to the mode in which the electric field is transverse to the direction of propagation (the z axis). The electric field lines along the waveguide are parallel to the plane containing the x and y axis. In other words, in the TE modes (also called the H-modes) the Ez=0. In the TM mode (also called the E-mode), the magnetic field is transverse to the direction of propagation. The magnetic field loops along the length of the waveguide are always parallel to the plane formed by the x and y axis (Bz=0).

Microwave Applicators: The applicator is a device through which the electromagnetic energy is transmitted to the target. Its design must be optimized to ensure high efficiency conversion of MW energy to the target.

Aluminum, copper and stainless steels are widely used in the fabrication of commercially available applicators. The irradiation of the target area has to be engineered carefully to excite and sustain the electric field patterns of interest. The applicator is very dependent on the application and how the desired irradiation is defined.

Multimode applicators find world-wide applications covering almost every application of microwave power. Single mode applicators or resonant cavities are designed to sustained well defined field patterns. The establishment of a well defined electric field pattern inside the metallic enclosure in single mode cavities allows uniform heating of samples having small dimensions.

The quality factor of an applicator, Q, of a resonant circuit at the frequency of resonance is defined as:

$Q=2\pi$(energy stored/energy dissipated per cycle).

Magnetic Flux Applicators:

One simple magnetic flux applicator of the invention is a multi-turn solenoidal coil. FIG. 49A is a schematic of a multi-turn solenoidal coil 220 showing the projection of the magnetic field along the longitudinal axis. FIG. 49B is a schematic of another multi-turn solenoidal coil 220 showing the projection of the magnetic field along the longitudinal axis. A target to be treated would be placed along the longitudinal axis. FIG. 50 is a schematic of bird cage coil 230 showing the projection of the magnetic field in a radial direction. A target to be treated would be placed along the radial direction. There are various RF coils used for magnetic resonance which can have application to the invention for delivery of magnetic flux to the target. Each coil configuration has advantages and disadvantaged depending on the application. These coils include but are not limited to: Alderman-Grant Coil, Bird Cage, Butterfly Coil, Dome Resonator, Gradiometer, Implantable, Inside Out (Schlumberger Coil), Intravascular Coil, Ladder, Loop-Gap Resonator, Loop-Stick, Meanderline, Transmission Line (TEM) (Slotted Tube), Truncated Spiral, Superconducting Coil, Mouse Coil, Multi-Turn Solenoid, Ribbonator, Phased Array Volume, Saddle Coil, Scroll Coil, Single Turn Solenoid, Surface Coil and Spiral Coil.

The bird cage coil construction has been routinely used in practice for MRI imaging of the head and brain. Meanwhile, the single turn solenoid, which is a single-turn solenoid (STS) is a tubular inductor with a capacitive gap running along the length of the tube, has been used for extremity exposure, such as the breasts and the wrist. The phased array coil allows the coupling of energy with more controlled method for coupling to various species within a media.

MRI machines are particularly attractive as noted above, given the industrial base in existence in the medical field. A conventional MRI does not use of ionizing radiation to produce images. However, a conventional MRI does make use of strong magnetic fields, radio frequency energy, time varying magnetic fields, magnetic field gradients, cryogenic liquids to cool the magnets (to produce very strong magnetic fields).

The installed base of MRI equipment is estimated at more than 10,000 units. The number of MRI scans exceeds 75,000,000 MRI scans per year worldwide. Original Equipment Manufacturers (OEMs) of MRIs include among others large multinational companies including: General Electric Medical Systems, Siemens Medical Solutions, Toshiba Medical Systems, Philips Medical Systems, Hitachi Medical Systems and Fonar.

When gases are ionized (or formed into a plasma) and electrons are freed from the binding energies of their respective nuclei, the electrons can travel with a mean free path that depends on the pressure within the containment chamber and the nature of gas. Furthermore, electron in the presence of a magnetic field (as applied from an MRI machine) can enter a precession motion or ECR, as discussed earlier. The ECR frequency depends on their masses and is dependent directly on the magnitude of the magnetic field.

Figure 51A:
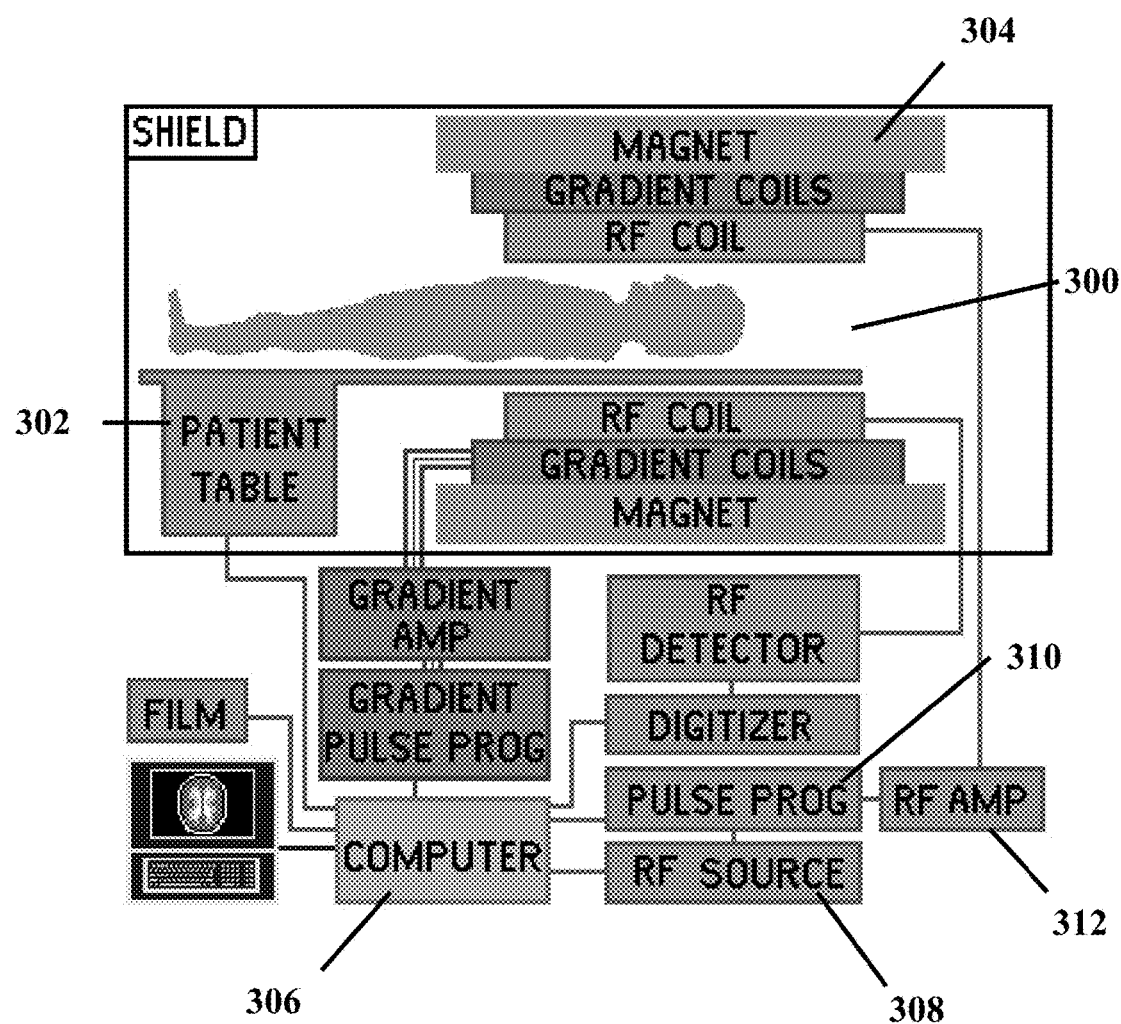
FIG. 51A is a schematic of a MRI arrangement suitable for the invention and representative of a typical commercial MRI system.
Figure 51B:
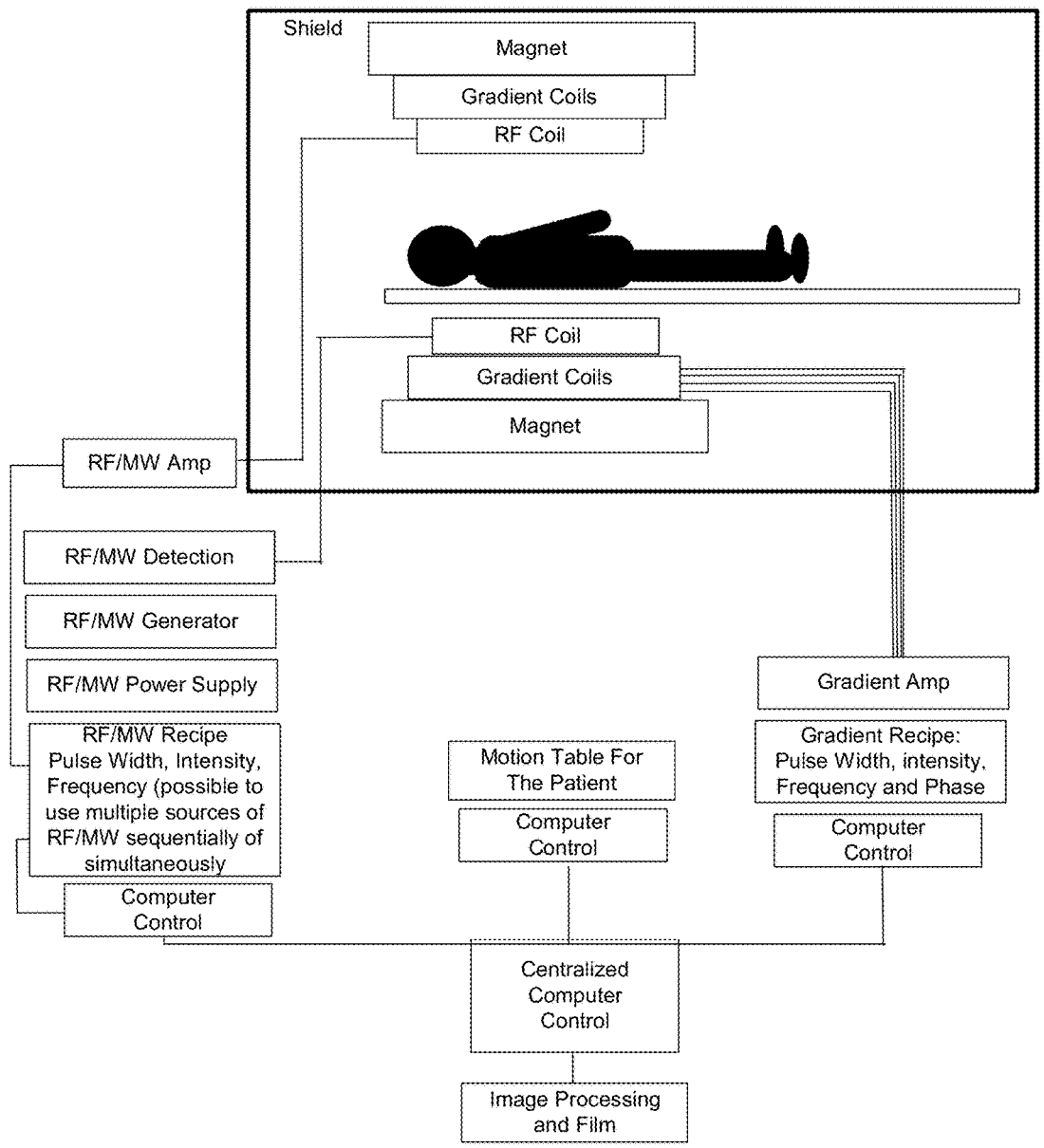
FIG. 51B is a schematic of providing more operational detail to the MRI arrangement shown in FIG. 59A.

FIG. 51A is a schematic of a MRI arrangement suitable for the invention and representative of a typical commercial MRI system. In one embodiment of the invention, a target medium or a patient 300 is placed on a precision table 302 (that has for example an accuracy of 1 mm). The table 302, with the target or patient, is introduced in a large cylindrical structure containing a magnet 304 with a very homogeneous magnet field in the axis of the magnetic cylinder. Superconducting coils are typically used in the MRI machines to produce the strong magnetic field from 1 Tesla to 11 Tesla. In one embodiment of the invention, the applied magnetic field from the MRI is applied in conjunction with a microwave field or a radio frequency field to induce a plasma in the up conversion gas containers of the invention. FIG. 51B is a schematic of providing more operational detail to the MRI arrangement shown in FIG. 51A.

The operation can be computer controlled by computer 306. The RF components including the radio frequency source 308 and pulse programmer 310 can be adjusted. The RF amplifiers 312 can increase the pulses power from the mW range to the kW range, which is typical of RF powers in MRI imaging, where the presence of a Radio Frequency pulse (in the MHz range) with an orientation 90 degrees and 180 degrees orientation vis-à-vis the uniform and axial magnetic field can be used to generate plasmas in the gas containing UCC structures of the invention. As with the commercial MRI imaging, the magnetic fields (or gradients thereof) in one embodiment of the invention would be computer controlled in terms of the shape and amplitude of each of the three gradient fields.

In one embodiment of the invention, it is advantageous to include gases with characteristics such as: para-magnetism, unpaired electrons, asymmetrical charge distribution, well pronounced electrical dipoles, low ionization potentials and the ability to emit in the UV range. In one embodiment of the invention, gas isotopes can be contained in the gas containers. For example, $Xe^{129}$ has been demonstrated to be quite successful as an imaging gas for MRI. Thus, in this embodiment, conventional MRI can be used to image the position of the UCC structures in the target organ before microwave or RF activation.

It is possible to use MRI techniques with materials other than $Xe^{129}$ to ensure that the delivery of bio-therapeutic agents has been successfully accomplished. For example, it is possible in one embodiment of the invention to use magnetic materials or ionic species with magnetic properties, as part of the silicate structure of the UCC material composition to act as tracers for imaging. When using magnetic "dopants" for imaging in MRI, care is taken to ensure that magnetic tracers have the right concentration in order to avoid causing magnetic induction effects that may in turn lead to heating. The concentration of $Fe^{3+}$ in the ppm level compared to the silicate network formers ought to be sufficient for imaging but not for localized over heating and magnetic induction.

Figure 52:
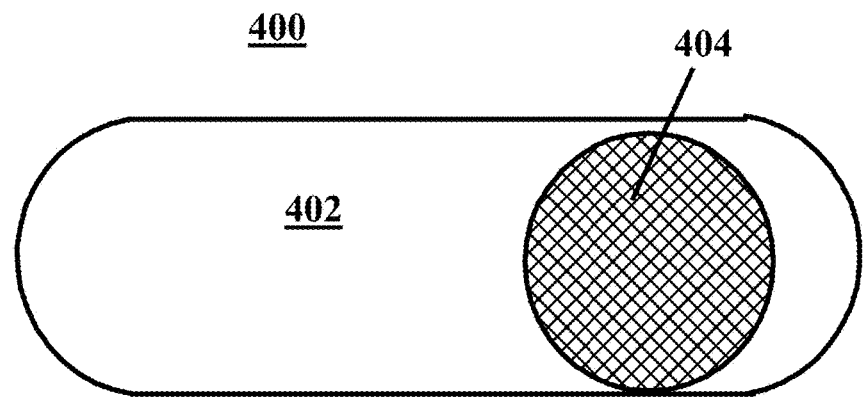
FIG. 52 is a schematic of a UCC structure including a capsule-type region for holding an upconverting gas and a down converting media.

After the imaging step using MRI is performed, the activation process using microwave and RF can be executed to achieve up conversion; however, the UCC can contain an up converting media (such as gases prone to ionization leading to plasma generation and hence UV emission) and a down converting media (such as doped $Y_2O_3$) at the same time. FIG. 52 shows a UCC structure 400 including a capsule-type region 402 for holding an upconverting gas (not shown) and a down converting media 404. In this embodiment, an X-Ray treatment can be used to induce a desirable down conversion to generate UV emissions in the proper range suitable for photo-activating chemotherapeutic agents of choice 410, as shown in FIG. 53. More generally, FIG. 53 is a schematic of a UCC structure including a capsule-type region for holding an upconverting gas and a down converting media where an activatable agent is attached thereto.

Figures 1A, 54:
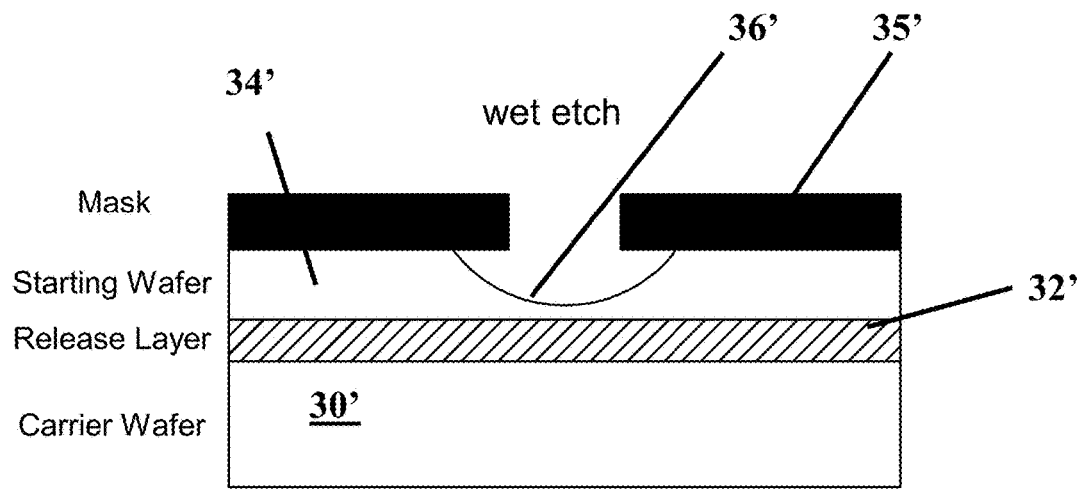
Figures 1B, 54:
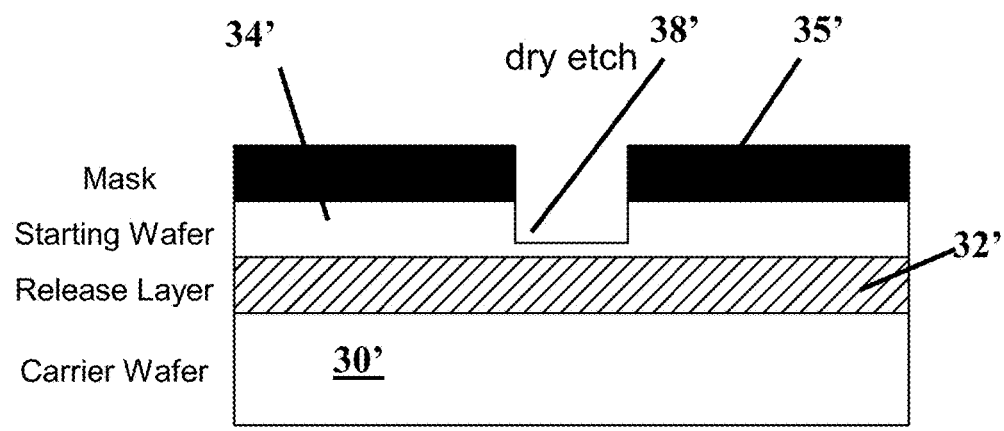

Magnetic Field Induction:

FIGS. 54-1A to 54-1*l* are a group of schematics depicting various processes for depositing a magnetic membrane structure according to one embodiment of the invention. The process is similar and uses many of the techniques discussed above with regard to FIGS. 13-22.

In FIG. 54-1A, a carrier wafer 30' having a release layer 32' and starting wafer 34 disposed thereon is provided. A mask 35' is deposited and thereafter has an opening defined thereon to expose the starting wafer 34'. A wet etch is used to generate the undercut portions 36'. In FIG. 54B, a plasma etch is used to generate the undercut portions 38'. Differences between wet etch and plasma etch have been discussed before. Plasma etching is anisotropic and leads to a trench definition having more rectangular edges than typically possible with wet etching. A mask 34' is deposited and thereafter has an opening defined thereon to expose the starting wafer 32'. As shown in FIG. 54-1A, a dry etch is typically used to generate the trench-like portions 36'.

Figures 2A, 54:
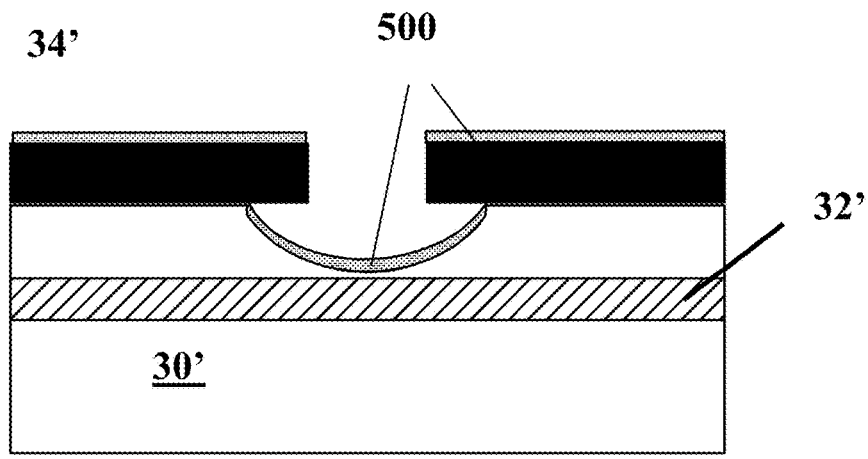

In FIG. 54-2A, deposition of a magnetic film 500 occurs using for example molecular beam epitaxy (MBE) or by alternating target laser ablation deposition (ATLAD) c to deposit for example a $BaFe_{10.5}Mn_{1.5}O_{19}$ film. The $BaFe_{10.5}Mn_{1.5}O_{19}$ film has a suitably high magnetic susceptibility and would therefore couple efficiently to electromagnetic frequencies described below. Other magnetic materials (as discussed below) can also be used in various embodiments of the invention. Alternating target laser ablation deposition is described elsewhere and the following patent documents describing alternating target laser ablation deposition are incorporated herein by reference in their entirety: U.S. Pat. No. 5,173,441 and U.S. Pat. Appl. Publ. No. 2004/0033702.

Other magnetic films and magnetic materials are also possible in various embodiments of the invention. Examples of such materials include but are not limited to: Fe—Si—Al materials (in a flake or other form), ZnCo-substituted W-type hexaferrite materials, $Fe_2O_3$ materials (including particles and nano-particles of oleic acid hydrophobized magnetic $Fe_2O_3$), cobalt ferrite materials (including particles and nano-particles of cobalt ferrite $CoFe_2O_4$), Fe/Cr materials including multilayered films of Fe/Cr, Fe—Ag materials including Fe—Ag films, Fe—Ag materials having giant magneto-resistance (GMR effects), $FexAg_{1-x}$ alloys (x-0-0.045) materials (for example fabricated using an electron beam co-evaporation technique), a ferrite series of $[Ca(CoTi)_xFe_{12-2x}O_{19}]_{96.0}[La_2O_3]_{4.0}$ ferrite with x carrying from 0 to 1.0, and materials (including particles and nano particles) of $Fe^{3+}$ for example produced by a fermentation process such as described in U.S. Pat. No. 6,444,453, the entire contents of which are incorporated herein by reference.

Electron beam co evaporation techniques are described in U.S. Pat. Appl. Publ. No. 2002/0110698 and U.S. Pat. No. 7,393,416. The entire contents of which are both incorporated herein by reference.

Figures 2B, 54:
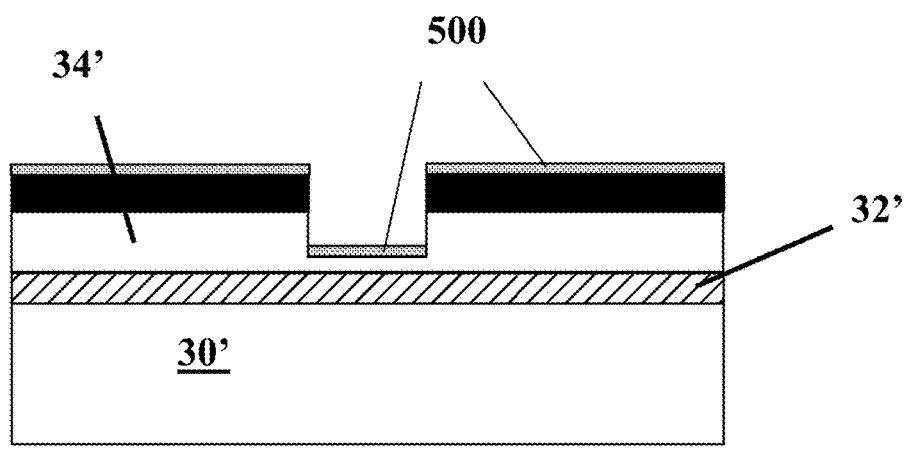

The magnetically coated wafers described in FIG. 54-2A and FIG. 54-2B are then etched to remove the mask layer through the use of solvent leading to lift off of the mask layer 35'. A magnetic film 500 is deposited within trench 36', and trench 38' is left behind. The wafer is subsequently cleaned and caped using wafer 40' using methods similar to those described before in FIG. 15.

FIG. 54-3A and FIG. 54-3B are schematics showing how after removal of the patterning resist, the starting wafer can be capped with the plate 40' (e.g., a flat quartz wafer) to form gas containers. The wafers in FIGS. 54-3A and 54-3B are removed flipped and transferred to another carrier wafer 31'. This is accomplished by removing the wafers 30' from the release layers shown in FIGS. 54-3A and 54-3B, after having been subsequently transferred to another carrier wafer 31' with another released layer 33' as shown in FIGS. 54-4A and 54-4B.

FIG. 54-5A is a schematic showing another embodiment of the invention and depicting after removal of the resist, that two mirror imaged wafers 42', 44' (using a wet etch) are joined to form the gas containers with the resultant magnetic membrane 500 in the middle. A more rounded container can be obtained prior to removing the release layer. FIG. 54-4B is another schematic showing that, after removal of resist, two mirror imaged wafers 46', 48' (using a dry etch) can be joined to form at least one gas container.

Figures 6C, 54:
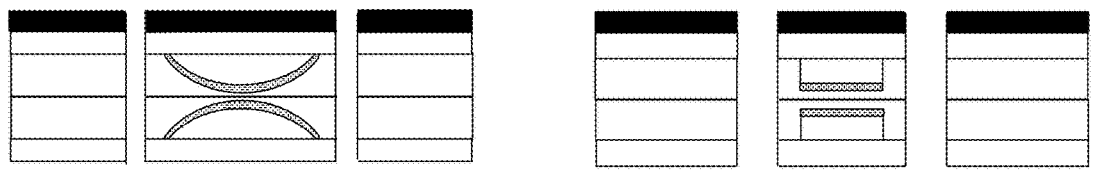
Figures 7, 54:
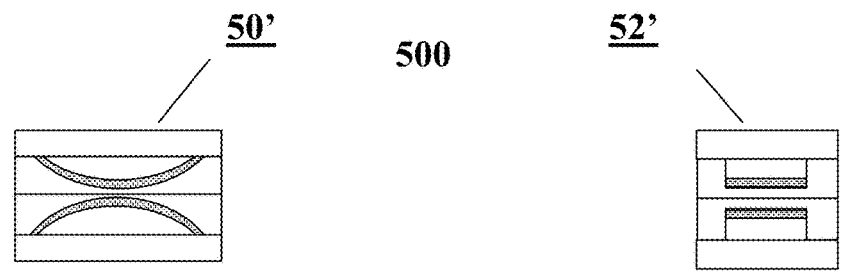

FIG. 54-6-A is a process schematic showing the release layer 32' having been removed, followed by patterning at step 54-6-A, the masking, and patterning at step 54-6-B, and the etching at step 62-6-C to release and separate the UCC structures from each other. In this embodiment, a dry etch is used to obtain the gas containers.

FIG. 54-7 is a process schematic showing two gas containers 50', 52' of the invention made using the large scale repeatable and reproducible processes discussed above. The gas containers 50' and 52' contain magnetic membranes 500 separating the two cambers within a gas container.

Figures 8, 54:
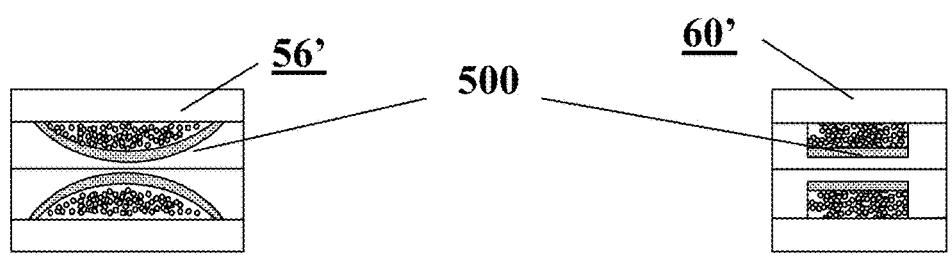
Figures 9, 54:
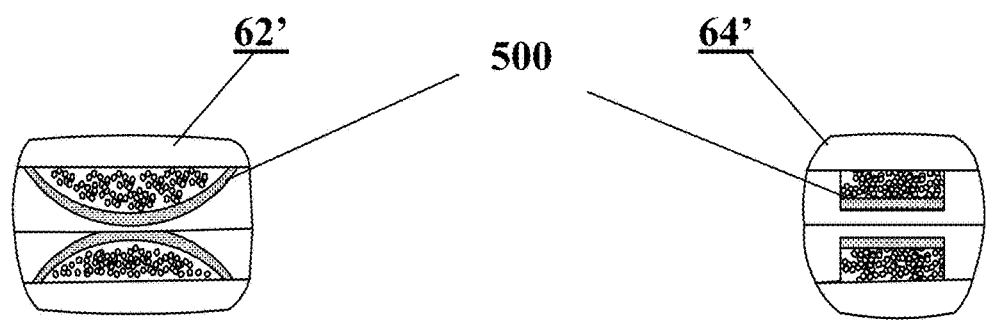
Figures 10, 54:
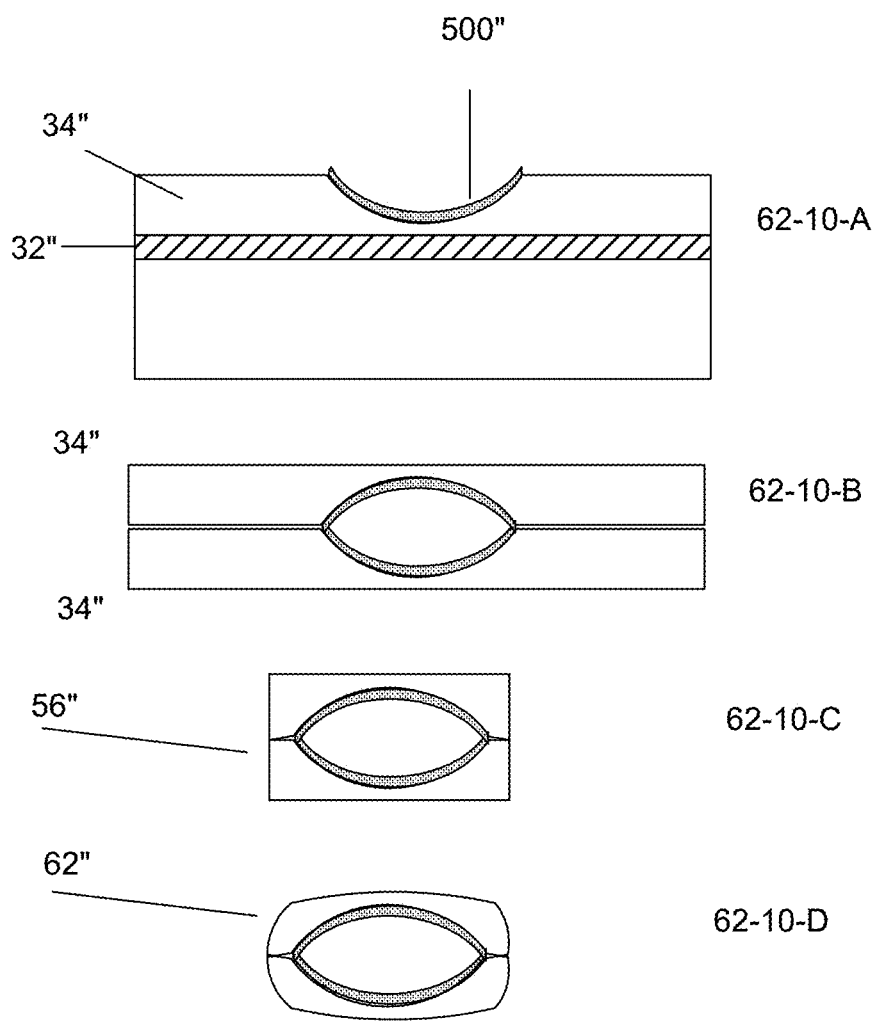
Figures 11, 54:
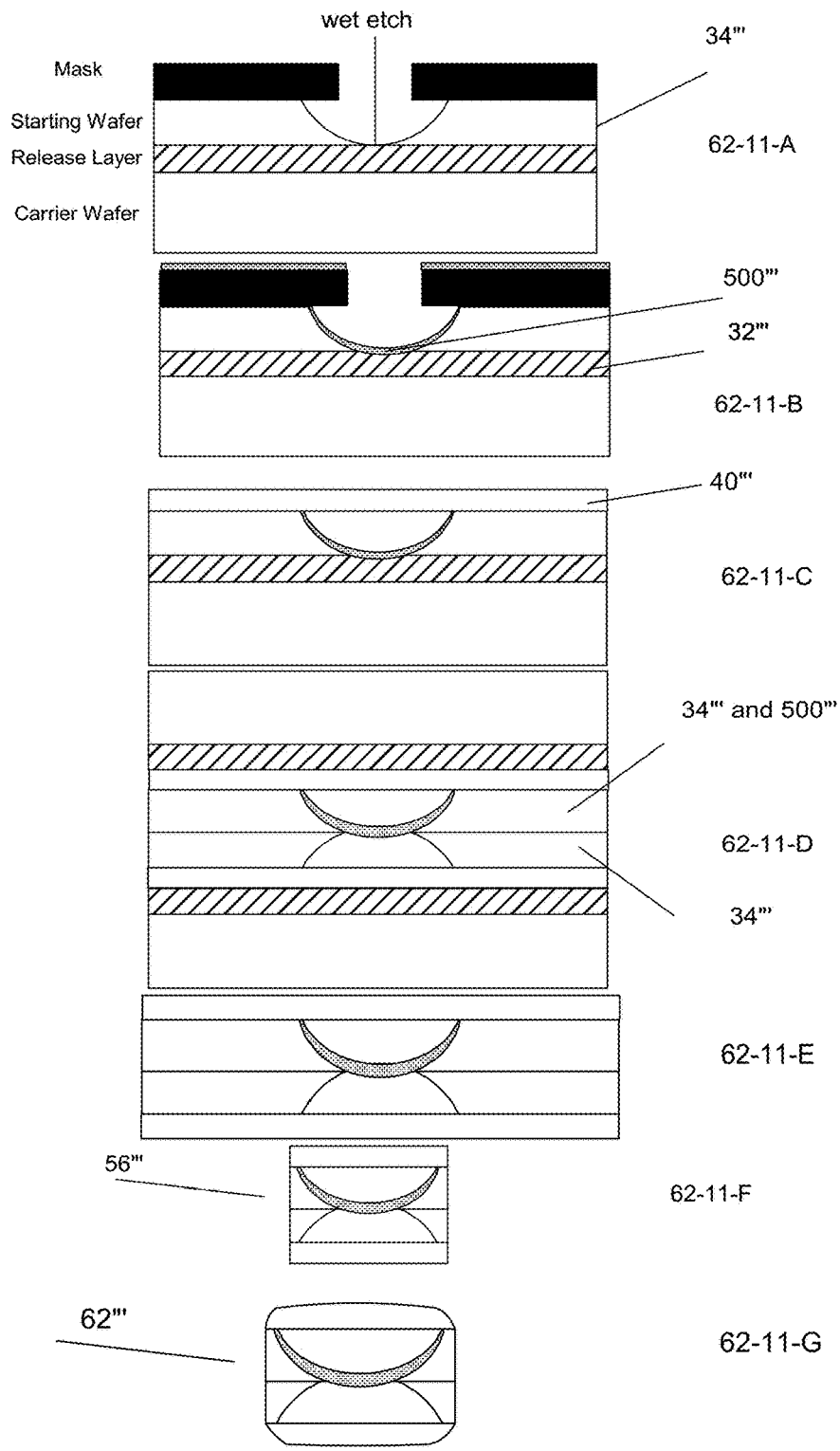

FIG. 54-8 is a process schematic showing the filling of the gas containers 56', 60' with the appropriate gases prior to sealing. In FIG. 54-8, each of the as containers 56', 60' have magnetic films contained within the sealed structure. FIG. 54-9 shows the treatment of the gaseous-filled up converters (for example with an HF treatment) to round the edges.

FIG. 54-10 describes the process through which a magnetic film 500" is deposited on the inner walls of the UCC. In this example, the fabrication process uses two mirror image coated wafers 34" with a magnetic film as depicted in FIG. 54-10-B. In this example, a continuous coating is provided around the inner walls of the UCC. This UCC structure 56" in FIG. 54-10-C can be treated with HF to yield a UCC with more rounded outer wall 62" as illustrated in FIG. 54-10-D.

The construction steps of a UCC with a single magnetic membrane are provided in FIG. 54-11A to FIG. 54-11-G. In this example, the wet etch process performed on wafer 34''' is continued until the etching front reaches the outer wall of wafer 34'''. Subsequently a magnetic film deposition is performed (similar to the deposition techniques described in the previous figures) to layout a magnetic membrane. The wafer 34''' having a magnetic membrane is sealed in the presence of a preselected gas. The sealing process typically involves pressing wafer 34" against wafer 40'''. The formed composite shown in FIG. 54-11-C is then released from release layer 32''' and then sealed against a mirror wafer 34''' that does not a magnetic coating (see FIG. 54-11-D). The sealed wafers are detached from release layer 32'''. The wafers shown in FIG. 54-11-E are etched to yield UCC structures 52''' in FIG. 54-11-F. The UCC structures 52''' can be HF treated to yield the resultant UCC structures 62" in FIG. 54-11-G.

Similar to the previous descriptions, the UCC 52", 52''', 62" and 62''' are compatible with Au coating techniques described before for single and double Au shells that can lead to plasmonic activity. Furthermore UCC 52", 52''', 62" and 62''' can have CNT attached to them using similar techniques to those described before.

The magnetic films depicted in the embodiments shown in the FIG. 54 group of schematics (described above) form a double or a single membrane within the double gas container structure. In other embodiments of the invention, a UCC structure only needs one magnetic layer and one gas container. In either case, upon heating, the magnetic membranes would be stressed above their modulus of rupture to break the barrier between the tow chambers within the UCC. Once this barrier is broken the chemical(s) that were separated now chemically react. For example chemiluminescent materials are made to react and emit light upon breaking the magnetic barrier.

In other cases, the magnetic barrier of strong susceptibility (or absorption) can assist in plasma ignition of gases. For the case of the double gas container structure, the rupture would lead to the merging of the two chambers formed within the gas containers. Upon rupture, the magnetic membrane would release for example magnetic flakes and/or magnetic particles. These magnetic flakes and/or particles are expected to participate in further magnetically induced rotation or RF/MW and magnetic induction thorough dipolar coupling of energy. Either one mechanism would lead to further heating causing more friction with the appropriate gas chemistries and ultimately leading to plasma ignition.

Similar to what was described before the gases such as Ne, Xe, He, Hg, $H_2$, $N_2$, Ar, Kr can be used as the fill gases. Also gas mixtures Ne+He, Ne+He+5% Xe, Ne+5-10% Xe can be used. The percent Xe addition is by atomic percent. Hg+Ar emit at the 360 nm; Ne+1% Ar also emits at 365 nm. Furthermore, other gas combinations can be used, including iodine vapor with various impurities. After the gas fill, the gas containers can be treated to an HF solution to treat their edges to produce the UCC structures 62', 64'.

Figure 55:
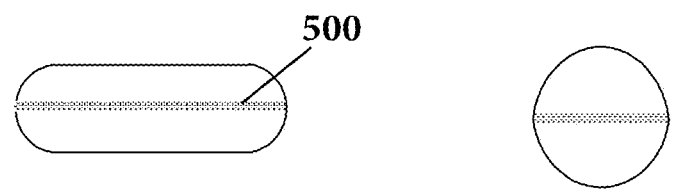
FIG. 55 is a side view schematic depicting up converters of one embodiment of the invention having magnetic layers contained therein.
Figure 56:
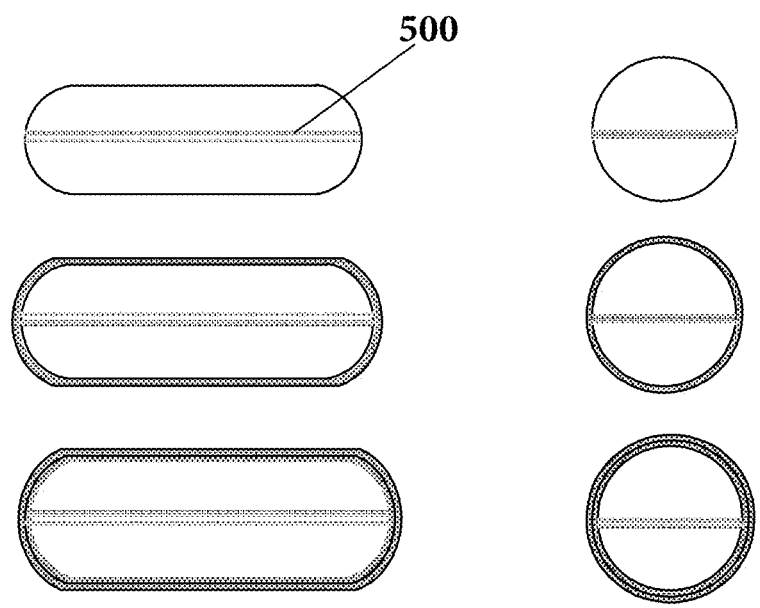
FIG. 56 is a side view schematic showing magnetically loaded containers having single coating or double coating for plasmonic resonance effects.

FIG. 55 is a side view schematic showing that the shape of up converter structures of one embodiment of the invention having magnetic layers 500 contained therein can be controlled and further illustrating that elongated and spherical shapes can be manufactured in a reproducible manner. FIG. 56 is a side view schematic showing that the magnetically loaded containers can be coated with Au for single coating or a double coating 502, both of which can lead to plasmonic resonance effects. Similar to the descriptions and examples provided before, the outer surfaces of the gas containers (which in this embodiment can include membranes or particles with magnetic properties) can be coated with metallic coatings of Au and Ag for plasmonic activity. It possible therefore in this embodiment, through similar or identical process as described before, to also achieve a single metallic or a double metallic coating for plasmonic resonance.

Figure 57:
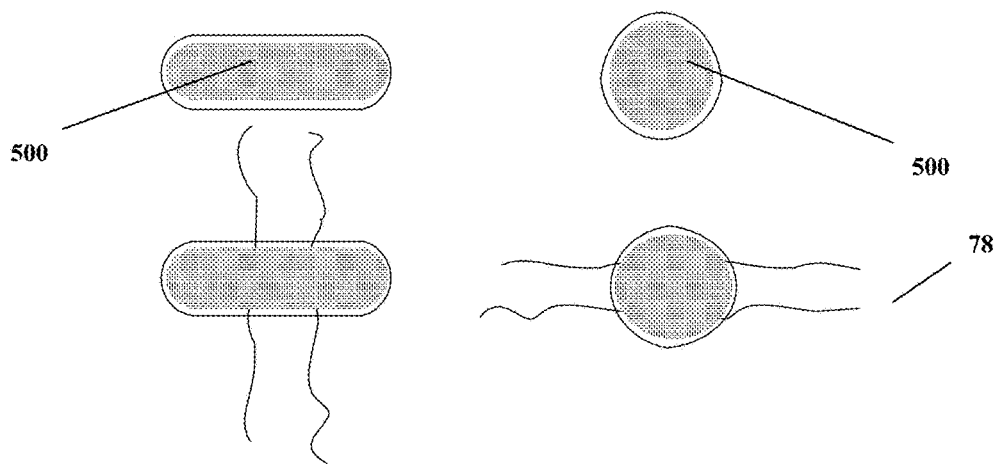
FIG. 57 a top view schematic showing up converters of one embodiment of the invention having magnetic layers contained therein.

Similar to the descriptions and processes described before, the up converter structures (in this embodiment where the up converters include membranes or particles with magnetic properties) can be built to include carbon-nanotubes (CNTs) which can protrude inside the enclosure. These CNTs are added for the purpose of facilitating the RF/MW coupling and plasma ignition or initiation. FIG. 57 a top view schematic showing of the shape of up converters having magnetic layers 500 contained therein. The shapes can be controlled. In various embodiments, elongated shapes and spherical shaped up converter structures can be manufactured in a reproducible manner using the lithographic techniques described above. The attachment of CNTs is illustrated for both shapes shown in FIG. 57.

The magnetic films 500 respond to an oscillating magnetic field for example in an electromagnetic wave of an alternating magnetic field generated using the flow of alternating current flow inside a solenoid. The energy coupling of a magnetic material to the electromagnetic wave of an alternating B field is characterized by the magnetic susceptibility of the film. A couple of factors affecting energy coupling are magnetic permeability and magnetic loss. Almost all magnetically susceptible materials readily absorb RF/MW because RF/MW radiation are electromagnetic waves that have an electric field and an orthogonal magnetic field of the same frequency.

Typically RF applicators operate at low frequencies below 110 MHz and operate up to 300 MHz, at which point in frequency the energy can typically no longer be contained between ground and the electrically hot electrodes. While the demarcation between RF and MW is not exact in terms of a definition, it is generally agreed that at 100's of MHz, the electromagnetic radiation is characterized as MW electromagnetic radiation. MW radiation typically propagates from and is not confined by the generating network. Frequencies in the microwave regime propagate in free space unless the MW radiation is contained inside an enclosure.

There are various ways of building the RF applicators of the invention. The configuration of the RF electrodes can easily be modified and can take different size and shapes. In general, the length of the electrode does not impact the uniformity of the RF field distribution. Over a length of one meter, the voltage across an electrode would drop by less than 3% which is negligible. The RF generators can also vary; but because of the stability of solid state generators and their wide use enabled through wireless applications and cell phones, solid state generators are cost effective and often utilized to power electrodes in an RF applicator. Some RF applicator configurations of interest are described below.

Figure 58:
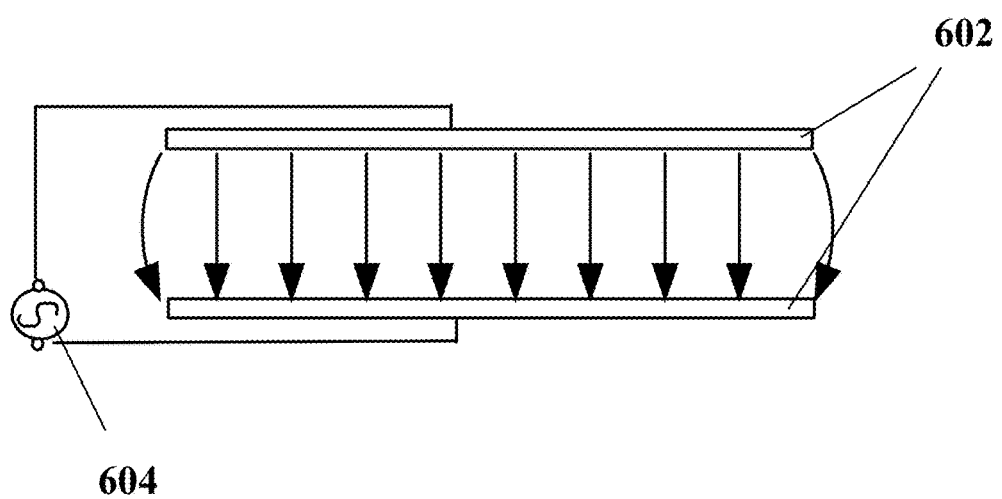
FIG. 58 is schematic of an RF plate capacitor configuration.
Figure 59:
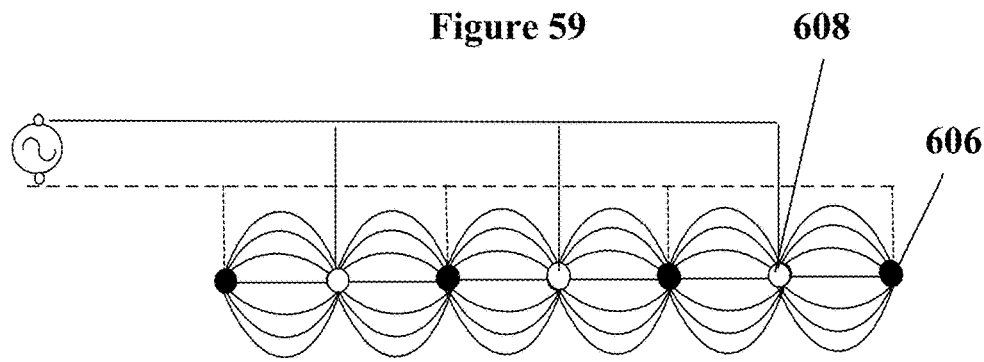
FIG. 59 is a schematic of an RF stray field applicator configuration.
Figure 60:
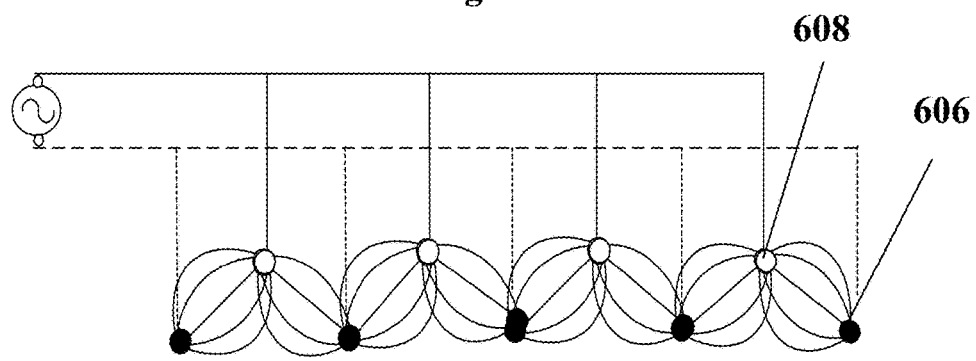
FIG. 60 is a schematic description of a staggered RF stray field applicator configuration.

FIG. 58 is schematic of an RF plate capacitor configuration. Parallel plate electrodes 602 can be any dimension and can be used to apply from an RF source 604 an electric field of small to high strength. FIG. 59 is a schematic of an RF stray field applicator configuration. The electric field is strongest between the electrodes 606, 608 and decay in strength with distance from ground to the powered electrode 608. Alternatively, FIG. 60 is a schematic description of a staggered RF stray field applicator configuration. The electric field is redistributed in three dimensions, and is no longer predominantly confined to a plane.

The capacitive plate, the stray field, and the staggered stray field configurations could be used to treat (for example) tumors that are close to the surface and that are not deep within the body. Other RF applicators capable of deep treatment (as discussed below) may be more desirable for controlled treatment and plasma initiation of the gaseous media if the tumor site is deep within the body. The RF applicators capable of deep treatment may also be capable of treating the surface.

Figure 61:
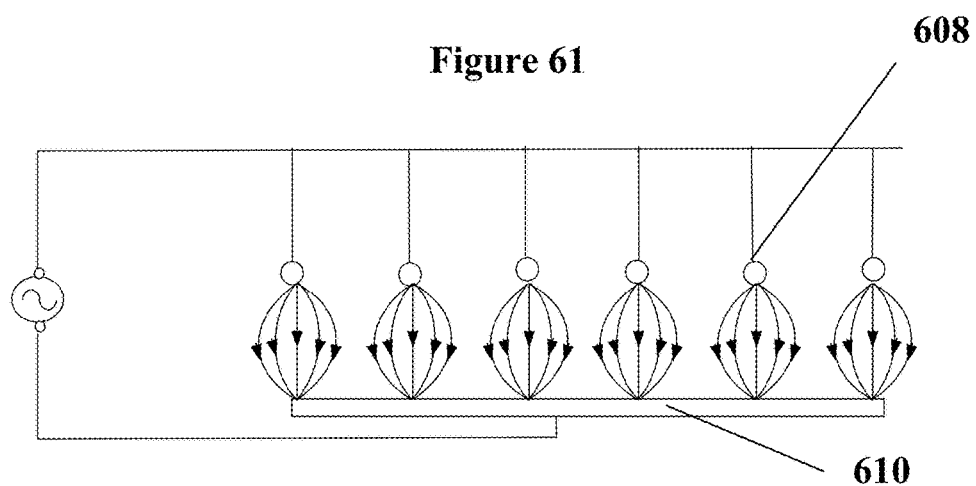
FIG. 61 is a schematic description of a hybrid RF applicator where adjustable electrodes are illustrated.
Figure 62:
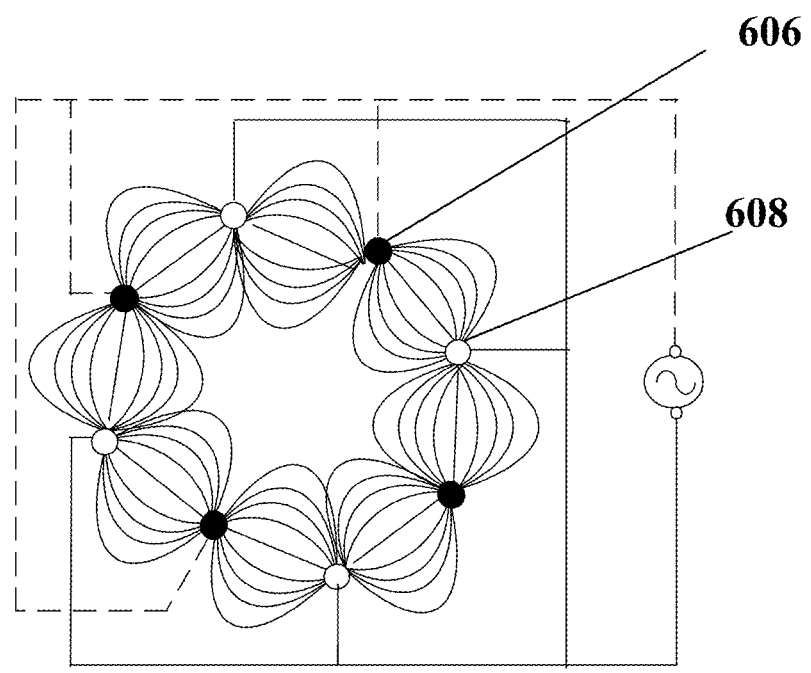
FIG. 62 is a schematic description of a staggered cylindrical RF applicator configuration.

FIG. 61 is a schematic description of a hybrid RF applicator where adjustable electrodes are illustrated. This configuration allows more flexibility as compared to the RF configurations shown above. The height between the electrode 608 and ground electrode 610 can be adjustable. Alternatively, FIG. 62 is a schematic description of a staggered cylindrical RF applicator configuration. The electrodes 606, 608 are positioned in a circular/cylindrical pattern which provides more control over the deliverable energy patterns.

Figure 63:
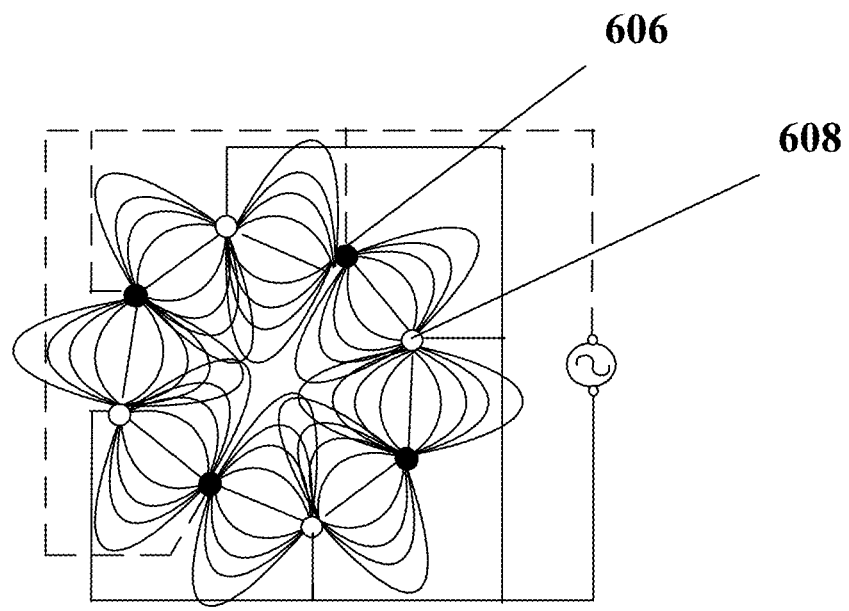
FIG. 63 is a schematic description of a cylindrically configured staggered cylindrical RF applicator is presented.

FIG. 63 is a schematic description of a cylindrically configured staggered cylindrical RF applicator. The electrodes 606, 608 are positioned in a circular/cylindrical pattern which provides more control over the deliverable energy patterns. The size of this applicator can be variable depending on the size of the part of the workpiece or human body to be treated or if the workpiece or entire human body is to be treated.

Figure 64:
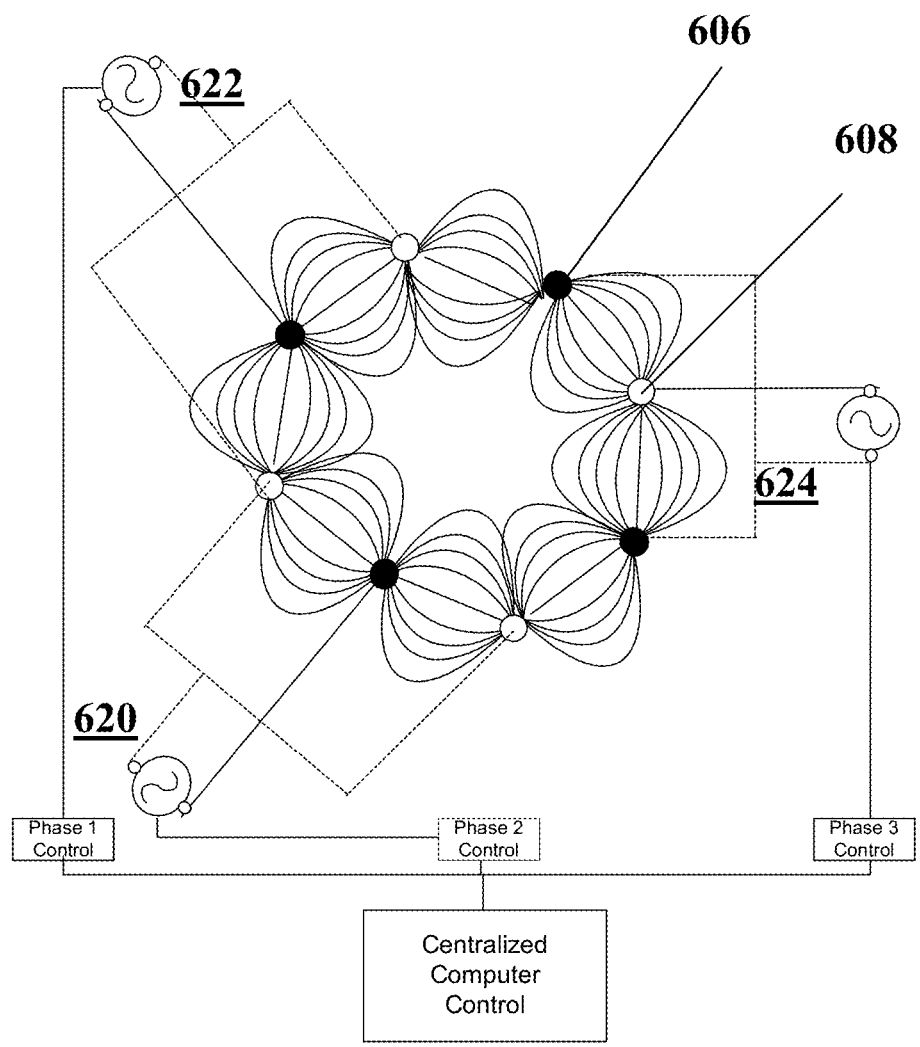
FIG. 64 is a schematic description of a cylindrically configured staggered cylindrical RF applicator configuration.

FIG. 64 is a schematic description of a cylindrically configured staggered cylindrical RF applicator configuration. The electrodes 606, 608 are positioned in a circular/cylindrical pattern which provides more control over the deliverable energy patterns. Three sections 620, 622, and 624 power the electrodes 606, 608. The size of this applicator can be made variable depending on the size of the part of the workpiece or human body to be treated or if the workpiece or entire human body is to be treated. Furthermore the control of the applicator is accomplished in sections such that the RF treatment can be performed in series, with each controlled section powered sequentially and programmed to deliver a suitable recipe in terms of power and frequency.

The RF applicator with sections 620, 622, and 624 operating in phase can be operated over a large frequency range and depending on the site to be treated and the magnitude of the operating magnetic field. Different frequencies may be used !! the higher the magnitude of the magnetic field, typically the higher frequency the operational frequency which would be used.

Figure 65:
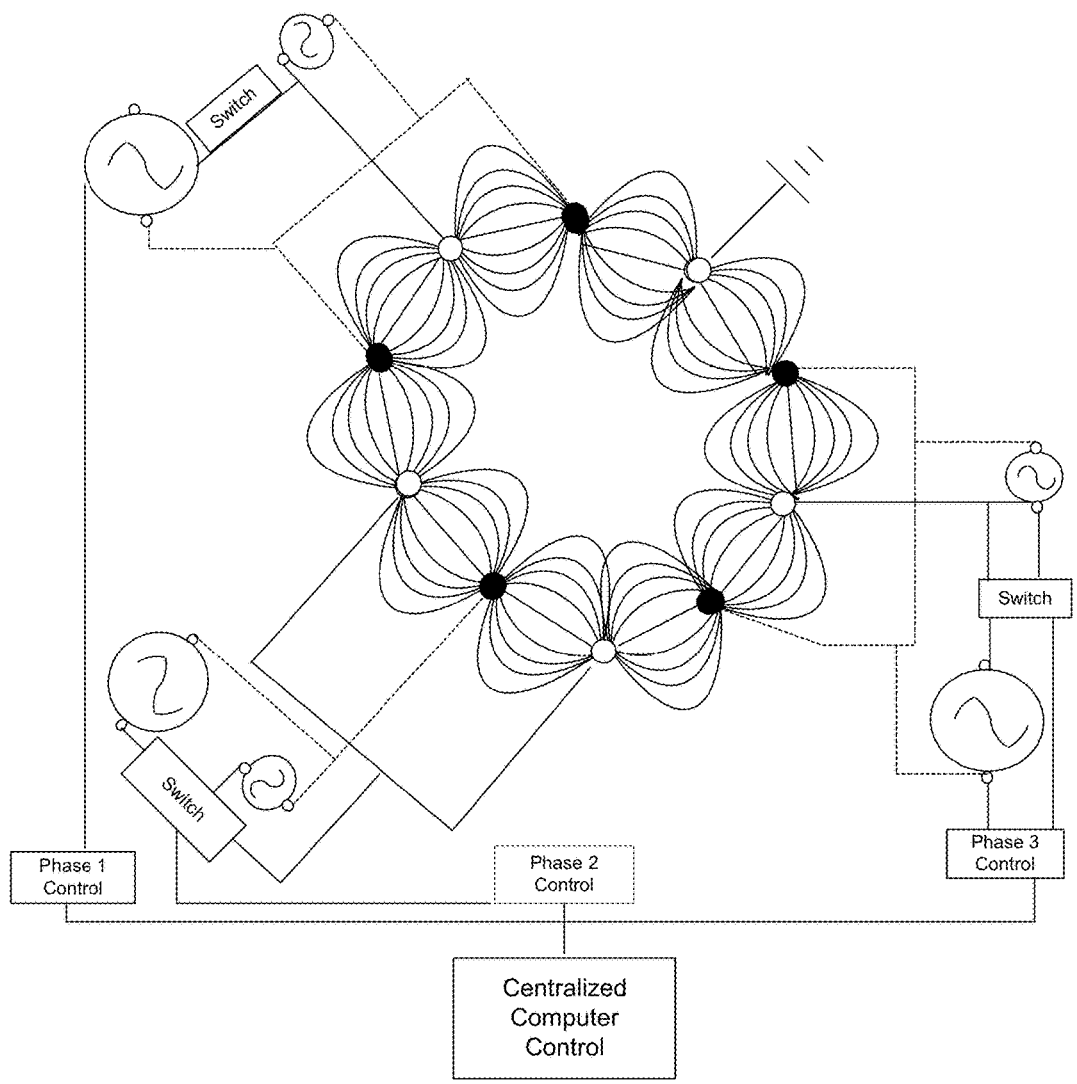
FIG. 65 is a schematic of a phased RF applicator capable of delivering different frequencies.

The three sections 620, 622, and 624 can also be powered out phase. FIG. 65 is a schematic of a phased RF applicator capable of delivering different frequencies. The waveform used in the generators depicted in FIG. 65 can be controlled at a centralized computer controller to inject programmable phase delays between the various electrodes.

In FIG. 65, the electrodes can be made to operate independently or in synchronization with one another. The electrode sets corresponding to one generator can be made to operate in phase or out of phase. The generators themselves can be pulsed on and off as may desirable by a treatment recipe. A switching network can be utilized to energize the electrode by one set of frequencies for a period of time and then switch to another set of generators to operate at a different frequency regime. The first regime could be in the KHz, and the second regime could be in the MHz.

In one embodiment of the invention, the RF applicators can be adjustable in frequency provided that the generator is capable of doing so. If not, separate generators (capable of delivering power at different frequencies) can be utilized to energize the electrodes.

The RF applicators shown above are capable of delivering a large amount of powers in a short pulse as needed. The microwave applicators and the RF applicators can be designed to work in conjunction with an MRI machine (such as the one described above) to take advantage of the capability of the magnetic gradients and the uniform cylindrical magnetic field.

In one embodiment of the invention, the RF and MW applicators are configured with a preferential orientation of the electric field, where the electric field is orthogonal to a cylindrical magnetic field. In this configuration, the electrons generated during plasma generation precess along the magnetic field lines.

Targeted Magnetic Field Applications

It is possible to exercise various aspects of the invention without the need for an MRI machine. In these embodiments, the utilized magnetic coils can constructively trigger rotational movements in the gases contained in the UCC structures. Various ways of triggering a magnetic field can be applied constructively to achieve the desired result. By considering a coil magnet first, a series of coils magnets can be energized using current flow. In this case, no MRI machine is needed to generate the up conversion.

In various embodiments, multi-head coils are operated at low frequency from 1 KHz to 400 MHz and are engineered to be out of phase with one another. Furthermore, the magnetic fields emanating from each coil can have different (or similar) orientations. The resulting magnetic field orientation hence formed in this series of magnetic coils (that are operable out of phase with one another) can lead to the triggering of magnetic field pulses each in a different orientation. In one embodiment, each magnetic field pulse tends to orient the paramagnetic gases, the magnetic dipoles within the magnetic films, and/or magnetic dipoles of the magnetically susceptible nano particles. The series of the magnetic coils is designed to orient the magnetic dipoles (contained with the UCC structures) in a synchronized fashion for maximized coupling and the inducement of rotary movement of gases which can lead to collisions and plasma ignition.

The number of magnetic heads can be made variable depending on the susceptibility of the UCC. The more susceptibility the less number of magnetic head needed to trigger plasma ignition and up conversion. The magnetic heads can be made close or far apart depending on the application (treatment).

Figure 66A:
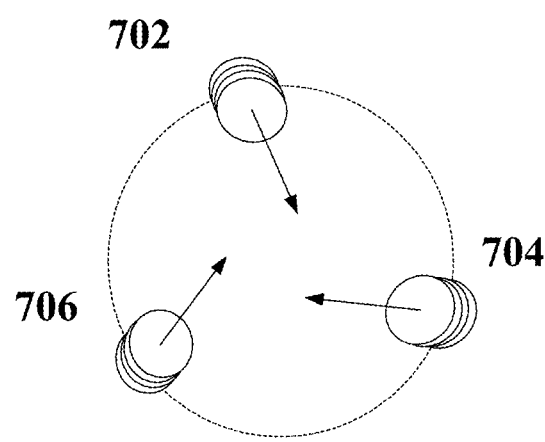
FIGS. 66A, 66B and 66C are schematics of different sets of solenoid coils in different configurations designed to excite and stimulate rotational movements of paramagnetic gases and magnetic dipoles contained in various UCC structures of the invention.
Figure 66B:
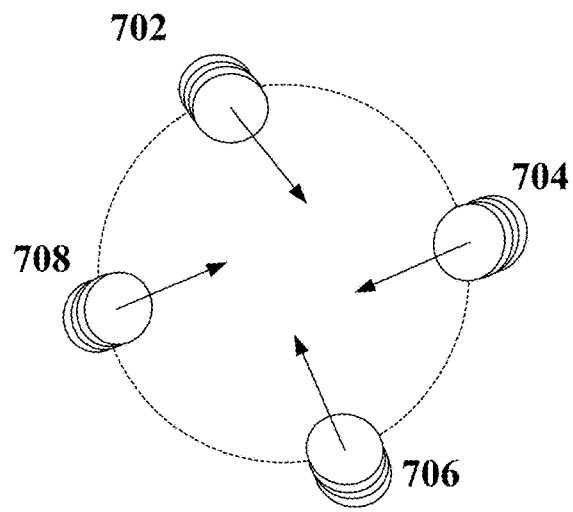
Figure 66C:
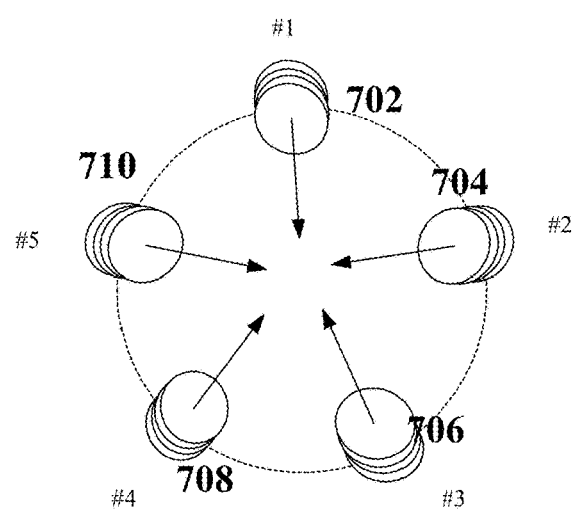

FIGS. 66A, 66B and 66C are schematics of different sets of solenoid coils in different configurations designed to excite and stimulate rotational movements of paramagnetic gases and the magnetic dipoles contained in magnetic films and magnetic nano particles that are in turn formed as part of the UCC structures of the invention, described above.

In FIG. 66A, three solenoids 702, 704, 706 are configured in a circle and oriented such that their respective protruding magnetic field is oriented toward the general direction of the center of the circumference formed by the three coil magnets. The magnetic field can protrude slightly off center. In FIG. 66B, four solenoids 702, 704, 706, 708 are configured in a circle and oriented such that their respective protruding magnetic field is oriented toward the general direction of the center of the circumference formed by the four coil magnets. The magnetic field can protrude slightly off center. In FIG. 66C, five solenoids 702, 704, 706, 708, 710 are configured in a circle and oriented such that their respective protruding magnetic field is oriented toward the general direction of the center of the circumference formed by the five coil magnets. The magnetic field can protrude slightly off center.

In one example of this embodiment of the invention, these five solenoids can be employed in a way that maximizes the torque applied to the magnetic dipole and dielectric dipole. In this case a solenoid #1 (702) would be activated followed by solenoid #3 (706), followed by solenoid #5 (710), followed by solenoid #2 (704), followed solenoid #4 (708) followed by solenoid #1 (702); so fort and so on. In other words, every other solenoid is sequentially activated. The solenoids to be powered would then operated out-of-phase to be able to take full advantage of the rotary motion imparted to the magnetically susceptible matter in the UCCs.

Figure 67:
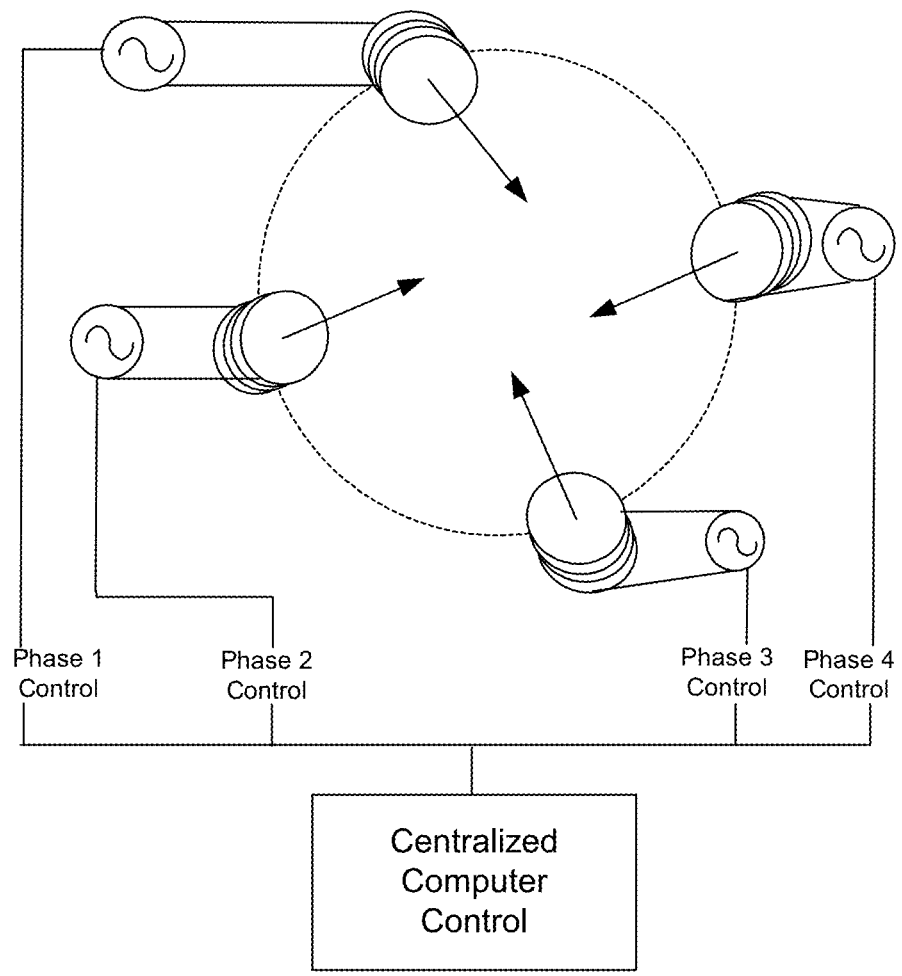
FIG. 67 is schematic of a configuration for a serialized operation of four coil magnets that can operate out of phase.

FIG. 67 illustrates the operation of a series of coil magnets that is out-of-phase. Indeed, FIG. 67 is schematic of configuration for serialized operation of four coil magnets operating out of phase with one another to maximize the rotational imparted into the magnetic and dielectric matter contained in the UCC. This configuration can be used for the purpose of igniting a plasma for a brief interval of time sufficient to photo initiate an agent in the medium of the UCC structure, and in particular for activation of a therapeutic agent, with a time frame not sufficient to cause tissue damage.

The RF, MW or magnetic susceptibility of nano particles or carbon nano tubes that can be engineered within the UCC can assist in heating and lowering the ionization of gas mixtures described elsewhere and can facilitate plasma ignition. Furthermore, as in the embodiments described above, a number of different gasses can be used to generate the needed light emission to activate a therapeutic agent or other activating agent in the medium about the UCC structure.

To further elaborate on the coil magnets and the mechanisms thereof capable of constructively operating to trigger up conversion by plasma initiation; other configurations and modifications are described below.

In one embodiment, two coils are made to operate simultaneously in cooperation with one another. In this case for the five solenoids example, solenoid #1 and solenoid 3 are operated at the same time in different direction (this is done by circulating an electrical current in solenoid #1 and a current in the opposite direction in solenoid 3) in such way to create a re-entrant magnetic field path as illustrated of FIG. 68 (see solid magnetic line). In a similar fashion, the magnetic field between 2 and 4 forms a reentrant magnetic field (see broken dashed magnetic line) and in turn the magnetic field between 3 and 5 forms a reentrant magnetic field (see broken dotted magnetic line).

Figure 68:
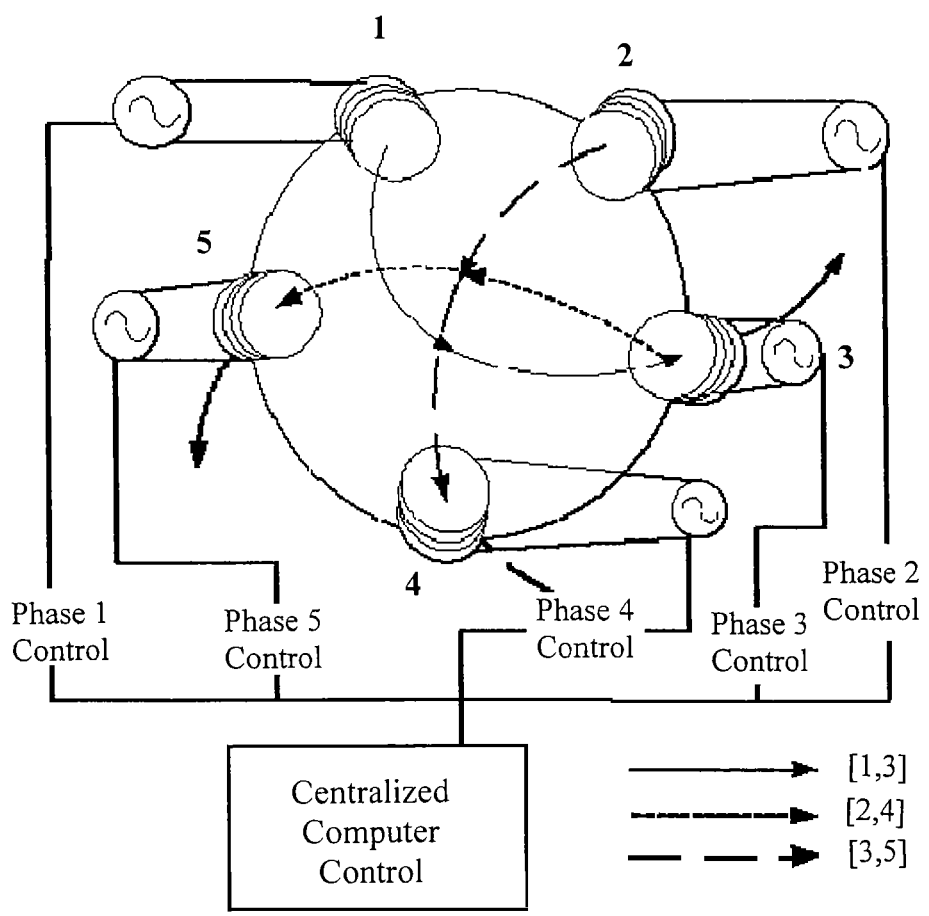
FIG. 68 is a schematic depicting the operation of paired solenoids to create a re-entrant magnetic field path, where the paired solenoids are operated in a serialized manner and/or out of phase between the pairs

The waveform used in the generators depicted in FIG. 68 is controlled at the centralized computer controller to inject programmable phase delays between the various coils. The current fed into select coils can be in phase with one another, or out of phase with one another or have a phase delay between a pair of coils. In the example shown in FIG. 68, the paired coils 1 and 3 are 180° out of phase and operate simultaneously. In the same example, the paired coils 2 and 4 are 180° out of phase and operate simultaneously. However, the operation of the two pairs can be 90° out of phase. In this manner, the various generators operate in a controlled manner and have engineered reentrant magnetic field pathways.

Figure 69:
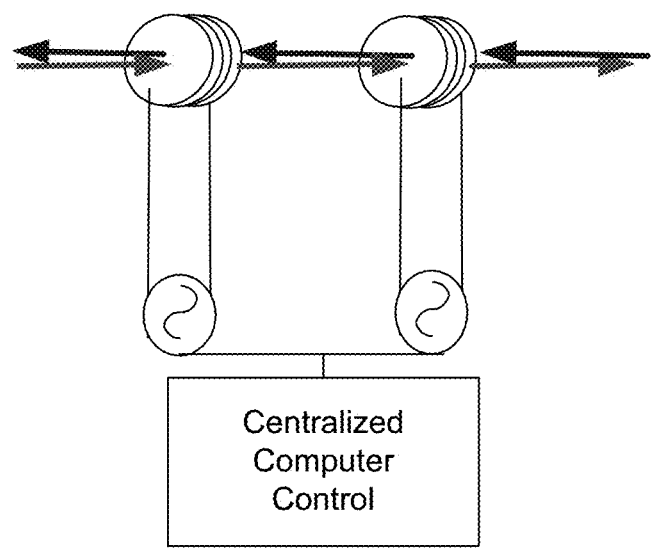
FIG. 69 is a schematic of two electromagnetic coils working in conjunction with one another to form a reentrant magnetic field which can penetrate an object when the field emanates from one coil to the other.

FIG. 69 is a schematic of two electromagnetic coils working in conjunction with one another to form a reentrant magnetic field which can penetrate an object when the field emanates from one coil to the other. In general, reentrant magnetic fields can be formed from many coil and magnet configurations. The configuration selected would depend on the number of electromagnetic coils juxtaposed in a constructive way. The higher the number of electromagnets, the more flexibility one has in engineering a magnetic path that is suitable for use through a work piece, a patient or a part of a work piece or a part of a patient. However, in one embodiment of the invention (as illustrated in FIG. 69), a reentrant magnetic field can be achieved by only two electromagnetic coils. This configuration would be suitable for example if the patient or one of the patient's part is outside of the coils. In other words, a reentrant magnetic field would be used when the work piece or patient or any part of the work piece or patient is to be left outside of the coil region for treatment.

Figure 70A:
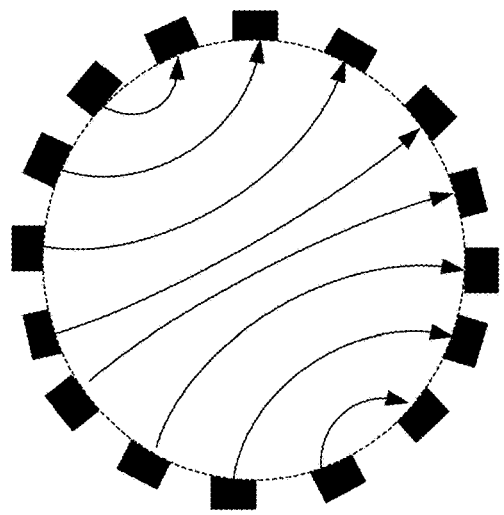
FIG. 70A is a schematic depicting a number of electromagnets disposed around a work piece or a patient where the magnetic field paths are configurable.
Figure 70B:
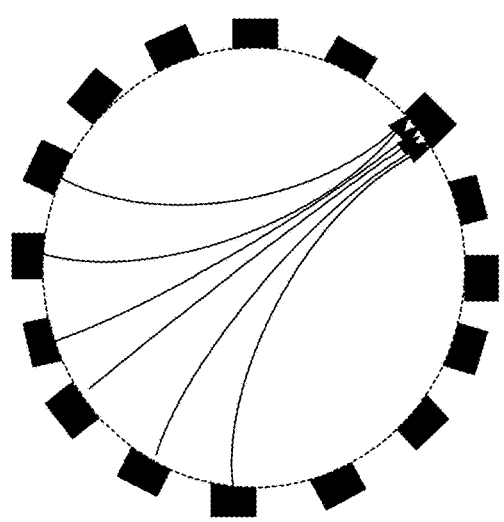
FIG. 70B is a schematic of a magnetic configuration illustrated for aligning and strengthening the magnetic field.

If a large number of magnets is used, then in one embodiment of the invention a large number of configurations (i.e., available magnetic path ways) are possible for directing and collimating the magnetic field. FIGS. 70A and 70B illustrate a configuration with a series of coil magnets or electromagnets which can be used to engineer a variety of magnetic patterns that can be time varying patters according to the way the electromagnets are powered. In particular, FIG. 70A is a schematic depicting a large number of electromagnets (16 electromagnets) that can be disposed around a work piece or a patient to create a large number of magnetic path ways. In particular, FIG. 70B is a schematic of a magnetic configuration illustrated for aligning the magnetic field and for strengthening the magnetic field for an elapsed amount of time. Conversely, a large number of electromagnets can be used around the work piece or patient to create other magnetic path ways that are useful.

The magnetic field achieved in FIG. 70B can be used to perform the same function as the one described in FIG. 68 (where by certain magnetic coils are operated out of phase to achieve rotational energy coupling to gases and to lossy magnetic and dielectric matter). However, another use for this multipath-way magnetic design is to concentrate the magnetic field sufficiently in one localized area of a work piece or a patient, to thereby reach a sufficiently high magnetic field strengths (e.g., at least 0.5 Tesla) which would permit the use of an additional gradient electromagnet in conjunction with RF to trigger a plasma and/or to created a plasma with ECR conditions.

Figure 71:
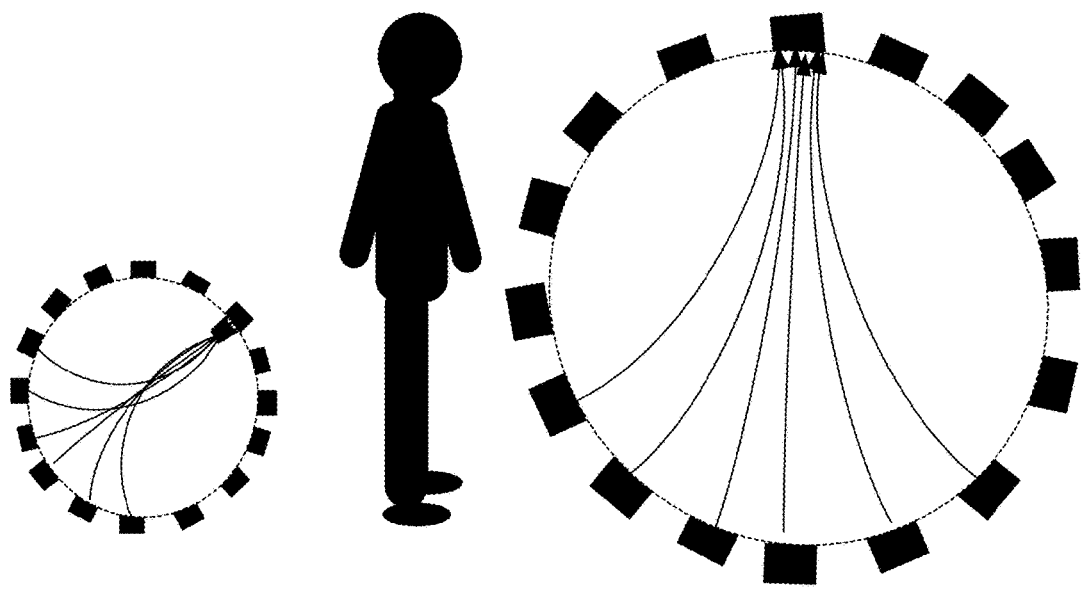
FIG. 71 is a schematic depicting the utilization of variable field strength multipath-way magnets, the size of which can be made large to host a patient or small to be used for localized treatment on a patient.
Figure 72:
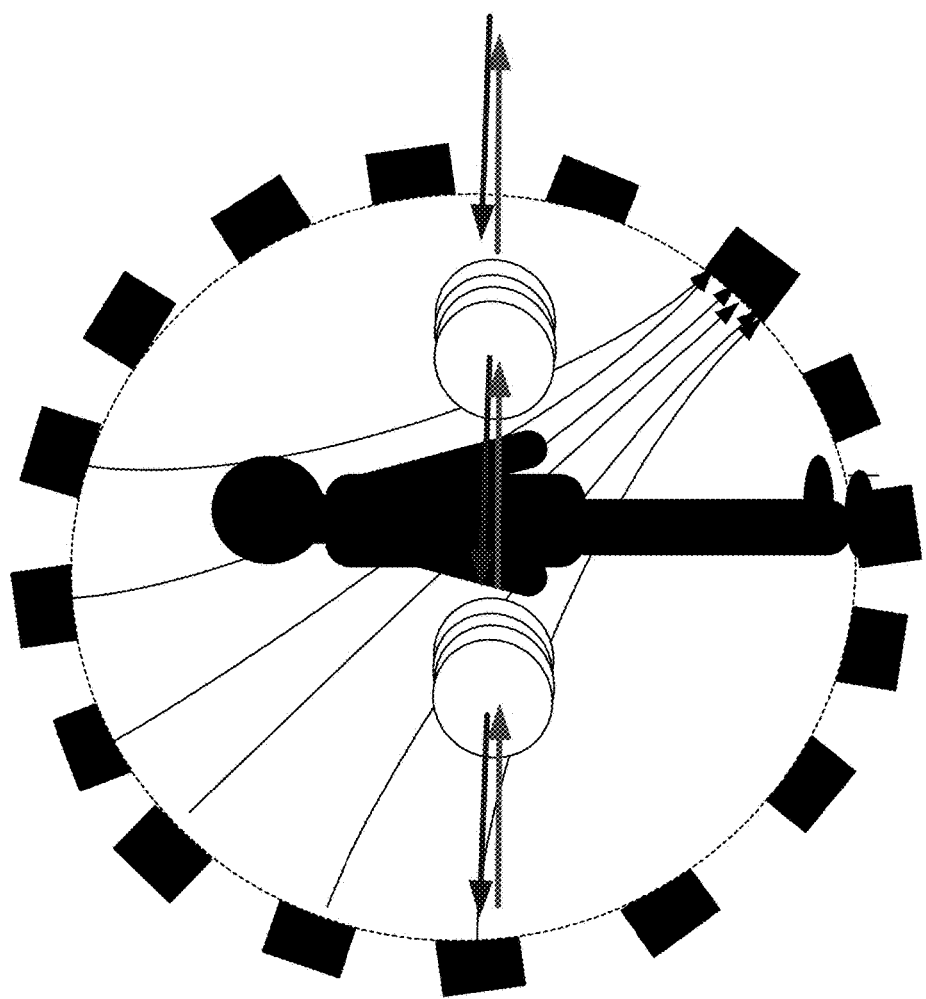
FIG. 72 is an illustration of a large multipath way magnet used in conjunction with a reentrant electromagnet.

FIG. 71 is a schematic depicting the utilization of variable field strength multipath-way magnets and their use in conjunction with each other. FIG. 72 is an illustration of a configuration where a large multipath way magnet can be used in conjunction with a (relatively small) reentrant electromagnet for the purpose of triggering up conversion. The multipath-magnet (when operated in a focused mode) could replace the role of an MRI, and would be more cost effective due to its simplicity and basic hardware and computer control. The multipath-way magnet can be used with two reentrant magnets, in this embodiment, to achieve up conversion of a gaseous media in the UCC structure of the invention. The multipath-way magnet would be congruent with the use of four of five phased reentrant solenoids.

Figure 73A:
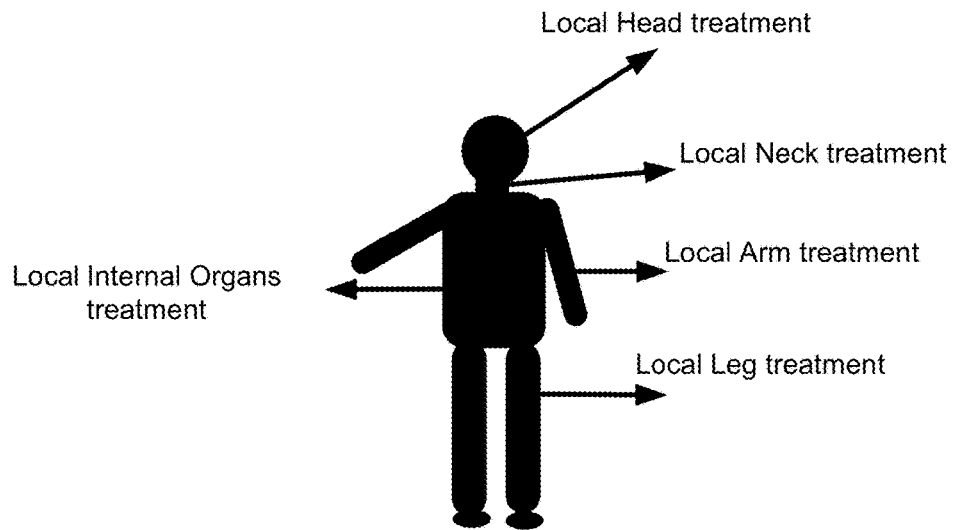
FIGS. 73A and 73B are schematics of various sets of solenoid coils each arranged in a configuration to treat local parts of an object or a patient.
Figure 73B:
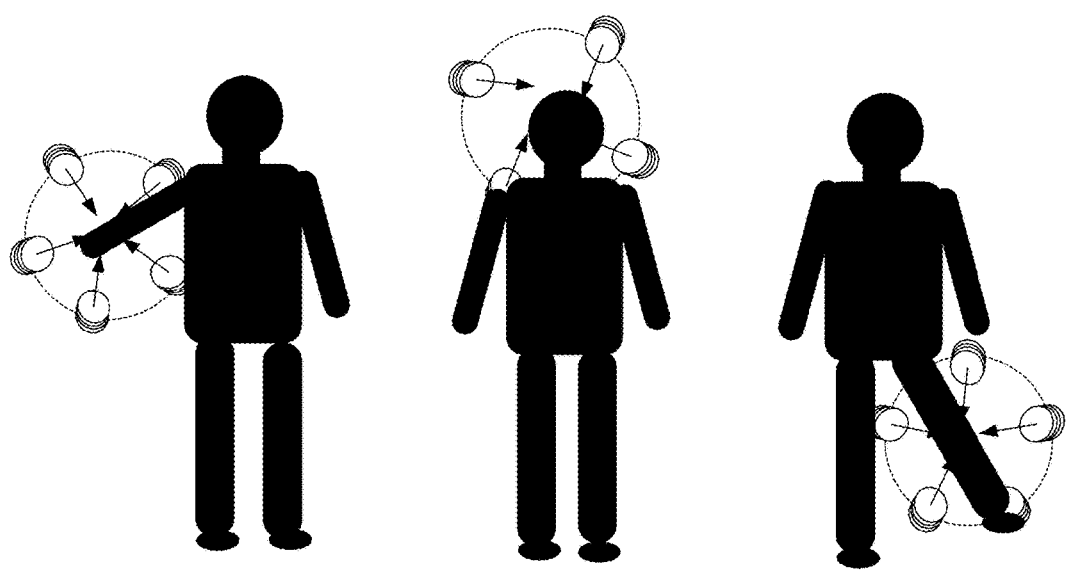

In the case of relatively smaller reentrant magnetic coils, as described before, FIGS. 73A and 74B are schematics of various sets of solenoid coils each arranged in a configuration to treat local parts of an object such as for example a human patient. The serial magnetic coil approach can be applied to localized parts of the body in this case smaller coils configured closer to one another can be used to achieve maximum coupling.

Figure 73C:
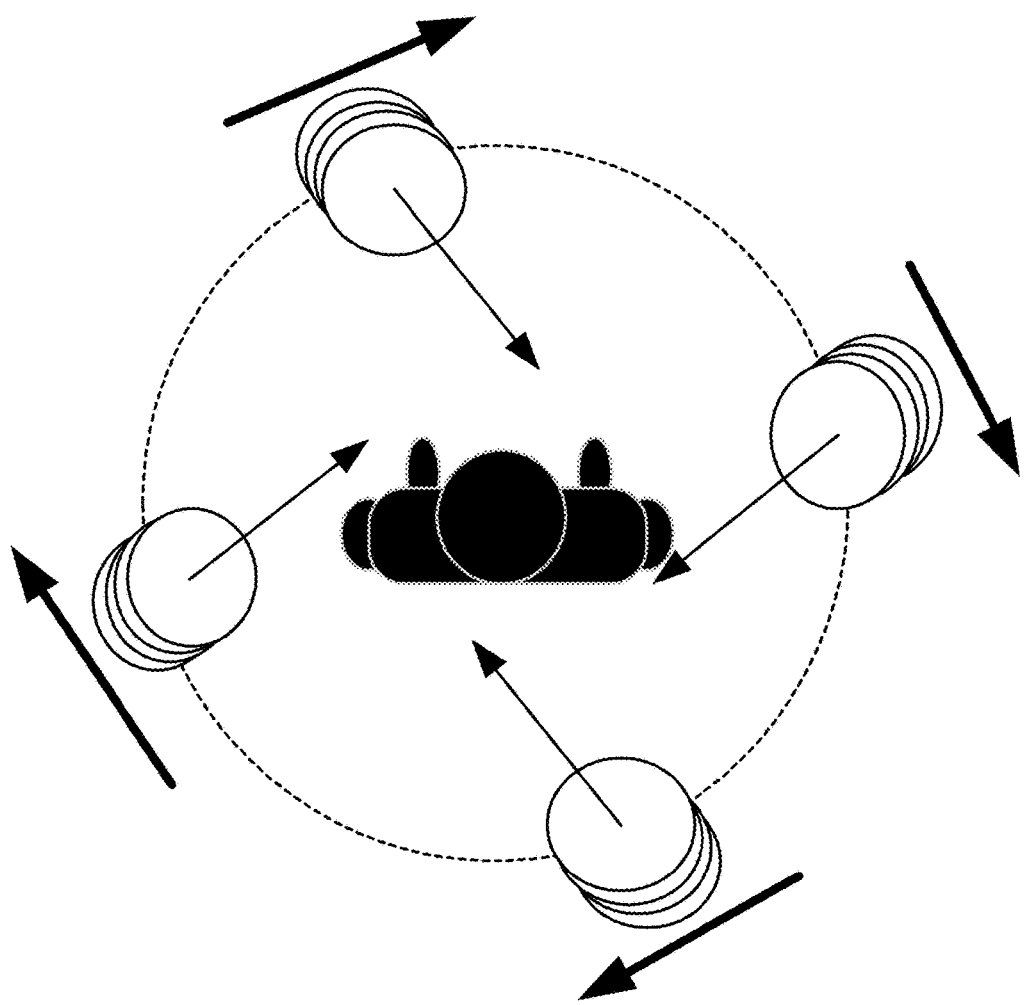
FIG. 73C is a schematic showing four magnetic coils spaced apart to host a patient and operate in series for the purpose of a targeted penetration into a work piece or patient and for the triggering of a plasma in the UCC structures of the invention.
Figure 74:
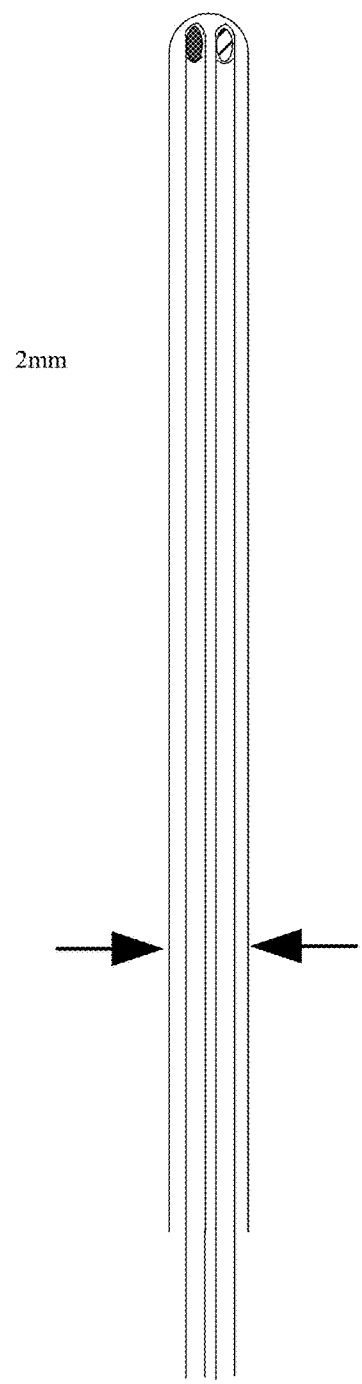
FIG. 74 is a schematic of a temperature, electric field, and magnetic field probe all of which can be measured simultaneously.

FIG. 73C is a schematic showing four magnetic coils spaced apart to host a patient and operate in series for the purpose of a targeted penetration into a work piece or patient and for the triggering of a plasma in the UCC structures of the invention to initiate a bio-therapeutic agent. In the above magnetic flux and RF/MW embodiments, it is of concern (when the object treated is a patient instead of an artificial medium) the quantity of the dose of RF and magnetic field applied. FIG. 74 is a schematic of a temperature, electric field, and magnetic field probe all of which can be measured simultaneously by feeding the difference in temperature rise between the two adjacent probes in the illustration to a computer and deriving the local field strength, one probe has a material susceptible to oscillating electric and magnetic fields while the other probe is measuring the environmental temperature. In FIG. 74, magnetic field strength and or the electric field strength can be measured using two fiber optic probes one with electromagnetic susceptible tip and the other one with air to act as the reference. The temperature rise and hence the difference between the two probes can yield the electric or magnetic field strength; hence, the treatment dose. If the probe is inserted inside a patient's body, then the environment temperature measured by the probe becomes the patient's body temperature and the electromagnetic energy is measured by the difference in the temperature between the two adjacent probes inside the patient's body.

Figure 75A:
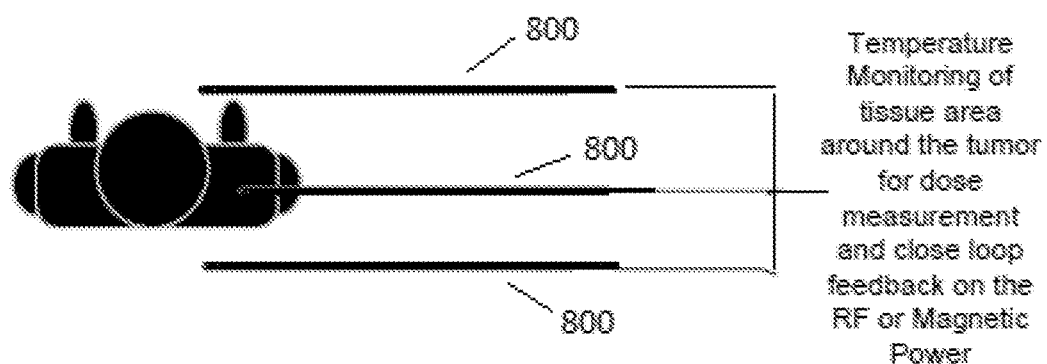
FIGS. 75A and 75B are schematics of sensors (including temperature, magnetic and electric field strengths) employable in various embodiments of the invention.
Figure 75B:
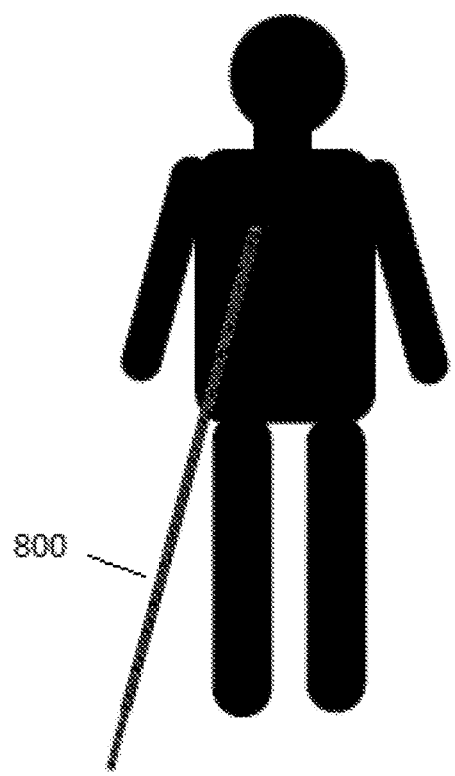

FIGS. 75A and 75B are schematics of sensors 800 (including temperature, magnetic and electric field strengths) employable in various embodiments of the invention. The probes 800 shown in these figures can be implanted in the body and positioned below and above the patient for mapping the environment of a patient or another workspace. The probe sensor information could be provided to the computer 306 shown in FIG. 39, for example, to be part of the treatment monitoring.

Figure 76:
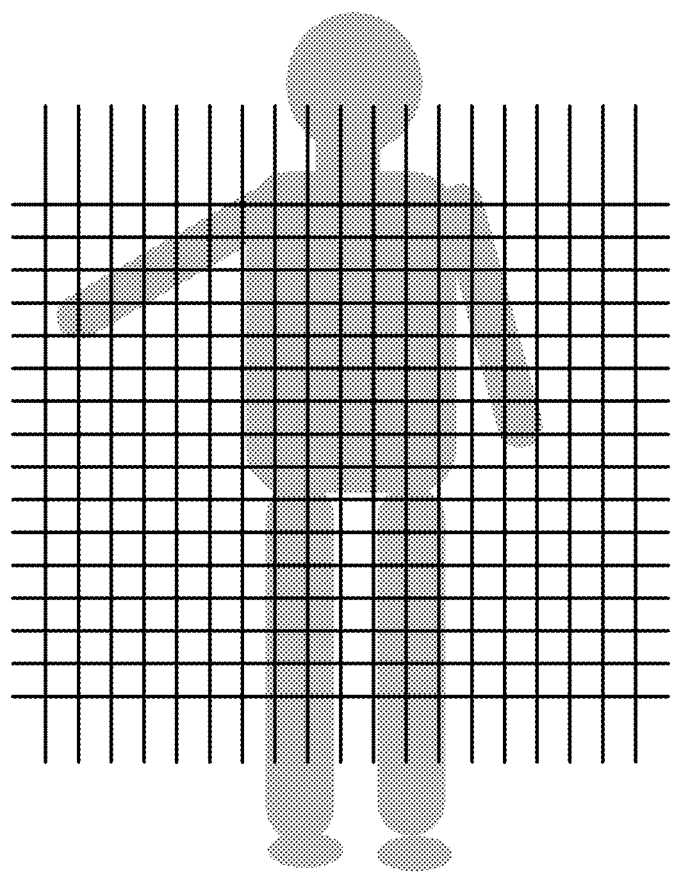
FIG. 76 is a schematic of an area array of sensors provided under and above a patient or a work piece to collect information and resolution of the field special distribution.

FIG. 76 is a schematic of an area array (mesh) of sensors provided under and above the patient to make precise measurements. This area array of probes can be use to ensure that the dose and the radiation is delivered to the patient at the deigned place and per the programmable instructions. In one embodiment, any deviations from what is deemed the procedure of record, an emergency shut down can be triggered.

In one embodiment of the invention, multiple probes can be used around or inside the patient to monitor the patient temperature and electromagnetic dose received during the treatment. This information can be used as feedback to the computer to regulate the Pulse width duration and frequency selection. In one embodiment of the invention, RF and MW are used sequentially, simultaneously and possibly with magnetic induction depending on the composition of the UCC. Once a dose is established (a dose calibration is done) the internal probes above and below the patient we can calculate the absorption in the patient without having to insert a field measurement probe inside a patient.

Three probes are shown: below, inside. and above the patient to monitor the patient temperature and feedback information to the computer to regulate the pulse width duration and frequency selection. In one embodiment of the invention, RF and MW are used sequentially, simultaneously and possibly with magnetic induction depending on the composition of the UCC. Once the probes above and below are calibrated, the absorption in the patient can be calculated without having to insert a field measurement probe.

Figure 77:
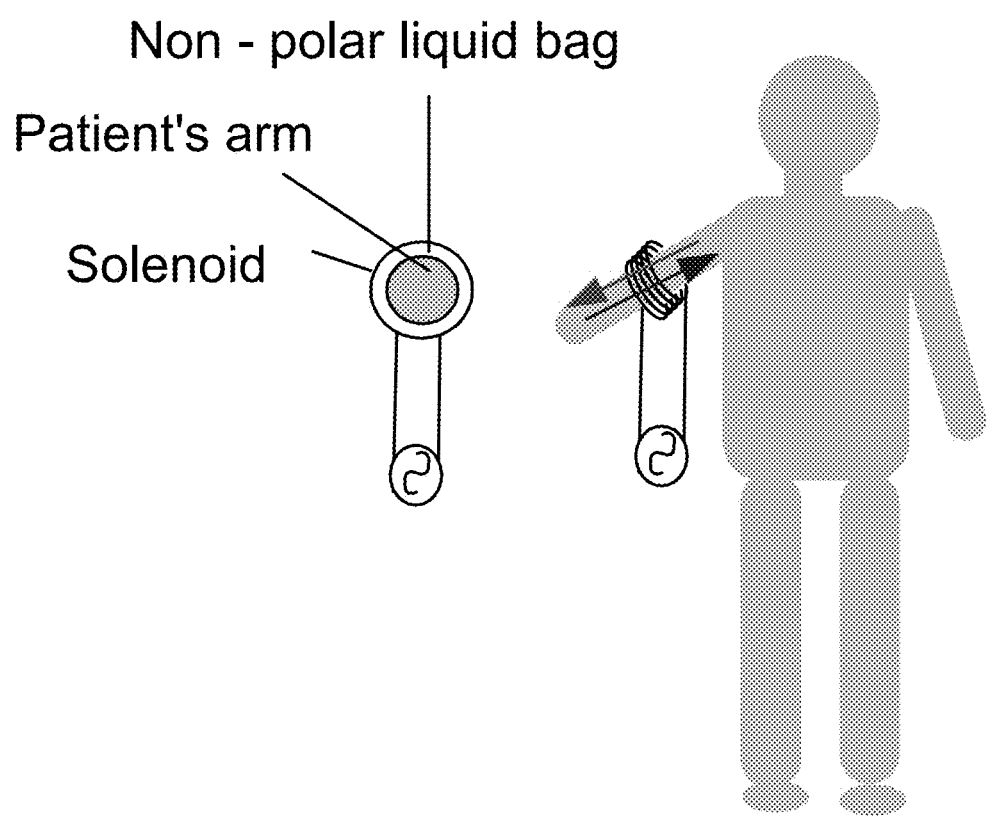
FIG. 77 is a schematic of the utilization of magnetic induction system if a patient requires treatment in a limb and not an internal organ.

FIG. 77 is a schematic of the utilization of magnetic induction if a patient requires treatment in a limb and not an internal organ. In a few cases, when the tumor is located the arm or the leg, it is possible to use magnetic induction using one coil. In this case a solenoid is activated using an alternating current and low frequencies (anywhere from the kHz to the MHz) to trigger the gaseous up conversion. A non polar liquid bag can be used with this local applicator around the site to be treated. De-ionized water can also be used with this local applicator.

Macroscopic Probes

While illustrated above with regard to microscopic size plasma containments, the invention is not limited to that size gas or plasma containments. For many applications, microscopic size plasma containments still provide unique advantages. The advantages here relate to the capability of the invention to initiate plasmas under conditions whereby ordinarily one would have not expected plasma ignition to be possible. As described above, the magnetic fields in conventional NMR or MRI machines had not been realized prior to the invention as being capable of participating in the igniting and sustaining a plasma (especially inside a medium and especially inside the human body). Yet, this work has realized this capability in millimeter and sub-millimeter size plasma containments.

In one illustration, a static magnetic field from a commercial MRI was used in conjunction with and RF source able to supply from 100 MHz to 400 MHz. The microwave power supply was connected to various antennas placed within the bore of the MRI magnet to ignite and sustain plasma contained within glass containers. In some cases the gas container was placed inside of a phantom and in others the gas container was in the vicinity of a well plate containing a cell culture and a photo-activated bio-therapeutic agent. RF power was supplied from the antenna. While demonstrated with magnetic fields from a commercial MRI, similar results in the presence of magnetic fields from rare-earth permanent magnets (with a magnetic field strength of about 1.5 Tesla) have been realized at remarkably low powers. In the presence of a magnetic field such as the MRI plasma were sustained inside glass containers at 5 Watts as opposed to 50 Watts.

While demonstrated with static (non-time varying) magnetic fields from the MRI (or permanent magnets), various embodiments of the invention vary the magnetic field in time, with spatial gradients to produce magnetic induction effects which can assist in the ignition and/or maintenance of a plasma in the gas container up converters of the invention. Additionally, motion of the gas container up converters having an electrode attached to it or a metallic loop relative to the magnetic field can likewise produce magnetic induction effects which can assist in the ignition and/or maintenance of a plasma in the gas container up converters of the invention.

Some work was also conducted in a modified commercial microwave oven to have feed-through to have a mechanical rod to move magnets around a gas container and to have the antenna of a Tesla coil reach inside the chamber and in proximity to the a phantom containing a gas container. The feed-through holes were equipped with chokes to eliminate leakage. The microwave antenna was polarized using an extended waveguide inside the cavity. In some of these cases, a fluidic conduit was connected to a glass tube that was not sealed and the open ends of the gas tubes were connected to a vacuum side on one side and the gas feed on the other. In this case scenario a plasma was generated having open ended ends that were connected to the appropriate pressure control and gas feed.

In this work, sealed glass tubes made of boro-silicates, soda-lime-silicates, lead glass, and quartz tubes of dimensions ranging from 30 mm down to 4 mm in length, and from 3 mm in thickness down to 900 microns in thickness. The sealed glass containers were evacuated and backfilled with a mixture argon, nitrogen, hydrogen, mercury vapor and sodium. The vacuum pressure ranged from 5 mTorr to 10 Torr. These gas containers were placed inside an MRI from GE Healthcare Technologies d Model 1.5T SIGNA MRi EXCITE HDx. In some cases we showed sustained plasma after ignition with a Tesla coil outside the bore of the magnet and in some cases they were ignited and sustained inside the bore of the magnet with a Tesla coil.

In one embodiment of the invention, the sealed containers were subjected to a cleaning process to "burn-off" organic contaminants from the inner walls of the containers. The cleaning process involved the following steps: placing electrodes at the end of the container, sealing the electrodes into the end of the container through a gas heated flame, followed by cooling and then performing a vacuum drawing followed by the backfill of the container using the desirable gas and gas mixtures like argon or nitrogen, and by adding any additives that could lower the ionization potential of the gas, then the electrodes on each side the tube were hooked up to a high voltage low current transformer to ignite a plasma and heat the tube using both the plasma and an external heater. The plasma was ignited and sustained with a 400 milliamps, 12,000 volt, 350 EC. The temperature of the containers was monitored each time to 400 EC on the outside. The internal temperature was exceeding 700 EC at which organics are decomposed. The container is then allowed to cool. The containers were then placed on an insulated table and heated locally by a high temperature flame to temperature sufficient to draw the glass. The glass was then pulled into smaller lengths. The glass walls were allowed to collapse and seal while at high temperature. This is how a 4 mm length glass was constructed. The starting inner diameter of the glass tube was 3 mm. From this 3 mm ID glass, a piece of 4 mm in length was successful drawn and ignited with RF energy. The electrodes at the end of the glass can be left as part of the glass containers or can be removed. Additional heating was provided to anneal the various glasses to remove or minimize trapped stresses inside the structure. In some cases, metals wires, metal coils, Carbon Nano Tubes, Nano Magnets were introduced inside the glass containers through a lateral aperture.

Besides work with the above-noted gasses, forming gas (i.e., a mixture of hydrogen up to 5.7% and nitrogen) was successfully tested.

In one embodiment of the invention, the sealed tubes were subjected to a cleaning process to "burn" organic contaminants from the tubes. The cleaning process involved an air plasma ignited and sustained with a 400 milliamps, 12,000 volt, 350 EC, plasma treatment.

This experimental work demonstrated ignition of plasma (even inside phantoms to be discussed below) with the assistance of a Tesla Coil, power pulsing and/or modulation, electric and magnetic field gradients and transients, CNT and metallic additives, and the above in combination with the presence of a magnetic field, especially a field from a MRI. Indeed, plasma operation in the gas containers inside the MRI have been sustained at power levels as low as 5 Watts.

Indeed, even when "phantoms" representing human blood were wrapped around the quartz tubes, plasma ignition still occurred. Phantoms of a thickness of about 2-15 cm have been tested successfully under different RF frequencies and antenna designs. Temperature sensors in the phantoms showed an acceptable level of heating of the phantom. Thus, in one embodiment of the invention, plasma ignition and light generation therefrom are possible in a human or animal body as the subject of light therapy or light treatments.

In other demonstrations, a RF frequency at 915 MHz was used to ignite a plasma inside container separated from the RF antenna by a phantom of a thickness about 2.5 cm. In that demonstration, the gas containers were built as described before.

One typical phantom recipe contains (by weight); 70% laboratory grade ethylene glycol, 28% distilled water and 2% noniodized table salt. Tissue equivalent phantoms for performing power deposition specific absorption rate (SAR) studies of RF and microwave sources have been constructed from numerous materials. For example, even solid gelled phantoms have been used. The Table below describes the properties of various phantom mixtures.

Weight percentage components for liquid and solid phantom models of human liver tissue at 915 MHz.

| Phantom components | Desired properties | Mixture 1 | Mixture 2 | Mixture 3 | Mixture 4 | Mixture 5 |
|---|---|---|---|---|---|---|
| Liquid phantoms | | | | | *** | |
| Water | | 4.93 | 8.89 | 28 | 28.5 | 44.54 |
| Ethylene Glycol | | 93.9 | 90 | 70.5 | 69.85 | 54.1 |
| NaCl | | 1.17 | 1.11 | 1.5 | 1.65 | 1.36 |
| Dielectric constant | 55 ± 6 | 33.7 | 39.5 | 49.1 | 51.0 | 57.3 |
| Conductivity (S/m) | 1.0 ± 0.2 | 0.93 | 1.05 | 1.02 | 0.99 | 1.28 |
| Solid phantoms | | *** | | | | |
| Water | | 51.02 | 52.96 | 51.6 | 52.4 | |
| Sugar | | 46.01 | 43.88 | 46.56 | 45 | |
| NaCl | | 0.82 | 1.02 | 1.24 | 1.4 | |
| HEC *5000, **3400 | | 2.05* | 2.04** | 0.52* | 1.0 | |
| Dowicil 75 | | 0.1 | 0.1 | 0.1 | 0.1 | |
| Dielectric constant | 55 ± 6 | 51.3 | 51.4 | 52.0 | 54.7 | |
| Conductivity (S/m) | 1.0 ± 0.2 | 0.96 | 1.02 | 1.13 | 1.38 | |
| | | | More solid | More liquid | Muscle (6) | |

*HEC 5000;
**HEC 3400;
***Bold = preferred mixtures

The following papers incorporated herein by reference in their entirety provide descriptions of phantoms: 1) Chou C K, Chen G, Guy A W, Luk K H. Formulas for preparing phantom muscle tissue at various radiofrequencies. Bioelectromag. 1984; 5:435-41; 2) Hartsgrove G, Kraszewski A, Surowiec A. Simulated biological materials for electromagnetic radiation absorption studies. Bioelectromag. 1987; 8:29-36; 3) Stauffer P R, Rossetto F, Prakash M, Neuman D G, Lee T. Phantom and animal tissues for modelling the electrical properties of human liver. Int J Hyperthermia. 2003; 19(1):89-101; and 4) Neuman D G, Stauffer P R, Jacobsen S, Rossetto F. SAR pattern perturbations from resonance effects in water bolus layers used with superficial microwave hyperthermia applicators. Int J Hyperthermia. 2002; 18(3):180-93.

In one demonstration, a SigmaEye pelvic applicator was used to activate various gas containers having a small electrode with RF excitation when the gas container was positioned in the middle of a 15 cm diameter saline phantom load inside a full waterbolus inside the SigmaEye pelvic applicator. The gas container in this demonstration was more or less centered inside the SigmaEye applicator which is an oval (eye) shape of 47×56 cm so the gas container was located deep in water load as well as in the saline (body) load. A discussion of various applicators (including the SigmaEye applicator) is given below.

In one embodiment, the RF or microwave power applied is applied at one power for plasma ignition then at a lower power for plasma maintenance.

In one embodiment the plasma ignition is achieved through a Tesla coil capable of producing a high voltage gradient around its antenna. Bringing the Tesla coil in proximity or in contact with the glass container produced ignition. The plasma is then sustained using RF energy in the presence or absence of a magnetic field.

Alternatively, other mechanisms for ionization such as ionization in the gas container up converter by x-rays or high energy particles can be used to ignite the plasma. Alternatively, other mechanisms for ionization such as the application of energy from a Tesla coil can be used to ignite the plasma.

Figure 78A:
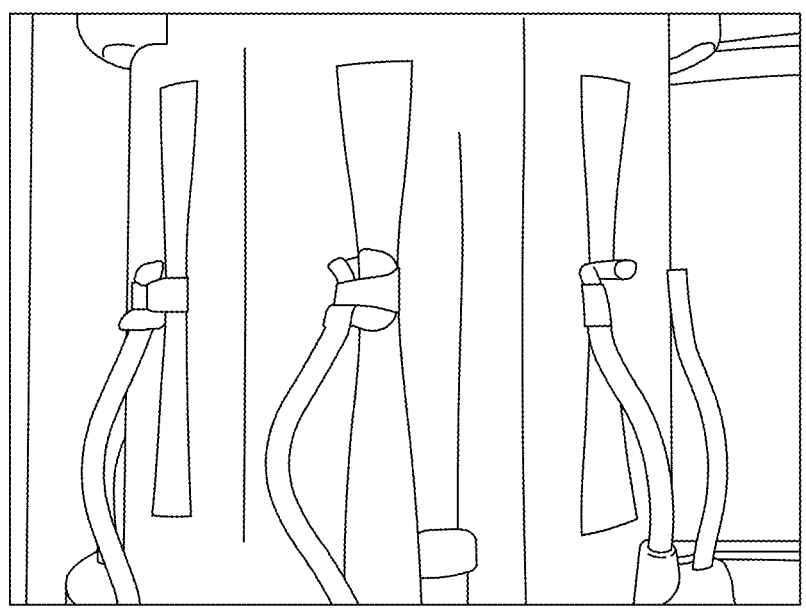
FIG. 78A is a schematic depiction of a phased array of dipole antennas surrounding a phantom.

In one demonstration of the invention, a 140 MHz phased array of dipole antennas has been used to couple power through a phantom. FIG. 78A is a photographic depiction of a phased array of dipole antennas surrounding a phantom.

In another demonstration, a single dipole antenna operated at 140 MHz ignited and sustained a plasma inside a phantom at a depth of 6 cm. In this demonstration, the array delivered a power of 200 W to 50 W to gas containers located 10 cm from the array. A phantom covered the gas containers.

In one embodiment of the invention, the RF or microwave power applied is applied in a duty cycle to reduce the heating of the medium in which the gas container up converters are disposed. In one embodiment, the RF or microwave power applied is applied with a phased array of antennas to reduce the overall heating of the medium in which the gas container up converters are disposed while increasing the field strength locally at a position inside the medium where the emitted light is need to induce a change in the medium.

In particular, a Spin Echo pulse sequence has been used to demonstrate the ability to activate gas ionization and plasma generation and sustainment with only the RF coils in the MRI bore, which emit very short RF pulses during MRI pulse sequences to excite the proton spins. Using spin echo pulse sequences, which feature the highest power pulses achievable with commercial pulse sequences, gases in millimeter size quartz tubes in a phantom were ignited at the frequency of the RF pulses. This was performed using the RF body coil and the quadrature transmit/receive head coil, both within the clinical specific absorption rate (SAR) limits. Better ignition could be achieved with customized pulse sequences with longer RF pulse duration. Up to 1.4 Kilowatt pulses could be applied, without excessively heating the phantom. The pulse frequency was changed from 1000 milliseconds to 500 ms, 250 ms, 100 ms, 50 ms and 35 ms.

Frequency Hopping has been demonstrated to activate plasma emission in gas containers at a lower power than otherwise possible. In this mode of operation, the operational frequency is switched between a first and second frequency regime (both of which show a good match (minimum impedance mismatch). By rapidly switching frequencies from one frequency regime leading to another frequency regime of good match lower power plasma emission was demonstrated. Moreover, this effect was enhanced in the presence of a magnetic field (especially near or inside an MRI).

High Power Pulse Modulation by way of a power-modulated signal with very high power and very short pulse width is a way to generate high field strengths with sufficiently low average power to activate plasma emission without overheating tissue. Such pulse modulation techniques could work on any antenna design.

Flux transients demonstrate the ability to activate plasma emission at a lower power than otherwise possible. By rapidly moving the plasma container through the field or physically tapping the lamp, flux transients have demonstrated plasma emission at a lower power than otherwise possible. In one demonstration, when a conductive loop built into a gas container was passed through an electromagnetic field, its increased energy coupling lead to plasma ignition.

Phase Shifting/Switching demonstrate the ability to activate florescence with lower power level than otherwise possible by rapidly switching phase between adjacent or opposing antennas.

X-Ray assistance has demonstrate that, when inner walls of the gas containers are coated with a material that would generate secondary electrons upon X-Ray exposure, the secondary electrons enter into high energy excitations due to RF and/or MW energy, thereby producing lower power plasma ignitions. Higher energy excitations are possible in the presence of a magnetic field.

In one embodiment of the invention, free-standing microwave and rf receptors can be used to receive incident electromagnetic radiation (transmitted through an optically opaque medium, such as biological and/or human tissue) and generate visible or ultraviolet light. Indeed, in one embodiment of the invention, the wavelength of light generated is determined by the gas (or gasses) in the receptors. Moreover, in one embodiment of the invention, the use of one or more of gasses such as hydrogen, argon, nitrogen, xenon, ammonia, iodine vapor; mercury vapor; an organic gas, and hydrogen-nitrogen mixtures, and/or mixtures thereof not only serve to "tune" the wavelength, but are considered of assistance (especially the low ionization potential gasses such as iodine vapor; mercury vapor; and organic gasses) for ignition of the plasma. Low ionization materials such as sodium and barium strontium oxide have shown a propensity for assisting in plasma initiation and maintenance.

Moreover, in one embodiment of the invention, the gas container can include structures which provide a source of electrons (from electric field induced emission, for example) into the gas of the containment to assist in ionization. Thus, the gas container can include at least one of a carbon structure, a carbon nanotube, a single wall carbon nanotube, a double wall carbon nanotube, grapheme, and metal materials made of aluminum or copper.

This work has realized that macroscopic and microscopic gas containing upconverter structures can be used in various applications and particularly medical applications for light therapy or light treatments inside a living animal or person.

In one example, macroscopic or a plurality of microscopic gas containing up converter structures of the invention can be mounted on catheters for insertion into a patient. Catheters have been and are widely used in medical applications. Catheters have been particularly useful in treating for example enlarged prostates by microwave treatment. In this medical application, a catheter is inserted into the urethra of the man to be treated until an inflatable balloon, which is located at the front insertion end of the catheter, is positioned in the urinary bladder. The balloon is then inflated and held stationary within the bladder. Subsequently, in this prior microwave treatment, a microwave antenna was inserted through an inner lumen of the catheter until it is located adjacent to the prostate. The antenna was arranged at the front end of an antenna cable, while the other end of the cable, which protruded from the catheter, was connected to a microwave energy source.

Here, the need to internally supply microwave power through the inner lumen of the catheter imposes restrictions on the catheter, the space within the catheter, and the power transfer to the end of the catheter. Furthermore, any stray microwave radiation would locally heat the prostate. Catheters for the conventional microwave treatment of prostate frequently used a catheter tube made of polyvinylchloride (PVC) or polytetrafluoroethylene (PTFE). Such catheters are highly flexible and can form the basis for the catheter of this embodiment of the invention. Typically, a catheter tube has a wall thickness of between 0.1 and 0.3 mm. The outer catheter layer can be made microporous PTFE which has good padding properties. This is advantageous when the catheter is moved through bends of the body such as the urethra. Furthermore, microporous PTFE has very good sliding properties.

The outer layer of the catheter of this invention can be made from a tape of microporous PTFE which is wrapped around the carrier tube, or a separate tube of microporous PTFE which is applied over the carrier tube or can be extruded onto the carrier tube, either simultaneously or subsequently.

Figure 78B:
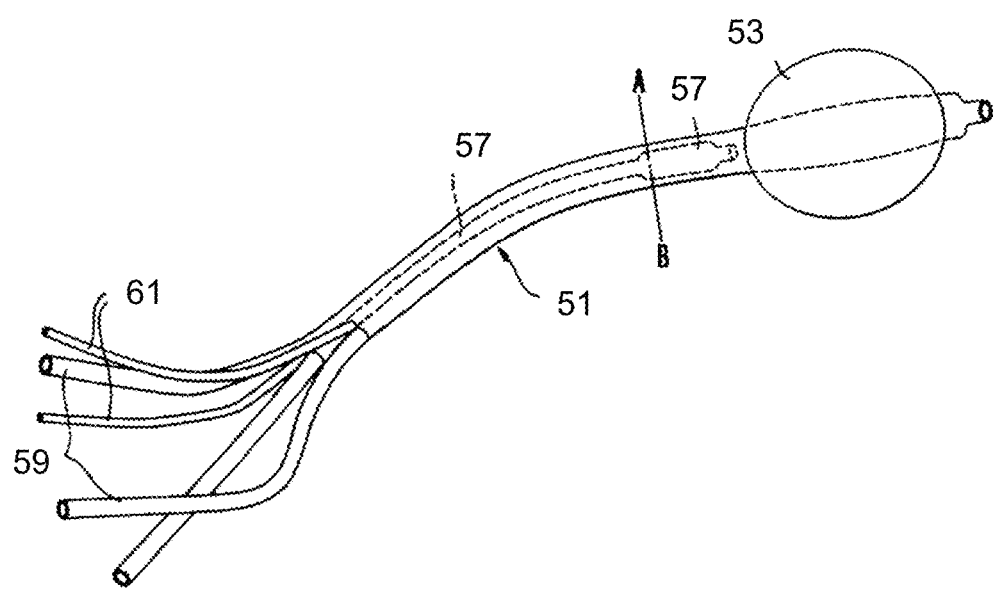
FIG. 78B is a schematic of a catheter of the invention having a gas container upconverter at or near the distal end of the catheter.

FIG. 78B is a schematic of catheter 51 of the invention having a gas container upconverter 57 at or near the distal end of the catheter. At the end of the catheter which is inserted first, there can be disposed an inflatable balloon 53 which is shown in the inflated state in FIG. 78. At the end of the catheter 51 opposite to the insertion end, the gas container upconverter 57 is disposed. Cooling water tubes 59 and sensor lines 61 can also be also disposed in the catheter 51.

In this arrangement, the gas container upconverter 57 can be positioned inside the human body in a vicinity of the organ to be treated. A human person having the catheter with gas container upconverter 57 in place can then (or beforehand) be positioned in an NMR unit, as described above. Powering of the NMR then activates the ionizable gas in gas container upconverter 57 producing UV or visible light for phototherapy or light treatments of the organ. Appropriate phototherapies are described in U.S. patent application Ser. No. 12/389,946, PCT/US2009/050514 application, U.S. provisional application 61/171,158, U.S. patent application Ser. No. 12/417,779, U.S. patent application Ser. No. 12/725,108, the entire contents of which are incorporated herein by reference. A discussion of various phototherapies useful in this invention by way of light from gas containing upconverter structures of this invention is included below.

In general, numerous microwave and RF applicators have been demonstrated by one or more of the inventors. Microwave applicators operating at frequencies like 433 and 915 MHz typically heat superficial tissue regions within about 3-4 cm of skin surface. Thus, a rapidly attenuating field penetrates somewhat deeper, but the primary field and thus effective heating is limited to about 3-4 cm. Radiofrequency fields from about 70-200 MHz have much longer wavelength and can penetrate deeper into tissue under an antenna. While still attenuating with depth, it is possible to obtain a local maximum (focal hot spot) as deep as the body axis by aiming multiple antennas with correct phase relationship to have fields add at depth. In one embodiment of the invention, microwave and RF applicators as discussed above and elaborated on below can be used in the invention to excite the gasses in the gas containing upconverter structures of the invention.

Of interest here are applicators already available from hyperthermia medical treatment apparatus. The following papers incorporated herein by reference in their entirety provide descriptions of applicators suitable for the invention and provide descriptions of their configuration and operating frequencies: 1) Lee E R. Electromagnetic superficial heating technology. In: Seegenschmiedt M H, Fessenden P, Vernon C C, editors. Thermo-radiotherapy and Thermo-chemotherapy. Berlin, Heidelberg: Springer-Verlag; 1995. p. 193-217; 2) Hand J W, Hind A J. A review of microwave and RF applicators for localized hyperthermia. In: Hand J W, James J R, editors. Physical Techniques in Clinical Hyperthermia. Letchworth, Hertfordshire, England: Research Studies Press; 1986. p. 98-148; 3) Stauffer P R. Thermal therapy techniques for skin and superficial tissue disease. In: Ryan T P, editor. A critical review, matching the energy source to the clinical need. Bellingham Wash.: SPIE Optical Engineering Press; 2000. p. 327-67; 4) Stauffer P R. Evolving technology for thermal therapy of cancer. Int J Hyperthermia. 2005; 21(8):731-44; 5) Stauffer P R, Diederich C J, Pouliot J. Thermal therapy for cancer. In: Thomadsen B, Rivard M, Butler W, editors. Brachytherapy Physics, Second Edition, Joint AAPM/ABS Summer School, Med Phys Monograph No 312005. p. 901-32; 6) Sneed P K, Stauffer P R, Li G, Sun X, Myerson R. Hyperthermia. In: Phillips T, Hoppe R, Roach M, editors. Textbook of Radiation Oncology Third Edition. Philadelphia: Elsevier Saunders Co; 2010. p. 1564-93.

For both radiofrequency (RF) and microwave (MW) radiation, absorbed power density decreases exponentially with depth in tissue. In order to select the optimum frequency of EM field for depositing energy in a tumor, the critical factors are tumor size and depth below the tissue surface relative to EM wavelength, and proximity to adjacent critical normal tissue structures. For the practical range of frequencies used in hyperthermia and applicable here in the invention for plasma excitation from 1-1000 MHz, the wavelengths in soft tissue vary from about 4.5 cm at 1000 MHz up to 2 m at the lower RF frequencies. The maximum spatial resolution of power deposition (focal spot size) is approximately one half this wavelength. The effective heating depth may decrease further as a result of power deposition peaks in the spatially complex antenna near field, and heterogeneities of tissue properties which increase reflection and refraction perturbations of the EM field at tissue interfaces. In general, it may be expected that the upper microwave frequencies may be expected to provide localized heating of skin and surface tissues while the lower RF frequencies will heat larger and deeper regions of the body.

Microwave waveguide: The most basic EM applicator used for heating superficial tissue is the microwave waveguide with single linearly polarized monopole feed. Aperture size is generally designed with one side at least a half wavelength long. The interior is often filled or lined with high dielectric constant material to reduce the effective wavelength in the waveguide structure. Electromagnetic horn applicators are a close variant of the waveguide applicator, with tapered openings to control the divergence of radiated field. In general, horns provide somewhat larger effective field size than equivalent size waveguides. Flared horns with the two sides parallel to the electric field replaced with low εr Lucite to expand the SAR distribution in the H-plane have been used. A six (6) element array of Lucite Cone Applicators (LCA) has demonstrated uniformity of heating. The LCA applicators have been used in up to 3H2 arrays, treating surface areas up to 600 cm². The following papers incorporated herein by reference in their entirety provide descriptions of microwave waveguides suitable for the invention and provide descriptions of their configuration and operating frequencies: 1) Rietveld P J M, Van Putten W L J, Van Der Zee J, Van Rhoon G C. Comparison of the clinical effectiveness of the 433 MHz Lucite cone applicator with that of a conventional waveguide applicator in applications of superficial hyperthermia. International Journal of Radiation Oncology Biology Physics. 1999; 43(3):681-7; 2) Van Rhoon G C, Rietveld P J M, Van Der Zee J. A 433 MHz Lucite cone waveguide applicator for superficial hyperthermia. Int J Hyperthermia. 1998; 14(1):13-27' 3) Chan K W, McDougall J A, Chou C K. FDTD simulations of Clini-Therm applicators on inhomogeneous planar tissue models. Int J Hyperthermia. 1995; 11(6):809-20; 4) Straube W L, Myerson R J, Emami B, Leybovich L B. SAR patterns of external 915 MHz microwave applicators. Int J Hyperthermia. 1990; 6(3):665-70; 5) Turner P F, Kumar L. Computer solution for applicator heating patterns. National Cancer Institute Monograph. 1982; 61:521-3.

Conformal Antennas—For heating large areas of superficial disease such as chest wall recurrence of breast carcinoma, large multi-element microwave arrays are generally preferred to uniformly cover large contoured regions of the torso. Examples include the Dual Concentric Conductor based Conformal Microwave Array (CMA) which was tested in this preliminary exercise. Heating is typically <2-3 cm depth. Another example is a 915 MHz sixteen (16) element planar waveguide array applicator Microtherm 1000 (Labthermics Technologies Corp., Champaign Ill.) which was shown suitable for treating superficial tissue regions up to 13H13H1.5 cm. Another array heating approach makes use of inductive loop coupled Current Sheet Applicators (CSA) which are smaller (7.3H5.9H3.3 cm) and lighter in weight than typical waveguide applicators and can be connected together in hinged flexible arrays for contoured surfaces A 433 MHz four element CSA array demonstrated more uniform and higher overall temperature distributions than possible with earlier devices, with tumor heating temperatures of 41.0±1.5° C. and 42.2±1.4° C., respectively obtained.

Another example is a printed circuit board (PCB) based microstrip antenna technology have received attention due to the ability to form almost arbitrarily large arrays from relatively low cost, lightweight and flexible PCB material. Microstrip patches, slot apertures, and spiral microstrip antennas have been used. Microstrip applicators appear best suited to tumors that extend up to and include the tissue surface rather than those located beneath a layer of high resistivity fat. Contact Flexible Microstrip Applicators (CFMA) are available in several different sizes that can be used at frequencies ranging from 40 MHz to 915 MHz. The applicators have been shown to produce large effective field sizes up to 400 cm² with relatively uniform SAR patterns Conformal Microwave Array (CMA) applicators consisting of an array of square radiating apertures etched from a single layer of flexible copper foil and driven non-coherently at 915 MHz have been used. Subsequently, radiation patterns from the square annular slot Dual Concentric Conductor (DCC) apertures were analyzed theoretically with Finite Difference Time Domain (FDTD) simulations for a variety of aperture sizes and design configurations, and the simulations verified with measurements of SAR in muscle equivalent phantoms.

The following papers incorporated herein by reference in their entirety provide descriptions of conformal applicators suitable for the invention and provide descriptions of their configuration and operating frequencies: 1) Gelvich E A, Mazokhin V N. Contact flexible microstrip applicators (CFMA) in a range from microwaves up to short waves. IEEE Trans Biomed Eng. 2002; 49:1015-23; 2) Lee E R, Wilsey T R, Tarczy-Hornoch P, Kapp D S, Fessenden P, Lohrbach A W, et al. Body conformable 915 MHz microstrip array applicators for large surface area hyperthermia. IEEE Trans Biomed Eng. 1992; 39(5):470-83; and 3) Stauffer P, Maccarini P, Arunachalam K, Craciunescu O, Diederich C, Juang T, et al. Conformal microwave array (CMA) applicators for hyperthermia of diffuse chest wall recurrence. Int J Hyperthermia. 2010; 26(7):686-98.

Another device that can deposit energy deep in the body with a single external power source is the Coaxial TEM applicator. This device consists of a coaxial cable like structure that is large enough to place the entire patient inside a hollow 60 cm diameter "inner conductor" chamber that is filled with coupling water. With only a single 70 MHz power generator to produce an axially directed electric field, partial steering of the SAR around the body cross section is possible by shifting patient position within the 60 cm aperture cross section. Since it is desirable to both penetrate deep in the body and restrict heating to specific tumor containing regions at depth, there have been a number of electromagnetic radiating array applicators developed which are designed to steer energy deposition within the body. One such device is the four wave guide array or Matched Phased Array (MPA) system which allows custom positioning of waveguide sources on the patient surface accompanied by phase and amplitude adjustments of all four sources to steer power deposition at depth. This device has demonstrated the ability to generate low to moderate temperatures (40-41° C.) in deep tumors in clinical studies since 1987.

Radiofrequency Phased-Array—Deep heating antenna arrays have been constructed from concentric ring arrays of dipole radiators mounted on a plexiglass cylinder or elliptical shape form. Arrays with 8 dipoles connected in pairs to four RF power amplifiers have been constructed in annular phased arrays for arms, legs and pelvis and more recently into Magnetic Resonance Thermal Imaging compatible arrays with one ring or three rings of 4 dipole pairs. In one example, an Annular Phased Array System (APAS) having 4 amplifiers driving 8 dipole antennas positioned in a fixed pattern around the patient circumference and coupled with deionized water bolus has been developed by BSD Medical Corp. Subsequent development produced the Sigma-60 applicator operating providing increased flexibility of control from four independent phase and amplitude controls for the 8 dipoles as well as a more patient friendly interface, as seen in FIG. 15. Improved localization has been reported for this device as well as clinical utility in a number of deep tissue sites. BSD Medical Corp extended its product line with a new series of Sigma-Eye applicators operating at 100 MHz, which provide axial as well as lateral steering of power deposition with three rings of 8 dipole antennas each. This later configuration has sufficient adjustability that an MRI-compatible heat applicator system along with an MRI magnet that facilitates pre-treatment planning scans of the patient in the intended treatment configuration. Moreover, associated software is available to non-invasively monitor deep tissue temperature and physiologic changes during heat treatment is available.

In one embodiment of the invention, the temperature surrounding the gas containers can be noninvasively measured using magnetic resonance thermometry (MRT), which can produce 2D images of the temperature changes in the tissue surrounding the lamps. Several methods have been developed for performing MRT in vivo, which can then be used to determine the heat distribution in the body caused by RF and argon tube heating. These methods can be applied to a number of different applicators and regions of the body. T The following papers incorporated herein by reference in their entirety provide descriptions of magnetic resonance thermometry (MRT) suitable for the invention: 1) Carter, D. L., J. R. MacFall, S. T. Clegg, X. Wan, D. M. Prescott, H. C. Charles, and T. V. Samulski, Magnetic resonance thermometry during hyperthermia for human high-grade sarcoma. Int J Radiat Oncol Biol Phys, 1998. 40(4): p. 815-22; 2) Wyatt C R., Soher, B J., Maccarrini, P., Stauffer, P., MacFall, J R. Hyperthermia MRI Temperature Measurement: Evaluation of Measurement Stabilization Strategies for Extremity and Breast Tumors. International Journal of Hyperthermia, 25(6): 422-433. D01:10.1080/02656730903133762.

The following papers incorporated herein by reference in their entirety provide descriptions of phased array applicators suitable for the invention and provide descriptions of their configuration and operating frequencies: 1) Wust P, Beck R, Berger J, Fahling H, Seebass M, Wlodarczyk W, et al. Electric field distributions in a phased-array applicator with 12 channels: Measurements and numerical simulations. Med Phys. 2000; 27(11):2565-79; 2) Turner P, Schaefermeyer T, editors. Sigma Eye EM phased array and the BSD-2000 3D system. 16th Annual Meeting of the European Society for Hyperthermic Oncolgy; 1999; Berlin: Humbolt University; 3) Kato H, Uchida N, Kasai T, Ishida T. A new applicator utilizing distributed electrodes for hyperthermia: a theoretical approach. Int J Hyperthermia. 1995; 11(2):287-94; and 4) Kato H, Hand J W, Michael M V, Furukawa M, Yamamoto O, Ishida T. Control of specific absorption rate distribution using capacitive electrodes and inductive aperture-type applicators: implications for radiofrequency hyperthermia. IEEE Trans Biomed Eng. 1991; 38(7):644.

In this invention, these applicators (developed for hyperthermia) are usable to excite plasmas in the gas containing upconverter structures of the invention, thereby providing the capability to leverage this pre-existing technology base to provide photodynamic therapy in addition to, in conjunction with, or separate from a hyperthermia treatment.

A programmed Sigma-Eye applicator has been used with multiple antennas placed concentrically around a tissue load or phantom with the gas containing upconverter structures of the invention placed inside. The fields from each antenna are combined and there are regions of constructive phase addition and regions of destructive interference. The array is considered focused where the fields add constructively to produce a local maximum. In the center of a perfectly circular array with N antennas of equal power and phase, the field in the central focus is N2 as much as it would be from one antenna alone. If the phase angles are shifted appropriately to launch the wave from some antennas later than from other antennas, then the local field maximum will be shifted closer to the antennas with phase delay. By rapidly shifting the relative phase of all antennas between fixed patterns that produce local maximums in different locations of the central tissue load, the hot spot can be shifted around inside the tissue volume allowing higher power and field strengths but spreading the average power and heating around a larger volume. This effect was seen in the ability to selectively ignite plasmas in separate gas containers in separate regions of the phantom. Plasma emission can thus be achieved over larger areas for same increase in temperature.

In one embodiment of the invention, a Meta-material Lens Applicator can be used. This kind of applicator represents a new class of metamaterial antennas with great potential to increase effective penetration and even produce a minor focus of microwave energy at depth. The technology has demonstrated effective fields at depth using convenient low profile lightweight and power efficient antennas driven at 433 and 915 MHz. Maximum penetration and ability to phase focus is not yet determined but may increase to 4-6 cm at 433-915 MHz and more with phase addition of multiple antenna arrays. These antennas are described by Maccarini P, Aknine G, Wyatt C, Stauffer: P. in Characterization of the First Conformal Metamaterial Lens Applicator (CMLA) for Hyperthermia,. European Society Hyperthermic Oncology; Rotterdam 2010, the entire contents of which are incorporated herein by reference.

In one embodiment of the invention, a parabolic antenna could be used to produce a localized high intensity region for plasma ignition in the gas containing upconverter structures of the invention.

Photodynamic Therapy (PDT)

PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in Biomedical Photonics Handbook, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

$PA + h\nu \rightarrow {}^1PA^*(S)$ Excitation ${}^1PA^*(S) \rightarrow {}^3PA^*(T)$ Intersystem crossing for singlet to triplet state ${}^3PA^*(T) + O^*_2 \rightarrow {}^1O^*_2 + PA$ Energy transfer from the drug to singlet oxygen where PA=photo-active drug at the ground state; ${}^1PA^*(S)$ =excited singlet state; ${}^3PA^*(T)$=excited triplet state; ${}^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a photosensitizer to be clinically useful. Pharmacokinetics, pharmacodynamics, stability in vivo and acceptable toxicity play critical roles as well [Henderson B W, Gollnick S O, "Mechanistic Principles of Photodynamic Therapy", in Biomedical Photonics Handbook, Vo-Dinh T, Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitiser (PS) initiates chemical reactions that lead to the direct or indirect production of cytotoxic species such as radicals and singlet oxygen. The reaction of the cytotoxic species with subcellular organelles and macromolecules (proteins, DNA, etc) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "Synthetic Strategies in designing Porphyrin-Based Photosensitizers", in Biomedical Photonics Handbook, Vo-Dinh T., Ed., CRC Press, Boca Raton Fla. (2003)], chlorines, phthalocyanine, and naphthalocyanine have been investigated.

PDT retains several photosensitizers in tumors for a longer time than in normal tissues, thus offering potential improvement in treatment selectivity. See Corner C., "Determination of [3H]— and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favorable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Photoactivation Treatments

For the treatment of cell proliferation disorders, an initiation energy source (e.g, light from the gas containing up converter structures of the invention) can provide an initiation energy that activates an activatable pharmaceutical agent to treat target cells within a subject. In one embodiment, the initiation energy source is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject.

Although not intending to be bound by any particular theory or be otherwise limited in any way, the following theoretical discussion of scientific principles and definitions are provided to help the reader gain an understanding and appreciation of the present invention. As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable pharmaceutical agent" (alternatively called a "photoactive agent" or PA) is an agent that normally exists in an inactive state in the absence of an activation signal. When the agent is activated by a matching activation signal under activating conditions, it is capable of effecting the desired pharmacological effect on a target cell (i.e. preferably a predetermined cellular change).

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation (e.g, UV-A light from the gas containing up converter structures of the invention). Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic (electromagnetic) energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment can be by those methods described in U.S. application Ser. No. 11/935,655, filed Nov. 6, 2007 (incorporated by reference above), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; a nanostructure, or combinations thereof; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention. Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 lists some photoactivatable molecules capable of being photoactivated to induce an auto vaccine effect.

TABLE 1

SSET and TTET rate constants for bichromophoric peptides

| Compound | $\lambda_{ex}$ (nm) | $E_{SSET}$ | $k_s$ of donor (s⁻¹) | $k_{SSET}$ (s⁻¹) | $k_{SSET}$ (s⁻¹) (Average) | $R_0$ (Å) | $R$ (Å) | $R_{model}$ (Å) (Average) | $E_{TTET}$ | $k_{TTET}$ (s⁻¹) |
|---|---|---|---|---|---|---|---|---|---|---|
| 1B | 224 | 96.3 | $9.5 \times 10^3$ | $2.44 \times 10^8$ | $1.87 \times 10^3$ | 14.7 | 9 | 9.5 | | |
|  | 266 | 95 | | $1.8 \times 10^8$ | | | | | 2.5 | $5 \times 10^2$ |
|  | 280 | 94 | | $1.36 \times 10^8$ | | | | | | |
| 1A | 224 | 80 | $9.5 \times 10^6$ | $3.8 \times 10^7$ | $3.67 \times 10^7$ | 14.7 | 11.8 | 14.1 | | |
|  | 266 | 79 | | $3.6 \times 10^7$ | | | | | 2 | $3.6 \times 10^2$ |
|  | 280 | 79 | | $3.6 \times 10^7$ | | | | | | |
| 2B | 224 | 77 | $9.5 \times 10^5$ | $3.1 \times 10^7$ | $3.9 \times 10^7$ | 14.7 | 11.9 | 6.5 | | |
|  | 266 | 81 | | $3.9 \times 10^7$ | | | | | 32 | $9.4 \times 10^3$ |
|  | 280 | 83 | | $4.7 \times 10^7$ | | | | | | |
| 2A | 224 | 69 | $9.5 \times 10^5$ | $2.1 \times 10^7$ | $3 \times 10^7$ | 14.7 | 12.2 | 8.1 | 74.3 | $5.7 \times 10^4$ |
|  | 266 | 80 | | $3.7 \times 10^7$ | | | | | | |
|  | 280 | 77 | | $3.2 \times 10^7$ | | | | | | |

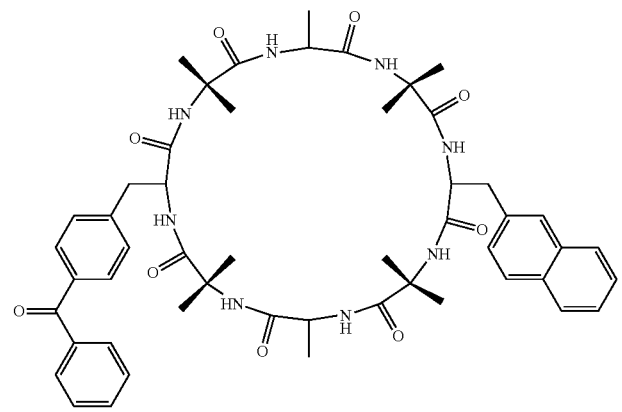

1A

TABLE 1-continued
SSET and TTET rate constants for bichromophoric peptides
| Compound | $\lambda_{ex}$ (nm) | $E_{SSET}$ | $k_s$ of donor (s$^{-1}$) | $k_{SSET}$ (s$^{-1}$) | $k_{SSET}$ (s$^{-1}$) (Average) | $R_0$ (Å) | $R$ (Å) | $R_{model}$(Å) (Average) | $E_{TTET}$ | $k_{TTET}$ (s$^{-1}$) |
|---|---|---|---|---|---|---|---|---|---|---|
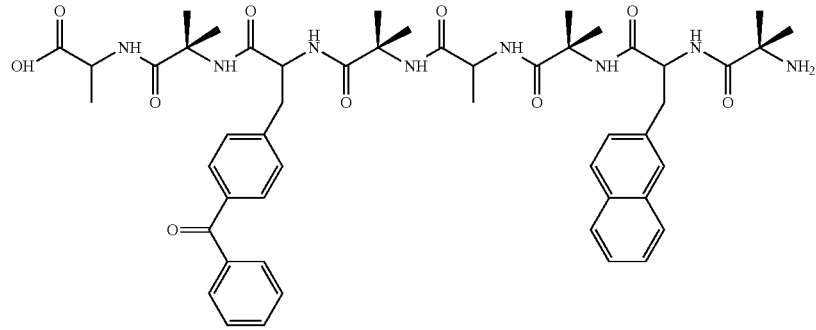
1B
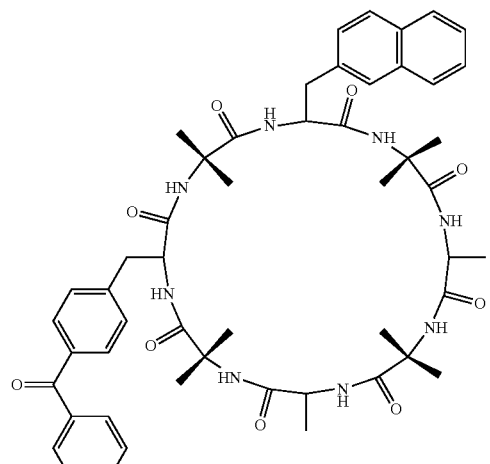
2A
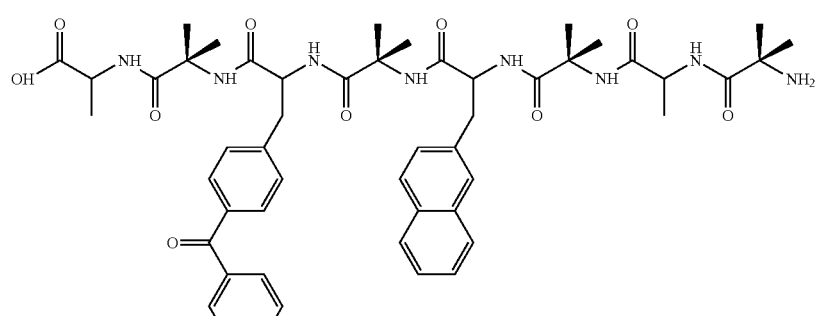
2B Table 2 lists some additional endogenous photoactivatable molecules.

TABLE 2

Biocompatible, endogenous fluorophore emitters.

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucelotide | 450 | 535 |
| reduced nicotinamide dinucelotide | 290, 351 | 440, 460 |
| reduced nicolinamide dinucelotide phosphate | 336 | 464 |
| Vitamins: | | |
| Vitamins A | 327 | 510 |
| Vitamins K | 335 | 480 |
| Vitamins D | 390 | 480 |
| Vitamins $B_5$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Cerold | 340-395 | 430-460, 540 |
| Porphyrins | 400-450 | 630, 690 |

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

Energy from light emitted from the gas containing up converter structures of the invention may be transferred from one molecule to another (intermolecular transfer) or from one part of a molecule to another part of the same molecule (intramolecular transfer). For example, the receives electromagnetic energy may be converted into thermal energy. Energy transfer processes are also referred to as molecular excitation.

Additionally, energy modulation agents may be included in the medium to be treated. The energy modulation agents may upon receiving of light from the gas containing up converter structures re-emit a light specific to a desired photo-driven reaction. Energy modulation agents (reacting to the light from the gas containing up converter structures) can have a very short energy retention time (on the order of fs-ns, e.g. fluorescent molecules) whereas others may have a very long half-life (on the order of seconds to hours, e.g. luminescent inorganic molecules or phosphorescent molecules). Suitable energy modulation agents include, but are not limited to, a biocompatible metal nanoparticle, metal coated with a biocompatible outer layer, a chemiluminescent molecule whose rate of luminescence is increased by microwave activation, fluorescing dye molecule, gold nanoparticle, a water soluble quantum dot encapsulated by polyamidoamine dendrimers, a luciferase, a biocompatible phosphorescent molecule, a biocompatible fluorescent molecule, a biocompatible scattering molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent or the gas containing up converter structures of the invention may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the UV-A emitting source in a specific target tumor.

Additionally, the energy modulation agent can be used alone or as a series of two or more energy modulation agents wherein the energy modulation agents provide an energy cascade from the light of the gas containing up converter structures. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

In general, photoactivatable agents may be stimulated by light of the gas containing up converter structures, leading to subsequent irradiation, resonance energy transfer, exciton migration, electron injection, or chemical reaction, to an activated energy state that is capable of effecting the predetermined cellular change desired. In a one embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the invention administers a photoactivatable agent to a patient, stimulates the photoactivatable agent by light of the gas containing up converter structures to induce cell damage, and generates an auto vaccine effect. In one further preferred embodiment, the photoactivatable agent is stimulated via a resonance energy transfer.

One advantage is that multiple wavelengths of emitted radiation from the light of the gas containing up converter structures may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

In another embodiment, the invention includes the administration of the activatable pharmaceutical agent, along with administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. The administration of the activatable pharmaceutical agent and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

In the PEPST embodiment of the present invention, the present invention is significantly different from the phototherapy technique often referred to as Photo-thermal Therapy (PTT). To illustrate the difference between the present invention PEPST, a form of photospectral therapy (PST) and the PTT technique, the photochemical processes involved in PST and PPT is discussed below.

When drug molecules absorb excitation light, electrons undergo transitions from the ground state to an excited electronic state. The electronic excitation energy subsequently relaxes via radiative emission (luminescence) and radiation-less decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the $S_n$ state deactivate rapidly, within $10^{-3}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ via an internal conversion (IC) process. IC processes are transitions between states of the same multiplicity. The molecule subsequently deactivates to the lowest vibronic levels of $S_{n-1}$ via a VR process. By a succession of IC processes immediately followed by VR processes, the molecule deactivates rapidly to the ground state $S_L$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of laser energy needed to induce local damage of the diseased cells, making the therapy method less invasive. A problem associated with the use of dye molecules is their photobleaching under laser irradiation. Therefore, nanoparticles such as gold nanoparticles and nanoshells have recently been used. The promising role of nanoshells in photothermal therapy of tumors has been demonstrated [Hirsch, L. R., Stafford, R. J., Bankson, J. A., Sershen, S. R., Rivera, B., Price, R. E., Hazle, J. D., Halas, N. J., and West, J. L., Nanoshell-mediated near-infrared thermal therapy of tumors under magnetic resonance guidance. PNAS, 2003. 100(23): p. 13549-13554].

The PST method of the invention, however, is based on the radiative processes (fluorescence, phosphorescence, luminescence, Raman, etc) whereas the PTT method is based on the radiationless processes (IC, VR and heat conversion) in molecules.

Various Light-Activated Pharmaceuticals

It has been reported that ferritin could be internalized by some tumor tissues, and the internalization was associated with the membrane-specific receptors [S. Fargion, P. Arosio, A. L. Fracanzoni, V. Cislaghi, S. Levi, A. Cozzi, A Piperno and A. G. Firelli, *Blood*, 1988, 71, 753-757; P. C. Adams, L. W. Powell and J. W. Halliday, *Hepatology*, 1988, 8, 719-721]. Previous studies have shown that ferritin-binding sites and the endocytosis of ferritin have been identified in neoplastic cells [M. S. Bretscher and J. N. Thomson, *EMBO J.*, 1983, 2, 599-603]. Ferritin receptors have the potential for use in the delivery of anticancer drugs into the brain [S. W. Hulet, S. Powers and J. R. Connor, *J Neurol. Sci.*, 1999, 165, 48-55]. In one embodiment, the invention uses ferritin or apoferritin to both encapsulate PA and energy modulation agent-PA systems and also target tumor cells selectively for enhanced drug delivery and subsequent phototherapy. In this case, no additional bioreactors are needed.

The photoactive drug molecules can be given to a patient by oral ingestion, skin application, or by intravenous injection. The photoactive drug molecules drugs travel through the blood stream inside the body towards the targeted tumor (either via passive or active targeting strategies). The invention treatment may also be used for inducing an auto vaccine effect for malignant cells, including those in solid tumors. To the extent that any rapidly dividing cells or stem cells may be damaged by a systemic treatment, then it may be preferable to direct the stimulating rf, microwave, or magnetic induction energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in one embodiment of the invention, it is most preferable to avoid production of an amount of singlet oxygen that would cause cell lysis, due to its indiscriminate nature of attack, lysing both target cells and healthy cells. Accordingly, it is most preferred in the invention that the level of singlet oxygen production caused by the initiation energy used or activatable pharmaceutical agent upon activation be less than level needed to cause cell lysis.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent and plasmonics compounds and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, the entire contents of which are incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

Methods of administering agents are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located.

It will also be understood that the order of administering the different agents is not particularly limited. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of this approach is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The methods described here can be used alone or in combination with other therapies for treatment of cell proliferation disorders. Additionally, the methods described can be used, if desired, in conjunction with recent advances in chronomedicine, such as that detailed in Giacchetti et al, *Journal of Clinical Oncology*, Vol 24, No 22 (Aug. 1), 2006: pp. 3562-3569, the entire contents of which are incorporated herein by reference.

In chronomedicine, it has been found that cells suffering from certain types of disorders, such as cancer, respond better at certain times of the day than at others. Thus, chronomedicine could be used in conjunction with the present methods in order to augment the effect of the treatments of the invention.

Photobiomodulation

Another object of the invention is to treat a condition, disorder or disease in a subject using an activatable pharmaceutical agent. Exemplary conditions, disorders or diseases may include, but are not limited to, cancer, autoimmune diseases, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthrisis, joint conditions, lymph node conditions, and cognitive and behavioral conditions.

Accordingly, the invention in one embodiment provides methods utilizing the principle of energy transfer to and among molecular agents to control delivery and activation of pharmaceutically active agents such that delivery of the desired pharmacological effect is more focused, precise, and effective than the conventional techniques. Here, the energy transfer can include light from the gas containing up converter structures of the invention.

Although not intending to be bound by any particular theory or be otherwise limited in any way, the following theoretical discussion of scientific principles and definitions are provided to help the reader gain an understanding and appreciation of the present invention.

As used here, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmia and atrial fibrillation), photoangioplastic conditions (e.g., de novo atherosclerosis, restinosis), intimal hyperplasia, arteriovenous fistula, macular degeneration, psoriasis, acne, hopecia areata, portwine spots, hair removal, rheumatoid and inflammatory arthritis, joint conditions, and lymph node conditions.

As used here, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

As used here, an "energy modulation agent" refers to an agent that is capable of receiving an energy input from a source and then re-emitting a different energy to a receiving target. The energy modulation agents can be used in conjunction with gas containing up converter structures of the invention to assist in the transfer of energy from the light emitted from the gas containing up converter structures to the pharmaceutical agent or the photoactivatable agent or to the tissue being treated.

Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In various embodiments, the energy modulation agents (e.g., the gas containing up converter structures) receive RF or microwave energy and re-emits at higher energy (e.g. UV-A, UV-B, visible). In various embodiments, the energy modulation agents receive higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more other energy modulation agents wherein the energy modulation agents provide an energy cascade. Thus, the first energy modulation agent in the cascade will absorb the activation energy, convert it to a different energy which is then absorbed by the second energy modulation agent in the cascade, and so forth until the end of the cascade is reached with the final energy modulation agent in the cascade emitting the energy necessary to activate the activatable pharmaceutical agent.

Signals that may be used to activate a corresponding agent may include, but are not limited to, photons of specific wavelengths (e.g. x-rays, ultraviolet, or visible light), electromagnetic energy (e.g. radio or microwave), thermal energy, acoustic energy, or any combination thereof.

Activation of the agent may be as simple as delivering the signal to the agent or may further premise on a set of activation conditions. For example, an activatable pharmaceutical agent, such as a photosensitizer, may be activated by UV-A radiation from the gas containing up converter structures of the invention. Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

The initiation energy source can be any energy source capable of providing energy at a level sufficient to cause cellular changes directly or via a modulation agent which transfer the initiation energy to energy capable of causing the predetermined cellular changes. Also, the initiation energy source can be any energy source capable of providing energy at a level sufficient activate the activatable agent directly, or to provide the energy to a modulation agent with the input needed to emit the activation energy for the activatable agent (indirect activation). In one embodiment, the initiation energy is capable of penetrating completely through the subject. Within the context of the invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, UV light, visible light, IR radiation, x-rays, gamma rays, electron beams, microwaves and radio waves.

An additional embodiment of the invention is to provide a method for treatment of a condition, disease or disorder by the in-situ generation of energy in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to, chemical reaction such as chemiluminescence, or by conversion of an energy applied to the subject externally, which is converted in-situ to a different energy (of lower or higher energy than that applied), through the use of one or more energy modulation agents.

A further embodiment of the invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying an initiation energy which, directly or indirectly, activates the pharmaceutical agent. As noted elsewhere in this application, this initiation energy can be of any type, so long as it can be converted to an energy suitable for activating the pharmaceutical compound. In addition to applying this initiation energy, in this embodiment of the present invention, an energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the present invention methods to enhance the onset of apoptosis.

In one embodiment, heat can be generated by any desired manner. Preferably, the heat can be generated using the application of microwaves or NIR energy to the target structure or by the use of use of nanoparticles of metal or having metal shells. Heat can also be generated by the absorption of light from the gas containing up converter structures of the invention. Alternatively, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Natarajan A et al.: Thermal dosimetry predictive of efficacy of 111In-ChL6 NPAMF-induced thermoablative therapy for human breast cancer in mice. J. Nucl. Med.48(3), 437-444 (2007).)

In another embodiment, the patient's own cells are removed and genetically modified to provide photonic emissions. For example, tumor or healthy cells may be removed, genetically modified to induce bioluminescence and may be reinserted at the site of the disease or condition to be treated. The modified, bioluminescent cells may be further modified to prevent further division of the cells or division of the cells only so long as a regulating agent is present.

In a further embodiment, a biocompatible emitting source, such as a fluorescing metal nanoparticle or fluorescing dye molecule or the gas containing up converter structures of the invention, is selected that emits in the UV-A band. The UV-A emitting source is directed to the site of a disease or condition. The UV-A emitting source may be directed to the site of the disease or condition by systemically administering the UV-A emitting source. Preferably, the UV-A emitting source is concentrated in the target site, such as by physical insertion or by conjugating the UV-A emitting molecule with a specific carrier that is capable of concentrating the UV-A emitting source in a specific target structure, as is known in the art.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. Alternatively, a phosphorescent emitting source may be used. One advantage of a phosphorescent emitting source is that the phosphorescent emitting molecules or other source may be electroactivated or photoactivated prior to insertion into a target site either by systemic administration or direct insertion into the region of the target site. Alternatively, some of these materials can be activated, with the energy being "stored" in the activated material, until emission is stimulated by application of another energy. For example, see the discussion in U.S. Pat. No. 4,705,952 (incorporated by reference in its entirety) regarding infrared-triggered phosphors.

Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

In an additional embodiment, the photoactivatable agent can be a photocaged complex having an active agent contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

In one embodiment, the use of light (e.g. light emitted from the gas containing up converter structures) for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysipologically characterization of genetically defined cell populations. Accordingly, in an additional embodiment, a light-sensitive protein is introduced into cells or live subjects via a number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump halorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence can be used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures (e.g., the gas containing upconverters of the invention) to irradiate the target structure, after exposure to the lanthanide chelate and a photoactive molecule.

In another embodiment, a biocompatible, endogenous fluorophore emitter can be selected to stimulate resonance energy transfer to a photoactivatable molecule. A biocompatible emitter (e.g. the gas containing up converter structures) with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Skin photosensitivity is a major toxicity of photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. Some additional photosensitizers have been developed to induce type I responses, directly damaging cellular structures.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Motexafin lutetium (Lutetium texaphryin) is activated by light in the near infared region (732 nm). Absorption at this wavelength has the advantage of potentially deeper penetration into tissues, compared with the amount of light used to activate other photosensitizers (FIGS. 2A and 2B). Lutetium texaphryin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation an activatable molecule. The process may be a photopheresis process or may be similar to photophoresis. While photophoresis is generally thought to be limited to photonic excitation, such as by UV-light, other forms of radiation may be used as a part of a system to activate an activatable molecule. Light emission can stimulate the activation of an activatable molecule, such as 8-MOP. In one example, light emission from the gas containing up converter structures of the invention is directed at a solid tumor and stimulates, directly or indirectly, activation of 8-MOP.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the invention.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the invention also provides methods for producing an autovaccine, including: (1) providing a population of targeted cells; (2) treating the cells ex vivo with a psoralen or a derivative thereof; (3) activating the psoralen with an initiation energy source to induce a predetermined change in a target structure in the population of the target cells; and (4) returning the treated cells back to the host to induce an autovaccine effect against the targeted cell, wherein the treated cells cause an autovaccine effect.

In another aspect, heat can be generated in the target structure from the light from the at least one gas containing up converter structure, and the heat can enhance the induction of the predetermined change. In this embodiment, the predetermined change can modify the target structure and modulate the biological activity of the target structure thus treating a condition, disorder or disease affecting the target structure.

Figure 79A:
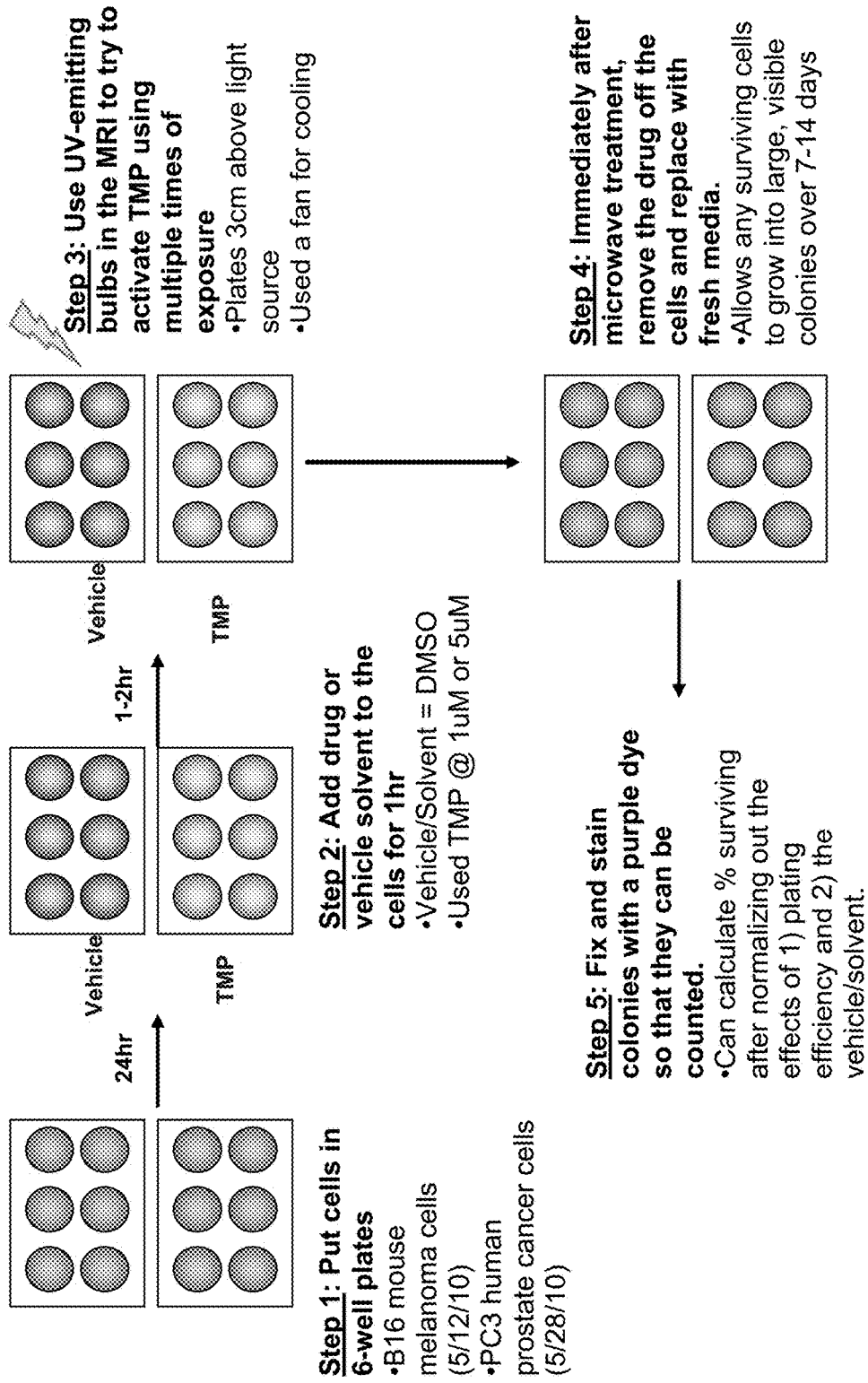
FIGS. 79A and 79B are schematic representations of the in-vitro assays and results thereof, where cells were exposed, through a phantom to mimic in-vivo penetration of the activation energy.
Figure 79B:
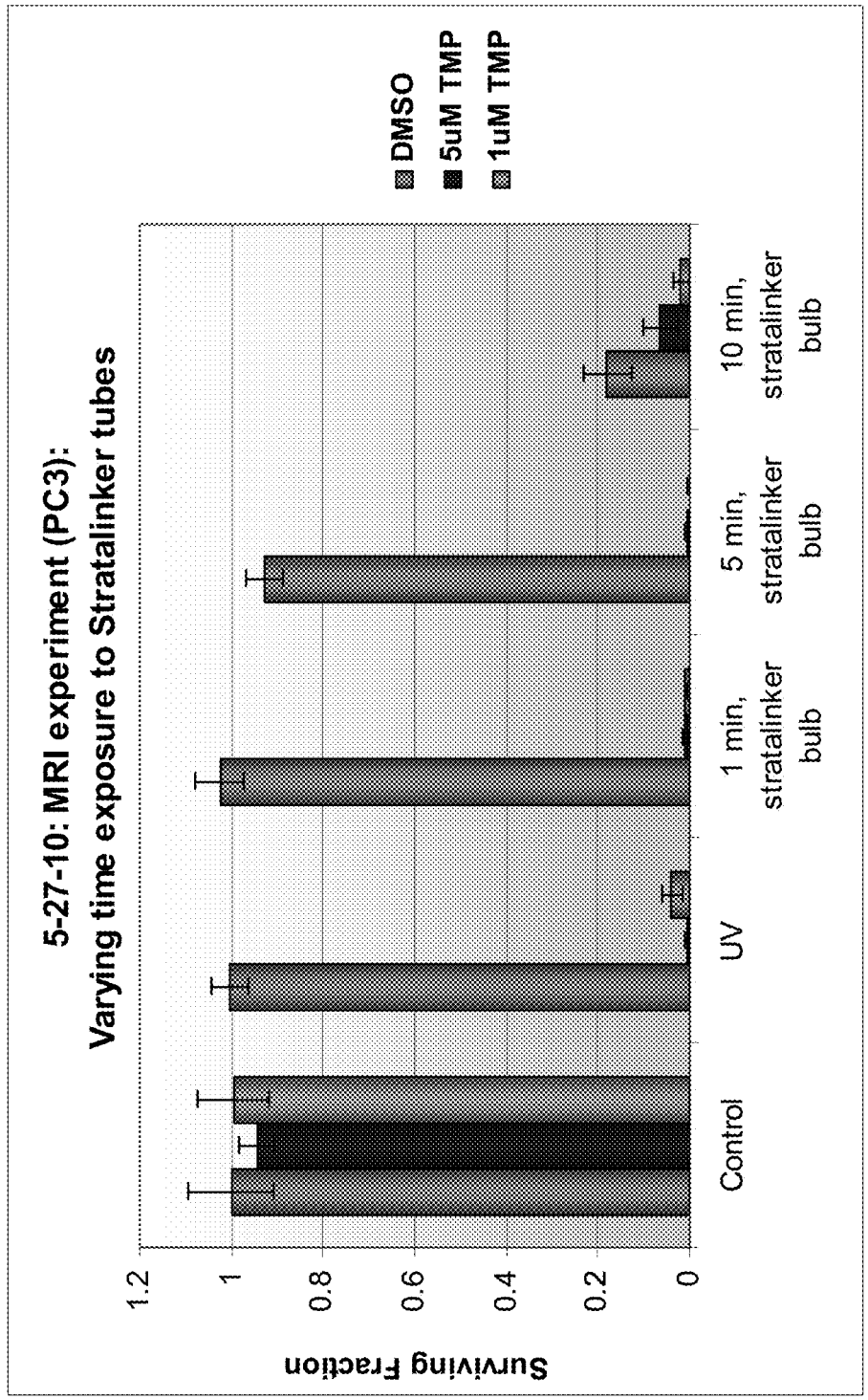

In one example of modulating biological activity, microwave driven plasma UV emission sources have been used to activate psoralen in test cultures containing B16 melanoma cancer cells or PC3 prostate tumor cells. FIG. 79A represents a schematic of the in-vitro assay depicting the clonogenic survival assays used to test if the microwaves can activate the drug TMP to kill cancer cells. Cells were exposed, through a phantom to mimic in-vivo penetration of the activation energy, to one, five or ten minutes of light generated via a microwave driven plasma UV emission. Compared to controls, significantly more cancer cells were killed with the TMP activated by plasma generated UV light. For the longer exposure times, 5 minutes and greater, some of the cell kill can likely be attributed to hyperthermia effects. FIG. 79B shows that the MRI seems very efficient with UV-stratalinker bulbs at activating TMP in PC3 cells. Even as little as a 1 min exposure was sufficient to kill almost all the cells. The decrease in survival seen in the DMSO/vehicle groups treated at 5 min and 10 min exposures is likely due to hyperthermic cell kill. The temperatures of the media post-10 min exposure ranged from 39-43° C., which is high enough to negatively effect survival.

Generalized Upconversion

The invention as described above can be viewed for its aspects of exposing an up converter to one source of light or radiation (an initiation source for exampled of a relatively low energy) and having the up converter produce light or radiation at a relatively higher energy. In one embodiment of the invention, a change is produced in a medium. The change is produced by (1) placing in a vicinity of the medium the upconverter or an otherwise upconverting structure, and (2) applying the initiation energy from an energy source through the artificial container to the medium, wherein the emitted light directly or indirectly produces the change in the medium. As explained above, for the upconverter to be placed in a vicinity of the medium to be changed (i.e. the upconverter can be within the medium, partly inside or outside the medium, or segregated outside the medium). The resultant of the upconverter being placed in a vicinity of the medium is that emitted light from the upconverter is incident on the medium, thereby directly or indirectly producing the change in the medium.

The upconverter or the otherwise upconverting structure in one embodiment is configured, upon exposure to a first wavelength $\lambda_1$ of radiation, to generate a second wavelength $\lambda_2$ of radiation having a higher energy than the first wavelength $\lambda_1$. The upconverter or the otherwise upconverting structure in one embodiment includes a metallic shell encapsulating at least a fraction of the nanoparticle.

The change produced can cure a radiation-curable medium by activating a photoinitiator in the radiation-curable medium. In this case, the emitted light can be of a wavelength appropriate to induce photo-catalytic effects such as coupling to a photo-initiator or a UV cross-linking agent to produce curing in the uncured medium. Curing or polymerization of the medium results in the formation of a partial or complete three-dimensional network. The radiation-curable medium can be cured by activating a photo-initiator in the radiation-curable medium. For way of contrast, an uncured state of a material can be considered a state at which the material exhibit liquid-like behavior with a viscosity that can be high or that can be low. The cured state typically results in a state at which the material exhibits solid-like or rubbery-like behavior or a visco-elastic behavior and can result in a state where limited flow under an applied stress is produced.

The change produced can result in a photo-stimulated change to a medium. The change produced can result in a radiation cured medium. The change produced can result in a sterilized medium. The change produced can activate a therapeutic drug.

For many applications, the initiation source may well be low frequency sources such as microwave or radio frequency irradiation, where in one embodiment of the invention localized heating of the agent enhances generation of a secondary light and in another embodiment localized field enhancements from the microwave field present in the medium enhance fluorescence, as described in "Microwave- Accelerated Metal-Enhanced Fluorescence (Mamef) With Silver Colloids in 96-Well Plates: Application to Ultra Fast and Sensitive Immunoassays, High Throughput Screening and Drug Discovery," by Aslan et al in Journal of Immunological Methods 312 (2006) 137-147.

For many applications, the initiation source is a low frequency source such as microwave or radiofrequency irradiation, where in one embodiment of the invention absorption of the microwave radiation by the gas containing up converter structures results in subsequent emission at higher energies toward the infrared, visible, and ultraviolet. The degree to which the upconverted radiation is applicable to the applications described above will be dependent on the conversion efficiencies and will be dependent on the efficiency of a recipient molecule linked to the specific metal shell/dielectric core nanostructures to absorb the upconverted light. The recipient molecule may linked to the upconverters to absorb the upconverted light.

For many applications, the initiation source may well be low frequency sources such as microwave or radio frequency irradiation, where in one embodiment of the invention the low frequency sources and even ultrasound sources interact with a component in the up converting structure to produce light for example by plasma excitation of a gas in the upconverting structure or activation of a chemical reaction in the upconverting structure.

In one embodiment, the invention utilizes microwave or radiofrequency energy to promote light generation from the upconverter or upconverting gas structure, whose light emission in turn produces a number of the physical and biological changes described above.

In one embodiment of the invention, the initiation energy source is at least one of x-rays, high energy particles, microwaves, radio waves, or magnetic induction. The x-rays and high energy particles may used as sources for generating free electrons inside the gas containing up converters of the invention. The generated free electrons ay then gain energy through the applied microwaves, radio waves, or magnetic induction fields.

In one embodiment of the invention, at least one activatable pharmaceutical agent that is capable of activation a predetermined cellular change when activated is administering to a subject. Light from the at least one upconverter interacts with the at least one activatable pharmaceutical agent to activate the activatable pharmaceutical agent in situ, thus causing the predetermined cellular change to occur in the medium of the subject.

In one embodiment of the invention, the initiation energy is capable of penetrating completely through the subject.

In one embodiment of the invention, the cell proliferation disorder is at least one member selected from the group consisting of cancer, bacterial infection, viral infection, immune rejection response, autoimmune disorders, aplastic conditions, and combinations thereof. In one embodiment of the invention, the activatable pharmaceutical agent is a photoactivatable agent. The activatable pharmaceutical agent can be selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

In one embodiment of the invention, the pharmaceutical agent is a psoralen, a coumarin, a porphyrin or a derivative thereof. In one embodiment of the invention, the pharmaceutical agent is 8-MOP or AMT. In one embodiment of the invention, the activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

In one embodiment of the invention, the activatable pharmaceutical agent is coupled to a carrier that is capable of binding to a receptor site. The carrier can be one selected from insulin, interleukin, thymopoietin or transferrin. In one embodiment of the invention, the activatable pharmaceutical agent is coupled to the carrier by a covalent bond. In one embodiment of the invention, the activatable pharmaceutical agent is coupled to the carrier by non-covalent bond. In one embodiment of the invention, the receptor site is one selected from nucleic acids of nucleated cells, antigenic sites on nucleated cells, or epitopes.

In one embodiment of the invention, the pharmaceutical agent has affinity for a target cell. In one embodiment of the invention, the activatable pharmaceutical agent is capable of being preferentially absorbed by a target cell. In one embodiment of the invention, the predetermined cellular change is apoptosis in a target cell.

In one embodiment of the invention, the activatable pharmaceutical agent causes an auto-vaccine effect in the subject that reacts with a target cell. The auto-vaccine effect can be generated in a joint or lymph node. In one embodiment of the invention, the activatable pharmaceutical agent is a DNA intercalator or a halogenated derivative thereof.

In one embodiment of the invention, light from the at least one upconverter is applied to a target structure in a subject in need of treatment, wherein the light contacts the target structure and induces a predetermined change in the target structure in situ in the medium of the subject, and the predetermined change modifies the target structure and modulates the biological activity of the target structure. In this embodiment, the initiation energy can be capable of penetrating completely through the subject. In this embodiment, the light can induce a predetermined change in the target structure with or without an energy modulator or photoactive agent.

In this embodiment, an energy modulation agent can be administered to the subject which adsorbs, intensifies or modifies the light into an energy that effects the predetermined change in the target structure. In this embodiment, the energy modulation agent can be specifically located around, on, or in the target structure. In this embodiment, the energy modulation agent can also transform the initiation electromagnetic energy into a photonic or another electromagnetic energy that effects the predetermined change in the target structure. In this embodiment, the energy modulation agent can decrease the wavelength of the initiation energy. In this embodiment, the energy modulation agent can increase the wavelength of the initiation energy. In this embodiment, the energy modulation agent(s) can include one or more members selected from a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

In this embodiment, the predetermined change can or can not result in destruction, lysis or inactivation of the target structure. In this embodiment, the predetermined change can enhance an activity of the target structure. The activity enhanced can be energy emission from the target, which then mediates, initiates or enhances a biological activity of other target structures in the subject, or of a second target structure.

In this embodiment, the target structure can be at least one of a eukaryotic cell, a prokaryotic cell, a subcellular structure. The subcellular structure can be a cell membrane, a nuclear membrane, cell nucleus, nucleic acid, mitochondria, ribosome, or other cellular organelle or component. In this embodiment, the target structure can be at least one of an extracellular structure, a virus or prion, a cellular tissue.

In this embodiment, the predetermined change can result in treatment of a condition, disorder or disease in the subject. The condition, disorder or disease can be at least one of a cancer, a disease occurring in a soft tissue and/or cartilage, a disease occurring in bone tissue, a chronic pain, an autoimmune disease, a prion, viral, bacterial, fungal, or parasitic infection, a disease characterized by varicose veins, a disease characterized by an enlarged prostate, a disease characterized by retinal injuries and other ocular diseases, a disease characterized by a behavioral, perceptional and/or cognitive disorder, or Parkinson's disease.

In this embodiment, the predetermined change can be a wound healing, an enhancement of tissue growth, nerve regeneration or sensory regeneration/restoration, reduction or removal of fat deposits (liposuction), nerve (brain) imaging and stimulation or direct control of brain cell activity with light, modulation of cell death (apoptosis), modulating cell growth and division, modulation of an activity, quantity, or number of intracellular components in a cell, or modulation of an activity, quantity, or number of extracellular components produced by, excreted by, or associated with a cell.

In this embodiment, heat can be generated in the target structure from the light from the at least one upconverter, and the heat can enhance the induction of the predetermined change. In this embodiment, the predetermined change can modify the target structure and modulate the biological activity of the target structure thus treating a condition, disorder or disease affecting the target structure.

In one embodiment, there is provided a system for energy upconversion. The system includes at least one upconverter configured in such a way that upon exposure to a first set of radiation having a wavelength $\lambda_1$ or centered around wavelength $\lambda_1$ (also known as a frequency window centered around frequency f1 or $V_1$), to generate a second set of radiation centered around wavelength $\lambda_2$ having a higher quantum energy level than the first set of radiation centered around or having wavelength $\lambda_1$. The range of frequencies in a frequency window centered on a desirable center frequency can be very narrow, and under ideal conditions, the frequency window contains only one monochromatic radiation having a single frequency.

In another embodiment, there is provided a system for producing a photostimulated reaction in a medium. The system includes at least one upconverter configured, upon exposure to a first radiation having wavelength $\lambda_1$, to generate a second radiation having wavelength $\lambda_2$ with a higher quantum energy level than the first radiation having wavelength $\lambda_1$.

Sterilization and Cold Pasteurization of Fluids

Table 1 included below shows appropriate intensities for germicidal destruction with UV light irradiation.

TABLE 1

| Germicidal energies needed to destroy Approximate intensity ($\mu W/cm^2$) required for 99% destruction of microorganisms: | |
|---|---|
| Bacteria | 10 400 |
| Protozoa (single celled organism) | 105 000 |
| Paramecium (slipper shaped protozoa) | 200 000 |
| Chlorella (unicellular fresh-water alga) | 13 000 |
| Flagellate (protozoan or alga with flagella) | 22 000 |
| Sporozoan (parasitic protozoans) | 100 000 |
| Virus | 8 000 |

In this application, it is known that ultraviolet (UV) with a wavelength of 254 nm tends to inactivate most types of microorganisms. Most juices are opaque to UV due to the high-suspended solids in them and hence the conventional UV treatment, usually used for water treatment, cannot be used for treating juices. In order to make the process efficient, a thin film reactor constructed from glass has been used with the juice flowing along the inner surface of a vertical glass tube as a thin film. See "Ultraviolet Treatment of Orange Juice" by Tran et al. published in Innovative Food Science & Emerging Technologies (Volume 5, Issue 4, December 2004, Pages 495-502), the entire contents of which are incorporated herein by reference. Tran et al. reported that decimal reduction doses required for the reconstitute orange juices (OJ; 10.5° Brix) were 87±7 and 119±17 $mJ/cm^2$ for the standard aerobic plate count (APC) and yeast and moulds, respectively. They also reported that the shelf life of fresh squeezed orange juice was extended to 5 days with a limited exposure of UV (73.8 $mJ/cm^2$). The effect of UV on the concentration of Vitamin C was investigated using both HPLC and titration methods of measurements. The degradation of Vitamin C was 17% under high UV exposure of 100 $mJ/cm^2$, which was similar to that usually found in thermal sterilization. Enzyme pectin methylesterase (PME) activity, which is the major cause of cloud loss of juices, was also measured. The energy required for UV treatment of orange juice (2.0 kW h/$m^3$) was much smaller than that required in thermal treatment (82 kW h/$m^3$). The color and pH of the juice were not significantly influenced by the treatment.

The invention described herein offers advantages over this approach in that the up converters of the invention can be placed inside fixtures such as quartz or glass (encapsulation structures) within the orange juice (or other fluid medium) and irradiated with microwave or RF power supplied to activate the encapsulated upconverter structures of the invention in the orange juice.

While discussed with regard to orange juice, any other medium to be sterilized including food products, medical products and cosmetic products could be treated using the technique of the invention described herein.

Sterilization of Blood Products

U.S. Pat. No. 6,087,141 (the entire contents of which are incorporated herein by reference) describes an ultraviolet light activated psoralen process for sterilization of blood transfusion products. The invention can be applied for the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, anthroquinones, porphycene, rubyrin, rosarin, hexaphyrin, sapphyrin, chlorophyl, chlorin, phthalocynine, porphyrazine, bacteriochlorophyl, pheophytin, texaphyrin macrocyclic-based component, or a metalated derivative thereof. These photoactivatable agents serve as recipients for the secondarily generated light induced by the down conversion or upconversion.

The recipient in this and other embodiments of the invention can include at least one of a laser dye, a fluorophore, a lumophore, or a phosphor. The laser dye can be at least one of p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2, 7-dichlorofluorescein, rhodamine 65, and rhodamin 19 perchlorate, rhodamine b, and derivatives of these laser dyes that are modified by addition the addition of appropriate substituents to modify solubility or tune their interactions within the biological milieu.

In various embodiments of the invention, the recipients are secondary agents performing other functions. Suitable secondary agents for the invention include secondary emitters, cytotoxic agents, magnetic resonance imaging (MRI) agents, positron emission tomography (PET) agents, radiological imaging agents, or photodynamic therapy (PDT) agents.

These photoactivatable agents (recipients and secondary agents) are introduced into the blood product (or a patient's blood stream). Microwave or RF power is applied to the blood product (or to the patient). The gas containing up converter structures of the invention (either included in the blood product) or in encapsulated structures generate secondary light such as UV light which activates the photoactivatable agents in the blood products. In one embodiment, the gas containing up converter structures of the invention are complexed with the X-ray down converting particles or other energy modulation agents permitting for example X-ray irradiation to also assist in this process.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof.

Waste Water Detoxification

Photocatalysis has also been used as tertiary treatment for wastewater to comply with regulatory discharge limits and to oxidize compounds that have not been oxidized in the biological treatment. Photocatalysis has been used to reduce or eliminate several pollutants (e.g., alkanes, alkenes, phenols, aromatics, pesticides) with great success. In many cases, total mineralization of the organic compounds has been observed. Several photocatalysts, such as CdS, $Fe_2O_3$, ZnO, $WO_3$, and ZnS, have been studied, but the best results have been achieved with $TiO_2$ $P_{25}$. These photocatalyst can be used in the invention.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

It is known that photocatalysis can be used for waste water reduction remediation. U.S. Pat. No. 5,118,422 (the entire contents of which are incorporated herein by reference) to Cooper et al. describe an ultraviolet driven photocatalytic post-treatment technique for purifying a water feedstock containing an oxidizable contaminant compound. In this work, the water feedstock was mixed with photocatalytic semiconductor particles (e.g., $TiO_2$, ZnO, CdS, CdSe, $SnO_2$, $SrTiO_3$, $WO_3$, $Fe_2O_3$, and $Ta_2O_5$ particles) having a particle size in the range of about 0.01 to about 1.0 micron and in an amount of between about 0.01% and about 0.2% by weight of the water. The water including the semiconductor mixture is exposed to band-gap photons for a time sufficient to affect an oxidation of the oxidizable contaminant to purify the water. Crossflow membrane filtration was used to separate the purified water from the semiconductor particles. Cooper et al. show that the organic impurity carbon content of simulated reclamation waters at nominal 40 PPM level were reduced to parts per billion using a recirculation batch reactor.

Cooper et al. identified that one important aspect of the photocatalytic process is the adsorption of the organic molecules onto the extremely large surface area presented by the finely divided powders dispersed in the water. Cooper et al. further indicated that, in photoelectrochemical applications, advantage is taken of the fact that the solid phase (a metal oxide semiconductor) is also photo-active and that the generated charge carriers are directly involved in the organic oxidation. The adsorption of the band-gap photon by the semiconductor particle results in the formation of an electron ($e^-$)/hole($h^+$) pair. Cooper et al. explain that the electrons generated in the conduction band react with solution oxygen forming the dioxygen anion ($O_{2-}$) species which subsequently undergo further reactions resulting in the production of the powerfully oxidizing hydroxyl radical species, OH. These powerful oxidants are known to oxidize organic compounds by themselves. Additionally, Cooper et al. explain that the strongly oxidizing holes generated in the valence band have sufficient energy to oxidize all organic bonds.

In the reactor of Cooper et al., turbulence is necessary in order to ensure that the waste water contaminants and the photocatalytic titania particles are exposed to the UV light. Cooper et al. explain that the most basic considerations of photocatalyst light adsorption and its relationship to convective mixing. For a 0.1 wt % photocatalyst loading, experiments have shown that 90% of the light is absorbed within 0.08 cm. This is primarily due to the large UV absorption coefficient of the photocatalyst and therefore, most of the photoelectrochemistry occurs within this illuminated region. By operating the reactor of Cooper et al. with a Reynolds number (Re) of 4000, a significant portion of the photoactive region is ensured of being within the well mixed turbulent zone.

Santos et al. have reported in "Photocatalysis as a tertiary treatment for petroleum refinery wastewaters" published in Braz. J. Chem. Eng. vol. 23, No. 4, 2006 (the entire contents of which are incorporated herein by reference), photocatalysis for tertiary treatment for petroleum refinery wastewaters which satisfactorily reduced the amount of pollutants to the level of the regulatory discharge limits and oxidized persistent compounds that had not been oxidized in the biological treatment. The treatment sequence used by the refinery (REDUC/PETROBRAS, a Brazilian oil refinery) is oil/water separation followed by a biological treatment. Although the process efficiency in terms of biological oxygen demand (BOD) removal is high, a residual and persistent COD and a phenol content remains. The refining capacity of the refinery is 41,000 $m^3$/day, generating 1,100 $m^3$/h of wastewater, which are discharged directly into the Guanabara Bay (Rio de Janeiro). Treating the residual and persistent COD remains a priority.

Santos et al. conducted a first set of experiments carried out in an open 250 mL reactor containing 60 mL of wastewater. In the second set of experiments, a Pyrex® annular reactor containing 550 mL of wastewater was used (De Paoli and Rodrigues, 1978). The reaction mixtures inside the reactors were maintained in suspension by magnetic stirring. In all experiments, air was continuously bubbled through the suspensions. A 250 W Phillips HPL-N medium pressure mercury vapor lamp (with its outer bulb removed) was used as the UV-light source (radiant flux of 108 $J \cdot m^{-2} \cdot s^{-1}$ at 8>254 nm). In one set of experiments, the lamp was positioned above the surface of the liquid at a fixed height (12 cm). In the second set, the lamp was inserted into the well. All experiments by Santos et al. were performed at 25±1° C. The catalyst concentration ranged from 0.5 to 5.5 g $L^{-1}$ and the initial pH ranged from 3.5 to 9.

In one embodiment of the invention described herein, the up converters of the invention would be placed inside quartz or glass fixtures within the waste water or would be placed on silica encapsulated structures within the waste water which, like the photocatalytic $TiO_2$, could be entrained in the waste water during the irradiation.

Upon irradiation with for example microwave or RF power activation of the gas containing upconverter structures of the invention would generate UV light in nearby presence of the photocatalytic agent. In other words for this embodiment, the gas containing upconverter structures of the invention are mixed along with the photocatalytic semiconductor particles in the waste water fluid stream, and the exterior activation energy source penetrates the container (e.g., a plastic or aluminum container) and irradiates the bulk of the waste water, producing UV light throughout the waste water which in turn drives the photocatalytic reactions. In one embodiment, the upconverters of the invention are complexed with the X-ray down converting particles or other energy modulation agents permitting for example X-ray irradiation to also assist in this process.

In other embodiment, light from the gas containing upconverter structures would be used in conjunction with more conventional microwave chemical processing to facilitate the chemical processing. U.S. Pat. Nos. 4,946,797 and 5,840,583 (both of which are incorporated herein by reference)

U.S. Pat. No. 4,946,797 describes a process where microwave energy is applied to an acid/sample mixture at the beginning of, and thereafter during protein digestion. After the application of microwave energy is discontinued, the digestate is diluted by pulsed addition of water, followed by continuous addition of water. Dilution in this manner prevents a sudden surge in gas evolution, and eliminates the need for an intervening cooling step, thereby reducing processing time. In the present invention, the application of light from the gas containing upconverter structures of the invention, especially in the UV wavelength range would facilitate in the digestion of these mixtures either directly or through the use of the catalyst as described above.

U.S. Pat. No. 5,840,583 describes a method for microwave assisted chemical processes that comprises applying sufficient microwave radiation to a temperature-monitored mixture of reagents, with at least one of the reagents being thermally responsive to electromagnetic radiation in the microwave range, and based on the monitored temperature, to maintain the added reagents at or closely about a predetermined temperature while substantially avoiding thermal dilution (or before substantial thermal dilution can occur) that otherwise would have been caused by the addition of the reagents to one another. The '583 patent describes that treatments usually represent oxidation of samples and thus include conversion of carbon to carbon dioxide and hydrogen to water or water vapor. Some of the oxidation procedures that use liquid oxidizing agents such as the mineral acids are referred to as "wet ashing," "wet-oxidation," or "digestion." In the present invention, the application of light from the gas containing upconverter structures of the invention, can further assist the thermally responsive agents (the liquid oxidizing agents) in the digestion of these mixtures either directly or through the use of the catalyst as described above.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

Workers have found that UV irradiation could realize an effective graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photo-grafting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of the upconverter structures of the invention in dispersion in the fluid medium being used for photostimulation. Upon microwave or RF power irradiation, the upconverters of the invention would generate UV light permitting batch or bulk type processing to occur in parallel inside the container.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Wanting to stop the fermentation process is all good in and of itself. But unfortunately, there is really no practical way to successfully stop a fermentation dead in its tracks. Additives such as sulphite and sorbate can be added to stabilize a fermented product and stop additional fermentation. Many winemakers will turn to sulfites such as that found in Sodium Bisulfite or Campden tablets for the answer. But, these two items are not capable of reliably killing enough of the yeast to guarantee a complete stop of the activity—at least not at normal doses that leave the wine still drinkable.

Once the bulk of the sulfites from either of these ingredients dissipate from the wine into the air—as sulfites do—there is a very strong chance that the remaining few live yeast cells will start multiplying and fermenting again if given enough time. This usually happens at a most inconvenient time, like after the wine has been bottled and stowed away.

Potassium sorbate is another ingredient that many winemakers consider when trying to stop a wine from fermenting any further. There is a lot of misunderstanding surrounding this product. It is typically called for by home wine making books when sweetening a wine. This is a situation where the fermentation has already completed and is ready for bottling. One adds the potassium sorbate along with the sugar that is added for sweetening.

The potassium sorbate stops the yeast from fermenting the newly added sugar. So, many winemakers assume potassium sorbate can stop an active fermentation as well, but, potassium sorbate does not kill the yeast at all, but rather it makes the yeast sterile. In other words, it impairs the yeast's ability to reproduce itself. But, it does not hinder the yeast's ability to ferment sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above could be used for the application described here. For non-liquid products, energy modulation agents with little and preferably no toxicity (e.g. Fe oxides or titanium oxides) could be added. Here, the concentration of these additives would likely be limited by any unexpected changes in taste.

Here, UV light produced by the up converters of the invention would deactivate the yeasts.

Photoactivated Cross-linking and Curing of Polymers

In this application, the upconverters of the invention are provided and distributed into an uncured polymer based medium for the activation of photosensitive agents in the medium to promote cross-linking and curing of the polymer based medium. In one embodiment, the upconverters of the invention are complexed with other down-converting luminescent particles or other energy modulation agents prior to being added to the polymer.

For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the upconverters of the invention are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with, for example, carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silione resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of the invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio) phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4,6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis (.eta..sup.5-2,4-cyclopentadien-1-yl)-bis[2,6-difluoro-3-(1H-pyrrol-1-yl)phenyl]titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 urn. Other Q-CEL products are shown below in tabular form. Another commercially available hollow glass microsphere is sold by Kish under the trade name SPHERICEL. SPHEREICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCH-LITE tradename.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescent particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are the upconverter structures of the invention. These compositions can then be applied to surfaces of objects to be fixed together or to surfaces where a hard coating is desired or cast in a curable form for the production of molded objects. These compositions upon activation will produce radiant light for photoactivated cure of the luminescent particle containing polymer composition. The density of the upconverter structures in these compositions will depend on the "light transparency" of the luminescent particle containing composition. Where these compositions contain a significant amount of the inorganic filler as discussed above, the concentration of the upconverter structures can be reduced for example as compared to a composition with a black color pigment where the light transparency will be significantly reduced.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C(200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the upconverters are added to these Bach et al. compositions. Due to the fact that the exterior energy source penetrates deeper into the entirety of the Bach et al. compositions, thicker surface coatings can be realized. Further, the coatings can be applied to intricate surfaces having for example been prepared with recesses or protrusions.

Electromagnetic Field Visualization Probe

The gas containing up converter structures of the invention in one embodiment are designed to produce plasma ignition under low Q, low field conditions such that inadvertent heating does not occur in the medium where the upconverters are dispersed. This capability permits then the upconverters of the invention to be used in encapsulations on or near (or removable and insertable) high power electromagnetic sources. For example, in the testing and development of microwave circuitry, one often has to infer as to the paths of microwave leakage (especially if the paths of microwave leakage or operating at harmonic frequencies). In on embodiment, isolated gas cavities filled with ioniozable gas can be packing for example in a wand made of an electrically insulating material to protect the user. The wand would then be used as a test probe to probe regions of high electric field strength. Alternatively, in one embodiment, the wand would include a microwave antenna connected to a microwave power supply. The field strength from the antenna would not normally (in absence of an external field) produce plasma ignitions in the isolated gas cavities.

At low powers, the wand could physically probe the microwave field strength with areas of high field strength producing plasma ignition and optical emission from the wand which would be visible to the user. The small size of the cavities in the broad band upconverters of the invention would be advantageous for not drawing significant power from the microwave circuit being evaluated.

In another embodiment, the wand could be designed for the testing of high power AC and RF circuits or transformers. In this embodiment, the wand could also include the afore-mentioned microwave antenna providing a local source of microwave power to the isolated gas cavities. The power level would be set below an ignition threshold of the gas cavity. However, as the wand and the isolated gas cavities were moved into a region of high electric field, the high electric field would supplement energy from the microwave antenna and produce plasma ignitions.

In another embodiment, the wand would include isolated gas cavities where different ones of the gas cavities would be filled with gases of different ionization potentials or at different pressures. The gases igniting first would have one color, while gases igniting later at higher potentials would show a different color. In this way, a relative magnitude of the electric field would be manifest by the different colors. For example, blue emission could be established with argon, and a red emission could be established with nitrogen such that the blue would be regarded by the user to the representative of a relatively low electric field strength and the red emission would be representative of a relatively higher electric field strength.

In some environments, workers for example on high power, high tension electrical lines would use the wands as safety checks on the presence of power. In this aspect, no contact of the wand to the high tension device is required to ascertain the presence of power on the lines.

Light Sources

The gas containing up converter structures of the invention in one embodiment are designed to produce plasma ignition under low Q, low field conditions such that inadvertent heating does not occur in the medium where the upconverters are dispersed. This capability permits then the upconverters of the invention to be used as light sources similar to the microcavity light sources described above. The microcavity light sources described above depend on capacitive electric field coupling to generate the plasma responsible for light emission. This power coupling mechanism inherently heats the anode of the lighting device, ultimately limiting power to a point where local heating destroys the material of the microcavity light source. Conversely, this power coupling mechanism requires a high value of electric field strength and voltage to sustain a plasma. Indeed, the microcavity light sources described above typically requires 100's of volts for plasma operation.

Microwave coupling avoids these issues and is an electrodeless way to couple power without then the anode loss problem.

Inspection Probes

As noted above, microwave coupling avoids these issues and is an electrodeless way to couple power without then the anode loss problem. While this may permit higher luminance from microcavity devices to be obtained, it may also permit lower powers to be used to obtain emission.

Because of the sensitivity of the human eye and modern detectors, even low level luminoscity devices can be of utility in diagnostic areas. For example, in the inspection of many macroscopic construction articles, (such as for example steel structures, metal castings, concrete pourings, plastic moldings, asphalt pavings, etc.), the human eye and staining techniques are typically used. Beyond that, more expensive x-ray and ultrasound techniques are used.

Here, the gas containing up converter structures of the invention in one embodiment are of a microscopic size such that the upconverters could be applied to the surface of an article of manufacture. For example, the upconverters could be suspended in a solution and washed over the piece to be tested for cracks. The microscopic size would mean that the broad band upconverters would preferentially be retained in the non-surface areas (e.g., in the cracks or pits of the concrete). Irradiation with a hand held microwave source (or placement of the piece inside a microwave resonator) would produce plasma emission whose intensity would show more strongly where more of the upconverters had settled. Digital cameras could then be used to document where the defects occurred.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A method for producing a change in a fluid medium, comprising:
    (1) placing into the fluid medium at least one gas-containing upconverter including a gas for plasma ignition,
    said gas-containing upconverter configured, upon exposure to initiation energy, to generate and emit light into the fluid medium; and
    (2) applying the initiation energy to the gas-containing upconverter, wherein the emitted light directly or indirectly produces the change in the fluid medium.

2. The method of claim 1, wherein said fluid medium is waste water, and wherein applying comprises applying the initiation energy to the waste water to reduce contaminants in the waste water.

3. The method of claim 1, wherein applying comprises applying the initiation energy to the fluid medium to sterilize the fluid medium.

4. The method of claim 3, wherein the fluid medium is a blood product.

5. The method of claim 1, wherein applying comprises applying the initiation energy to alter a surface structure of an article in the fluid medium.

6. The method of claim 5, wherein applying comprises photo-grafting a molecular species onto a surface of the article.

7. The method of claim 1, wherein said applying comprises
    applying microwave radiation or radiofrequency radiation by which said gas-containing upconverter generates emitted light in the infrared, visible, or ultraviolet range to produce at least one of physical and biological changes in the fluid medium.

8. The method of claim 1 wherein the gas-containing upconverter comprises a free-standing receptor having outside dimensions of millimeters or below to a first wavelength $\lambda_1$ of radiation, and
    upon interaction of said initiation energy with the receptor, generating radiation in the infrared, visible, or ultraviolet wavelength range.

9. The method of claim 1, further comprising:
    irradiating a fluidized bed including a plurality of gas-containing upconverters; and
    generating from said plurality of gas-containing upconverters radiation to treat the fluid medium about the fluidized bed.

10. The method of claim 1, wherein the fluid medium is an uncured radiation-curable resin and the change in the fluid medium is curing of the uncured radiation-curable resin.

11. A system for medical therapy comprising:
    a photosensitive therapeutic agent activatable at a selected optical wavelength;
    a gas-containing container including a gaseous medium configured to produce said optical wavelength via plasma generation;
    said container disposed proximate to said therapeutic agent, said container being at least partially transmissive at said optical wavelength;
    a magnetic field source configured to apply a magnetic field to said gaseous medium; and
    an applicator configured to apply microwave or rf energy to said gaseous medium to produce a plasma from said gaseous medium in said container, thereby generating said optical wavelength for activating the photosensitive therapeutic agent.

12. The system of claim 11, wherein said container comprises at least one of glasses and ceramics, polymers, microporous and nanoporous materials, molecular sieves and zeolites, and microporous silica.

13. The system of claim 11, wherein said container comprises a dielectric capsule further comprising a conductive element.

14. The system of claim 13, wherein said conductive element comprises at least one of carbon nanotubes and graphene.

15. The system of claim 11, wherein said container comprises a glass microballoon.

16. The system of claim 11, wherein said container comprises a plasmonic active coating thereon.

17. The system of claim 16, wherein said plasmonic active coating comprises at least a layer of gold.

18. The system of claim 17, wherein said gaseous medium comprises a gas composition capable of emitting UV light and comprises at least one of hydrogen, argon, nitrogen, xenon, ammonia, iodine vapor; mercury vapor; sodium vapor, an organic gas, and hydrogen-nitrogen mixtures, and mixtures thereof.

19. The system of claim 17, wherein said magnetic field is applied by a magnetic resonance imaging system.

20. The system of claim 11, wherein said microwave or rf energy is applied by a device comprising at least one of inductive loops, coaxial antennas, waveguide launchers, and quasi-optical applicators.

21. A system for generating a response in a fluid medium, comprising:
    an rf or microwave electromagnetic flux source configured to direct rf or microwave radiation to the fluid medium;
    an energy receptor comprising a gas-containing container having outside dimensions of millimeters or below and disposed in the fluid medium and configured, upon exposure to the rf or microwave radiation, to generate a direct or indirect response in the fluid medium from secondary radiation emitted into the fluid medium of a higher energy than said rf or microwave radiation.

22. The system of claim 21, wherein the electromagnetic flux source comprises at least one of a rf applicator or a microwave applicator, or both.

23. The system of claim 21, further comprising a magnetic flux source.

24. A medical catheter comprising:
- a gas-containing containment sealed with an ionizable gas which upon receipt of first wavelength $\lambda_1$ of microwave or rf energy emits light in the visible or ultraviolet wavelength range;
- an insertion sleeve including at a distal end thereof the gas-containing containment for insertion into a patient.

25. A method for producing light within the body of a human or animal subject, comprising:
- placing inside the body a gas-containing containment sealed with an ionizable gas;
- irradiating the body with microwave or rf energy; and
- igniting a plasma in the gas of the gas-containing containment to thereby produce light within the body of the subject.

26. A system for treating or diagnosing a human or animal subject, comprising:
- a gas-containing containment sealed with an ionizable gas, the gas-containing containment configured to be disposed inside the human or animal subject;
- a source of microwave or rf energy configured to broadcast the microwave or rf energy into the human or animal subject; and
- said source at least partially having the capability to generate a plasma in the gas of the gas-containing containment to thereby produce light within the body of the human or animal subject.

* * * * *

UNITED STATES PATENT AND TRADEMARK OFFICE
CERTIFICATE OF CORRECTION

Page 1 of 2

PATENT NO. : 10,080,275 B2
APPLICATION NO. : 14/688687
DATED : September 18, 2018
INVENTOR(S) : Frederic A. Bourke et al.

It is certified that error appears in the above-identified patent and that said Letters Patent is hereby corrected as shown below:

On the Title Page

On page 3, Column 1, item (56), other publications, Line 18, "Opportunites" should read --Opportunities--

In the Specification

Column 6, Line 22, "alumino-silcate" should read --alumino-silicate--

Column 15, Line 15, "Gyrtrons," should read --Gyrotrons,--

Column 23, Line 18, "of the of the" should read --of the--

Column 25, Line 40, "and or" should read --and/or--

Column 26, Line 38, "and or" should read --and/or--

Column 30, Line 64, "alumino-silcate" should read --alumino-silicate--

Column 32, Lines 57-58, "chmistries." should read --chemistries.--

Column 32, Lines 59-60, "chmistries." should read --chemistries.--

Column 47, Line 30, "cambers" should read --chambers--

Column 48, Line 10, "tow" and should read --two--

Column 53, Line 62, "and or" should read --and/or--

Column 64, Line 31, "Oncolgy" should read --Oncology--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,080,275 B2

Column 64, Line 32, "Humbolt" should read --Humboldt--

Column 70, Line 4, "napththoquinones," should read --naphthoquinones,--

Column 73, Line 19, "dinucelotide" should read --dinucleotide--

Column 73, Line 20, "dinucelotide" should read --dinucleotide--

Column 78, Line 26, "cyclodextran." should read --cyclodextrin.--

Column 79, Line 4, "manitol," should read --mannitol,--

Column 81, Line 10, "ablasion" should read --ablation--

Column 81, Line 12, "restinosis)," should read --restenosis),--

Column 81, Line 14, "hopecia areata," should read --alopecia areata,--

Column 81, Line 45, "ablasion" should read --ablation--

Column 81, Line 47, "restinosis)," should read --restenosis),--

Column 81, Line 49, "hopecia areata," should read --alopecia areata,--

Column 84, Line 18, "napththoquinones," should read --naphthoquinones,--

Column 87, Lines 24-25, "electrophysipologically" and should read --electrophysiologically--

Column 87, Lines 52-53, "aminoinethyltrimethylpsoralen" should read --aminomethyltrimethylpsoralen--

Column 102, Line 15, "urn." should read --µm.--